(12) United States Patent
Taniguchi et al.

(10) Patent No.: US 9,579,407 B2
(45) Date of Patent: Feb. 28, 2017

(54) RADIOLABELED COMPOUNDS AND THEIR USE AS RADIOTRACERS FOR QUANTITATIVE IMAGING OF PHOSPHODIESTERASE (PDE10A) IN MAMMALS

(75) Inventors: Takahiko Taniguchi, Kanagawa (JP); Shotaro Miura, Kanagawa (JP); Tomoaki Hasui, Kanagawa (JP); Christer Halldin, Stockholm (SE); Vladimir Stepanov, Stockholm (SE); Akihiro Takano, Stockholm (SE)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/237,234

(22) PCT Filed: Aug. 21, 2012

(86) PCT No.: PCT/JP2012/071523
§ 371 (c)(1),
(2), (4) Date: Feb. 5, 2014

(87) PCT Pub. No.: WO2013/027845
PCT Pub. Date: Feb. 28, 2013

(65) Prior Publication Data
US 2014/0178304 A1 Jun. 26, 2014

(30) Foreign Application Priority Data

Aug. 22, 2011 (SE) ........................ 1150757
Aug. 15, 2012 (SE) ........................ 1250925

(51) Int. Cl.
*A61K 51/00* (2006.01)
*A61M 36/14* (2006.01)
*A61K 51/04* (2006.01)
*C07D 401/14* (2006.01)
*C07D 405/14* (2006.01)
*C07D 413/14* (2006.01)
*C07D 403/04* (2006.01)
*C07D 403/14* (2006.01)
*C07D 417/14* (2006.01)
*C07D 498/08* (2006.01)

(52) U.S. Cl.
CPC ...... *A61K 51/0459* (2013.01); *A61K 51/0463* (2013.01); *A61K 51/0468* (2013.01); *C07D 401/14* (2013.01); *C07D 403/04* (2013.01); *C07D 403/14* (2013.01); *C07D 405/14* (2013.01); *C07D 413/14* (2013.01); *C07D 417/14* (2013.01); *C07D 498/08* (2013.01)

(58) Field of Classification Search
CPC ............ A61K 51/0459; A61K 51/0463; A61K 51/0468; C07D 401/14; C07D 405/14; C07D 413/14; C07D 403/04; C07D 403/14; C07D 417/14; C07D 498/08

USPC .......................................................... 424/1.81
See application file for complete search history.

(56) References Cited

U.S. PATENT DOCUMENTS

| 5,877,175 A | 3/1999 | Sargent et al. |
|---|---|---|
| 8,178,538 B2 | 5/2012 | Alberati et al. |
| 8,354,411 B2 | 1/2013 | Taniguchi et al. |
| 8,435,995 B2 | 5/2013 | Taniguchi et al. |
| 8,513,251 B2 | 8/2013 | Taniguchi et al. |
| 2008/0207902 A1 | 8/2008 | Kohno et al. |
| 2010/0152193 A1 | 6/2010 | Alberati et al. |
| 2010/0197651 A1 | 8/2010 | Taniguchi et al. |
| 2012/0028951 A1 | 2/2012 | Taniguchi et al. |
| 2012/0064005 A1 | 3/2012 | Cox et al. |
| 2012/0277204 A1 | 11/2012 | Taniguchi et al. |
| 2012/0277430 A1 | 11/2012 | Taniguchi et al. |
| 2012/0277431 A1 | 11/2012 | Taniguchi et al. |
| 2013/0137675 A1 | 5/2013 | Taniguchi et al. |
| 2013/0150344 A1 | 6/2013 | Yoshikawa et al. |

FOREIGN PATENT DOCUMENTS

| WO | 2010/063610 | 6/2010 |
|---|---|---|
| WO | 2010/090737 | 8/2010 |

(Continued)

OTHER PUBLICATIONS

Lin et al. Nucl. Med. Biol. 2005, 415-422.*
Zhang et al. Curr. Top. Med. Chem. 2007, 1817-1828.*
International Search Report issued Nov. 2, 2012 in International (PCT) Application No. PCT/JP2012/071523.
Iwata et al., "Radiosynthesis of O[$^{11}$C]methyl-L-tyrosine and O[$^{18}$F]Fluoromethyl-L-tyrosine as potential PET tracers for imaging amino acid transport", Journal of Labelled Compounds and Radiopharmaceuticals, vol. 46, 2003, pp. 555-566.

(Continued)

*Primary Examiner* — Michael G Hartley
*Assistant Examiner* — Sean R Donohue
(74) *Attorney, Agent, or Firm* — Wenderoth, Lind & Ponack, L.L.P.

(57) ABSTRACT

The present invention provides radiolabeled compounds useful as radiotracers for quantitative imaging of PDE10A in mammals. The compound of the present invention is represented by the formula (I): wherein each symbols are as defined in the specification.

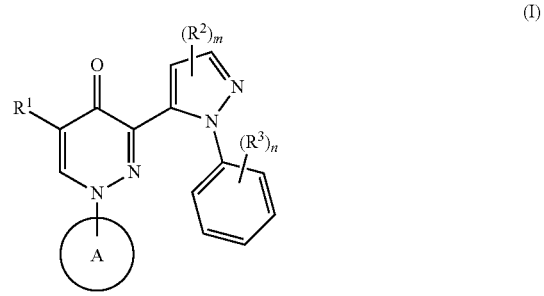

(I)

12 Claims, 20 Drawing Sheets

(56) References Cited

FOREIGN PATENT DOCUMENTS

| WO | 2010/138577 | 12/2010 |
|---|---|---|
| WO | 2012/018059 | 2/2012 |
| WO | 2012/020780 | 2/2012 |

OTHER PUBLICATIONS

Lourenco et al., "Characterization of R-[$^{11}$C]rolipram for PET imaging of phosphodiesterase-4: in vivo binding, metabolism, and dosimetry studies in rats", Nuclear Medicine and Biology, vol. 28, No. 4, 2001, pp. 347-358.
Green et al., "Longitudinal studies of cognition and functional outcome in schizophrenia: implications for Matrics", Schizophrenia Research, vol. 72, 2004, pp. 41-51.
Harvey et al., "Cognitive Functioning in Schizophrenia: A Consensus Statement on Its Role in the Definition and Evaluation of Effective Treatments for the Illness", Journal of Clinical Psychiatry, vol. 65, No. 3, 2004, pp. 361-372.
Ross et al., "Neurobiology of Schizophrenia", Neuron, vol. 52, Oct. 5, 2006, pp. 139-153.
Krebs et al., "Current schizophrenia drugs: efficacy and side effects", Expert Opinion on Pharmacotherapy, vol. 7, No. 8, 2006, pp. 1005-1016.
Menniti et al., "Phosphodiesterases in the CNS: targets for drug development", Nature Reviews Drug Discovery, vol. 5, Aug. 2006, pp. 660-667.
Menniti et al., "Phosphodiesterase 10A inhibitors: A novel approach to the treatment of the symptoms of schizophrenia", Current Opinion in Investigational Drugs, vol. 8, No. 1, 2007, pp. 54-59.
Bender et al., "Cyclic Nucleotide Phosphodiesterases: Molecular Regulation to Clinical Use", Pharmacological Reviews, vol. 58, No. 3, 2006, pp. 488-520.
Fujishige et al., "Enzymology: Cloning and Characterization of a Novel Human Phosphodiesterase That Hydrolyzes Both cAMP and cGMP (PDE10A)", The Journal of Biological Chemistry, vol. 274, No. 26, 1999, pp. 18438-18445.
Loughney et al., "Isolation and characterization of PDE10A, a novel human 3',5'—cyclic nucleotide phosphodiesterase", Gene, vol. 234, 1999, pp. 109-117.
Soderling et al., "Isolation and characterization of a dual-substrate phosphodiesterase gene family: PDE10A", Proceedings of the National Academy of Sciences, vol. 96, Jun. 1999, pp. 7071-7076.
Seeger et al., "Immunohistochemical localization of PDE10A in the rat brain", Brain Research, vol. 985, 2003, pp. 113-126.
Xie et al., "Cellular and Subcellular Localization of PDE10A, A Striatum-Enriched Phosphodiesterase", Neuroscience, vol. 139, 2006, pp. 597-607.
Coskran et al., "Immunohistochemical Localization of Phosphodiesterase 10A in Multiple Mammalian Species", Journal of Histochemistry & Cytochemistry, vol. 54, No. 11, 2006, pp. 1205-1213.
Siuciak et al., "Genetic deletion of the striatum-enriched phosphodiesterase PDE10A: Evidence for altered striatal function", Neuropharmacology, vol. 51, 2006, pp. 374-385.
Siuciak et al., "Inhibition of the striatum-enriched phosphodiesterase PDE10A: A novel approach to the treatment of psychosis", Neuropharmacology, vol. 51, 2006, pp. 386-396.
Graybiel, A., "Neurotransmitters and neuromodulators in the basal ganglia", Trends in Neurosciences, vol. 13, No. 7, 1990, pp. 244-254.
Graybiel, A., "The basal ganglia", Current Biology, vol. 10, 2000, pp. 509-511.
Van de Bittner et al., "A Philosophy for CNS Radiotracer Design", Acc. Chem. Res., vol. 47, 2014, pp. 3127-3134.
Halldin et al., "PET Studies with Carbon-11 Radioligands in Neuropsychopharmacological Drug Development", Current Pharmaceutical Design, vol. 7, 2001, pp. 1907-1929.

* cited by examiner

RADIOLABELED COMPOUNDS AND THEIR USE AS RADIOTRACERS FOR QUANTITATIVE IMAGING OF PHOSPHODIESTERASE (PDE10A) IN MAMMALS

TECHNICAL FIELD

The invention relates generally to novel radiolabeled compounds and to their use as radiotracers for quantitative imaging of phosphodiesterase 10A (PDE10A) in mammals.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, tumor imaging, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lives of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}TC$, $^{201}Tl$ and $^{123}I$.

In the last two decades, one of the most active areas of nuclear medicine research has been the development of receptor imaging radiotracers. These tracers bind with high affinity and specificity to selective receptors and neuroreceptors. Successful examples include radiotracers for imaging the following receptor or transporter systems: estrogen, muscarinic, serotonin, dopamine, opiate, neuropeptide-Y, cannabinoid-1 and neurokinin-1.

Schizophrenia is a devastating neuropsychiatric syndrome that typically strikes in late adolescence or early adulthood. Positive or psychotic symptoms, including delusions and hallucinations, are the most apparent manifestation of the disorder. These emerge episodically and usually trigger the first hospitalization in early adulthood. Chronic aspects of the disorder include negative symptoms such as social withdrawal, flattened affect, and anhedonia as well as pervasive cognitive deficits. The latter have been closely linked to a poor function outcome and long-term prognosis (Green et al., Schizophr. Res. (2004) 72: 41-51; Harvey et al., J. Clin. Psychiatry (2004) 65: 361-372). Although dopamine $D_2$ receptor antagonists are effective for positive symptoms, these drugs are not effective for negative and cognitive symptoms of schizophrenia, suggesting that other systems (e.g., NMDA receptor hypofunction and GABAergic hypofunction) than excessive subcortical dopaminergic activity may have also implicated in the pathophysiology of schizophrenia (Ross et al., Neuron (2006) 52: 139-153). $D_2$ antagonists (typical antipsychotics) are known to cause extrapyramidal side effects (EPS) and hyperprolactinemia by excessive $D_2$ receptor antagonism in the brain (Michael et al., Expert Opin. Pharmacother. (2006) 7: 1005-1016). Although atypical antipsychotics, such as olanzapine and risperidone, have a lower incidence of EPS than typical antipsychotics, these drugs still have problem of hyperprolactinemia as well as serious metabolic side effects including hyperglycemia, weight gain, diabetes, and abnormal lipid profile due to interaction with multiple neurotransmitter receptors (Michael et al., Expert Opin. Pharmacother. (2006) 7: 1005-1016). Thus novel drugs with potent efficacy against not only positive symptom but also negative and cognitive symptoms, as well as better safety profile, would be of considerable therapeutic value.

It has recently been hypothesized that inhibition of the cyclic nucleotide phosphodiesterase (PDE) will provide a new therapeutic approach to the treatment of schizophrenia (Frank et al., Nat. Rev. Drug Disc. (2000) 5: 660-670; Frank et al., Curr. Opin. Investig. Drugs (2000) 8: 54-59). PDE superfamily of enzymes was encoded by 21 genes and subdivided into 11 distinct families according to structural and functional properties (Andrew et al., Pharmacol. Rev. (2006) 58: 488-520). These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

PDE10 has the most restricted distribution within known PDE families; the PDE10 mRNA is highly expressed only in the brain and testis (Fujimoto et al., J. Biol. Chem. (1999) 274: 18438-18445; Loughney et al., Gene (1999) 234: 109-117; Soderling et al., Proc. Natl. Acad. Sci. USA (1999) 96: 7071-7076). PDE10 protein is also highly expressed in the brain with restricted distribution in the periphery in multiple mammalian species (Thomas et al., Brain Research (2003) 985: 113-126). In the mammalian brain, mRNA and protein of PDE10 are highly enriched in medium spiny neurons (MSNs) of the striatum (Thomas et al., Brain Research (2003) 985: 113-126; Xie et al., Neuroscience (2006) 139: 597-607; Timothy et al., J. Histochem. Cyto. (2006) 54: 1205-1213), where it regulates striatal output by its effects on both the cAMP and cGMP signaling cascades (Judith et al., Neuropharmacology (2006) 51: 374-385; Judith et al., Neuropharmacology (2006) 51: 386-396). MSNs are mainly divided into two pathways: a direct (striatonigral) pathway that expresses $D_1$ dopamine receptors and an indirect (striatopallidal) pathway that expresses $D_2$ dopamine receptors (Graybiel et al., Trends Neurosci. (1990) 13: 244-254; Graybiel et al., Curr. Biol. (2000) 10: 509-511). These pathways have opposing effects on striatal output. As PDE10 is expressed in both pathways, PDE10 inhibition and the resulting elevation of striatal cyclic nucleotide levels would potentially have the effects of $D_2$ antagonism, the standard treatment for psychosis, along with $D_1$ agonism which may minimize extrapyramidal side effect liabilities. This unique distribution and function in the brain indicates that PDE10 represents an important new target for the treatment of neurological and psychiatric disorders, in particular psychotic disorders like schizophrenia.

PET (Positron Emission Tomography) radiotracers and imaging technology may provide a powerful method for clinical evaluation and dose selection of PDE10A inhibitors. Thus, the invention herein is directed to radiolabeled PDE10A inhibitors that would be useful for exploratory and diagnostic imaging applications, both in vitro and in vivo, and for competition studies using radiolabeled and unlabeled PDE10A inhibitors.

SUMMARY OF THE INVENTION

Problems to be Solved by the Invention

The present invention aims to provide novel radiolabeled compounds useful as radiotracers for quantitative imaging of PDE10A in mammals.

Means of Solving the Problems

The present inventors have conducted intensive studies in an attempt to solve the aforementioned problems and found that the compounds represented by the below-mentioned formula (I) and formula (I') are useful as radiotracers for quantitative imaging of PDE10A in mammals. Further studies made by the present inventors based on these findings have resulted in the completion of the present invention.

Accordingly, the present invention relates to
[1] A compound represented by the formula (I):

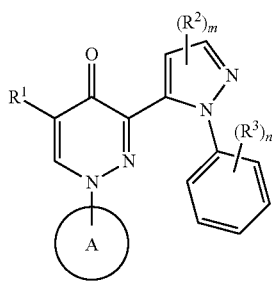

(I)

wherein:
ring A is selected from the group consisting of
(1) a benzene,
(2) a pyrazole,
(3) a thiazole,
(4) a piperidine, and
(5) a tetrahydropyridine,
wherein said ring A may optionally be substituted by 1 to 4 substituents selected from the group consisting of halogens, an optionally substituted $C_{1-4}$ alkyl, an optionally substituted $C_{1-4}$ alkoxy, an optionally substituted $C_{7-14}$ aralkyl, an optionally substituted $C_{2-4}$ alkenyl, an optionally substituted $C_{2-4}$ alkynyl, and a cyclic group which may optionally be substituted (provided that a cyclic group represented by the formula

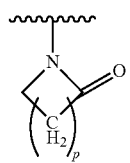

(wherein p is 1 to 4) which may optionally be substituted, is excluded), $R^1$ is an optionally substituted $C_{1-4}$ alkoxy, wherein the optionally substituted $C_{1-4}$ alkoxy is radiolabeled,
$R^2$ and $R^3$ are each substituent,
m is 0 to 2,
n is 0 to 5;
provided that
1-(2-fluorophenyl)-5-[$^{11}$C]methoxy-3-(1-phenyl-1H-pyrazol-5-yl)pyridazin-4(1H)-one,
1-[4-(3,5-dimethylisoxazol-4-yl)-2-fluorophenyl]-5-$^{11}$C-methoxy-3-(1-phenyl-1H-pyrazol-5-yl)pyridazin-4(1H)-one and
1 (2 fluoro-4-(morpholin-4-yl)phenyl)-5-$^{11}$C-methoxy-3-(1-phenyl-1H-pyrazol-5-yl)-pyridazin-4(1H)-one
are excluded;
or a salt thereof (hereinafter to be sometimes abbreviated as compound (I)).
[2] The compound according to [1], or a salt thereof, wherein a compound represented by the formula (I) is a compound represented by the formula (I'):

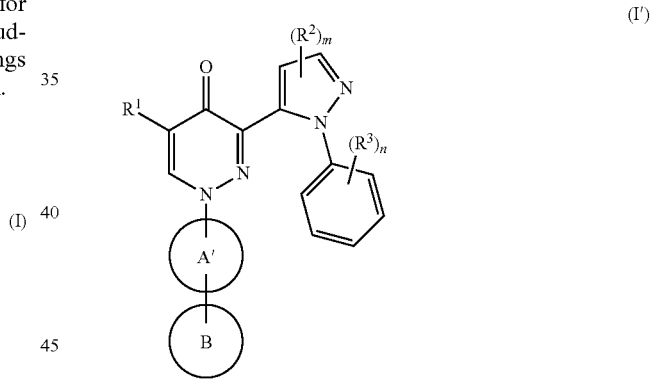

(I')

wherein:
ring A' is selected from the group consisting of
(1) a benzene,
(2) a piperidine, and
(3) a tetrahydropyridine,
wherein said ring A' may optionally be substituted by 1 to 4 substituents selected from the group consisting of halogens, $C_{1-4}$ alkyl, and $C_{1-4}$ alkoxy,
ring B is an optionally substituted cyclic group (provided that a group represented by the formula

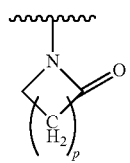

(wherein p is 1 to 4) which may optionally be substituted, is excluded) (hereinafter to be sometimes abbreviated as compound (I')).

[3] The compound according to [2], or a salt thereof, wherein ring B is selected from the group consisting of
(1) an optionally substituted $C_{3-12}$ cycloalkyl,
(2) an optionally substituted dihydropyranyl,
(3) an optionally substituted tetrahydropyranyl,
(4) an optionally substituted azetidinyl,
(5) an optionally substituted pyrrolidinyl,
(6) an optionally substituted piperidinyl,
(7) an optionally substituted imidazolyl,
(8) an optionally substituted isoxazolyl,
(9) an optionally substituted pyrazolyl,
(10) an optionally substituted dihydropyrazolyl,
(11) an optionally substituted pyridyl,
(12) an optionally substituted pyrrolyl,
(13) an optionally substituted dihydropyrrolyl,
(14) an optionally substituted phenyl,
(15) an optionally substituted morpholinyl,
(16) an optionally substituted thiazolyl,
(17) an optionally substituted oxazolidinyl,
(18) an optionally substituted imidazolidinyl,
(19) an optionally substituted oxaazabicyclooctyl, and
(20) an optionally substituted oxazepanyl.

[4] The compound according to [1], or a salt thereof, wherein $R^1$ is an optionally substituted $C_{1-4}$ alkoxy radiolabeled with $^{11}C$ or $^{18}F$.

[5] The compound according to [1], or a salt thereof, wherein $R^1$ is an optionally substituted $^{11}CH_3O$—, an optionally substituted $^{18}FCH_2O$—, an optionally substituted $^{18}FCD_2O$—, an optionally substituted $^{18}FCH_2CH_2O$— or an optionally substituted $^{18}FCD_2CD_2O$—.

[6] The compound according to [1], or a salt thereof, wherein $R^1$ is an optionally substituted $^{11}CH_3O$—, $^{18}FCD_2O$— or $^{18}FCD_2CD_2O$—.

[7] The compound according to [1], or a salt thereof, wherein both m and n are 0.

[8] The compound according to [2], or a salt thereof, wherein the ring A' is benzene which may optionally be substituted by one halogen atom.

[9] The compound according to [2], or a salt thereof, wherein ring B is selected from the group consisting of
(1) an optionally substituted tetrahydropyranyl, and
(2) an optionally substituted azetidinyl.

[10] 1-[2-Fluoro-4-(tetrahydro-2H-pyran-4-yl)phenyl]-5-$^{11}C$-methoxy-3-(1-phenyl-1H-pyrazol-5-yl)pyridazin-4 (1H)-one or a salt thereof.

[11] 1-[4-(3,3-Difluoroazetidin-1-yl)-2-fluorophenyl]-5-$^{11}C$-methoxy-3-(1-phenyl-1H-pyrazol-5-yl)pyridazin-4 (1H)-one or a salt thereof.

[12] 5-([$^{18}F$]Fluoro-methyloxy-$d_2$)-1-(2-fluoro-4-(tetrahydro-2H-pyran-4-yl)phenyl)-3-(1-phenyl-1H-pyrazol-5-yl)pyridazin-4(1H)-one or a salt thereof.

[13] 5-(2-[$^{18}F$]Fluoro-ethyloxy-$d_4$)-1-(2-fluoro-4-(tetrahydro-2H-pyran-4-yl)phenyl)-3-(1-phenyl-1H-pyrazol-5-yl)pyridazin-4(1H)-one or a salt thereof.

[14] A method for quantitative imaging of PDE10A in a mammal, which comprises administering to the mammal in need of such imaging an effective amount of the compound of [1], or a salt thereof, and obtaining an image useful for quantifying PDE10A in the mammal using positron emission tomography.

[15] A method for quantitative imaging of PDE10A in the brain in a mammal, which comprises administering to the mammal in need of such imaging an effective amount of the compound of [1], or a salt thereof, and obtaining an image useful for quantifying PDE10A in the brain in the mammal using positron emission tomography.

[16] A method for diagnostic imaging of a neurological or psychiatric disorder associated with PDE10A dysfunction in a mammal, which comprises administering to the mammal in need of such diagnostic imaging an effective amount of the compound of [1], or a salt thereof, and obtaining an image useful for quantifying PDE10A in the brain in the mammal using positron emission tomography.

[17] A method for diagnostic imaging of a neurological or psychiatric disorder associated with striatal hypofunction or basal ganglia dysfunction in a mammal, which comprises administering to the mammal in need of such diagnostic imaging an effective amount of the compound of [1], or a salt thereof, and obtaining an image useful for quantifying PDE10A in the brain in the mammal using positron emission tomography.

[18] A method for the quantification of PDE10A in mammalian tissue, which comprises contacting such mammalian tissue in which quantification is desired with an effective amount of the compound of [1], or a salt thereof, and detecting or quantifying the PDE10A using positron emission tomography.

[19] A sterile composition which comprises a compound of [1], or a salt thereof, dissolved in saline.

[20] Use of a compound of [1], or a salt thereof, for imaging a tissue, cells or a host, in vitro or in vivo.

[21] A method of imaging a tissue, cells or a host, which comprises contacting a compound of [1], or a salt thereof, with or administering to a tissue, cells or a host, and imaging the tissue, cells or host with a PET imaging system

[22] A compound of [1], or a salt thereof, which is for use of quantitative imaging of PDE10A.

Effect of the Invention

According to the present invention, novel radiolabeled compounds useful as radiotracers for quantitative imaging of PDE10A in mammals can be provided.

DETAILED DESCRIPTION OF THE INVENTION

The present invention will be explained in detail below.

Unless otherwise specifically stated, in this specification, examples of the "halogen" include fluorine, chlorine, bromine and iodine.

Unless otherwise specifically stated, in this specification, the phrase "can be halogenated" or the term "halogeno" means that one or more (e.g., 1 to 3) halogen atoms can be present as substituents.

Unless otherwise specifically stated, in this specification, examples of the "alkyl (group)" include $C_{1-10}$ alkyl (group), preferably $C_{1-6}$ alkyl (group).

Unless otherwise specifically stated, in this specification, examples of the "$C_{1-10}$ alkyl (group)" include methyl, ethyl, propyl, isopropyl, butyl, isobutyl, sec-butyl, tert-butyl, pentyl, isopentyl, neopentyl, and hexyl. In the present specification, the "$C_{1-6}$ alkyl (group)" is alkyl having a carbon number of 1 to 6, from among the above-mentioned "$C_{1-10}$ alkyl (group)", and the "$C_{1-4}$ alkyl (group)" is alkyl having a carbon number of 1 to 4, from among the above-mentioned "$C_{1-10}$ alkyl (group)".

Unless otherwise specifically stated, in this specification, the term "$C_{1-10}$ alkyl (group) that can be halogenated" means $C_{1-10}$ alkyl (group) which can be substituted by halogen, and examples thereof include trifluoromethyl.

Unless otherwise specifically stated, in this specification, examples of the "alkenyl (group)" include $C_{2-6}$ alkenyl (group).

Unless otherwise specifically stated, in this specification, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl. In the present specification, the "$C_{2-4}$ alkenyl (group)" is alkenyl having a carbon number of 2 to 4, from among the above-mentioned "$C_{2-6}$ alkenyl (group)".

Unless otherwise specifically stated, in this specification, examples of the "alkynyl (group)" include $C_{2-6}$ alkynyl (group).

Examples of "$C_{2-6}$ alkynyl (group)" include ethynyl, 1-propyn-1-yl, 2-propyn-1-yl, 4-pentyn-1-yl, and 5-hexyn-1-yl. In the present specification, the "$C_{2-4}$ alkynyl (group)" is alkynyl having a carbon number of 2 to 4, from among the above-mentioned "$C_{2-6}$ alkynyl (group)".

Unless otherwise specifically stated, in this specification, examples of the "$C_{3-7}$ cycloalkyl-$C_{2-6}$ alkynyl (group)" include cyclopropylethyl.

Unless otherwise specifically stated, in this specification, examples of the "$C_{3-12}$ cycloalkyl (group)" include cyclopropyl, cyclobutyl, cyclopentyl, and cyclohexyl. In the present specification, the "$C_{3-7}$ cycloalkyl (group)" is cycloalkyl having a carbon number of 3 to 7, from among the above-mentioned "$C_{3-12}$ cycloalkyl (group)".

Unless otherwise specifically stated, in this specification, examples of the "$C_{6-14}$ aryl (group)" include phenyl, 1-naphthyl, 2-naphthyl, 2-biphenylyl, 3-biphenylyl, 4-biphenylyl, and 2-anthryl.

Unless otherwise specifically stated, in this specification, examples of "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylmethyl, 3-biphenylmethyl, and 4-biphenylmethyl. In the present specification, the "$C_{7-14}$ aralkyl (group)" is aralkyl having a carbon number of 7 to 14, from among the above-mentioned "$C_{7-16}$ aralkyl (group)".

Unless otherwise specifically stated, in this specification, examples of "$C_{6-14}$ aryl-$C_{2-6}$ alkenyl (group)" include styryl.

Unless otherwise specifically stated, in this specification, the "cyclic group" includes "$C_{3-12}$ cycloalkyl (group)" (preferably, $C_{3-7}$ cycloalkyl), "$C_{6-14}$ aryl (group)" and "heterocyclic group".

Unless otherwise specifically stated, in this specification, the "heterocyclic group" (and a heterocyclic moiety in a substituent) is a non-aromatic heterocyclic group, or a heteroaryl group (i.e., aromatic heterocyclic group), and examples thereof include 3- to 14-membered heterocyclic group having 1 to 5 hetero atoms selected from nitrogen, sulfur and oxygen. This "heterocyclic group" can be monocyclic, bicyclic or tricyclic.

Examples of the "3- to 14-membered heterocyclic group" include 3- to 14-membered aromatic heterocyclic group having 1 to 5 hetero atoms selected from nitrogen, sulfur and oxygen such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, indolyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-1]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl); and saturated or unsaturated 3- to 14-membered non-aromatic heterocyclic group having 1 to 5 hetero atoms selected from nitrogen, sulfur and oxygen such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydropyrazolyl, dihydropyrrolyl, dihydroquinolyl, oxaazabicyclooctyl and oxazepanyl.

Unless otherwise specifically stated, in this specification, examples of the "5- to 10-membered heterocyclic groups" include those having 5- to 10-members among the aforementioned "3- to 14-membered heterocyclic group".

Unless otherwise specifically stated, in this specification, examples of the "aromatic heterocyclic group" (and an aromatic heterocyclic moiety in a substituent) include the "3- to 14-membered aromatic heterocyclic group having 1 to 5 hetero atoms selected from nitrogen, sulfur and oxygen" as exemplified above as said "heterocyclic group".

Unless otherwise specifically stated, in this specification, examples of the "non-aromatic heterocyclic group" (and an aromatic heterocyclic moiety in a substituent) include the "saturated or unsaturated 3- to 14-membered non-aromatic heterocyclic group having 1 to 5 hetero atoms selected from nitrogen, sulfur and oxygen" as exemplified above as said "heterocyclic group".

Unless otherwise specifically stated, in this specification, examples of the "saturated heterocyclic group" (and a saturated heterocyclic moiety in a substituent) include those saturated among said "non-aromatic heterocyclic group". Specific examples thereof include tetrahydrofuryl, morpholinyl, thiomorpholinyl, piperidinyl, pyrrolidinyl, and piperazinyl group.

Unless otherwise specifically stated, in this specification, examples of the "5- to 6-membered saturated heterocyclic group" (and a saturated heterocyclic moiety in a substituent) include those having 5- to 6-members among said "saturated heterocyclic group".

Unless otherwise specifically stated, in this specification, examples of the "alkoxy (group)" include $C_{1-10}$ alkoxy (group).

Unless otherwise specifically stated, in this specification, examples of the "$C_{1-10}$ alkoxy (group)" include methoxy, ethoxy, propoxy, isopropoxy, butoxy, isobutoxy, sec-butoxy, pentyloxy and hexyloxy. In the present specification, the "$C_{1-4}$ alkoxy (group)" is alkoxy having a carbon number of 1 to 4, from among the above-mentioned "$C_{1-10}$ alkoxy (group)".

Unless otherwise specifically stated, in this specification, examples of the "$C_{3-7}$ cycloalkyloxy (group)" include cyclopropyloxy, cyclobutyloxy, cyclopentyloxy, cyclohexyloxy.

Unless otherwise specifically stated, in this specification, examples of the "$C_{6-14}$ aryloxy (group)" include phenyloxy, 1-naphthyloxy and 2-naphthyloxy.

Unless otherwise specifically stated, in this specification, examples of the "$C_{7-16}$ aralkyloxy (group)" include benzyloxy and phenethyloxy.

Unless otherwise specifically stated, in this specification, examples of the "alkyl-carbonyloxy (group)" include $C_{1-10}$ alkyl-carbonyloxy (group).

Unless otherwise specifically stated, in this specification, examples of the "$C_{1-10}$ alkyl-carbonyloxy (group)" include acetoxy and propionyloxy.

Unless otherwise specifically stated, in this specification, examples of the "alkoxy-carbonyloxy (group)" include $C_{1-10}$ alkoxy-carbonyloxy (group).

Unless otherwise specifically stated, in this specification, examples of the "$C_{1-10}$ alkoxy-carbonyloxy (group)" include methoxycarbonyloxy, ethoxycarbonyloxy, propoxycarbonyloxy and butoxycarbonyloxy.

Unless otherwise specifically stated, in this specification, examples of the "mono-alkyl-carbamoyloxy (group)" include mono-$C_{1-10}$ alkyl-carbamoyloxy (group).

Unless otherwise specifically stated, in this specification, examples of the "mono-$C_{1-10}$ alkyl-carbamoyloxy (group)" include methylcarbamoyloxy and ethylcarbamoyloxy.

Unless otherwise specifically stated, in this specification, examples of the "di-alkyl-carbamoyloxy (group)" include di-$C_{1-10}$ alkyl-carbamoyloxy (group).

Unless otherwise specifically stated, in this specification, examples of the "di-$C_{1-10}$ alkyl-carbamoyloxy (group)" include dimethylcarbamoyloxy and diethylcarbamoyloxy.

Unless otherwise specifically stated, in this specification, examples of the "$C_{6-14}$ aryl-carbonyloxy (group)" include benzoyloxy and naphthylcarbonyloxy.

Unless otherwise specifically stated, in this specification, examples of the "mono- or di-$C_{6-14}$ aryl-carbamoyloxy (group)" include phenylcarbamoyloxy and naphthylcarbamoyloxy.

Unless otherwise specifically stated, in this specification, examples of the heterocyclic moiety of the "heterocyclic-oxy (group)" include those similar to said "heterocyclic group" are included. Specifically, examples of the "heterocyclic-oxy (group)" include 5- to 14-membered heterocyclic-oxy (group) having 1 to 5 hetero atoms selected from nitrogen, sulfur and oxygen.

Unless otherwise specifically stated, in this specification, examples of the aromatic heterocyclic moiety of the "heterocyclic-oxy (group)" include those similar to the "aromatic heterocyclic group" as examples of said "heterocyclic group". Specifically, examples of the "aromatic heterocyclic-oxy (group)" include 3- to 14-membered aromatic heterocyclic-oxy (group) having 1 to 5 hetero atoms selected from nitrogen, sulfur and oxygen.

Unless otherwise specifically stated, in this specification, examples of the "$C_{1-10}$ alkylsulfonyloxy (group)" include methylsulfonyloxy and ethylsulfonyloxy.

Unless otherwise specifically stated, in this specification, examples of the "halogeno $C_{1-10}$ alkylsulfonyloxy (group)" include halogeno methylsulfonyloxy and halogeno ethylsulfonyloxy.

Unless otherwise specifically stated, in this specification, examples of the "alkylsulfanyl (group)" include $C_{1-10}$ alkylsulfanyl (group).

Unless otherwise specifically stated, in this specification, examples of the "$C_{1-10}$ alkylsulfanyl (group)" include methylsulfanyl, ethylsulfanyl, propylsulfanyl, isopropylsulfanyl, butylsulfanyl, sec-butylsulfanyl, and tert-butylsulfanyl.

Unless otherwise specifically stated, in this specification, examples of the "$C_{3-7}$ cycloalkylsulfanyl (group)" include cyclopropylsulfanyl, cyclobutylsulfanyl, cyclopentylsulfanyl and cyclohexylsulfanyl.

Unless otherwise specifically stated, in this specification, examples of the "$C_{6-14}$ arylsulfanyl (group)" include phenylsulfanyl, 1-naphthylsulfanyl and 2-naphthylsulfanyl.

Unless otherwise specifically stated, in this specification, examples of the "$C_{7-16}$ aralkylsulfanyl (group)" include benzylsufanyl and phenethylsulfanyl.

Unless otherwise specifically stated, in this specification, examples of the heterocyclic moiety of the "heterocyclic-sulfanyl (group)" include those similar to said "heterocyclic group". Specifically, examples of the "heterocyclic-sulfanyl (group)" include 5- to 14-membered heterocyclic-sulfanyl (group) having 1 to 5 hetero atoms selected from nitrogen, sulfur and oxygen.

Unless otherwise specifically stated, in this specification, examples of the "alkyl-carbonyl (group)" include $C_{1-10}$ alkyl-carbonyl.

Unless otherwise specifically stated, in this specification, examples of the "$C_{1-10}$ alkyl-carbonyl (group)" include acetyl, propionyl and pivaloyl.

Unless otherwise specifically stated, in this specification, examples of the "$C_{3-7}$ cycloalkyl-carbonyl (group)" include cyclopropylcarbonyl, cyclopentylcarbonyl and cyclohexylcarbonyl group.

Unless otherwise specifically stated, in this specification, examples of the "$C_{6-14}$ aryl-carbonyl (group)" include benzoyl, 1-naphthoyl and 2-naphthoyl group.

Unless otherwise specifically stated, in this specification, examples of the "$C_{7-16}$ aralkyl-carbonyl (group)" include phenylacetyl and 3-phenylpropionyl group.

Unless otherwise specifically stated, in this specification, examples of the heterocyclic moiety of the "heterocyclic-carbonyl (group)" include those similar to said "heterocyclic group". Specifically, examples thereof include 3- to 14-membered heterocyclic-carbonyl (group) having 1 to 5 hetero atoms selected from nitrogen, sulfur and oxygen. Further, specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidine-1-ylcarbonyl, pyrrolidine-2-ylcarbonyl, pyrrolidine-3-ylcarbonyl, piperidine-1-ylcarbonyl, piperidine-2-ylcarbonyl, piperidine-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazine-1-ylcarbonyl, 1,4-piperazine-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

Unless otherwise specifically stated, in this specification, examples of the "carboxy (group) that can be esterified" include carboxy, alkoxy-carbonyl which can be substituted, $C_{6-14}$ aryloxy-carbonyl which can be substituted, $C_{7-16}$ aralkyloxy-carbonyl which can be substituted, silyloxy-carbonyl which can be substituted (e.g., TMS-O—CO—, TES-O—CO—, TBS-O—CO—, TIPS-O—CO—, TBDPS-O—CO—, etc.)

Unless otherwise specifically stated, in this specification, examples of the "alkoxy-carbonyl (group)" include methoxycarbonyl, ethoxycarbonyl, propoxycarbonyl, and tert-butoxycarbonyl.

Unless otherwise specifically stated, in this specification, examples of the "$C_{6-14}$ aryloxy-carbonyl (group)" include phenoxycarbonyl.

Unless otherwise specifically stated, in this specification, examples of the "$C_{7-16}$ aralkyl-carbonyl (group)" include benzyloxycarbonyl and phenethyloxycarbonyl.

Unless otherwise specifically stated, in this specification, examples of the "alkylsulfonyl (group)" include $C_{1-10}$ alkylsulfonyl (group).

Unless otherwise specifically stated, in this specification, examples of the "$C_{1-10}$ alkylsulfonyl (group)" include methylsulfonyl and ethylsulfonyl.

Unless otherwise specifically stated, in this specification, examples of the "$C_{3-7}$ cycloalkylsulfonyl (group)" include cyclopropylsulfonyl, cyclobutylsulfonyl, cyclopentylsulfonyl and cyclohexylsulfonyl.

Unless otherwise specifically stated, in this specification, examples of the "$C_{6-14}$ arylsulfonyl (group)" include phenylsulfonyl, 1-naphthylsulfonyl and 2-naphthylsulfonyl.

Unless otherwise specifically stated, in this specification, examples of the heterocyclic moiety of the "heterocyclic-sulfonyl (group)" include those similar to said "heterocyclic group". Specifically, examples of the "heterocyclic-sulfonyl (group)" include 5- to 14-membered heterocyclic-sulfonyl (group) having 1 to 5 hetero atoms selected from nitrogen, sulfur and oxygen.

Unless otherwise specifically stated, in this specification, examples of the saturated heterocyclic moiety of the "saturated heterocyclic-sulfonyl (group)" include those similar to said "heterocyclic group". Specifically, examples of the "heterocyclic-sulfonyl (group)" include 5- to 14-membered heterocyclic-sulfonyl (group) having 1 to 5 hetero atoms selected from nitrogen, sulfur and oxygen.

Unless otherwise specifically stated, in this specification, examples of the "alkylsulfinyl (group)" include $C_{1-10}$ alkylsulfinyl (group).

Unless otherwise specifically stated, in this specification, examples of the "$C_{1-10}$ alkylsulfinyl (group)" include methylsulfinyl and ethylsulfinyl.

Unless otherwise specifically stated, in this specification, examples of the "$C_{3-7}$ cycloalkylsulfinyl (group)" include cyclopropylsulfinyl, cyclobutylsulfinyl, cyclopentylsufinyl, and cyclohexysulfinyl.

Unless otherwise specifically stated, in this specification, examples of the "$C_{6-14}$ arylsulfinyl (group)" include phenylsulfinyl, 1-naphthylsulfinyl and 2-naphthylsulfinyl.

Unless otherwise specifically stated, in this specification, examples of the heterocyclic moiety of the "heterocyclic-sulfinyl (group)" include those similar to said "heterocyclic group". Specifically, examples of the "heterocyclic-sulfinyl (group)" include 5- to 14-membered heterocyclic-sulfinyl (group) having 1 to 5 hetero atoms selected from nitrogen, sulfur and oxygen.

Unless otherwise specifically stated, in this specification, examples of the "alkyl-carbamoyl (group)" include $C_{1-10}$ alkyl-carbamoyl (group).

Unless otherwise specifically stated, in this specification, examples of the "$C_{1-10}$ alkyl-carbamoyl (group)" include methylcarbamoyl, ethylcarbamoyl and propylcarbamoyl.

Unless otherwise specifically stated, in this specification, examples of the "mono- or di-alkylamino (group)" include mono- or di-$C_{1-10}$ alkylamino (group).

Unless otherwise specifically stated, in this specification, examples of the "mono- or di-$C_{1-10}$ alkylamino (group)" include methylamino, ethylamino, propylamino, dimethylamino and diethylamino.

Unless otherwise specifically stated, in this specification, examples of the "alkyl-carbonylamino (group)" include $C_{1-10}$ alkyl-carbonylamino.

Unless otherwise specifically stated, in this specification, examples of the $C_{1-10}$ alkyl-carbonylamino (group)" include acetylamino, propionylamino and pivaloylamino.

Unless otherwise specifically stated, in this specification, examples of the heterocyclic moiety of the "heterocyclic-amino (group)" those similar to said "heterocyclic group". Examples of the "heterocyclic-amino (group)" include 2-pyridyl-amino.

Unless otherwise specifically stated, in this specification, examples of the "heterocyclic-carbonyl" of the "heterocyclic-carbonylamino (group)" those similar to said "heterocyclic-carbonyl". Examples of the "heterocyclic-carbonylamino (group)" include pyridyl-carbonylamino.

Unless otherwise specifically stated, in this specification, examples of the "heterocyclic (group)" of the "heterocyclic-oxycarbonylamino (group)" include those similar to said "heterocyclic group". Examples of the "heterocyclic-oxycarbonylamino (group)" include 2-pyridyl-oxycarbonylamino.

Unless otherwise specifically stated, in this specification, examples of the "heterocyclic (group)" of the "heterocyclic-sulfonylamino (group)" include those similar to said "heterocyclic group". Examples of the "heterocyclic-sulfonylamino (group)" include 2-pyridyl-sulfonylamino.

Unless otherwise specifically stated, in this specification, examples of the "alkoxy-carbonylamino (group)" include $C_{1-10}$ alkoxy-carbonylamino.

Unless otherwise specifically stated, in this specification, the $C_{1-10}$ alkoxy-carbonylamino (group)" include methoxycarbonylamino, ethoxycarbonylamino, propoxycarbonylamino and butoxycarbonylamino.

Unless otherwise specifically stated, in this specification, examples of the "alkyl-sulfonylamino (group)" include $C_{1-10}$ alkyl-sulfonylamino.

Unless otherwise specifically stated, in this specification, examples of the "$C_{1-10}$ alkyl-sulfonylamino (group)" include methylsulfonylamino and ethylsulfonylamino.

Unless otherwise specifically stated, in this specification, examples of the "mono- or di-$C_{3-7}$ cycloalkylamino (group)" include cyclopropylamino, cyclopentylamino and cyclohexylamino.

Unless otherwise specifically stated, in this specification, examples of the "$C_{3-7}$ cycloalkyl-carbonylamino (group)" include cyclopropylcarbonylamino, cyclopentylcarbonylamino and cyclohexylcarbonylamino.

Unless otherwise specifically stated, in this specification, examples of the "$C_{3-7}$ cycloalkyloxy-carbonylamino (group)" include cyclopropoxycarbonylamino, cyclopentyloxycarbonylamino and cyclohexyloxycarbonylamino.

Unless otherwise specifically stated, in this specification, examples of the "$C_{3-7}$ cycloalkyl-sulfonylamino (group)" include cyclopropylsulfonylamino, cyclopentylsulfonylamino and cyclohexylsulfonylamino.

Unless otherwise specifically stated, in this specification, examples of the "mono- or di-$C_{6-14}$ arylamino (group)" include phenylamino and diphenylamino.

Unless otherwise specifically stated, in this specification, examples of the "mono- or di-$C_{7-16}$ aralkylamino (group)" include benzylamino.

Unless otherwise specifically stated, in this specification, examples of the "$C_{6-14}$ aryl-carbonylamino (group)" include benzoylamino and naphthoylamino.

Unless otherwise specifically stated, in this specification, examples of the "$C_{6-14}$ aryl-sulfonylamino (group)" include phenylsulfonylamino, 2-naphthylsulfonylamino and 1-naphthylsulfonylamino.

Unless otherwise specifically stated, in this specification, when the groups, moieties and rings as explained in the present specification are substituted by plural substituents, the respective substituents may be the same or different.

Unless otherwise specifically stated, in this specification, examples of the substituents of "an optionally substituted $C_{1-4}$ alkyl", "an optionally substituted $C_{1-4}$ alkoxy", "an optionally substituted $C_{7-14}$ aralkyl", "an optionally substituted $C_{3-7}$ cycloalkyl", "an optionally substituted $C_{2-4}$ alkenyl", "an optionally substituted $C_{2-4}$ alkynyl", "a cyclic group which may optionally be substituted", "an optionally substituted $C_{3-12}$ cycloalkyl", "an optionally substituted dihydropyranyl", "an optionally substituted tetrahydropyranyl", "an optionally substituted azetidinyl", "an optionally substituted pyrrolidinyl", "an optionally substituted piperidinyl", "an optionally substituted imidazolyl", "an optionally substituted isoxazolyl", "an optionally substituted pyrazolyl", "an optionally substituted dihydropyrazolyl", "an optionally substituted pyridyl", "an optionally substituted pyrrolyl", "an optionally substituted dihydropyrrolyl", "an optionally substituted phenyl", "an optionally substituted morpholinyl", "an optionally substituted thiazolyl", "an optionally substituted oxazolidinyl", "an optionally substituted imidazolidinyl", "an optionally substituted oxaazabicyclooctyl", "an optionally substituted oxazepanyl" and "the formula

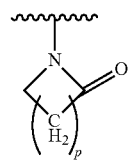

which may optionally be substituted" include substituents selected from the below described substituent group A. The number of the substituents ranges from 1 to the maximum number which can be substituted, preferably 1 to 3 and more preferably 1.

[Substituent Group A]

(1) a halogen atom;
(2) a nitro group;
(3) a cyano group;
(4) a carboxy group that can be esterified;
(5) an alkyl group which can be substituted;
(6) an alkenyl group which can be substituted;
(7) an alkynyl group which can be substituted (e.g., a $C_{3-7}$ cycloalkyl-$C_{2-6}$ alkynyl group which can be substituted);
(8) a $C_{3-7}$ cycloalkyl group which can be substituted;
(9) a $C_{6-14}$ aryl group which can be substituted;
(10) a $C_{7-16}$ aralkyl group which can be substituted;
(11) a $C_{6-14}$ aryl-$C_{2-6}$ alkenyl group which can be substituted;
(12) a heterocyclic group which can be substituted;
(13) a hydroxy group;
(14) an alkoxy group which can be substituted;
(15) a $C_{3-7}$ cycloalkyloxy group which can be substituted;
(16) a $C_{6-14}$ aryloxy group which can be substituted;
(17) a $C_{7-16}$ aralkyloxy group which can be substituted;
(18) an alkyl-carbonyloxy group which can be substituted;
(19) an alkoxy-carbonyloxy group which can be substituted;
(20) a mono-alkyl-carbamoyloxy group which can be substituted;
(21) a di-alkyl-carbamoyloxy group which can be substituted;
(22) a $C_{6-14}$ aryl-carbonyloxy group which can be substituted;
(23) a mono- or di-$C_{6-14}$ aryl-carbamoyloxy group which can be substituted;
(24) a heterocyclic-oxy group which can be substituted (e.g., aromatic heterocyclic-oxy group which can be substituted)
(25) a $C_{1-10}$ alkylsulfonyloxy (group) which can be substituted (e.g., halogeno $C_{1-10}$ alkylsulfonyloxy (group) which can be substituted);
(26) a mercapto group;
(27) an alkylsulfanyl group which can be substituted;
(28) a $C_{3-7}$ cycloalkylsulfanyl group which can be substituted;
(29) a $C_{6-14}$ arylsulfanyl group which can be substituted;
(30) a $C_{7-16}$ aralkylsulfanyl group which can be substituted;

(31) a heterocyclic-sulfanyl group which can be substituted;
(32) a formyl group;
(33) an alkyl-carbonyl group which can be substituted;
(34) a $C_{3-7}$ cycloalkylcarbonyl group which can be substituted;
(35) a $C_{6-14}$ arylcarbonyl group which can be substituted;
(36) a $C_{7-16}$ aralkylcarbonyl group which can be substituted;
(37) a heterocyclic-carbonyl group which can be substituted;
(38) an alkylsulfonyl group which can be substituted;
(39) a $C_{3-7}$ cycloalkylsulfonyl group which can be substituted;
(40) a $C_{6-14}$ arylsulfonyl group which can be substituted;
(41) a heterocyclic-sulfonyl group which can be substituted;
(42) an alkylsulfinyl group which can be substituted;
(43) a $C_{3-7}$ cycloalkylsulfinyl group which can be substituted;
(44) a $C_{6-14}$ arylsulfinyl group which can be substituted;
(45) a heterocyclic-sulfinyl group which can be substituted;
(46) a sulfo group;
(47) a sulfamoyl group;
(48) a sulfinamoyl group;
(49) a sulfenamoyl group;
(50) a thiocarbamoyl group;
(51) a carbamoyl group which can be substituted [e.g., alkyl-carbamoyl group which can be substituted];
(52) an amino group which can be substituted [e.g., amino,
mono- or di-alkylamino group which can be substituted,
mono- or di-$C_{3-7}$ cycloalkylamino group which can be substituted,
mono- or di-$C_{6-14}$ arylamino group which can be substituted,
mono- or di-$C_{7-16}$ aralkylamino group which can be substituted,
heterocyclic amino group which can be substituted,
$C_{6-14}$ aryl-carbonylamino group which can be substituted,
formylamino,
alkyl-carbonylamino group which can be substituted (e.g., mono-($C_{1-10}$ alkyl-carbonyl)-amino group which can be substituted),
$C_{3-7}$ cycloalkyl-carbonylamino group which can be substituted,
heterocyclic-carbonylamino group which can be substituted,
$C_{3-7}$ cycloalkyloxy-carbonylamino group which can be substituted,
heterocyclic-oxycarbonylamino group which can be substituted,
carbamoylamino group which can be substituted,
alkoxy-carbonylamino group which can be substituted,
alkylsulfonylamino group which can be substituted,
$C_{3-7}$ cycloalkyl-sulfonylamino group which can be substituted,
heterocyclic sulfonylamino group which can be substituted,
$C_{6-14}$ arylsulfonylamino group which can be substituted].
Among the aforementioned substituent group A, i.e., particularly,
the "alkoxy-carbonyl group which can be substituted",
the "alkyl group which can be substituted",
the "alkenyl group which can be substituted",
the "alkynyl group which can be substituted",
the "alkoxy group which can be substituted",
the "alkyl-carbonyloxy group which can be substituted",
the "alkoxy-carbonyloxy group which can be substituted",
the "mono-alkyl-carbamoyloxy group which can be substituted",
the "di-alkyl-carbamoyloxy group which can be substituted",
the "$C_{1-10}$ alkylsulfonyloxy group which can be substituted",
the "halogeno $C_{1-10}$ alkylsulfonyloxy group which can be substituted",
the "alkylsulfanyl group which can be substituted",
the "alkyl-carbonyl group which can be substituted",
the "alkylsulfonyl group which can be substituted",
the "alkylsulfinyl group which can be substituted",
the "alkyl-carbamoyl group which can be substituted",
the "mono- or di-alkylamino group which can be substituted",
the "alkyl-carbonylamino group which can be substituted",
the "mono-($C_{1-10}$ alkyl-carbonyl)-amino group which can be substituted"
the "carbamoylamino group which can be substituted",
the "alkoxy-carbonylamino group which can be substituted", and
the "alkylsulfonylamino group which can be substituted",
substituents thereof may be selected from, for example, the following substituent group B. The number of the substituents ranges from 1 to the maximum number which can be substituted, more preferably from 1 to 3 and further preferably 1.
[Substituent Group B]
Substituent group B consists of
(a) a halogen atom;
(b) a hydroxy group;
(c) a nitro group;
(d) a cyano group;
(e) a $C_{6-14}$ aryl group which can be substituted (the "$C_{6-14}$ aryl group" can be substituted with one or more substituents (preferably 1 to 3, more preferably 1) selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, alkoxy-carbonyl, $C_{6-14}$ aryloxy-carbonyl, $C_{7-16}$ aralkyloxy-carbonyl, alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl and so on);
(f) a $C_{6-14}$ aryloxy group which can be substituted (the "$C_{6-14}$ aryloxy group" can be substituted with one or more substituents (preferably 1 to 3, more preferably 1) selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl and so on);
(g) a $C_{7-16}$ aralkyloxy group which can be substituted (the "$C_{7-16}$ aralkyloxy group" can be substituted with one or more substituents (preferably 1 to 3, more preferably 1) selected from halogen atoms, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ arylcarbamoyl and so on);

(h) a mono- or di-5- to 10-membered heterocyclic group having 1 to 4 hetero atoms selected from nitrogen, sulfur and oxygen (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinoline-2-yl and the like) which can be substituted (the "mono- or di-5- to 10-membered heterocyclic group having 1 to 4 hetero atoms selected from nitrogen, sulfur and oxygen" can be substituted with one or more substituents (preferably 1 to 3, more preferably 1) selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, alkoxy-carbonyl, $C_{6-14}$ aryloxy-carbonyl, $C_{7-16}$ aralkyloxy-carbonyl, $C_{1-10}$ alkylsulfanyl, alkylsulfinyl, alkylsulfonyl, carbamoyl, thiocarbamoyl, mono- or di-$C_{1-10}$ alkylcarbamoyl, mono- or di-$C_{6-14}$ aryl-carbamoyl group and so on);

(i) an amino group which can be substituted [e.g., Amino group which can be substituted by one or two substituents selected from the group consisting of $C_{1-10}$ alkyl, $C_{2-6}$ alkenyl, $C_{6-14}$ aryl, $C_{7-16}$ aralkyl, heterocyclic group and heterocyclic-alkyl group (The $C_{1-10}$ alkyl, $C_{2-6}$ alkenyl, $C_{6-14}$ aryl, $C_{7-16}$ aralkyl, heterocyclic group and heterocyclic-alkyl group can be substituted with halogen atoms, hydroxy, cyano, amino, $C_{1-10}$ alkyl that can be halogenated (not the alkyl and alkenyl substituents), mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-10}$ alkylsulfanyl, $C_{3-7}$ cycloalkylsulfanyl, alkylsulfinyl, $C_{3-7}$ cycloalkylsulfinyl, $C_{1-10}$ alkylsulfonyl, $C_{3-7}$ cycloalkylsulfonyl, carbamoyl, thiocarbamoyl, mono- or di-$C_{1-10}$ alkylcarbamoyl, mono- or di-$C_{6-14}$ arylcarbamoyl group). "Heterocyclic" and "heterocyclic" in "heterocyclic-alkyl" are the same as the aforementioned "heterocyclic group"];

(j) a $C_{3-7}$ cycloalkyl;

(k) a $C_{1-10}$ alkoxy which can be substituted (the "$C_{1-10}$ alkoxy" can be substituted with one or more substituents (preferably 1 to 3, more preferably 1) selected from halogen, hydroxy, amino, mono- or di-$C_{1-10}$ alkylamino, mono- or di-$C_{6-14}$ arylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on);

(l) a formyl;

(m) a $C_{1-10}$ alkyl-carbonyl (e.g., acetyl);

(n) a $C_{3-7}$ cycloalkyl-carbonyl;

(o) a $C_{6-14}$ aryl-carbonyl;

(p) a $C_{7-16}$ aralkyl-carbonyl;

(q) a $C_{1-10}$ alkoxy-carbonyl;

(r) a $C_{6-14}$ aryloxy-carbonyl;

(s) a $C_{7-16}$ aralkyloxy-carbonyl;

(t) a $C_{1-10}$ alkylsulfanyl;

(u) a $C_{1-10}$ alkylsulfinyl;

(v) a $C_{1-10}$ alkylsulfonyl;

(w) a carbamoyl;

(x) a thiocarbamoyl;

(y) a mono-$C_{1-10}$ alkylcarbamoyl (e.g., methylcarbamoyl, ethylcarbamoyl, etc.);

(z) a di-$C_{1-10}$ alkylcarbamoyl (e.g., dimethylcarbamoyl, diethylcarbamoyl, ethylmethylcarbamoyl, etc.);

(aa) a mono- or di-$C_{6-14}$ aryl-carbamoyl (e.g., phenylcarbamoyl, 1-naphthylcarbamoyl, 2-naphthylcarbamoyl, etc.); and (bb) a mono- or di-5- to 7-membered heterocyclic-carbamoyl having 1 to 4 hetero atoms selected from nitrogen, sulfur and oxygen (e.g., 2-pyridylcarbamoyl, 3-pyridylcarbamoyl, 4-pyridylcarbamoyl, 2-thienylcarbamoyl, 3-thienylcarbamoyl, etc.).

Among the aforementioned substituent group A, i.e., particularly, the "$C_{6-14}$ aryloxy-carbonyl which can be substituted", the "$C_{7-16}$ aralkyloxy-carbonyl which can be substituted", the "$C_{3-7}$ cycloalkyl-$C_{2-6}$ alkynyl which can be substituted", the "$C_{3-7}$ cycloalkyl which can be substituted", the "$C_{6-14}$ aryl which can be substituted", the "$C_{7-16}$ aralkyl which can be substituted", the "$C_{6-14}$ aryl-$C_{2-6}$ alkenyl which can be substituted", the "heterocyclic group which can be substituted", the "$C_{3-7}$ cycloalkyloxy which can be substituted", the "$C_{6-14}$ aryloxy which can be substituted", the "$C_{7-16}$ aralkyloxy which can be substituted", the "$C_{6-14}$ aryl-carbonyloxy which can be substituted", the "mono- or di-$C_{6-14}$ aryl-carbamoyloxy which can be substituted", the "heterocyclic-oxy which can be substituted", the "aromatic heterocyclic-oxy which can be substituted", the "$C_{3-7}$ cycloalkylsulfanyl which can be substituted", the "$C_{6-14}$ arylsulfanyl which can be substituted", the "$C_{7-16}$ aralkylsulfanyl which can be substituted", the "heterocyclic-sulfanyl which can be substituted", the "$C_{3-7}$ cycloalkyl-carbonyl which can be substituted", the "$C_{6-14}$ aryl-carbonyl which can be substituted", the "$C_{7-16}$ aralkyl-carbonyl which can be substituted", the "heterocyclic-carbonyl which can be substituted", the "$C_{3-7}$ cycloalkylsulfonyl which can be substituted", the "$C_{6-14}$ arylsulfonyl which can be substituted", the "heterocyclic-sulfonyl which can be substituted", the "$C_{3-7}$ cycloalkylsulfinyl which can be substituted", the "$C_{6-14}$ arylsulfinyl which can be substituted", the "heterocyclic-sulfinyl which can be substituted", the "carbamoyl group which can be substituted", the "amino group which can be substituted", the "mono- or di-$C_{3-7}$ cycloalkylamino group which can be substituted", the "mono- or di-$C_{6-14}$ arylamino group which can be substituted", the "mono- or di-$C_{7-16}$ aralkylamino group which can be substituted", the "heterocyclic amino group which can be substituted", the "$C_{6-14}$ aryl-carbonylamino group which can be substituted", the "$C_{3-7}$ cycloalkyl-carbonylamino group which can be substituted", the "heterocyclic-carbonylamino group which can be substituted", the "$C_{3-7}$ cycloalkyloxy-carbonylamino group which can be substituted", the "heterocyclic-oxycarbonylamino group which can be substituted", the "$C_{3-7}$ cycloalkyl-sulfonylamino group which can be substituted", the "heterocyclic sulfonylamino group which can be substituted", and the "$C_{6-14}$ arylsulfonylamino group which can be substituted", substituents thereof may be selected from, for example, the aforementioned substituent group B and the following substituent group B'. The number of substituents ranges from 1 to the maximum number which can be substituted, more preferably from 1 to 3 substituents and further preferably 1 substituent.

[Substituent Group B']

Substituent group B' consists of (a) $C_{1-10}$ alkyl, which can be substituted by one or more substituents (preferably 1 to 3, more preferably. 1) selected from halogen, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on;

(b) $C_{2-6}$ alkenyl, which can be substituted by one or more substituents (preferably 1 to 3, more preferably 1) selected from halogen, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on; and (c) $C_{2-6}$ alkynyl, which can be substituted by one or more substituents (preferably 1 to 3, more preferably 1) selected from halogen atoms, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl group, and so on.

Symbols in the aforementioned formulas (Formula (I) and Formula (I')) will be explained below.

In the aforementioned formula, $R^1$ represents an optionally substituted $C_{1-4}$ alkoxy, wherein the optionally substituted $C_{1-4}$ alkoxy is radiolabeled.

Among them, $R^1$ is, for example, preferably a $C_{1-4}$ alkoxy which can be substituted by one or more substituents (preferably 1 to 3, more preferably 1) selected from a halogen atom, a $C_{1-10}$ alkoxy group, and a $C_{3-7}$ cycloalkyl group (e.g., methoxy, ethoxy, isopropoxy, cyclopropylmethoxy, difluoromethoxy, methoxyethoxy), and more preferably a $C_{1-4}$ alkoxy which can be substituted by one or more (preferably 1 to 3, more preferably 1) halogen atom, and further preferably a $C_{1-4}$ alkoxy group.

The "optionally substituted $C_{1-4}$ alkoxy" represented by $R^1$ is radiolabeled with any isotopes (e.g., $^3$H (also written as T), $^{11}$C, $^{18}$F, $^{35}$S, $^{125}$I, $^{82}$Br, $^{123}$I, $^{131}$I, $^{75}$Br, $^{15}$O, $^{13}$N, $^{211}$At, $^{75}$Br and the like), and the "optionally substituted $C_{1-4}$ alkoxy" which is radiolabeled may optionally be labeled with $^2$H (also written as D). Preferably, the "optionally substituted $C_{1-4}$ alkoxy" is radiolabeled with isotope(s) selected from $^{11}$C and $^{18}$F, wherein the $C_{1-4}$ alkoxy may optionally be labeled with $^2$H (D). In the radiolabeled "optionally substituted $C_{1-4}$ alkoxy", either "$C_{1-4}$ alkoxy" or "substituent" optionally possessed by said "$C_{1-4}$ alkoxy" may be radiolabeled. The radiolabeled "optionally substituted $C_{1-4}$ alkoxy" is preferably an optionally substituted $^{11}CH_3O-$, an optionally substituted $^{18}FCH_2O-$, an optionally substituted $^{18}FCD_2O-$, an optionally substituted $^{18}FCH_2CH_2O-$, or an optionally substituted $^{16}FCD_2CD_2O-$, more preferably an optionally substituted $^{11}CH_3O-$, and most preferably $^{11}CH_3O-$.

In another aspect of the present invention, the radiolabeled "optionally substituted $C_{1-4}$ alkoxy" is more preferably an optionally substituted $^{11}CH_3O-$, $^{18}FCD_2O-$ or $^{18}FCD_2CD_2O-$ and most preferably $^{11}CH_2O-$, $^{18}FCD_2O-$ or $^{18}FCD_2CD_2O-$.

In the aforementioned formula, ring A is selected from the group consisting of (1) a benzene,
(2) a pyrazole,
(3) a thiazole,
(4) a piperidine, and
(5) a tetrahydropyridine, wherein said ring A may optionally be substituted by 1 to 4 substituents selected from the group consisting of halogens, an optionally substituted $C_{1-4}$ alkyl, an optionally substituted $C_{1-4}$ alkoxy, an optionally substituted $C_{7-14}$ aralkyl, an optionally substituted $C_{2-4}$ alkenyl, an optionally substituted $C_{2-4}$ alkynyl, and a cyclic group which may optionally be substituted (provided that a cyclic group represented by the formula

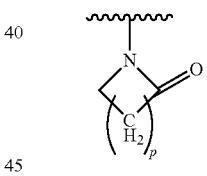

(p is 1 to 4) which may optionally be substituted, is excluded).

The number of substituents is preferably in the range of 1 to 3, more preferably one or two.

When the number of the substituents is two or more, the substituents on the Ring A can be combined to form a ring which can be substituted. The "ring" of the "ring which can be substituted" include a 5- to 6-membered heterocyclic ring containing one nitrogen atom or two oxygen atoms as heteroatoms.

The "ring" can be substituted by one or more (preferably, 1 to 5) substituents selected from the Substituent group A.

In another aspect of the present invention, preferred examples of the substituents of the Ring A include a halogen atom [e.g., iodine, bromine and fluorine], a $C_{1-4}$ alkyl group which can be substituted by 1 to 3 substituents selected from halogen atoms, $C_{6-14}$ aryl groups and $C_{3-7}$ cycloalkyl groups [e.g., trifluoromethyl and trifluoroethyl, cyclopropyl-methyl, cyclopropyl-ethyl, di-cyclopropyl-methyl, phenylethyl, isopropyl, isobutyl, cyclobutyl-methyl, cyclopropyl-butyl]), a C$_{2-4}$ alkenyl group [e.g., propenyl], a C$_{2-4}$ alkynyl group which may optionally be substituted by one C$_{3-7}$ cycloalkyl group [e.g., cyclopropylethynyl], a C$_{1-4}$ alkoxy group which can be substituted by 1 to 3 substituents selected from halogen atoms and C$_{6-14}$ aryl [e.g., methoxy group, difluoromethoxy group, trifluoromethoxy, difluoroethoxy, benzyloxy], a C$_{3-7}$ cycloalkyl group [e.g., cyclopropyl and cyclohexyl], a C$_{7-14}$ aralkyl group [e.g., benzyl], a C$_{6-14}$ aryl group which can be substituted by 1 to 3 substituents selected from halogen atoms and cyano [e.g., fluorophenyl, difluorophenyl, cyanophenyl], a 4- to 6-membered saturated heterocyclic group (preferably 4- to 6-membered saturated heterocyclic group containing 1 to 3 hetero atoms selected from nitrogen, oxygen and sulfur, which optionally has 1 to 5 substituents selected from halogen atoms, C$_{1-4}$ alkyl groups and oxo (provided that a cyclic group represented by the formula

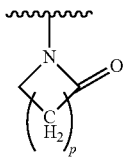

(p is 1 to 4) which may optionally be substituted, is excluded) [e.g., morpholinyl group, azetidinyl, tetrafluoropyrrolidinyl, difluoropiperidyl, dimethylmorpholinyl, oxaazabicyclooctyl, oxazepanyl piperidyl group, tetrahydropyranyl, fluoroazetidinyl, difluoroazetidinyl, difluoropyrrolidinyl, oxo-oxazolidinyl, oxo-morpholinyl, tert-butyl-oxoimidazolidinyl, difluoromethyl-oxoimidazolidinyl, trifluoromethylpyrrolidinyl, hydroxy-methylpiperidinyl, dimethyl-oxo-oxazolidinyl] and an unsaturated heterocyclic group (preferably 4- to 6-membered (preferably 5- to 6-membered) unsaturated heterocyclic group containing 1 to 3 hetero atoms selected from nitrogen, oxygen and sulfur, which optionally has 1 to 3 substituents selected from halogen atoms, C$_{1-4}$ alkoxy which may optionally be substituted, C$_{1-4}$ alkyl group which may be substituted, hydroxy, C$_{1-10}$ alkoxy-carbonyl groups and cyano [e.g., thiazolyl, pyrazolyl, difluoropyrrolyl, chloropyridyl, cyanopyridyl, methoxypyrazolyl, cyclopropylmethoxy-pyrazolyl, trifloroethoxy-pyrazolyl, dihydro-pyranyl, imidazolyl, dimethylisoxazolyl, methylpyrazolyl, difluoromethylpyrazolyl, oxazolyl, pyridyl, difluoropyrrolyl, ethylformyl-hydroxy-pyrazolyl, hydroxy-pyrazolyl, difluoromethyl-oxo-dihydro-pyrazolyl, dihydro-pyrrolyl].

Ring A is, for example, preferably
(i) a benzene,
(ii) a piperidine, or
(iii) a tetrahydropyridine,
wherein (i)-(iii) can be substituted by 1 to 4 substituents selected from
(1) a halogen atom,
(2) a C$_{1-4}$ alkyl group which can be substituted,
(3) a C$_{1-4}$ alkoxy group which can be substituted,
(4) a C$_{3-7}$ cycloalkyl group,
(5) a C$_{3-7}$ cycloalkyl-C$_{2-4}$ alkynyl group,
(6) a C$_{2-4}$ alkenyl group,
(7) a C$_{7-14}$ aralkyl group,
(8) a C$_{6-14}$ aryl group which can be substituted, and (9) a 4- to 6-membered heterocyclic group containing 0 or 1 oxygen atom, and 1 to 3 nitrogen atoms as heteroatoms which can be substituted by one or more substituents selected from a halogen atom, a hydroxy group, an oxo group, a C$_{1-10}$ alkoxy-carbonyl group, a C$_{1-10}$ alkoxy group which can be substituted, and a C$_{1-10}$ alkyl group which can be substituted.

Ring A is, for example, more preferably
(i) a benzene,
(ii) a piperidine, or
(iii) a tetrahydropyridine,
wherein (i)-(iii) can be substituted by 1 to 4 substituents selected from
(1) a halogen atom (e.g., fluorine, bromine, iodine),
(2) a C$_{1-4}$ alkyl group which can be substituted by 1 to 3 halogen atoms (e.g., methyl, trifluoromethyl),
(3) a C$_{1-4}$ alkoxy group which can be substituted by 1 to 3 halogen atoms (e.g., methoxy, difluoromethoxy, trifluoromethoxy),
(4) a C$_{3-7}$ cycloalkyl group (e.g., cyclopropyl),
(5) a C$_{3-7}$ cycloalkyl-C$_{2-4}$ alkynyl group (e.g., cyclopropylethynyl),
(6) a C$_{2-4}$ alkenyl group (e.g., propenyl),
(7) a C$_{7-14}$ aralkyl group (e.g., benzyl),
(8) a C$_{6-14}$ aryl group which can be substituted by 1 to 4 substituents selected from a halogen atom and cyano (e.g., fluorophenyl, difluorophenyl, cyanophenyl), and
(9) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a C$_{1-10}$ alkoxy-carbonyl group, a C$_{1-10}$ alkoxy group which can be substituted by halogen, and a C$_{1-10}$ alkyl group which can be substituted by halogen (e.g., fluoroazetidinyl, difluoroazetidinyl, difluoropyrrolidinyl, tetrafluoropyrrolidinyl, trifluoromethylpyrrolidinyl, difluoropiperidinyl, hydroxy-methylpiperidinyl, oxo-1,3-oxazolidinyl, morpholinyl, oxo-morpholinyl, dihydropyranyl, tetrahydropyranyl, oxo-imidazolidinyl, methyl-oxo-imidazolidinyl, tert-butyl-oxo-imidazolidinyl, difluoromethyl-oxo-imidazolidinyl, dihydro-1H-pyrrolyl, imidazolyl, thiazolyl, dimethyl-oxo-1,3-oxazolidinyl, dimethylisoxazolyl, difluoromethyl-oxo-2,5-dihydro-1H-pyrazolyl, pyrazolyl, methylpyrazolyl, chloro-1H-pyrazolyl, hydroxyl-pyrazolyl, difluoromethoxy-pyrazolyl, ethoxycarbonyl-hydroxyl-pyrazolyl, difluoropyrrolyl, difluoromethyl-pyrazolyl, 1,3-oxazolyl, pyridyl, chloropyridyl, cyanopyridyl).

In another aspect of the present invention, ring A is, for example, more preferably
(i) a benzene,
(ii) a piperidine, or
(iii) a tetrahydropyridine,
wherein (i)-(iii) can be substituted by 1 to 4 substituents selected from
(1) a halogen atom (e.g., fluorine, bromine, iodine),
(2) a C$_{1-4}$ alkyl group which can be substituted by 1 to 3 halogen atoms (e.g., methyl, trifluoromethyl),
(3) a C$_{2-4}$ alkoxy group which can be substituted by 1 to 3 halogen atoms (e.g., methoxy, difluoromethoxy, trifluoromethoxy),
(4) a C$_{3-7}$ cycloalkyl group (e.g., cyclopropyl),
(5) a C$_{3-7}$ cycloalkyl-C$_{2-4}$ alkynyl group (e.g., cyclopropylethynyl),
(6) a C$_{2-4}$ alkenyl group (e.g., propenyl),
(7) a C$_{7-14}$ aralkyl group (e.g., benzyl), (8) a $C_{6-14}$ aryl group which can be substituted by 1 to 4 substituents selected from a halogen atom and cyano (e.g., fluorophenyl, difluorophenyl, cyanophenyl), and (9) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen (e.g., fluoroazetidinyl, difluoroazetidinyl, difluoropyrrolidinyl, tetrafluoropyrrolidinyl, trifluoromethylpyrrolidinyl, difluoropiperidinyl, hydroxy-methylpiperidinyl, oxo-1,3-oxazolidinyl, oxo-morpholinyl, dihydropyranyl, tetrahydropyranyl, oxo-imidazolidinyl, methyl-oxo-imidazolidinyl, tert-butyl-oxo-imidazolidinyl, difluoromethyl-oxo-imidazolidinyl, dihydro-1H-pyrrolyl, imidazolyl, thiazolyl, dimethyl-oxo-1,3-oxazolidinyl, dimethylisoxazolyl, difluoromethyl-oxo-2,5-dihydro-1H-pyrazolyl, pyrazolyl, methylpyrazolyl, chloro-1H-pyrazolyl, hydroxyl-pyrazolyl, difluoromethoxy-pyrazolyl, ethoxycarbonyl-hydroxyl-pyrazolyl, difluoropyrrolyl, difluoromethyl-pyrazolyl, 1,3-oxazolyl, pyridyl, chloropyridyl, cyanopyridyl).

Ring A is, for example, further preferably a benzene ring which is substituted by 1 to 4 substituents selected from (1) a halogen atom (e.g., fluorine, bromine, iodine), (2) a $C_{1-4}$ alkyl group which can be substituted by 1 to 3 halogen atoms (e.g., methyl, trifluoromethyl), (3) a $C_{1-4}$ alkoxy group which can be substituted by 1 to 3 halogen atoms (e.g., methoxy, difluoromethoxy, trifluoromethoxy), (4) a $C_{3-7}$ cycloalkyl group (e.g., cyclopropyl), (5) a $C_{3-7}$ cycloalkyl-$C_{2-4}$ alkynyl group (e.g., cyclopropylethynyl), (6) a $C_{7-14}$ aralkyloxy (e.g., benzyloxy), and (7) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen (e.g., fluoroazetidinyl, difluoroazetidinyl, difluoropyrrolidinyl, tetrafluoropyrrolidinyl, trifluoromethylpyrrolidinyl, difluoropiperidinyl, hydroxy-methylpiperidinyl, oxo-1,3-oxazolidinyl, oxo-morpholinyl, dihydropyranyl, tetrahydropyranyl, oxo-imidazolidinyl, methyl-oxo-imidazolidinyl, tert-butyl-oxo-imidazolidinyl, difluoromethyl-oxo-imidazolidinyl, dihydro-1H-pyrrolyl, imidazolyl, dimethyl-oxo-1,3-oxazolidinyl, difluoromethyl-oxo-2,5-dihydro-1H-pyrazolyl, pyrazolyl, methylpyrazolyl, chloro-1H-pyrazolyl, hydroxyl-pyrazolyl, difluoromethoxy-pyrazolyl, ethoxycarbonyl-hydroxyl-pyrazolyl, difluoropyrrolyl, difluoromethyl-pyrazolyl, 1,3-oxazolyl, pyridyl), and particularly preferably a benzene ring which is substituted with (1) (a) 1 or 2 halogen atoms, or (b) one $C_{1-4}$ alkoxy group, and (2) one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen.

Most preferably, ring A is a benzene ring which may optionally be substituted by one halogen atom and one 4- to 6-membered heterocyclic group containing 0 or 1 oxygen atom, and 1 to 3 nitrogen atoms as heteroatoms which can be substituted by 1 to 4 halogen atoms (e.g., tetrahydropyranyl and difluoroazetidinyl).

Here, as the "one 4- to 6-membered heterocyclic group containing 0 or 1 oxygen atom, and 1 to 3 nitrogen atoms as heteroatoms", for example, preferred is a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

In another aspect of the present invention, ring A is, for example, further preferably (i) a piperidine, or (ii) a tetrahydropyridine, wherein (i) or (ii) is substituted by 1 to 4 substituents selected from (1) a $C_{2-4}$ alkenyl group (e.g., propenyl), (2) a $C_{7-14}$ aralkyl group (e.g., benzyl), (3) a $C_{6-14}$ aryl group which can be substituted by 1 to 4 substituents selected from a halogen atom and cyano (e.g., fluorophenyl, difluorophenyl, cyanophenyl), and (4) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen (e.g., thiazolyl, chloropyridyl, cyanopyridyl).

In the aforementioned formula, $R^2$ represents a substituent.

As the substituent, for example, the substituents selected from the aforementioned substituent group A can be included.

Preferable examples of the substituents include a halogen atom, an alkyl group which can be substituted and a $C_{6-14}$ aryl group which can be substituted, more preferable examples thereof include a halogen atom, an alkyl group which can be substituted by halogen, and a $C_{6-14}$ aryl group, further preferable examples thereof include an alkyl group (e.g., methyl).

In the aforementioned formula, m is 0 to 2. m is preferably 0 or 1 and more preferably 0.

In the aforementioned formula, $R^3$ represents a substituent.

As the substituent, for example, the substituents selected from the aforementioned substituent group A can be included.

Preferable examples of the substituents include a halogen atom, a $C_{1-10}$ alkyl group which can be substituted, a $C_{1-10}$ alkoxy group which can be substituted, and a $C_{7-16}$ aralkyloxy group which can be substituted, more preferable examples of the substituents include a halogen atom (e.g., chlorine, fluorine), a $C_{1-10}$ alkyl group which can be substituted by 1 to 5 (preferably 1 to 3) halogen atoms (e.g., methyl, isopropyl, isobutyl, trifluoromethyl), a $C_{1-10}$ alkoxy group which can be substituted by 1 to 5 (preferably 1 to 3) halogen atoms (e.g., methoxy, trifluoromethoxy) and a $C_{7-16}$ aralkyloxy group (e.g., benzyloxy), and further preferable examples of the substituents include a halogen atom, a $C_{1-10}$ alkyl group which can be substituted, a $C_{1-10}$ alkoxy group which can be substituted, and a $C_{7-16}$ aralkyloxy group which can be substituted, more preferable examples of the substituents include a halogen atom (e.g., chlorine, fluorine), a $C_{1-10}$ alkyl group which can be substituted by 1 to 5 (preferably 1 to 3) halogen atoms (e.g., methyl, isopropyl, isobutyl, trifluoromethyl), and a $C_{1-10}$ alkoxy group which can be substituted by 1 to 5 (preferably 1 to 3) halogen atoms (e.g., methoxy, trifluoromethoxy), and particularly preferable examples of the substituents include halogen atoms (e.g., fluorine atom, chlorine atom).

In the aforementioned formula, n is 0 to 5. n is preferably 0 to 3 and more preferably 0 or 1.

In the preferred embodiment of the present invention, both m and n are 0.

As the compound represented by the formula (I), a compound represented by the formula (I') is preferable.

In the aforementioned formula, ring A' is selected from the group consisting of
(i) a benzene,
(ii) a piperidine, and
(iii) a tetrahydropyridine,
wherein said ring A' may optionally be substituted by 1 to 4 substituents selected from the group consisting of halogens, $C_{1-4}$ alkyl and $C_{1-4}$ alkoxy.

Ring A' is, for example, preferably
(i) a benzene,
(ii) a piperidine, or
(iii) a tetrahydropyridine,
wherein (i)-(iii) can be substituted by 1 to 4 substituents selected from
(1) a halogen atom (preferably a fluorine atom) and
(2) a $C_{1-4}$ alkoxy group (preferably methoxy).

Ring A' is, for example, more preferably
(i) a benzene which can be substituted by 1 to 4 substituents selected from
(1) a halogen atom (preferably a fluorine atom) and
(2) a $C_{1-4}$ alkoxy group (preferably methoxy),
(ii) a piperidine, or
(iii) a tetrahydropyridine,
further preferably (i) a benzene which can be substituted by a halogen atom (preferably a fluorine atom),
particularly preferably (i) a benzene which is substituted by a halogen atom (preferably a fluorine atom).

In the aforementioned formula, ring B is an optionally substituted cyclic group (provided that a group represented by the formula

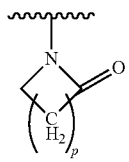

(p is 1 to 4) which may optionally be substituted, is excluded).

Preferable examples of the cyclic group represented by ring B include a 4- to 6-membered heterocyclic group containing 0 or 1 oxygen atom, and 1 to 3 nitrogen atoms as heteroatoms.

Ring B is, for example, preferably selected from the group consisting of
(1) an optionally substituted $C_{3-12}$ cycloalkyl,
(2) an optionally substituted dihydropyranyl,
(3) an optionally substituted tetrahydropyranyl,
(4) an optionally substituted azetidinyl,
(5) an optionally substituted pyrrolidinyl,
(6) an optionally substituted piperidinyl,
(7) an optionally substituted imidazolyl,
(8) an optionally substituted isoxazolyl,
(9) an optionally substituted pyrazolyl,
(10) an optionally substituted dihydropyrazolyl,
(11) an optionally substituted pyridyl,
(12) an optionally substituted pyrrolyl,
(13) an optionally substituted dihydropyrrolyl,
(14) an optionally substituted phenyl,
(15) an optionally substituted morpholinyl,
(16) an optionally substituted thiazolyl,
(17) an optionally substituted oxazolidinyl,
(18) an optionally substituted imidazolidinyl,
(19) an optionally substituted oxaazabicyclooctyl, and
(20) an optionally substituted oxazepanyl,
and more preferably selected from the group consisting of
(1) an optionally substituted tetrahydropyranyl, and
(2) an optionally substituted azetidinyl.

In one aspect of the present invention, preferred examples of the substituents of the Ring B include 1 to 4 substituents selected from a halogen atom (e.g., fluorine, chlorine), a hydroxy group, a cyano group, an oxo group, a $C_{1-10}$ alkoxy-carbonyl group (e.g., ethoxycarbonyl), a $C_{1-10}$ alkoxy group which can be substituted by halogen (e.g., difluoromethoxy), and a $C_{1-10}$ alkyl group which can be substituted by halogen (e.g., methyl, tert-butyl, difluoromethyl, trifluoromethyl).

Ring B is, for example, more preferably selected from the group consisting of
(1) dihydropyranyl,
(2) tetrahydropyranyl,
(3) azetidinyl,
(4) pyrrolidinyl,
(5) piperidinyl,
(6) imidazolyl,
(7) isoxazolyl,
(8) pyrazolyl,
(9) dihydropyrazolyl,
(10) pyridyl,
(11) pyrrolyl,
(12) dihydropyrrolyl,
(13) phenyl,
(14) morpholinyl,
(15) thiazolyl,
(16) oxazolidinyl, and
(17) imidazolidinyl,
wherein (1)-(17) may optionally be substituted by 1 to 4 substituents selected from a halogen atom (e.g., fluorine, chlorine), a hydroxy group, a cyano group, an oxo group, a $C_{1-10}$ alkoxy-carbonyl group (e.g., ethoxycarbonyl), a $C_{1-10}$ alkoxy group which can be substituted by halogen (e.g., difluoromethoxy), and a $C_{1-10}$ alkyl group which can be substituted by halogen (e.g., methyl, tert-butyl, difluoromethyl, trifluoromethyl),
and further preferably selected from the group consisting of
(1) tetrahydropyranyl, and
(2) azetidinyl,
wherein (1) or (2) may optionally be substituted by 1 to 4 substituents selected from a halogen atom (e.g., fluorine) and an oxo group,
and particularly preferably selected from the group consisting of
(1) tetrahydropyranyl, and
(2) azetidinyl,
wherein (1) or (2) may optionally be substituted 1 to 4 (preferably 2) halogen atoms (e.g., fluorine).

Further preferably, examples of the substituents, moieties and rings as explained in the present specification are used in combination.

Specific preferable examples of compound (I) include the following:

A compound of the formula (I), wherein
ring A is
(i) a benzene,
(ii) a piperidine, or
(iii) a tetrahydropyridine
wherein (i)-(iii) can be substituted by 1 to 4 substituents selected from
(1) a halogen atom,
(2) a $C_{1-4}$ alkyl group which can be substituted,
(3) a $C_{1-4}$ alkoxy group which can be substituted,
(4) a $C_{3-7}$ cycloalkyl group,
(5) a $C_{3-7}$ cycloalkyl-$C_{2-4}$ alkynyl group,
(6) a $C_{2-4}$ alkenyl group,
(7) a $C_{7-14}$ aralkyl group,
(8) a $C_{6-14}$ aryl group which can be substituted, and
(9) a 4- to 6-membered heterocyclic group containing 0 or 1 oxygen atom, and 1 to 3 nitrogen atoms as heteroatoms which can be substituted by one or more substituents selected from a halogen atom, a hydroxy group, an oxo group, a $C_{1-10}$ alkoxy-carbonyl group, a $C_{1-10}$ alkoxy group which can be substituted, and a $C_{1-10}$ alkyl group which can be substituted;

$R^1$ is a $C_{1-4}$ alkoxy group which can be substituted by one or more substituents selected from a $C_{1-4}$ alkoxy group, halogen atoms and a $C_{3-7}$ cycloalkyl group, wherein the optionally substituted $C_{1-4}$ alkoxy is radiolabeled;

$R^2$ is a halogen atom, a $C_{1-10}$ alkyl group which can be substituted or a $C_{6-14}$ aryl group which can be substituted;

$R^3$ is a halogen atom, a $C_{1-10}$ alkyl group which can be substituted or a $C_{1-10}$ alkoxy group which can be substituted;
m is 0 or 1; and
n is 0 to 3;
is preferable.

A compound of the formula (I), wherein
ring A is
(i) a benzene,
(ii) a piperidine, or
(iii) a tetrahydropyridine
wherein (i)-(iii) can be substituted by 1 to 4 substituents selected from
(1) a halogen atom (e.g., fluorine, bromine, iodine),
(2) a $C_{1-4}$ alkyl group which can be substituted by 1 to 3 halogen atoms (e.g., methyl, trifluoromethyl),
(3) a $C_{1-4}$ alkoxy group which can be substituted by 1 to 3 halogen atoms (e.g., methoxy, difluoromethoxy, trifluoromethoxy),
(4) a $C_{3-7}$ cycloalkyl group (e.g., cyclopropyl),
(5) a $C_{3-7}$ cycloalkyl-$C_{2-4}$ alkynyl group (e.g., cyclopropylethynyl),
(6) a $C_{2-4}$ alkenyl group (e.g., propenyl),
(7) a $C_{7-14}$ aralkyl group (e.g., benzyl),
(8) a $C_{6-14}$ aryl group which can be substituted by 1 to 4 substituents selected from a halogen atom and cyano (e.g., fluorophenyl, difluorophenyl, cyanophenyl), and
(9) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen (e.g., fluoroazetidinyl, difluoroazetidinyl, difluoropyrrolidinyl, tetrafluoropyrrolidinyl, trifluoromethylpyrrolidinyl, difluoropiperidinyl, hydroxy-methyl-piperidinyl, oxo-1,3-oxazolidinyl, morpholinyl, oxomorpholinyl, dihydropyranyl, tetrahydropyranyl, oxoimidazolidinyl, methyl-oxo-imidazolidinyl, tert-butyl-oxo-imidazolidinyl, difluoromethyl-oxo-imidazolidinyl, dihydro-1H-pyrrolyl, imidazolyl, thiazolyl, dimethyl-oxo-1,3-oxazolidinyl, dimethylisoxazolyl, difluoromethyl-oxo-2,5-dihydro-1H-pyrazolyl, pyrazolyl, methylpyrazolyl, chloro-1H-pyrazolyl, hydroxyl-pyrazolyl, difluoromethoxy-pyrazolyl, ethoxycarbonyl-hydroxyl-pyrazolyl, difluoropyrrolyl, difluoromethyl-pyrazolyl, 1,3-oxazolyl, pyridyl, chloropyridyl, cyanopyridyl);

$R^1$ is a $C_{1-4}$ alkoxy group which can be substituted by one or more substituents selected from halogen atoms, a $C_{1-4}$ alkoxy group and a $C_{3-7}$ cycloalkyl group (e.g., methoxy, ethoxy, isopropoxy, cyclopropylmethoxy, difluoromethoxy, methoxyethoxy), wherein the optionally substituted $C_{1-4}$ alkoxy is radiolabeled;

$R^2$ is a halogen atom, a $C_{1-10}$ alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), or a $C_{1-10}$ alkoxy group (e.g., methoxy);
m is 0 to 1; and
n is 0 or 1;
is more preferable.

Specific preferable examples of compound (I') (the compound (I') is included in the compound (I)) include the following:

A compound of the formula (I'), wherein
ring A' is
(i) a benzene,
(ii) a piperidine, or
(iii) a tetrahydropyridine
which can be substituted by 1 to 4 substituents selected from
(1) a halogen atom (preferably a fluorine atom) and
(2) a $C_{1-4}$ alkoxy group (preferably methoxy);
ring B is selected from the group consisting of
(2) dihydropyranyl,
(3) tetrahydropyranyl,
(4) azetidinyl,
(5) pyrrolidinyl,
(6) piperidinyl,
(7) imidazolyl,
(8) isoxazolyl,
(9) pyrazolyl,
(10) dihydropyrazolyl,
(11) pyridyl,
(12) pyrrolyl,
(13) dihydropyrrolyl,
(14) phenyl,
(15) morpholinyl,
(16) thiazolyl,
(17) oxazolidinyl,
(18) imidazolidinyl,
(19) oxaazabicyclooctyl, and
(20) oxazepanyl,
which may optionally be substituted by 1 to 4 substituents selected from a halogen atom (e.g., fluorine, chlorine), a hydroxy group, a cyano group, an oxo group, a $C_{1-10}$ alkoxy-carbonyl group (e.g., ethoxycarbonyl), a $C_{1-10}$ alkoxy group which can be substituted by halogen (e.g., difluoromethoxy), and a $C_{1-10}$ alkyl group which can be substituted by halogen (e.g., methyl, tert-butyl, difluoromethyl, trifluoromethyl);

$R^1$ is a $C_{1-4}$ alkoxy group which can be substituted by one or more substituents selected from a $C_{1-4}$ alkoxy group, halogen atoms and a $C_{3-7}$ cycloalkyl group, wherein the optionally substituted $C_{1-4}$ alkoxy is radiolabeled with $^{11}C$ or $^{18}F$;

$R^2$ is a halogen atom, a $C_{1-10}$ alkyl group which can be substituted or a $C_{6-14}$ aryl group which can be substituted;

$R^3$ is a halogen atom, a $C_{1-10}$ alkyl group which can be substituted or a $C_{1-10}$ alkoxy group which can be substituted;

m is 0 or 1; and n is 0 to 3;

is preferable.

A compound of the formula (I'), wherein ring A' is (i) a benzene which is substituted by 1 to 4 substituents selected from (1) a halogen atom (preferably a fluorine atom) and (2) a $C_{1-4}$ alkoxy group (preferably methoxy), (ii) a piperidine, or (iii) a tetrahydropyridine;

ring B is selected from the group consisting of (1) tetrahydropyranyl, and (2) azetidinyl, which may optionally be substituted by 1 to 4 substituents selected from a halogen atom (e.g., fluorine) and an oxo group;

$R^1$ is a $C_{1-4}$ alkoxy group which can be substituted by one or more substituents selected from halogen atoms, a $C_{1-4}$ alkoxy group and a $C_{3-7}$ cycloalkyl group (e.g., methoxy, ethoxy, isopropoxy, cyclopropylmethoxy, difluoromethoxy, methoxyethoxy), wherein the $C_{1-4}$ alkoxy is radiolabeled with $^{11}C$ or $^{18}F$;

$R^2$ is a halogen atom, an alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), or a $C_{1-10}$ alkoxy group (e.g., methoxy);

m is 0 to 1; and n is 0 or 1;

is more preferable.

In another aspect of a compound of the formula (I'), preferred examples of the ring A' is (i) a benzene which is substituted by 1 to 4 substituents selected from (1) a halogen atom (preferably a fluorine atom) and (2) a $C_{1-4}$ alkoxy group (preferably methoxy), (ii) a piperidine, or (iii) a tetrahydropyridine;

ring B is selected from the group consisting of (1) tetrahydropyranyl, and (2) azetidinyl, which may optionally be substituted by 1 to 4 substituents selected from a halogen atom (e.g., fluorine) and an oxo group;

$R^1$ is $^{11}CH_3O—$, $^{18}FCH_2O—$, $^{18}FCD_2O—$, $^{18}FCH_2CH_2O—$ or $^{18}FCD_2CD_2O—$ (more preferably $^{11}CH_3O—$, $^{18}FCD_2O—$ or $^{18}FCD_2CD_2O—$, most preferably $^{11}(CH_3O—)$;

$R^2$ is a halogen atom, an alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), or a $C_{1-10}$ alkoxy group (e.g., methoxy);

m is 0 to 1; and n is 0 or 1;

is more preferable.

A compound of the formula (I'), wherein ring A' is (i) a benzene which is substituted by 1 to 4 halogen atoms (preferably a fluorine atom);

ring B is selected from the group consisting of (1) tetrahydropyranyl, and (2) azetidinyl, which may optionally be substituted by 1 to 4 (preferably 2) halogen atoms (e.g., fluorine);

$R^1$ is a $C_{1-4}$ alkoxy group which can be substituted by one or more substituents selected from halogen atoms, a $C_{1-4}$ alkoxy group and a $C_{3-7}$ cycloalkyl group (e.g., methoxy, ethoxy, isopropoxy, cyclopropylmethoxy, difluoromethoxy, methoxyethoxy), wherein the $C_{1-4}$ alkoxy is radiolabeled with $^{11}C$ or $^{18}F$;

$R^2$ is a halogen atom, an alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), and a $C_{1-10}$ alkoxy group (e.g., methoxy);

m is 0 to 1; and n is 0 or 1;

is further preferable.

In another aspect of a compound of the formula (I'), preferred examples of the ring A' is (i) a benzene which is substituted by 1 to 4 halogen atoms (preferably a fluorine atom);

ring B is selected from the group consisting of (1) tetrahydropyranyl, and (2) azetidinyl, which may optionally be substituted by 1 to 4 (preferably 2) halogen atoms (e.g., fluorine);

$R^1$ is $^{11}CH_3O—$, $^{18}FCH_2O$, $^{18}FCD_2O—$, $^{18}FCH_2CH_2O—$ or $^{18}FCD_2CD_2O—$ (more preferably $^{11}CH_3O—$, $^{18}FCD_2O—$ or $^{18}FCD_2CD_2O—$, most preferably $^{11}CH_3O—$);

$R^2$ is a halogen atom, an alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), or a $C_{1-10}$ alkoxy group (e.g., methoxy);

m is 0 to 1; and n is 0 or 1.

A compound of the formula (I'), wherein ring A' is (i) a benzene which is substituted by 1 to 4 halogen atoms (preferably a fluorine atom);

ring B is selected from the group consisting of (1) tetrahydropyranyl, and (2) azetidinyl, which may optionally be substituted by 1 to 4 (preferably 2) halogen atoms (e.g., fluorine);

$R^1$ is $^{11}CH_2O—$, $^{18}FCH_2O—$, $^{18}FCD_2O—$, $^{18}FCH_2CH_2O—$ or $^{18}FCD_2CD_2O—$ (more preferably $^{11}CH_3O—$, $^{18}FCD_2O—$ or $^{18}FCD_2CD_2O—$, most preferably $^{11}CH_3O—$);

$R^2$ is a halogen atom, an alkyl group which can be substituted by halogen, or a $C_{6-14}$ aryl group;

$R^3$ is a halogen atom (e.g., chlorine, fluorine), a $C_{1-10}$ alkyl group (e.g., methyl, isopropyl, isobutyl), or a $C_{1-10}$ alkoxy group (e.g., methoxy);

m is 0 to 1; and n is 0 or 1;

is particularly preferable.

Specifically, compound (I) is preferably

1-[2-fluoro-4-(tetrahydro-2H-pyran-4-yl)phenyl]-5-$^{11}$C-methoxy-3-(1-phenyl-1H-pyrazol-5-yl)pyridazin-4(1H)-one or a salt thereof;

1-[4-(3,3-difluoroazetidin-1-yl)-2-fluorophenyl]-5-$^{11}$C-methoxy-3-(1-phenyl-1H-pyrazol-5-yl)pyridazin-4(1H)-one or a salt thereof;

5-([$^{18}$F]Fluoro-methyloxy-d$_2$)-1-(2-fluoro-4-(tetrahydro-2H-pyran-4-yl)phenyl)-3-(1-phenyl-1H-pyrazol-5-yl)pyridazin-4(1H)-one or a salt thereof; and 5-(2-[$^{18}$F]Fluoro-ethyloxy-d$_4$)-1-(2-fluoro-4-(tetrahydro-2H-pyran-4-yl)phenyl)-3-(1-phenyl-1H-pyrazol-5-yl)pyridazin-4(1H)-one or a salt thereof.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, etc.) and alkali earth metal salts (e.g., calcium salts, magnesium salts, barium salts, etc.) and ammonium salts are preferable. In contrast, in the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (I) includes isomers such as tautomers, optical isomers, steric isomers, reverse isomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound of the formula (I) can be a pharmaceutically acceptable co-crystal or a co-crystal salt. The term "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

The compound (I) can be provided as a solvate (for example, hydrate) or as a non-solvate and both are included in the compound (I).

The compounds labeled with isotopes (e.g., $^2$H (also written as D), $^3$H (also written as T), $^{11}$C, $^{14}$C, $^{18}$F, $^{35}$S, $^{125}$I, etc.) are also included in the compound (I).

[Manufacturing Methods]

The compound of the present invention and the compound as raw materials can be manufactured by the known means, for example, by the methods shown in the following schemes. Hereinafter, "room temperature" indicates a temperature generally ranging from 0 to 35° C. and "a low temperature" indicates a temperature generally from −78 to 0° C.

The compound (I) can be obtained, for example, by the method explained below or by a comparable method thereto. The methods of manufacturing the compound (I) is shown by the reaction schemes 1-6 described in detail in the following or a method according thereto.

The symbols used for the compounds in the reaction schemes indicate the same meanings as mentioned above. In this specification, a methyl group (CH$_3$) is sometimes abbreviated as Me.

In each of the following production methods, each starting material compound used for the production of compound (I) may form a salt. As such salt, those similar to the salt of compound (I) can be mentioned.

In addition, each starting material compound used for the production of compound (I) can also be used for the next reaction as a reaction mixture or as a crude product. It can also be isolated from a reaction mixture according to a conventional method, and can be easily purified by a means known per se, for example, separation means such as extraction, concentration, neutralization, filtration, distillation, recrystallization, chromatography and the like. Examples of the solvent used for the above-mentioned recrystallization include water, alcohols, ethers, hydrocarbons, amides, halogenated hydrocarbons, nitriles, ketones, esters, sulfoxides, organic acids and the like. These solvents can be used alone or in a mixture of two or more kinds of the solvents that are mixed at a suitable ratio, for example, 1:1 to 1:10 and the like. When a compound of a formula is commercially available, the commercially available product may be used as it is, or a compound produced by a method known per se, or a method according thereto may also be used.

When a substituent that compound (I) has contains a convertible functional group (e.g., a carboxyl group, an amino group, a hydroxy group, a carbonyl group, a mercapto group, a C$_{1-6}$ alkoxy-carbonyl group, a C$_{6-14}$ aryloxy-carbonyl group, a C$_{7-16}$ aralkyloxy-carbonyl group, a sulfo group, a halogen atom etc.), various compounds can be produced by converting such functional groups by a method known per se or a method according thereto.

In the case of a carboxyl group, for example, conversion is possible by esterification, reduction, amidation, conversion reaction to an optionally protected amino group, and the like.

In the case of an amino group, for example, conversion is possible by a reaction such as amidation, sulfonylation, nitrosation, alkylation, arylation, imidation and the like.

In the case of a hydroxy group, for example, conversion is possible by a reaction such as esterification, carbamoylation, sulfonylation, alkylation, arylation, oxidation, halogenation and the like.

In the case of a carbonyl group, for example, conversion is possible by a reaction such as reduction, oxidation, imination (including oximation, hydrazonation), (thio)ketalation, alkylidenation, thiocarbonylation and the like.

In the case of a mercapto group, for example, conversion is possible by a reaction such as alkylation, oxidation and the like.

In the case of a $C_{1-6}$ alkoxy-carbonyl group, a $C_{6-14}$ aryloxy-carbonyl group or a $C_{7-16}$ aralkyloxy-carbonyl group, for example, conversion is possible by a reaction such as reduction, hydrolysis and the like.

In the case of a sulfo group, for example, conversion is possible by a reaction such as sulfonamidation, reduction and the like.

In the case of a halogen atom, for example, conversion is possible by a reaction such as various nucleophilic substitution reactions, various coupling reactions and the like.

In each of the aforementioned reactions, when the compound is obtained in a free form, it may be converted to a salt according to a conventional method, and when the compound is obtained as a salt, it can also be converted to a free form or other salt according to a conventional method.

These functional groups can be converted by method known per se, for example, the method described in "Comprehensive Organic Transformations" (Richard C. Larock, Wiley-VCH, 1999) and the like.

In each reaction of the aforementioned production methods of compound (1) and each reaction of starting compound syntheses, when a starting compound has an amino group, a carboxyl group, a hydroxy group or a heterocyclic group as a substituent, a protecting group generally used in peptide chemistry and the like may be introduced into these groups. By removal of the protecting group as necessary after the reaction, the objective compound can be obtained.

As the amino-protecting group, for example, a formyl group; a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl (Alloc) group, a phenyloxycarbonyl group, a fluorenylmethoxycarbonyl (Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl(Z) etc.), a $C_{7-10}$ aralkyl group (e.g., benzyl etc.), a 2-(trimethylsilyl)ethoxymethyl (SEM) group, a trityl group, a phthaloyl group and/or an N,N-dimethylaminomethylene group etc., each optionally having substituent(s), and the like can be used. As these substituents, a phenyl group, a halogen atom (e.g., fluorine, chlorine, bromine, iodine etc.), a $C_{1-6}$ alkyl-carbonyl group (e.g., methylcarbonyl, ethylcarbonyl, butylcarbonyl etc.), a nitro group etc. can be used. The number of the substituents is about 1 to 3.

As the carboxyl-protecting group, for example, a $C_{1-6}$ alkyl group (e.g., methyl, ethyl, n-propyl, isopropyl, n-butyl, tert-butyl etc.), an allyl group, a benzyl group, a phenyl group, a trityl group and/or a trialkylsilyl group, each optionally having substituent(s), and the like can be used. As these substituents, a halogen atom (e.g., fluorine, chlorine, bromine, iodine etc.), a formyl group, a $C_{1-6}$ alkyl-carbonyl group (e.g., acetyl, ethylcarbonyl, butylcarbonyl etc.), a nitro group and the like can be used. The number of the substituents is about 1 to 3.

As the hydroxyl-protecting group, for example, a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group and/or a silyl group, each optionally having substituent(s), and the like can be used. As these substituents, a halogen atom (e.g., fluorine, chlorine, bromine, iodine etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like can be used. The number of the substituents is about 1 to 4.

These protecting groups may be introduced or removed by a method known per se, for example, the method described in "Protective Groups in Organic Synthesis, $3^{rd}$ Ed." (Theodora W. Greene, Peter G. M. Wuts, Wiley-Interscience, 1999) and the like.

When compound (I) presents as a configurational isomer, diastereomer, conformer or the like, they can be respectively isolated by known means. When compound (1) is an optically active form, a racemate can be separated into a (+) form and a (−) form by general optical resolution means.

When compound (I) contains optical isomer, stereoisomer, positional isomer, rotamer or tautomer, each of these can also be contained as compound (I), as well as can be obtained as a single product by a synthesis method and a separation method known per se.

For example, the method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENALTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [α-methoxy-α-(trifluoromethyl)phenylacetic acid], (−)-methoxyacetic acid, etc.) and the like are subjected to condensation reaction to give diastereomers in the ester form or in the amide form, respectively. When compound (I) has a carboxyl group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

A salt of compound (I) can be produced by a method known per se. For example, when compound (I) is a basic compound, it can be produced by adding an inorganic acid or organic acid, or when compound (I) is an acidic compound, by adding an organic base or inorganic base.

The solvent, acid and base used for the production methods of the compound of the present invention are explained below.

As the "alcohols", for example, methanol, ethanol, 1-propanol, 2-propanol, tert-butyl alcohol and the like can be used.

As the "ethers", for example, diethyl ether, diisopropyl ether, diphenyl ether, tetrahydrofuran, 1,4-dioxane, 1,2-dimethoxyethane and the like can be used.

As the "hydrocarbons", for example, benzene, toluene, cyclohexane, hexane and the like can be used.

As the "amides", for example, N,N-dimethylformamide, dimethylformamide, N,N-dimethylacetamide, N-methylpyrrolidine, hexamethylphosphoric triamide and the like can be used.

As the "halogenated hydrocarbons", for example, dichloromethane, chloroform, carbon tetrachloride, 1,2-dichloroethane, chlorobenzene and the like can be used.

As the "nitriles", for example, acetonitrile, propionitrile and the like can be used.

As the "ketones", for example, acetone, ethyl methyl ketone and the like can be used.

As the "esters", for example, ethyl acetate and the like can be used.

As the "sulfoxides", for example, dimethyl sulfoxide and the like can be used.

As the "organic acids", for example, formic acid, acetic acid, propionic acid, trifluoroacetic acid, citric acid, methanesulfonic acid, p-toluenesulfonic acid and the like can be used.

As the "mineral acids", for example, hydrochloric acid, sulfuric acid and the like can be used.

As the "Lewis acids", for example, boron trichloride, boron tribromide and the like can be used.

As the "inorganic bases", for example, sodium hydroxide, potassium hydroxide, lithium hydroxide, barium hydroxide and the like can be used.

As the "basic salts", for example, sodium carbonate, potassium carbonate, cesium carbonate, sodium hydrogen carbonate, sodium acetate, ammonium acetate and the like can be used.

As the "aromatic amines", for example, pyridine, lutidine and the like can be used.

As the "tertiary amines", for example, triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like can be used.

As the "alkali metal hydrides", for example, sodium hydride, potassium hydride and the like can be used.

As the "alkali metals", for example, sodium, lithium, potassium and the like can be used.

As the "metal amides", for example, sodium amide, lithium diisopropylamide, lithium hexamethyldisilazide and the like can be used.

As the "alkyl metals", for example, butyllithium, sec-butyllithium, tert-butyllithium and the like can be used.

As the "aryl metals", for example, phenyllithium and the like can be used.

As the "metal alkoxides", sodium methoxide, sodium ethoxide, sodium tert-butoxide, potassium tert-butoxide and the like can be used.

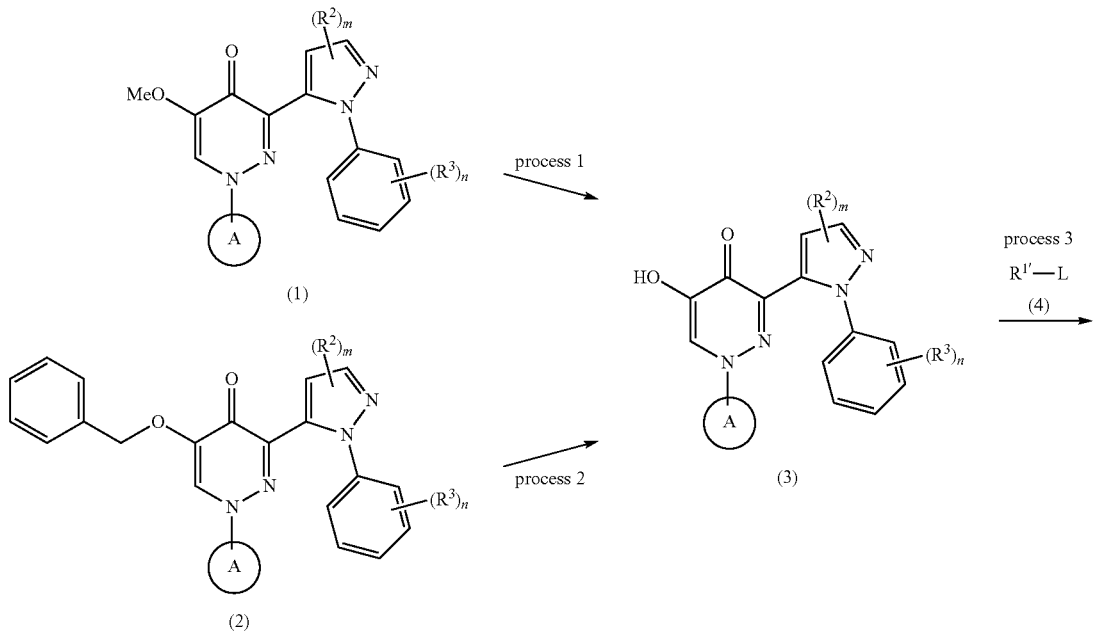

Reaction scheme 1

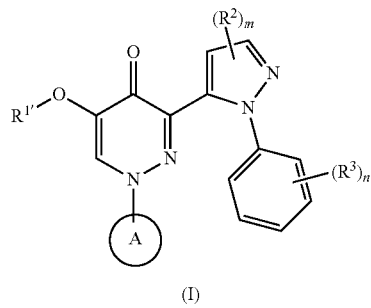

(I)

wherein $R^{1'}$ is a radiolabeled, optionally substituted $C_{1-4}$ alkyl group, L is a leaving group, and other symbols are as defined above.

Examples of the leaving group for L include halogen atom (e.g., chlorine, bromine, iodine), optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group which may optionally be substituted by a $C_{1-6}$ alkyl group (e.g., benzenesulfonyloxy, p-toluenesulfonyloxy), methanesulfonyl group and the like, with preference given to halogen atom and optionally halogenated $C_{1-6}$ alkylsulfonyloxy group.

Compound (1) can be produced by a method known per se or a method according thereto, or the method shown from the following reaction scheme 2 to reaction scheme 5, or a method analogous thereto. Compound (1) includes compound (1a), compound (1b) and compound (1c).

Compound (2) can be produced by a method known per se or a method according thereto, or the method shown by the following reaction scheme 6 or a method analogous thereto.

Compound (4) can be produced by a method known per se, for example, the method described in App. Radiat. Isot, 2009, 67(1), 106-110, Biooganic & Medicinal Chemistry, 2005, 13, 1811-1818, App. Radiat. Isot, 2002, 57(1), 335-342, or Journal of Fluorine Chemistry, 2004, 125, 1879-1886, or a method according thereto.

In process 1, compound (1) is reacted with trimethylsilyl chloride in the presence of sodium iodide to give compound (3). Sodium iodide is used in about 1-10 mol, preferably 1 to 5 mol, per 1 mol of compound (1). Trimethylsilyl chloride is also used in about 1-10 mol, preferably 1 to 5 mol, per 1 mol of compound (1). While the solvent is not particularly limited as long as the reaction proceeds, for example, nitriles are preferable. The reaction temperature is generally room temperature to 200° C., and 80° C. is preferable. The reaction time is generally 1 to 20 hr, preferably 3 to 10 hr.

In process 2, compound (2) is reacted with acid, or with palladium carbon under a hydrogen atmosphere to give compound (3).

For reaction with an acid, the acid is not particularly limited as long as the reaction proceeds and, for example, hydrogen bromide-containing acetic acid and trifluoroacetic acid are preferable. The reaction temperature is generally room temperature to 200° C., and 50° C. to 100° C. is preferable. The reaction time is generally 1 to 20 hr, preferably 3 to 12 hr.

For reaction with palladium carbon, palladium carbon is used in about 0.01 to 5 mol, preferably 0.05 to 0.3 mol, per 1 mol of compound (2). While the solvent is not particularly limited as long as the reaction proceeds, for example, alcohols are preferable. The reaction temperature is generally 0° C. to 150° C., and room temperature is preferable. The reaction time is generally 10 min to 10 hr, preferably 30 min to 5 hr.

In process 3, compound (3) is reacted with compound (4) to give compound (I). Generally, the necessary amount is not particularly limited as long as the reaction proceeds, and compound (3) may be used in an excess amount relative to compound (4). When desired, the reaction in this step may be performed in the presence of a base. While the solvent is not particularly limited as long as the reaction proceeds, for example, acetone is preferable. The reaction temperature is generally 0° C. to 150° C., and room temperature is preferable. The reaction time is generally 10 sec to 2 hr, preferably 30 sec to 20 min.

As an alternative method, compound (I) can also be obtained using a method described below.

Compound (I) can also be synthesized by monoalkylating compound (3) with L-$(CH_2)_n$-L or L-$(CD_2)_n$-L (n: as defined above but not 0) in the presence of a base such as NaH, and reacting the resulting compound with a nucleophile such as $^{18}F$ minus ion.

The amounts of L-$(CH_2)_n$-L or L-$(CD_2)_n$-L and NaH to be used are not particularly limited and generally each 1-10 mol relative to 1 mol of compound (3). The reaction solvent is not particularly limited as long as the reaction proceeds. For example, solvents such as halogenated hydrocarbons, amides, sulfoxides, ethers, nitriles, esters, hydrocarbons, water and the like, and the mixed solvent thereof and the like are preferable.

While the reaction time varies depending on the kind of the reagent and the solvent to be used, it is generally 0.1-24 hr, preferably 0.5-12 hr.

The reaction temperature is generally 0-200° C., preferably 0-100° C.

The nucleophile such as $^{18}F$ minus ion is used in an excess amount relative to 1 mol of alkylated compound (3).

When desired, the reaction in this step may be performed in the presence of a base. While the solvent is not particularly limited as long as the reaction proceeds, for example, acetonitrile, dimethyl sulfoxide and N,N-dimethylformamide are preferable. The reaction temperature is generally 0° C. to 150° C., and room temperature is preferable. The reaction time is generally 10 sec to 2 hr, preferably 30 sec to 20 min.

Reaction scheme 2

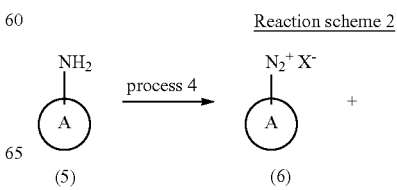

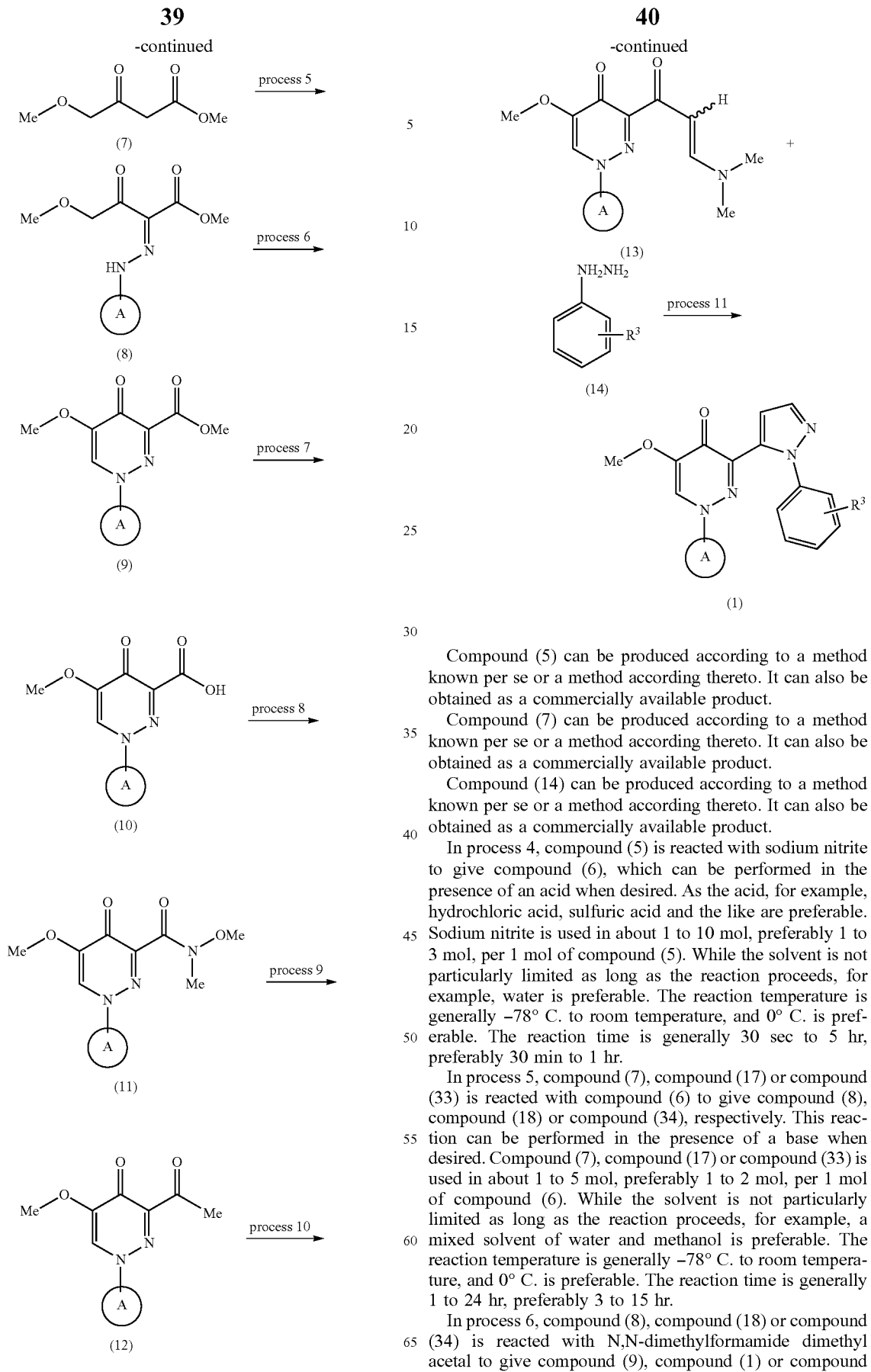

Compound (5) can be produced according to a method known per se or a method according thereto. It can also be obtained as a commercially available product.

Compound (7) can be produced according to a method known per se or a method according thereto. It can also be obtained as a commercially available product.

Compound (14) can be produced according to a method known per se or a method according thereto. It can also be obtained as a commercially available product.

In process 4, compound (5) is reacted with sodium nitrite to give compound (6), which can be performed in the presence of an acid when desired. As the acid, for example, hydrochloric acid, sulfuric acid and the like are preferable. Sodium nitrite is used in about 1 to 10 mol, preferably 1 to 3 mol, per 1 mol of compound (5). While the solvent is not particularly limited as long as the reaction proceeds, for example, water is preferable. The reaction temperature is generally −78° C. to room temperature, and 0° C. is preferable. The reaction time is generally 30 sec to 5 hr, preferably 30 min to 1 hr.

In process 5, compound (7), compound (17) or compound (33) is reacted with compound (6) to give compound (8), compound (18) or compound (34), respectively. This reaction can be performed in the presence of a base when desired. Compound (7), compound (17) or compound (33) is used in about 1 to 5 mol, preferably 1 to 2 mol, per 1 mol of compound (6). While the solvent is not particularly limited as long as the reaction proceeds, for example, a mixed solvent of water and methanol is preferable. The reaction temperature is generally −78° C. to room temperature, and 0° C. is preferable. The reaction time is generally 1 to 24 hr, preferably 3 to 15 hr.

In process 6, compound (8), compound (18) or compound (34) is reacted with N,N-dimethylformamide dimethyl acetal to give compound (9), compound (1) or compound (35), respectively. N,N-Dimethylformamide dimethyl acetal is used in about 1 to 30 mol, preferably 1 to 3 mol, per 1 mol of compound (8), compound (18) or compound (34). While the solvent is not particularly limited as long as the reaction proceeds and the reaction can also be performed without solvent, for example, DMF is preferable. The reaction temperature is generally room temperature to 200° C., and 100 to 150° C. is preferable. The reaction time is generally 1 to 24 hr, preferably 1 to 15 hr.

In process 7, compound (9) is reacted with a base to give compound (10). As the base, for example, aqueous sodium hydroxide solution is preferable. An aqueous sodium hydroxide solution is used in about 1 to 10 mol, preferably 1 to 3 mol, per 1 mol of compound (9). While the solvent is not particularly limited as long as the reaction proceeds, for example, methanol is preferable. The reaction temperature is generally 0° C. to 100° C., and room temperature is preferable. The reaction time is generally 1 to 24 hr, preferably 1 to 15 hr.

In process 8, compound (10) is reacted with N,O-dimethylhydroxylamine in the presence of a condensing agent and an activator to give compound (11). As the condensing agent, for example, 1-ethyl-3-(3-dimethylaminopropyl)carbodiimide hydrochloride and the like are preferable. As the activator, for example, 1-hydroxybenzotriazole and the like are preferable. The condensing agent is used in about 1 to 5 mol, preferably 1 to 3 mol, per 1 mol of compound (10). The activator is used in about 1 to 5 mol, preferably 1 to 3 mol, per 1 mol of compound (10). N,O-Dimethylhydroxylamine is used in about 1 to 3 mol, preferably 1 to 2 mol, per 1 mol of compound (10). While the solvent is not particularly limited as long as the reaction proceeds, for example, DMF is preferable. The reaction temperature is generally 0° C. to 100° C., and room temperature is preferable. The reaction time is generally 1 to 24 hr, preferably 1 to 15 hr.

In process 9, compound (11) is reacted with methylmagnesium bromide or methyllithium and the like to give compound (12). Methylmagnesium bromide or methyllithium is used in about 1 to 5 mol, preferably 1 to 3 mol, per 1 mol of compound (11). While the solvent is not particularly limited as long as the reaction proceeds, for example, THF or diethyl ether is preferable. The reaction temperature is generally −78° C. to room temperature, and −78° C. is preferable. The reaction time is generally 1 to 24 hr, preferably 1 to 15 hr.

In process 10, compound (12) is reacted with N,N-dimethylformamide dimethyl acetal to give compound (13). N,N-Dimethylformamide dimethyl acetal is used in about 1 to 30 mol, preferably 1 to 3 mol, per 1 mol of compound (12). While the solvent is not particularly limited as long as the reaction proceeds and the reaction can also be performed without solvent, for example, DMF is preferable. The reaction temperature is generally room temperature to 200° C., and 100 to 150° C. is preferable. The reaction time is generally 1 to 24 hr, preferably 1 to 15 hr.

In process 11, compound (13) or compound (35) is reacted with compound (14) to give compound (1) or compound (2), respectively. This reaction can be performed in the presence of an acid when desired. The acid is, for example, acetic acid, trifluoroacetic acid and the like. Compound (14) is used in about 1 to 5 mol, preferably 1 to 3 mol, per 1 mol of compound (13) or compound (35). While the solvent is not particularly limited as long as the reaction proceeds, for example, acetic acid, ethanol and the like are preferable. The reaction temperature is generally −20° C. to 100° C., and room temperature is preferable. The reaction time is generally 1 to 24 hr, preferably 1 to 15 hr.

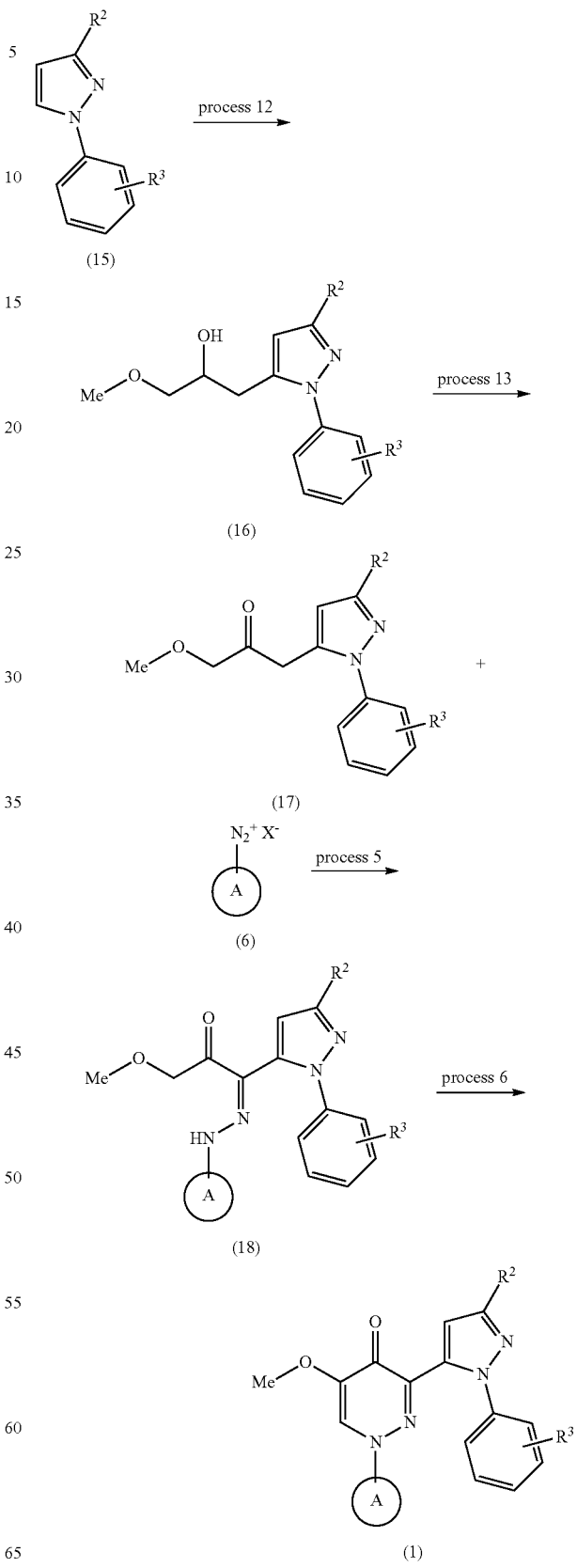

Compound (15) can be produced according to a method known per se or a method according thereto. It can also be obtained as a commercially available product.

In process 12, organolithium compound prepared from compound (15) and n-butyllithium is reacted with glycidyl methyl ether to give compound (16). n-Butyllithium is used in about 1 to 10 mol, preferably 1 to 3 mol, per 1 mol of compound (15). Glycidyl methyl ether is used in about 1 to 10 mol, preferably 1 to 5 mol, per 1 mol of compound (15). While the solvent is not particularly limited as long as the reaction proceeds, for example, THF is preferable. For preparation of the organolithium compound, the reaction temperature is generally −78° C. to 0° C., and −78° C. is preferable. For reaction with glycidyl methyl ether, the reaction temperature is generally −78° C. to 50° C., and room temperature is preferable. The reaction time is generally 10 min to 5 hr, preferably 30 min to 1 hr in both steps.

In process 13, compound (16) is reacted with an oxidant prepared from DMSO and trifluoroacetic anhydride and the like to give compound (17). DMSO is used in about 1 to 10 mol, preferably 1 to 5 mol, per 1 mol of compound (16). Trifluoroacetic anhydride is used in about 1 to 5 mol, preferably 1 to 2 mol, per 1 mol of compound (16). While the solvent is not particularly limited as long as the reaction proceeds, for example, THF is preferable. The reaction temperature is generally −78° C. to room temperature, and 0° C. is preferable. The reaction time is generally 10 min to 5 hr, preferably 30 min to 2 hr.

Reaction scheme 4

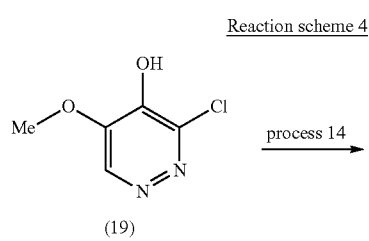
(19)

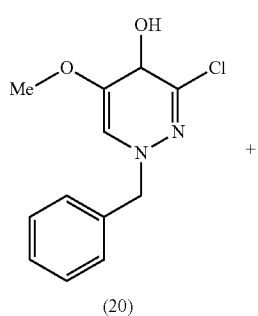
(20)

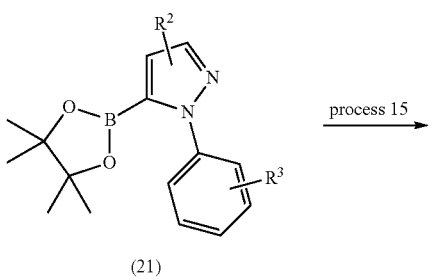
(21)

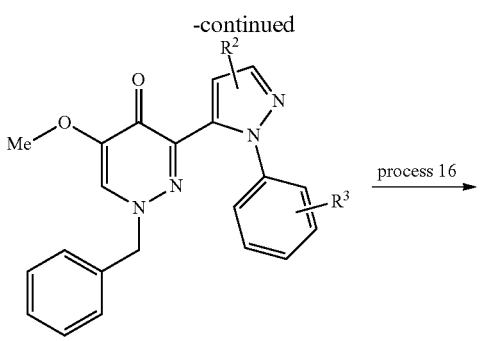
(22)

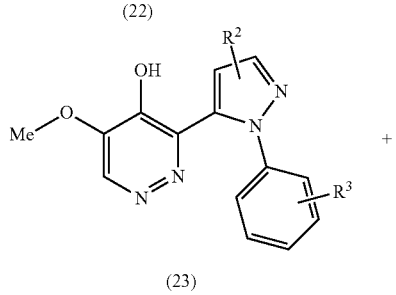
(23)

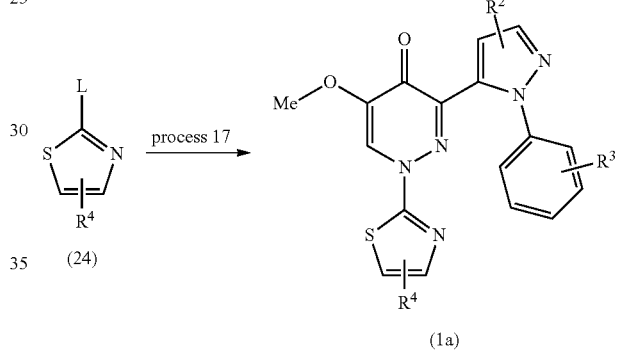
(24) (1a)

wherein $R^4$ is an alkyl group or an aryl group, L is a leaving group, and other symbols are as defined above.

Compound (19) can be produced according to a method known per se or a method according thereto.

Compound (21) can be produced according to a method known per se or a method according thereto.

Compound (24) can be produced according to a method known per se or a method according thereto. It can also be obtained as a commercially available product.

In process 14, compound (19) is reacted with benzyl bromide to give compound (20). This reaction can be performed in the presence of a base when desired. Benzyl bromide is used in about 1 to 3 mol, preferably 1 to 1.5 mol, per 1 mol of compound (19). While the solvent is not particularly limited as long as the reaction proceeds, for example, DMF is preferable. The reaction temperature is generally 0° C. to 50° C., and room temperature is preferable. The reaction time is generally 1 hr to 48 hr, preferably 3 hr to 25 hr.

In process 15, compound (20) and compound (21) are subjected to a coupling reaction in the presence of a palladium catalyst to give compound (22). As the palladium catalyst, for example, $PdCl_2\{Pt\text{-}Bu_2(Ph\text{-}p\text{-}NMe_2)\}_2$ and the like are preferable. This reaction can be performed in the presence of a base when desired. Compound (21) is used in about 1-3 mol, preferably 1 to 1.5 mol, per 1 mol of compound (20). The palladium catalyst is used in about 0.0001 to 2 mol, preferably 0.001 to 0.5 mol, per 1 mol of compound (20). While the solvent is not particularly limited as long as the reaction proceeds, for example, toluene is preferable. The reaction temperature is generally room temperature to 200° C., and 100° C. to 120° C. is preferable. The reaction time is generally 1 hr to 48 hr, preferably 3 hr to 25 hr.

In process 16, compound (22) is reacted with palladium carbon under a hydrogen atmosphere to give compound (23). Palladium carbon is used in about 0.01 to 5 mol, preferably 0.05 to 0.5 mol, per 1 mol of compound (22). While the solvent is not particularly limited as long as the reaction proceeds, for example, alcohols are preferable. The reaction temperature is generally 0° C. to 100° C., and room temperature is preferable. The reaction time is generally 10 min to 72 hr, preferably 1 hr to 60 hr.

In process 17, compound (23) is reacted with compound (24) to give compound (1a). This reaction can be performed in the presence of a base when desired. Compound (24) is used in about 1 to 5 mol, preferably 1 to 3 mol, per 1 mol of compound (23). While the solvent is not particularly limited as long as the reaction proceeds, for example, DMF is preferable. The reaction temperature is generally room temperature to 200° C., and 150° C. is preferable. The reaction time is generally 30 min to 24 hr, preferably 1 hr to 12 hr.

Reaction scheme 5
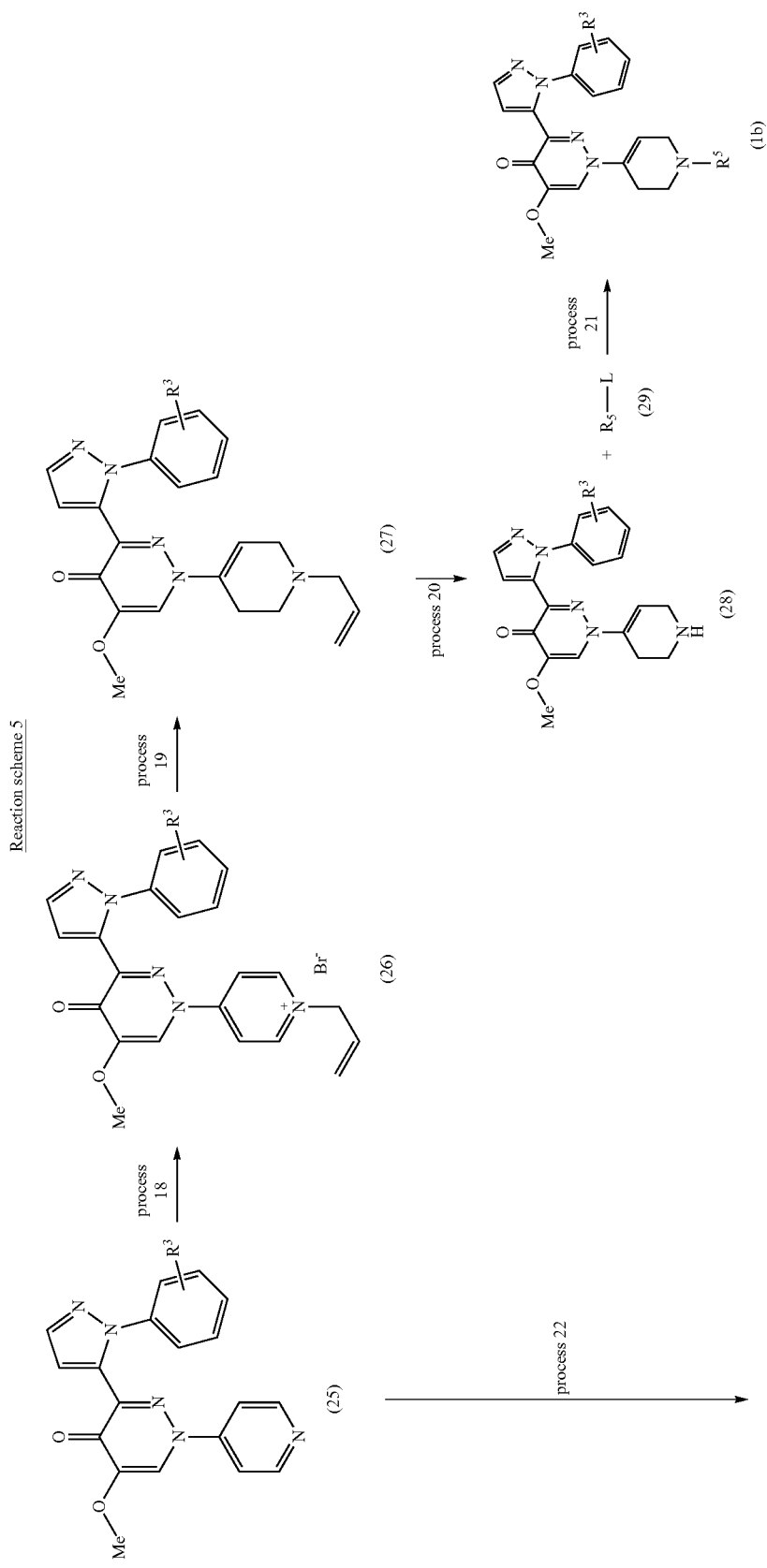

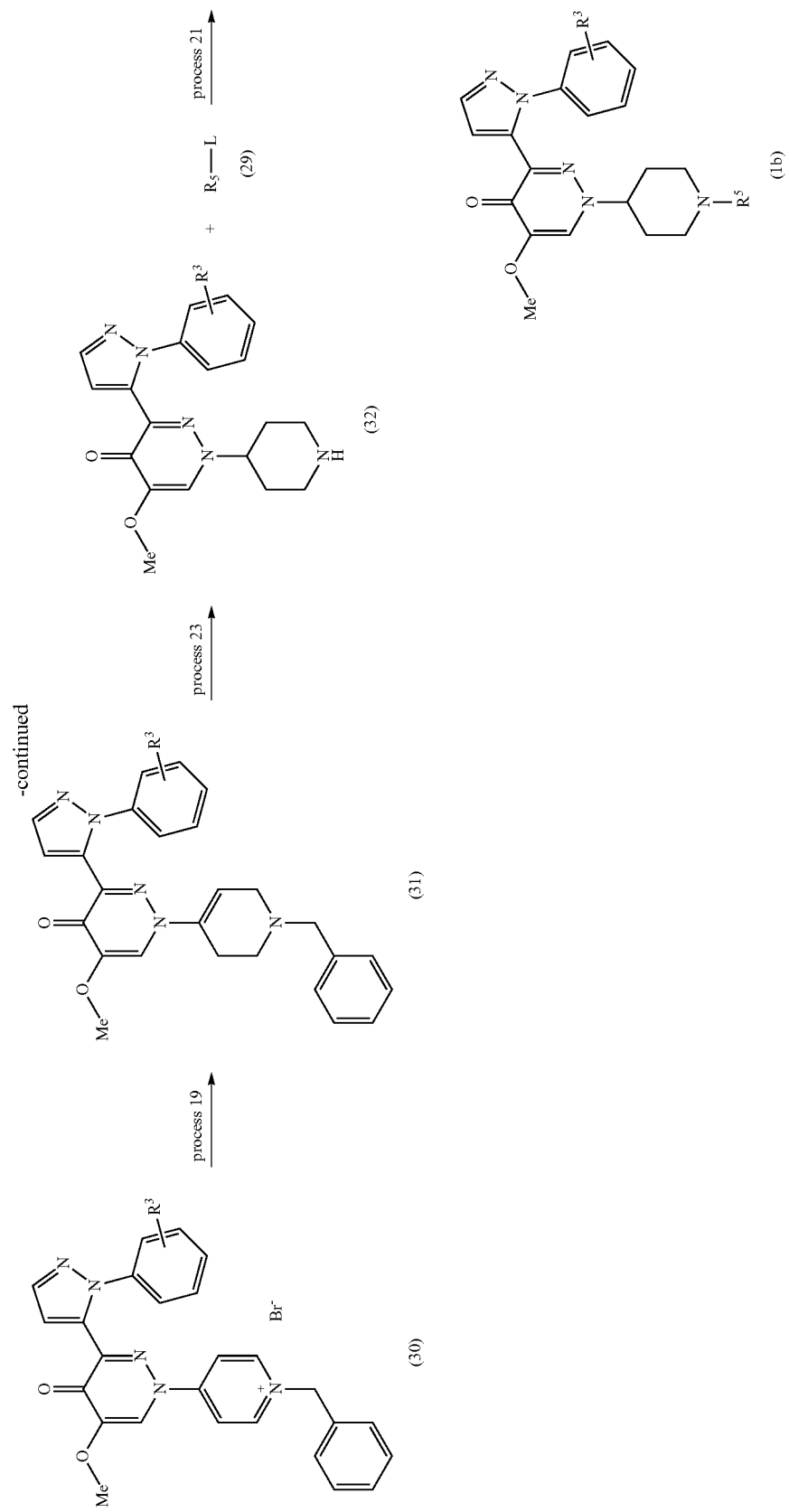

wherein R⁵ is an alkyl group or an aryl group, L is a leaving group, and other symbols are as defined above.

Compound (25) can be produced according to reaction scheme 1 or reaction scheme 2, or a method analogous thereto.

Compound (29) can be obtained as a commercially available product, or can be produced by a method known per se or a method according thereto.

In process 18, compound (25) is reacted with allyl bromide to give compound (26). Allyl bromide is used in about 1 to 5 mol, preferably 1 to 3 mol, per 1 mol of compound (25). While the solvent is not particularly limited as long as the reaction proceeds, for example, acetonitrile is preferable. The reaction temperature is generally room temperature to 150° C., and 80° C. is preferable. The reaction time is generally 30 min to 10 hr, preferably 1 hr to 4 hr.

In process 19, compound (26) or compound (30) is reacted with sodium borohydride and the like to give compound (27) or compound (31). Sodium borohydride is used in about 1 to 10 mol, preferably 1 to 5 mol, per 1 mol of compound (26) or compound (30). While the solvent is not particularly limited as long as the reaction proceeds, for example, methanol is preferable. The reaction temperature is generally −20° C. to 80° C., and room temperature is preferable. The reaction time is generally 1 hr to 24 hr, preferably 1 hr to 12 hr.

In process 20, compound (27) is reacted with 1,3-dimethylbarbituric acid in the presence of a palladium catalyst to give compound (28). The palladium catalyst is, for example, tetrakistriphenylphosphinepalladium and the like. 1,3-Dimethylbarbituric acid is used in about 1 to 10 mol, preferably 1 to 3 mol, per 1 mol of compound (27). While the solvent is not particularly limited as long as the reaction proceeds, for example, toluene is preferable. The reaction temperature is generally room temperature to 200° C., and 120° C. is preferable. The reaction time is generally 1 hr to 24 hr, preferably 1 hr to 12 hr.

In process 21, compound (28) or compound (32) is reacted with compound (29) to give compound (1b) or compound (1c). This reaction can be performed in the presence of a base when desired. Compound (29) is used in about 1 to 5 mol, preferably 1 to 3 mol, per 1 mol of compound (28) or compound (32). While the solvent is not particularly limited as long as the reaction proceeds, for example, THF is preferable. The reaction temperature is generally −20° C. to 150° C., and room temperature is preferable. The reaction time is generally 1 hr to 24 hr, preferably 1 hr to 12 hr.

In process 22, compound (25) is reacted with benzyl bromide to give compound (30). Benzyl bromide is used in about 1 to 5 mol, preferably 1 to 3 mol, per 1 mol of compound (25). While the solvent is not particularly limited as long as the reaction proceeds, for example, acetonitrile is preferable. The reaction temperature is generally room temperature to 150° C., and 80° C. is preferable. The reaction time is generally 30 min to 10 hr, preferably 1 hr to 4 hr In process 23, compound (31) is reacted with palladium hydroxide carbon and the like under a hydrogen atmosphere to give compound (32). Palladium hydroxide carbon is used in about 0.01 to 5 mol, preferably 0.05 to 1 mol, per 1 mol of compound (31). While the solvent is not particularly limited as long as the reaction proceeds, for example, methanol is preferable. The reaction temperature is generally room temperature to 100° C., and 50° C. is preferable. The reaction time is generally 30 min to 24 hr, preferably 1 hr to 12 hr.

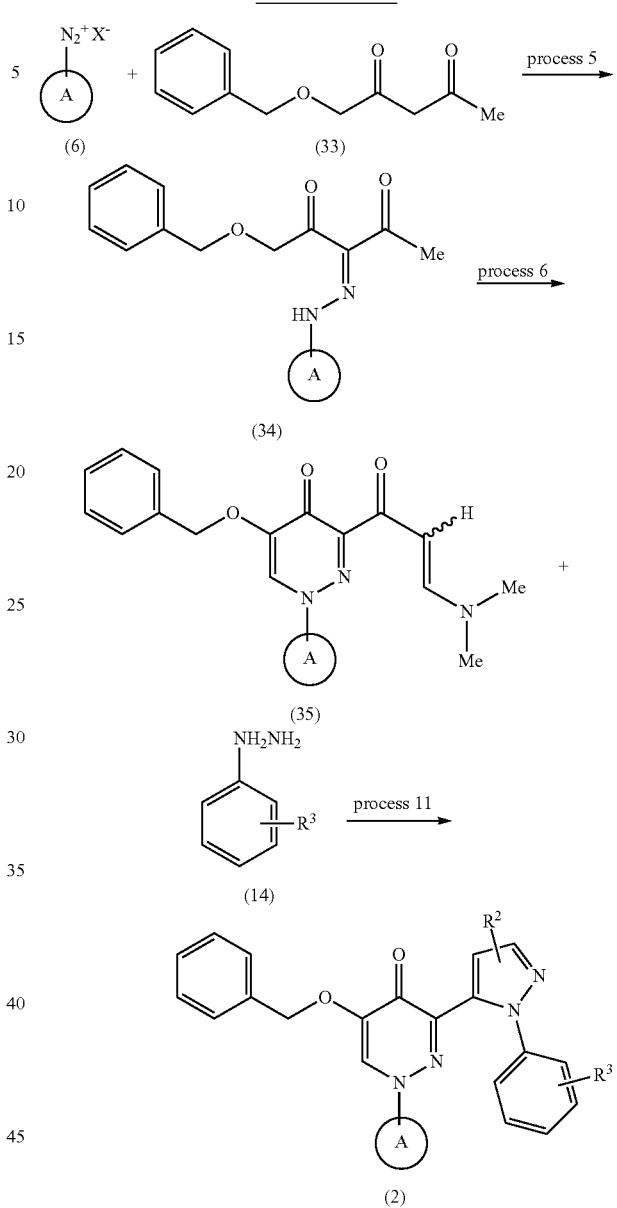

Reaction scheme 6

Compound (33) can be produced according to a method known per se or a method according thereto.

Compound (I) of the present invention obtained by the above methods can be purified by chromatography. In addition, compounds (1), (2) and (3) can be isolated and purified by, for example, a general separation means such as recrystallization, distillation, chromatography and the like.

In any of the above-mentioned production methods and steps, when desired, compound (I) can be synthesized by a known protection and deprotection, acylation reaction, alkylation reaction, hydrogenation reaction, oxidation reaction, reduction reaction, carbon chain extension reaction, substituent exchange reaction and the like, which may be used alone or in a combination of two or more thereof.

As in the case of the compound (I), a prodrug of the compound (I) can be used. The prodrug of the compound (I) is a compound that is converted to a compound (I) by reactions using enzymes or gastric acid under physiological conditions in vivo. Namely, it includes a compound that is converted to a compound (I) by enzymatic oxidation, reduction and hydrolysis or a compound that is converted to a compound (I) by hydrolysis using gastric acid.

Prodrugs of the compound (I) include compounds wherein an amino group in the compound (I) is acylated, alkylated or phosphorylated (e.g., the amino group in the compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); the hydroxyl group in the compound (I) is acylated, alkylated, phosphorylated or borated (e.g., the hydroxyl group in the compound (I) is acetylated, palmitoylated, propanoylated, pivaloylated, succinylated, fumarylated, alanylated, dimethylaminomethylcarbonylated); the carboxyl group in the compound (I) is esterified or amidated (e.g., the carboxyl group in the compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds can be produced from the compound (I) by the known methods. Prodrugs of the compound (I) can be converted to the compound (I) under the physiological conditions as described in "Development of Drugs" Vol. 7 Molecular Design published in 1990 by Hirokawa Shoten, page 163 to 198.

In an embodiment, the compounds of the present invention may be labeled as radiotracers for in vitro imaging. In another embodiment, the compounds of the invention may be prepared as Positron Emission Tomograph (PET) tracers for in vivo imaging and quantification of PDE10A.

Suitable radionuclides that may be incorporated in the instant compounds include, but not limited, $^{3}H$ (also written as T) $^{11}C$, $^{18}F$, $^{35}S$, $^{125}I$, $^{82}Br$, $^{123}I$, $^{131}I$, $^{75}Br$, $^{15}O$, $^{13}N$, $^{211}At$ or $^{77}Br$. The radionuclide that is incorporated in the instant radiolabeled compounds will depend on the specific analytical or pharmaceutical application of that radiolabeled compound.

Thus, for in vitro imaging of PDE10 and competition assays, compounds that incorporate $^{3}H$, $^{35}S$, $^{125}I$ or $^{82}Br$ will generally be most useful. For PET tracers, compounds that incorporate a radionuclide selected from $^{11}C$, $^{18}F$, $^{123}I$, $^{75}Br$, $^{76}Br$ or $^{77}Br$ are preferred. In certain applications incorporation of a chelating radionuclide such as $Tc^{99m}$ may also be useful. In other applications $^{18}F$ may be preferable over $^{11}C$ because with the longer half-life of $^{18}F$, imaging can be carried out long enough to allow a more specific signal to develop and improved conditions for receptor quantification studies. Compounds can be radiolabeled with either positron or gamma emitting radionuclides.

Radiolabeled PDE10A inhibitors, when labeled with the appropriate radionuclide, are potentially useful for a variety of in vitro and/or in vivo imaging applications. Specific examples of possible imaging applications include, but are not limited to, determining the location of, the relative activity of and/or quantifying PDE10A, radioimmunoassays of PDE10A inhibitors, and autoradiography to determine the distribution of PDE10A in a mammal or an organ or tissue sample thereof. Using a fluorine-18 or carbon-11 labeled radiotracer that provides a PDE10A-specific image in the brain and other tissues, the dose required to effectively inhibit the PDE10A enzyme can be determined by the blockade of the PET radiotracer image in humans.

In a specific embodiment, the instant radiolabeled PDE10A inhibitors when labeled with the positron emitting radionuclide, such as $^{11}C$, $^{18}F$, $^{15}O$ and $^{13}N$, are useful for positron emission tomographic (PET) imaging of PDE10A in the brain of living humans and experimental animals. These radiolabeled PDE10A inhibitors may be used as research tools to study the interaction of unlabeled PDE10A inhibitors with PDE10A in vivo via competition between the unlabeled drug and the radiolabeled compound for binding to the receptor. These types of quantitative studies are useful for determining the relationship between PDE10A occupancy and the dose of unlabeled PDE10A inhibitor, as well as for studying the duration of blockade of the receptor by various doses of the unlabeled PDE10A antagonist, agonists, and inverse agonists. As a clinical tool, the radiolabeled PDE10A inhibitors may be used to help define a clinically efficacious dose of a PDE10A inhibitor. In animal experiments, the radiolabeled PDE10A inhibitors can be used to provide information that is useful for choosing between potential drug candidates for selection for clinical development. The radiolabeled PDE10A inhibitors may also be used to study the regional distribution and concentration of PDE10A in the living human brain, as well as the brain of living experimental animals and in tissue samples. The radiolabeled PDE10A inhibitors may also be used to study disease or pharmacologically related changes in PDE10A concentrations.

In specific embodiments of the invention, PET tracers such as the present radiolabeled PDE10A inhibitors and currently available PET technology can be used, but is not limited to, to obtain the following information: relationship between level of receptor occupancy by candidate PDE10A inhibitors and clinical efficacy in patients; dose selection for clinical trials of PDE10A inhibitors prior to initiation of long term clinical studies; comparative potencies of structurally novel PDE10A inhibitors; investigating the influence of PDE10A inhibitors on in vivo transporter affinity and density during the treatment of clinical targets with PDE10A inhibitors and other agents; changes in the density and distribution of PDE10A, for example, 1) during the active stage of a psychiatric disease or condition, 2) for the evaluation of efficacy during treatment, or 3) during remission; changes in PDE10A expression and distribution in CNS disorders; imaging neurodegenerative disease when PDE10A is upregulated; imaging neurodegenerative disease when PDE10A is involved; and the like.

Isotopically-labeled compounds of formula (I) can generally be prepared by conventional techniques known to those skilled in the art or by processes analogous to those described in the accompanying Examples using appropriate isotopically-labeled reagents in place of the non-labeled reagent previously employed to produce radiolabeled derivatives.

The radiolabeled PDE10A inhibitors of the present invention have utility in imaging PDE10A or for diagnostic imaging with respect to any of the mentioned neurological and psychiatric disorders associated with PDE10A dysfunction.

The present invention is also directed to a method for quantitative imaging of PDE10A in a mammal which comprises administering to a mammal in need of such quantitative imaging an effective amount of the radiolabeled compound of the present invention.

The present invention is also directed to a method for quantitative imaging of tissues bearing PDE10A in a mammal which comprises administering to a mammal in need of such quantitative imaging an effective amount of the radio-labeled compound of the present invention.

The present invention is also directed to a method for quantitative imaging of PDE10A in tissues of a mammalian species which comprises administering to the mammalian species in need of such quantitative imaging an effective amount of the radiolabeled compound of the present invention.

The present invention is also directed to a method for quantitative imaging of PDE10A in the brain in a mammal which comprises administering to a mammal in need of such quantitative imaging an effective amount of the radiolabeled compound of the present invention.

The present invention is further directed to a method for the detection or quantification of PDE10A in mammalian tissue which comprises administering to a mammal in which such quantification is desired an effective amount of the radiolabeled compound of the present invention.

In a specific embodiment of the methods of the present invention, the mammal is a human.

The radiolabeled compound of the present invention is utility in imaging PDE10A or for diagnostic imaging with respect to the following diseases and symptoms in mammals (e.g., humans, cows, horses, dogs, cats, monkeys, mice, rats, etc. particularly in humans):

psychotic disorder (e.g., brief psychotic disorder, shared psychotic disorder);
psychosis induced by alcohol, amphetamine, cannabis, cocaine, hallucinogens, obesity, inhalants, opioids, or phencyclidine;
delusional disorder;
anxiety disorder;
movement disorder;
mood disorder;
major depressive disorder;
a major depressive disorder superimposed on a psychotic disorder comprising a delusional disorder or schizophrenia;
major depressive episode of the mild, moderate or severe type;
manic or mixed mood episode;
hypomanic mood episode;
depressive episode with atypical features;
depressive episode with melancholic features;
depressive episode with catatonic features;
mood episode with postpartum onset;
post-stroke depression;
dysthymic disorder;
minor depressive disorder;
autism;
drug addiction;
neurodegenerative disorder;
neurodegeneration associated with cerebral trauma;
neurodegeneration associated with stroke;
neurodegeneration associated with cerebral infarct;
hypoglycemia-induced neurodegeneration;
neurodegeneration associated with epileptic seizure;
neurodegeneration associated with neurotoxin poisoning;
multi-system atrophy;
Alzheimer's disease;
dementia;
multi-infarct dementia;
alcoholic dementia or other drug-related dementia;
dementia associated with intracranial tumors or cerebral trauma;
dementia associated with Huntington's disease or Parkinson's disease;
AIDS-related dementia;
Fronto temporal dementia;
delirium;
amnestic disorder;
post-traumatic stress disorder;
mental retardation;
learning disorder (e.g., reading disorder, mathematics disorder, or a disorder of written expression);
attention-deficit/hyperactivity disorder;
age-related cognitive decline;
premenstrual dysphoric disorder;
post-psychotic depressive disorder of schizophrenia;
bipolar disorder comprising bipolar I disorder, bipolar II disorder;
cyclothymic disorder;
Parkinson's disease;
Huntington's disease;
paranoid;
schizophrenia (e.g., paranoid schizophrenia, disorganized schizophrenia, disorganized schizophrenia, catatonic schizophrenia, undifferentiated schizophrenia, residual schizophrenia);
schizophreniform disorder;
schizoaffective disorder of the delusional type or the depressive type;
personality disorder of the paranoid type;
personality disorder of the schizoid type;
obesity;
metabolic syndrome;
non-insulin dependent diabetes (NIDDM);
glucose intolerance.

In particular, the radiolabeled compound of the present invention is useful for imaging PDE10A or for diagnostic imaging with respect to schizophrenia in humans.

The compound of the present invention can be administered safely, as it is, or in a dosage form which is manufactured, alone or together, in suitable dosage unit formulations containing conventional non-toxic pharmaceutically acceptable carriers, adjuvants and vehicles appropriate for each route of administration, according to a per se known method for manufacturing pharmaceutical formulations (e.g., methods described in Japanese Pharmacopoeia) such as tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection, ICV, intracisternal injection), drip infusion, implant, percutaneous absorbent, ointment, lotion, patch, suppositories (e.g., rectal suppository, vaginal suppository), pellets, transnasal preparations, pulmonary preparations (inhalant), inhalation spray, eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, nasal, vaginal, rectal sublingual, directly to lesion).

Here, as a pharmaceutical acceptable carrier, common organic or inorganic carrier substances are used as formulation raw materials. Carriers are added as vehicles, lubricants, binders and disintegrants in the solid formulations; and as solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light silicic anhydride, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light silicic anhydride and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzylbenzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene-hardened castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, red iron oxide).

Favorable examples of the sweeteners include sodium saccharin, dipotassium glycyrrhizate, aspartame and stevia.

The medical compositions of the present invention can be manufactured by the common methods in the field of formulation technology, for example, methods listed in the Japanese pharmacopoeia. Specific manufacturing methods for formulations are described in detail below.

The content of the compound of the present invention in the medical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

The compounds can be administered as the sole active agent or in combination with other pharmaceutical agents such as other agents used in the treatment of psychosis, especially schizophrenia and bipolar disorder, obsessive-compulsive disorder, major depression, Parkinson's disease, Alzheimer's disease, cognitive impairment and/or memory loss, e.g., nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigimine, and galantamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Haloperidol, Clozapine, Olanzapine, Risperidone, Aripiprazole, Ziprasidone, Paliperidone, Quetiapine fumarate, Lurasidone HCl and PDE10A inhibitors; bipolar disorder drug, including, but not limited to, Lithium, Olanzapine, Aripiprazole, and Valproic acid; Parkinson's disease drugs, including, but not limited to, Levodopa, Bromocriptine, Pergolide, Pramipexole, Tolcapone, Procyclidine, Trihexyphenidyl, and Benztropine; agents used in the treatment of major depression, including, but not limited to, Amitriptyline, Protriptyline, Desipramine, Nortriptyline, Paroxetine, Fluoxetine, Sertraline, Bupropion, Escitalopram, Mirtazapine, Venlafaxine, Duloxetine; agents used in the treatment of Alzheimer's disease, including, but not limited to, Galantamine, Tacrine, Donepezil, Rivastigmine, Memantine, Neotropin, Selegiline, Estrogen and Iodoquinol; agents used in the treatment of dementia, including, but not limited to, Thioridazine, Haloperidol, Risperidone, Tacrine, Donepezil, and Rivastigmine; agents used in the treatment of epilepsy, including, but not limited to, Phenyloin, Phenobarbital, Carbamazepine, Valproic acid, Ethosuximide, Gabapentin, Phenobarbital, Solfeton and Felbatol; agents used in the treatment of multiple sclerosis, including, but not limited to, Tolterodine, Oxybutynin, Oxycodone, Interferon beta-1b, Interferon beta-1a, Azathioprine, Methotrexate and Glatiramer; agents used in the treatment of Huntington's disease, including, but not limited to, Amitriptyline, Protriptyline, Desipramine, Nortriptyline, Paroxetine, Fluoxetine, Setraline, Tetrabenazine, Haloperidol, Chlorpromazine, Thioridazine, Sulpiride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlopropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metformin, e.g., Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

The form of administration of concomitant drugs with the compound of the present invention is not particularly limited and is acceptable as long as the compound of the present invention is combined with concomitant drugs at the time of administration. Examples of such forms of administration are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug. (For example, administration in the order of the composition of the present invention a concomitant drug, or administration in the reversed order). These forms of administration are summarized below and abbreviated as a concomitant agent of the present invention.

When administering the concomitant agent of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, drug forms and methods of administration. For example, when a concomitant drug is administered first, the compound of the present invention can be administered within 1 min. to 3 days, preferably within 10 min. to 1 day and more preferably within 15 min. to 1 hour after the concomitant drug is administered. However, if the compound of the present invention is administered first, a concomitant drug can be administered within 1 min. to 1 day, preferably within 10 min. to 6 hours and more preferably within 15 min. to 1 hour after the compound of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with schizophrenia (adults, bodyweight of approximately 60 kg), a normal daily dosage ranges from about 0.1 to 20 mg/kg bodyweight, preferably from about 0.2 to 10 mg/kg bodyweight and more preferably from about 0.5 to 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The concomitant agent of the present invention exhibits low toxicity. For example, the compound of the present invention or (and) the aforementioned concomitant drug can be combined with a pharmaceutically acceptable carrier according to the known method to prepare a medical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal and venous routes).

The pharmaceutically acceptable carriers that can be used for manufacturing the concomitant agent of the present invention can be the same as those used in the medical composition of the present invention as mentioned above.

A mixing ratio between the compound of the present invention and a concomitant drug in the concomitant agent of the present invention can be selected appropriately based on the administration subjects, administration routes and diseases.

The aforementioned concomitant drugs can be combined at an appropriate proportion if two or more drugs are combined.

A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug can be used in an amount ranging from 0.01 to 100 parts by weight relative to 1 part by weight of the compound of the present invention.

For example, the content of the compound of the present invention in the concomitant agent of the present invention varies with the drug form of formulations. Generally, it is present in a range from about 0.01 to 99.9 wt %, preferably from about 0.1 to 50 wt % and more preferably from about 0.5 to 20 wt % relative to the entire formula.

The content of a concomitant drug in the concomitant agent of the present invention varies with the drug form of formulations. Generally it is present in a range from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the drug form of formulations. Generally it is present in a range from about 1 to 99.99 wt % and preferably from about 10 to 90 wt % relative to the entire formula.

When the compound of the present invention and a concomitant drug are formulated independently, the same contents can be applied.

Since the dosages may fluctuate under various conditions as mentioned above, a dosage less than the aforementioned dosages may be sufficient or it may be necessary to administer at a dosage exceeding the range.

When the compounds of the invention are radiolabeled and/or are used as PET tracers, it is preferable that administration be done intravenously. Radiotracers labeled with positron emitting radionuclides are generally administered via intravenous injection within one hour of their synthesis due to the short half-life of the radionuclides involved, which is typically 20 and 110 minutes for $^{11}$C and $^{18}$F, respectively. When the radiolabeled PDE10A inhibitors of the invention are administered to a human subject, the amount required for imaging will normally be determined by the prescribing physician with the dosage generally varying according to the quantity of emission from the radionuclide used. Those with ordinary skill in the art would appreciate that in most instances, an effective amount will be the amount of compound sufficient to produce emissions in the range of from about 1-5 mCi. The mass associated with a PET tracer is in the form of the natural isotope, for example, $^{12}$C for an $^{11}$C PET tracer and $^{18}$F for an $^{18}$F PET tracer, respectively. This mass comprises from about 0.1 μg to about 50 μg of a radiolabeled PDE10A inhibitor in order to avoid significant inhibition of PDE10A.

The following illustrative procedure may be utilized when performing PET imaging studies on patients in a clinical setting. The human subject is either unmedicated or premedicated with unlabeled PDE10A inhibitor or other pharmacological intervention some time prior to the day of the experiment and is fasted for at least 12 hours allowing water intake ad libitum. A 20 G two inch venous catheter is inserted into the contralateral ulnar vein for radiotracer administration. Administration of the PET tracer is often timed to coincide with time of maximum ($T_{max}$) or minimum ($T_{min}$) of PDE10A inhibitor (or other compound of intervention) concentration in the blood.

The human subject is positioned in the PET camera and a tracer dose of [$^{11}$C] Compound (I) (<20 mCi) is administered via i.v. catheter. Either arterial or venous blood samples are taken at appropriate time intervals throughout the PET scan in order to analyze and quantitate the fraction of umetabolized [$^{11}$C] (Compound (I)) in plasma. Images are acquired for up to 120 minutes. Within ten minutes of the injection of radiotracer and at the end of the imaging session, 1 ml blood samples are obtained for determining the plasma concentration of any unlabeled PDE10A inhibitor (or other compound of intervention) which may have been administered before the PET tracer.

Tomographic images are obtained through image reconstruction. For determining the distribution of radiotracer, regions of interest (ROIs) are drawn on the reconstructed image including, but not limited to, the striatum, cerebellum and other specific brain regions or areas of the central nervous system. Radiotracer uptakes over time in these regions are used to generate time activity curves (TAC), including those obtained in the absence of any intervention or in the presence of PDE10A inhibitors or other compound of intervention at the various dosing paradigms examined. Data are expressed as radioactivity per unit time per unit volume (μCi/cc/mCi injected dose). TAC data are processed with various methods well-known in the field to yield quantitative parameters, such as Binding Potential (BP), that are proportional to the density of unoccupied PDE10A. Inhibition of PDE10A is then calculated based on the change of BP in the presence of PDE10A inhibitors at the various dosing paradigms as compared to the BP in the unmedicated state. Inhibition curves are generated by plotting the above data vs the dose (concentration) of PDE10A inhibitors. The $ID_{50}$ values are obtained by curve fitting the dose-rate/inhibition curves with the following equation:

$$B = A_0 - A_0 * I / (ID_{50} + I) + NS$$

where B is the %-Dose/g of radiotracer in tissues for each dose of clinical candidate, $A_0$ is the specifically bound radiotracer in a tissue in the absence of PDE10A inhibitors, I is the injected dose of antagonist, $ID_{50}$ is the dose of compound which inhibits 50% of specific radiotracer binding to PDE10A, and NS is the amount of non-specifically bond radiotracer.

The subject compounds are further useful in a method for the prevention, treatment, control, amelioration, or reduction of risk of the diseases, disorders and conditions noted herein. The dose of the active ingredient in the composition may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets being adhered to by the patient, concurrent medication, and other factors which those skilled in the art will recognize. Generally, dosage levels between 0.01 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 mg of the active ingredient, such as, 1, 5, 10, 15, 20, 25, 50, 75, 100, 150, 200, 250, 300, 400, 500, 600, 750, 800, 900, and 1000 mg of the active ingredient for the symptomatic adjustment of the dosage to the patient to be treated. The compounds may be administered on a regimen of 1 to 4 times per day, preferably in a regimen of once or twice per day.

The compounds of the following examples had activity in inhibiting the human PDE10A enzyme as described in the biological assay that follows, generally with an $IC_{50}$ of less than about 1 μM. Many of the compounds within the present invention had activity in inhibiting the human PDE10A enzyme in the aforementioned assay, generally with an $IC_H$ of less than about 0.1 μM. Such a result is indicative of the intrinsic activity of the compounds in use as inhibitors of the PDE10A enzyme. In general, one of ordinary skill in the art would appreciate that a substance is considered to effectively inhibit PDE10A activity if it has an $IC_{50}$ of less than or about 1 μM, preferably less than or about 0.1 μM. The present invention also includes compounds within the generic scope of the invention which possess activity as inhibitors of other phosphodiesterase enzymes.

The PDE10A $IC_{50}$ is a measure of the ability of the test compound to inhibit the action of the PDE10A enzyme. To determine the selectivity of the test compounds for PDE10A, the $IC_{50}$ of the compound was determined for PDEs 1-9, and 11. In the table that follows, the selectivity is defined as the $IC_{50}$ of the test compound for the most potently inhibited PDE other than PDE10A, divided by the $IC_{50}$ for PDE10A. The PDE enzyme most potently inhibited other than PDE10A is listed.

The compounds of the present invention exhibit superior BBB (Brain-Blood Barrier) penetration. In addition, the compound of the present invention exhibit preferably 1-10%, more preferably 2-3.5% at the % ID values which is calculated as total radioactivity in the brain (MBq)×100/Injected radioactivity (MBq). The compounds of present invention exhibit high specific binding to putamen which is PDE10A rich region. In addition, the washout from nonspecific region (ex. cerebellum and frontal cortex) in brain shows faster than that from specific region (ex. putamen), making them more attractive as potential PET radioligands. Since the compounds of the present invention show efficacy exhibition, they are useful as PET radioligands of PDE10A.

EXAMPLES

The present invention will be explained in detail below with reference to the reference examples, embodiments, formulation examples and experimental examples. Since these are simply examples, the present invention will not be limited to these examples and the present invention can be modified in the range not deviating from the scope of the present invention.

The materials or intermediates of the present invention can be manufactured by the method known per se or the method disclosed in WO2010-090737.

In the following reference examples and embodiments, "room temperature" indicates generally approximately 10° C. to 35° C. As for %, % in terms of yields indicates mol/mol %, % in terms of the solvent used for chromatography indicates vol %, and % in other cases indicates wt %. In the proton NMR spectrum, OH and NH protons that cannot be identified due to broad bands are not recorded in the data and 1,3-dicarbonyl compounds may optionally be observed as enol-form compounds or mixture of keto-form compounds and enol-form compounds. Kieselgel 60 by Merck & Co., Inc. was used in silica gel chromatography and Chromatorex NH by Fuji Silysia Chemical Ltd. was used in basic silica gel chromatography.

Abbreviations used in other sections of the text imply the following meanings.
s: singlet
d: doublet
dd: doublet of doublets
dt: doublet of triplets
t: triplet
tt: triplet of triplets
td: triplet of doublets
q: quartet
septet: septet
m: multiplet
br: broad
J: coupling constant
Hz: hertz
$CDCl_3$: deuterochloroform
DMSO-$d_6$: deutero-dimethyl sulfoxide
$^1$H-NMR: proton nuclear magnetic resonance
HPLC: high performance liquid chromatography
AcOEt: ethyl acetate
THF: tetrahydrofuran
DMF: N,N-dimethylformamide
DMSO: dimethylsulfoxide
IPE: isopropyl ether
NMP: N-methylpyrrolidone
HOBt: 1-hydroxybenzotriazole
WSC: 1-ethyl-3-(3-dimethylaminopropyl)-carbodiimide hydrochloride
HATU: hexafluorophosphate 2-(7-aza-1H-benzotriazole-1-yl)-1,1,3,3-tetramethyluronium
DMTMM: 4-(4,6-dimethoxy-1,3,5-triazin-2-yl)-4-methylmorpholinium chloride n-hydrate
DBU: 1,8-diazabicyclo[5.4.0]-7-undecene
LC-MS: liquid chromatography/mass spectroscopy
ESI: electrospray ionization
CDI: 1,1'-carbonyldiimidazole
dba: dibenzylideneacetone
DIBAL: diisobutylaluminium hydride
DME: 1,2-dimethoxyethane
DPPA: diphenylphosphoryl azide
HMPA: hexamethylphosphoric triamide
selectfluor: 1-chloromethyl-4-fluoro-1,4-diazoniabicyclo[2.2.2]octane bis(tetrafluoroborate)
TEA: triethylamine
TFA: trifluoroacetic acid
Tf: trifluoromethylsulfonyl
TMSCl: trimethylsilyl chloride
Xantphos: 4,5-bis(diphenylphosphino)-9,9-dimethylxanthene
Rt: retention time
PBS: phosphate-buffered saline All reagents and solvents were of commercial quality and used without further purification. Column chromatography was performed using Merck silica gel 60 (230-400 mesh). The compounds and/or intermediates were purified by preparative high performance liquid chromatography (prep. HPLC) using a Gilson High Through Put Purification System.

The columns were reversed phase YMC CombiPrep Pro C18, S-5 μm, 19×50 mm. A gradient elution was used (flow rate 20 mL/min), typically starting with 5% acetonitrile/95% water and progressing to 100% acetonitrile over a Period of 7 min. All solvents contained 0.1% trifluoroacetic acid (TFA).

Mass spectrometric analysis was performed according to liquid chromatography/mass spectroscopy (LCMS) methods. The method employed a Waters LC-MS System (Agilent HP1100 HPLC and a Micromass ZMD mass spectrometer for the LCMS instrument, a CAPCELL PAK C18, UG120, S-3 μm, 1.5×35 mm for the chromatography column, and a solvent system that was a 5-95% gradient of acetonitrile in water with 0.04% TFA over a 3.60 min period (flow rate 0.5 mL/min molecular weight range 200-800; cone Voltage 20 V; column temperature 40° C.). All masses were reported as those of the protonated parent ions.

Reference Example 1

1-[2-(Difluoromethoxy)phenyl]-5-methoxy-3-(1-phenyl-1H-pyrazol-5-yl)pyridazin-4(1H)-one

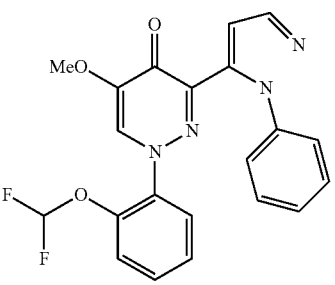 [SMILES: COc1cn(-c2ccccc2OC(F)F)nc(/C(=C/C=N)Nc2ccccc2)c1=O]

A solution of 1-[2-(difluoromethoxy)phenyl]-3-[3-(dimethylamino)prop-2-enoyl]-5-methoxypyridazin-4(1H)-one (0.50 g, 1.369 mmol) and phenylhydrazine (0.269 mL, 2.74 mmol) in AcOH (5 mL) was refluxed for 2 hr. After cooling to room temperature, the mixture was concentrated under reduced pressure. The residue was diluted with AcOEt, washed successively with 1 M HCl aqueous solution, saturated NaHCO$_3$ aqueous solution, and brine, dried over MgSO$_4$, and concentrated under reduced pressure. The residue was purified by silica gel column chromatography eluting with hexane/AcOEt (7/3-0/10) to give the title compound (0.38 g, 68% yield) as an off-white amorphous solid: $^1$H NMR (300 MHz, CDCl$_3$): δ ppm 3.88 (3H, s), 6.37 (1H, t, J=72.3 Hz), 6.57 (1H, dd, J=8.1, 1.7 Hz), 7.09-7.16 (1H, m), 7.22-7.25 (2H, m), 7.34-7.42 (6H, m), 7.76-7.78 (2H, m). LC-MS (ESI) m/z 411 [M+H]$^+$. Anal. Calcd. for C$_{21}$H$_{16}$F$_2$N$_4$O$_3$: C, 61.15; H, 4.07; N, 13.79. Found: C, 61.23; H, 4.11; N, 13.71.

Reference Example 2

5-Methoxy-3-(1-phenyl-1H-pyrazol-5-yl)-1-[3-(trifluoromethyl)phenyl]pyridazin-4(1H)-one

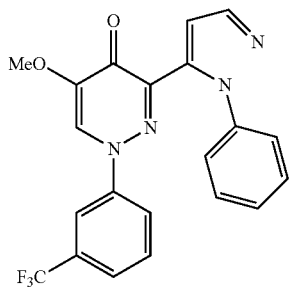 [SMILES: COc1cn(-c2cccc(C(F)(F)F)c2)nc(/C(=C/C=N)Nc2ccccc2)c1=O]

A solution of 3-[3-(dimethylamino)prop-2-enoyl]-5-methoxy-1-[3-(trifluoromethyl)phenyl]pyridazin-4(1H)-one (3.41 g, 9.29 mmol) and phenylhydrazine (1.83 mL, 18.6 mmol) in AcOH (25 mL) was refluxed for 2 hr. After cooling to room temperature, the reaction mixture was concentrated under reduced pressure. The residue was diluted with AcOEt, washed successively with 1 M HCl aqueous solution, 1 M NaOH aqueous solution, and brine, dried over MgSO$_4$, and concentrated under reduced pressure. The residue was purified by silica gel column chromatography eluting with AcOEt and crystallized from hexane/AcOEt to give the title compound (2.70 g, 71% yield) as colorless crystals: mp 139-141° C.; $^1$H NMR (300 MHz, CDCl$_3$): δ ppm 3.98 (3H, s), 7.05 (1H, dd, J=1.9, 7.9 Hz), 7.19 (1H, s), 7.34-7.47 (7H, m), 7.56 (1H, d, J=7.9 Hz), 7.80 (1H, d, J=1.9 Hz), 7.92 (1H, s). LC-MS (ESI) m/z 413 [M+H]$^+$. Anal. Calcd for C$_{21}$H$_{15}$F$_3$N$_4$O$_2$: C, 61.17; H, 3.67; N, 13.59. Found: C, 61.15; H, 3.65; N, 13.57.

Reference Example 3

1-(2-Fluoro-4-iodophenyl)-5-methoxy-3-(1-phenyl-1H-pyrazol-5-yl)pyridazin-4(1H)-one

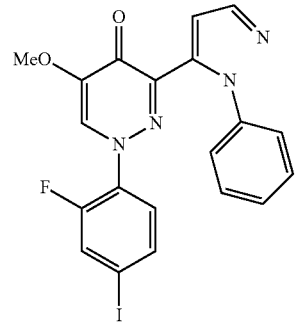 [SMILES: COc1cn(-c2ccc(I)cc2F)nc(/C(=C/C=N)Nc2ccccc2)c1=O]

A mixture of 3-acetyl-1-(2-fluoro-4-iodophenyl)-5-methoxypyridazin-4(1H)-one (2.02 g, 5.2 mmol) and N,N-dimethylformamide dimethyl acetal (30 ml) was refluxed for 6 hr. After cooling to room temperature, the reaction mixture was concentrated under reduced pressure.

A solution of the residue and phenylhydrazine (1.54 mL, 15.6 mmol) in AcOH (20 mL) was refluxed for 2 hr. After cooling to room temperature, the reaction mixture was concentrated under reduced pressure. The residue was diluted with AcOEt, washed successively with 1 M HCl aqueous solution, 1 M NaOH aqueous solution, and brine, dried over MgSO$_4$, and concentrated under reduced pressure. The residue was purified by silica gel column chromatography eluting with AcOEt and recrystallized from MeOH to give the title compound (1.14 g, 45% yield) as pale yellow crystals: mp 194-196° C.; $^1$H NMR (300 MHz, CDCl$_3$): δ ppm 3.90 (3H, s), 6.04 (1H, t, J=8.5 Hz), 7.30-7.47 (7H, m), 7.54 (1H, dd, J=1.9, 10.6 Hz), 7.76 (1H, d, J=2.3 Hz), 7.78 (1H, d, J=2.3 Hz). LC-MS (ESI) m/z 489 [M+H]$^+$. Anal. Calcd for C$_{20}$H$_{14}$FIN$_4$O$_2$: C, 49.20; H, 2.89; N, 11.47. Found: C, 48.94; H, 3.01; N, 11.54.

Reference Example 4

1-[2-Fluoro-4-(trifluoromethyl)phenyl]-5-methoxy-3-(1-phenyl-1H-pyrazol-5-yl)pyridazin-4(1H)-one

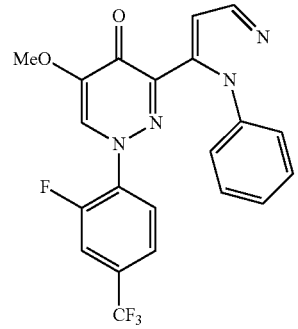 [SMILES: COc1cn(-c2ccc(C(F)(F)F)cc2F)nc(/C(=C/C=N)Nc2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.50 mmol), FSO$_2$CF$_2$CO$_2$Me (0.318 mL, 2.5 mmol), HMPA (0.435 mL, 2.5 mmol), and CuI (114 mg, 0.6 mmol) in DMF (2.5 mL) was stirred for 24 hr at 90° C. under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) and recrystallized from hexane/AcOEt to give the title compound (71.7 mg, 33% yield) as off-white crystals: mp 169-171° C.; $^1$H NMR (300 MHz, CDCl$_3$): δ ppm 3.92 (3H, s), 6.42-6.47 (1H, m), 7.22-7.26 (1H, m), 7.37-7.49 (7H, m), 7.80 (1H, d, J=1.9 Hz), 7.84 (1H, d, J=2.3 Hz). LC-MS (ESI) m/z 431 [M+H]$^+$. Anal. Calcd for C$_{21}$H$_{14}$F$_4$N$_4$O$_2$: C, 58.61; H, 3.28; N, 13.02. Found: C, 58.50; H, 3.36; N, 12.93.

Reference Example 5

5-Ethoxy-3-(1-phenyl-1H-pyrazol-5-yl)-1-[3-(trifluoromethyl)phenyl]pyridazin-4(1H)-one

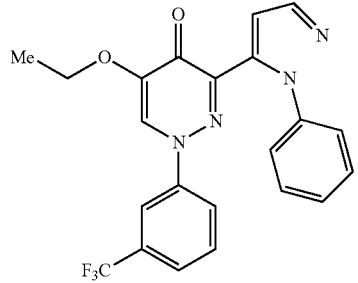 [SMILES: CCOc1cn(-c2cccc(C(F)(F)F)c2)nc(/C(=C/C=N)Nc2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), iodoethane (0.040 mL, 0.50 mmol), and K$_2$CO$_3$ (104 mg, 0.75 mmol) in DMF (1 mL) was stirred for 24 hr at room temperature. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) to give the title compound (94.1 mg, 88% yield) as an off-white amorphous solid: $^1$H NMR (300 MHz, CDCl$_3$): δ ppm 1.52 (3H, t, J=6.8 Hz), 4.21 (2H, q, J=6.8 Hz), 7.03 (1H, dd, J=1.9, 7.9 Hz), 7.18 (1H, s), 7.33-7.46 (7H, m), 7.55 (1H, d, J=7.9 Hz), 7.80 (1H, d, J=1.9 Hz), 7.94 (1H, s). LC-MS (ESI) m/z 427 [M+H]$^+$. Anal. Calcd for C$_{22}$H$_{17}$F$_3$N$_4$O$_2$: C, 61.97; H, 4.02; N, 13.14. Found: C, 61.82; H, 4.15; N, 13.17.

Reference Example 6

5-(1-Methylethoxy)-3-(1-phenyl-1H-pyrazol-5-yl)-1-[3-(trifluoromethyl)phenyl]pyridazin-4(1H)-one

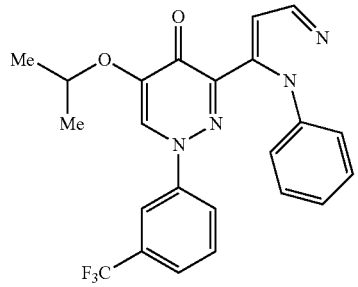 [SMILES: CC(C)Oc1cn(-c2cccc(C(F)(F)F)c2)nc(/C(=C/C=N)Nc2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), 2-iodopropane (0.050 mL, 0.50 mmol), and K$_2$CO$_3$ (104 mg, 0.75 mmol) in DMF (1 mL) was stirred for 20 hr at 60° C. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) and crystallized from hexane/AcOEt to give the title compound (79.5 mg, 72% yield) as colorless prisms: mp 137-139° C.; $^1$H NMR (300 MHz, CDCl$_3$): δ ppm 1.38 (6H, d, J=6.4 Hz), 4.96-5.09 (1H, m), 7.05 (1H, dd, J=1.9, 7.9 Hz), 7.18 (1H, s), 7.33-7.46 (7H, m), 7.55 (1H, d, J=7.9 Hz), 7.80 (1H, d, J=1.9 Hz), 8.01 (1H, s). LC-MS (ESI) m/z 441 [M+H]$^+$. Anal. Calcd for C$_{23}$H$_{19}$F$_3$N$_4$O$_2$: C, 62.72; H, 4.35; N, 12.72. Found: C, 62.74; H, 4.40; N, 12.81.

Reference Example 7

5-(Cyclopropylmethoxy)-3-(1-phenyl-1H-pyrazol-5-yl)-1-[3-(trifluoromethyl)phenyl]pyridazin-4(1H)-one

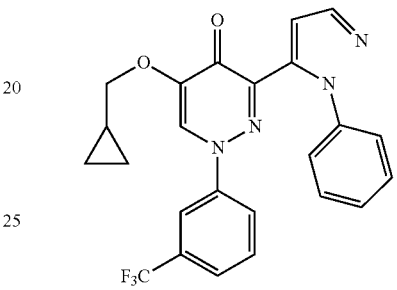

A suspension of 5-hydroxy-3-(1-phenyl-1H-pyrazol-5-yl)-1-[3-(trifluoromethyl)phenyl]pyridazin-4(1H)-one (100 mg, 0.25 mmol), (bromomethyl)cyclopropane (0.048 mL, 0.50 mmol), and K$_2$CO$_3$ (104 mg, 0.75 mmol) in DMF (1 mL) was stirred for 20 hr at room temperature. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) and crystallized from MeOH to give the title compound (103 mg, 91% yield) as colorless prisms: mp 72-s 78° C.; $^1$H NMR (300 MHz, CDCl$_3$): δ ppm 0.32-0.47 (2H, m), 0.60-0.76 (2H, m), 1.26-1.39 (1H, m), 4.06 (2H, d, J=7.2 Hz), 7.04 (1H, dd, J=2.3, 8.3 Hz), 7.18 (1H, s), 7.33-7.46 (7H, m), 7.55 (1H, d, J=7.9 Hz), 7.80 (1H, d, J=1.9 Hz), 7.99 (1H, s). LC-MS (ESI) m/z 453 [M+H]$^+$. Anal. Calcd for C$_{24}$H$_{19}$F$_3$N$_4$O$_2$.0.5H$_2$O: C, 62.47; H, 4.37; N, 12.14. Found: C, 62.19; H, 4.41; N, 12.15.

Reference Example 8

5-(Difluoromethoxy)-3-(1-phenyl-1H-pyrazol-5-yl)-1-[3-(trifluoromethyl)phenyl]pyridazin-4(1H)-one

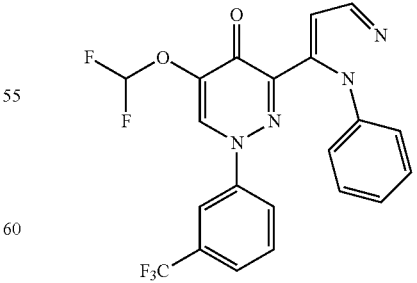

A mixture of 5-hydroxy-3-(1-phenyl-1H-pyrazol-5-yl)-1-[3-(trifluoromethyl)phenyl]pyridazin-4(1H)-one (398 mg, 1.0 mmol), CF$_2$ClCO$_2$Na (305 mg, 2.0 mmol), K$_2$CO$_3$ (207 mg, 1.5 mmol), DMF (2 mL), and H$_2$O (0.4 mL) was stirred for 6 hr at 100° C. After cooling to room temperature, the reaction mixture was poured into water and extracted with AcOEt. The extract was washed with brine, dried over MgSO4, and concentrated under reduced pressure. The residue was purified by basic silica gel column chromatography eluting with hexane/AcOEt (3/1) and crystallized from hexane/AcOEt to give the title compound (267 mg, 59% yield) as colorless prisms: mp 132-134° C.; $^1$H NMR (300 MHz, CDCl$_3$): δ ppm 7.06 (1H, dd, J=2.3, 8.3 Hz), 7.16-7.66 (10H, m), 7.82 (1H, d, J=1.9 Hz), 8.33 (1H, s). LC-MS (ESI) m/z 449 [M+H]$^+$. Anal. Calcd for C$_{21}$H$_{13}$F$_5$N$_4$O$_2$: C, 56.26; H, 2.92; N, 12.50. Found: C, 55.98; H, 2.82; N, 12.43.

Reference Example 9

5-(Difluoromethoxy)-1-(2-fluorophenyl)-3-(1-phenyl-1H-pyrazol-5-yl)pyridazin-4(1H)-one

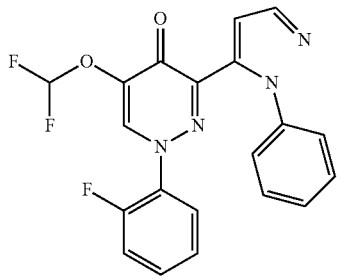 [SMILES: N=C/C=C(\Nc1ccccc1)c1nn(-c2ccccc2F)cc(OC(F)F)c1=O]

A mixture of 1-(2-fluorophenyl)-5-hydroxy-3-(1-phenyl-1H-pyrazol-5-yl)pyridazin-4(1H)-one (557 mg, 1.6 mmol), CF$_2$ClCO$_2$Na (488 mg, 3.2 mmol), K$_2$CO$_3$ (332 mg, 2.4 mmol), DMF (3 mL), and H$_2$O (0.6 mL) was stirred overnight at 100° C. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with hexane/AcOEt (2/1) and crystallized from hexane/AcOEt to give the title compound (485 mg, 76% yield) as colorless prisms: mp 109-114° C.; $^1$H NMR (300 MHz, CDCl$_3$): δ ppm 6.46 (1H, dd, J=1.5, 7.9 Hz), 7.00-7.06 (1H, m), 7.08-7.59 (9H, m), 7.80 (1H, d, J=1.9 Hz), 8.20 (1H, s). LC-MS (ESI) m/z 399 [M+H]$^+$. Anal. Calcd for C$_{20}$H$_{13}$F$_3$N$_4$O$_2$: C, 60.30; H, 3.29; N, 14.07. Found: C, 60.50; H, 3.41; N, 14.20.

Reference Example 10

5-(2-Methoxyethoxy)-3-(1-phenyl-1H-pyrazol-5-yl)-1-[3-(trifluoromethyl)phenyl]pyridazin-4(1H)-one

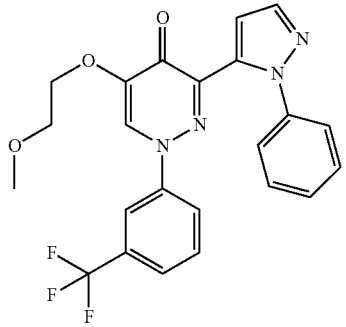 [SMILES: COCCOc1cn(-c2cccc(C(F)(F)F)c2)nc(-c2ccnn2-c2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), 2-bromoethyl methyl ether (0.070 mL, 0.75 mmol), and K$_2$CO$_3$ (104 mg, 0.75 mmol) in DMF (1 mL) was stirred for 24 hr at room temperature. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/2) to give the title compound (89.9 mg, 79% yield) as a pale yellow amorphous solid: $^1$H NMR (300 MHz, CDCl$_3$): δ ppm 3.45 (3H, s), 3.78-3.81 (2H, m), 4.42-4.44 (2H, m), 7.02 (1H, dd, J=1.9, 7.9 Hz), 7.20 (1H, s), 7.34-7.45 (7H, m), 7.55 (1H, d, J=7.9 Hz), 7.80 (1H, d, J=1.9 Hz), 8.29 (1H, s). LC-MS (ESI) m/z 457 [M+H]$^+$. Anal. Calcd for C$_{23}$H$_{19}$F$_3$N$_4$O$_3$.0.25H$_2$O: C, 59.93; H, 4.26; N, 12.16. Found: C, 59.87; H, 4.09; N, 12.15.

Reference Example 11

1-[2-Fluoro-4-(trifluoromethoxy)phenyl]-5-methoxy-3-(1-phenyl-1H-pyrazol-5-yl)pyridazin-4(1H)-one

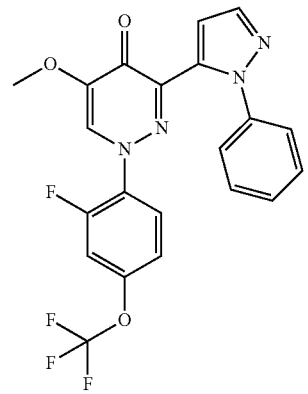 [SMILES: COc1cn(-c2ccc(OC(F)(F)F)cc2F)nc(-c2ccnn2-c2ccccc2)c1=O]

A solution of 3-acetyl-1-[2-fluoro-4-(trifluoromethoxy)phenyl]-5-methoxypyridazin-4(1H)-one (2.8 g, 8.1 mmol) and N,N-dimethylformamide diisopropyl acetal (8.5 mL, 40 mmol) in toluene (50 mL) was refluxed for 5 hr. After stirring at room temperature overnight, the mixture was concentrated under reduced pressure.

A solution of the residue and phenylhydrazine (2.0 mL, 20 mmol) in AcOH (30 mL) was refluxed for 3 hr. After stirring at room temperature overnight, the mixture was concentrated under reduced pressure. The residue was diluted with AcOEt, and washed with saturated NaHCO$_3$ aqueous solution and brine. The organic layer was dried over MgSO$_4$, filtered and concentrated under reduced pressure. The residue was chromatographed on silica gel (10/90-100/0 AcOEt/hexane) to give 2.4 g of the crude product.

One gram of the crude product was purified by preparative HPLC, and the combined fraction was concentrated under reduced pressure. The residual solution was basified with saturated NaHCO$_3$ aqueous solution and extracted with AcOEt. The organic layer was washed with brine, dried over MgSO$_4$, filtered and concentrated under reduced pressure. The residual crystals were recrystallized from AcOEt/ hexane to give the title compound (0.66 g) as white crystals: mp 117-118° C.; $^1$H NMR (300 MHz, CDCl$_3$): δ ppm 3.90 (3H, s), 6.43 (1H, t, J=8.7 Hz), 6.85-6.90 (1H, m), 7.09 (1H, dd, J=11.5, 1.7 Hz), 7.34 (1H, d, J=1.9 Hz), 7.35-7.47 (5H, m), 7.77 (1H, d, J=2.3 Hz), 7.78 (1H, d, J=1.9 Hz). LC-MS (ESI) m/z 447 [M+H]$^+$. Anal. Calcd. for C$_{21}$H$_{14}$F$_4$N$_4$O$_3$: C, 56.51; H, 3.16; N, 12.55. Found: C, 56.51; H, 3.14; N, 12.61.

Preparative HPLC was performed at the conditions described below.

Column: Waters SunFire Column C18 (30×50 mm S-5 μm)

Column temp: 25° C.

Mobile phase: (A) 0.1% TFA in distilled water, (B) 0.1% TFA in acetonitrile

Gradient: 0 min (A/B=90/10)→1 min (A/B=90/10)→4.75 min (A/B=0/100)→7.40 min (A/B=0/100)→7.41 min (A/B=90/10)→8.50 min (A/B=90/10)

Flow rate: 70 mL/min

Detector: UV 220 nm

Concentration: 100 mg/mL

Inject volume: 10 mL

Reference Example 12

1-(3-Bromo-2-fluorophenyl)-5-methoxy-3-(1-phenyl-1H-pyrazol-5-yl)pyridazin-4(1H)-one

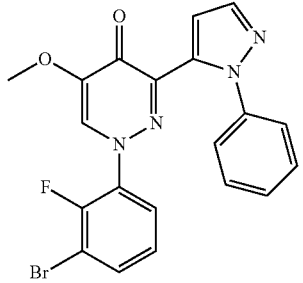 [SMILES: COc1cn(-c2cccc(Br)c2F)nc(-c2ccnn2-c2ccccc2)c1=O]

A mixture of 3-acetyl-1-(3-bromo-2-fluorophenyl)-5-methoxypyridazin-4(1H)-one (2.98 g, 8.74 mmol) in N,N-dimethylformamide dimethyl acetal (30 mL) was heated to reflux for 3.5 hr. The mixture was concentrated under reduced pressure. To the residue were added AcOH (30 mL) and phenylhydrazine (1.72 mL, 17.5 mmol). The mixture was heated to reflux for 4 hr. The mixture was diluted with 1 M HCl aqueous solution, extracted with AcOEt, washed with saturated NaHCO$_3$ aqueous solution, dried over Na$_2$SO$_4$, filtered, concentrated under reduced pressure, purified by column chromatography on basic silica gel (hexane/AcOEt=50/50 to 0/100) and recrystallized with EtOH to yield the title compound (2.29 g, 59% yield) as a yellow solid: mp 186-191° C. $^1$H NMR (DMSO-d$_6$, 300 MHz): δ ppm 3.77 (3H, s), 6.99 (1H, d, J=1.9 Hz), 7.08-7.15 (1H, m), 7.17-7.26 (1H, m), 7.28-7.47 (5H, m), 7.74-7.86 (2H, m), 8.55 (1H, d, J=2.3 Hz). Anal. Calcd for C$_{20}$H$_{14}$BrFN$_4$O$_2$: C, 54.44; H, 3.20; N, 12.70. Found: C, 54.70; H, 3.30; N, 12.82.

Reference Example 13

1-[4-(Cyclopropylethynyl)-2-fluorophenyl]-5-methoxy-3-(1-phenyl-1H-pyrazol-5-yl)pyridazin-4(1H)-one

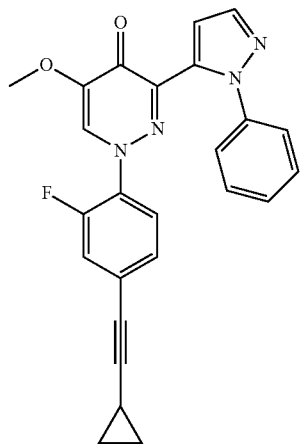 [SMILES: COc1cn(-c2ccc(C#CC3CC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (255 mg, 0.5 mmol), cyclopropylethylene (0.0846 mL, 1.0 mmol), i-Pr$_2$NEt (0.348 mL, 2.0 mmol), CuI (9.5 mg, 0.05 mmol), Pd(PPh$_3$)$_2$Cl$_2$ (17.5 mg, 0.025 mmol) and PPh$_3$ (6.6 mg, 0.025 mmol) in DMF (1 ml) was heated to 40° C. for 90 min under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane to yield the title compound (181 mg, 85% yield) as a yellow solid: mp 145-146° C. $^1$H NMR (DMSO-d$_6$, 300 MHz): δ ppm 0.74-0.82 (2H, m), 0.88-0.98 (2H, m), 1.58 (1H, tt, J=8.2, 5.1 Hz), 3.77 (3H, s), 6.91-7.01 (2H, m), 7.20 (1H, dd, J=8.3, 1.1 Hz), 7.28-7.51 (6H, m), 7.78 (1H, d, J=1.9 Hz), 8.47 (1H, d, J=1.9 Hz). Anal. Calcd for C$_{25}$H$_{19}$FN$_4$O$_2$: C, 70.41; H, 4.49; N, 13.14. Found: C, 70.33; H, 4.60; N, 13.08.

Reference Example 14

1-(4-Cyclopropyl-2-fluorophenyl)-5-methoxy-3-(1-phenyl-1H-pyrazol-5-yl)pyridazin-4(1H)-one

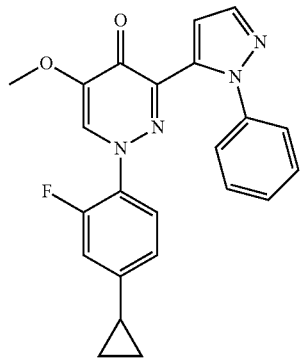 [SMILES: COc1cn(-c2ccc(C3CC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (255 mg, 0.5 mmol), cyclopropylboronic acid (55.8 mg, 0.65 mmol), K$_3$PO$_4$ (372 mg, 1.75 mmol), Pd(OAc)$_2$ (5.6 mg, 0.025 mmol) and tricyclohexylphosphine (14 mg, 0.05 mmol) in toluene (2.25 mL) and water (0.11 mL) was heated to 100° C. for 4 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane to yield the title compound (128 mg, 64% yield) as a white solid: mp 140-142° C. $^1$H NMR (DMSO-d$_6$, 300 MHz): δ ppm 0.70-0.82 (2H, m), 0.96-1.10 (2H, m), 1.94-2.09 (1H, m), 3.76 (3H, s), 6.87-7.01 (3H, m), 7.09-7.18 (1H, m), 7.28-7.50 (5H, m), 7.78 (1H, d, J=1.9 Hz), 8.44 (1H, d, J=1.9 Hz). Anal. Calcd for C$_{23}$H$_{19}$FN$_4$O$_2$: C, 68.65; H, 4.76; N, 13.92. Found: C, 68.47; H, 4.82; N, 13.84.

Reference Example 15

1-[4-(3,6-Dihydro-2H-pyran-4-yl)-2-fluorophenyl]-5-methoxy-3-(1-phenyl-1H-pyrazol-5-yl)pyridazin-4(1H)-one

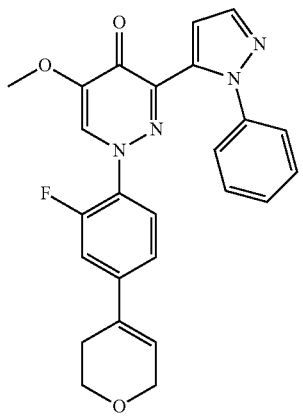 [SMILES: COc1cn(-c2ccc(C3=CCOCC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (459 mg, 0.9 mmol), 3,6-dihydro-2H-pyran-4-boronic acid pinacol ester (210 mg, 1.0 mmol), Pd(PPh$_3$)$_4$ (52 mg, 0.045 mmol), Na$_2$CO$_3$ (212 mg, 2.0 mmol), DME (4 mL), and H$_2$O (1 mL) was refluxed overnight under Ar atmosphere. After cooling to room temperature, the precipitate was collected by filtration and recrystallized from THF/MeOH to give the title compound (364 mg, 91% yield) as a white solid: mp 229-231° C.; $^1$H NMR (300 MHz, DMSO-d$_6$): δ ppm 2.40-2.50 (2H, m), 3.77 (3H, s), 3.82 (2H, t, J=5.5 Hz), 4.22-4.27 (2H, m), 6.43-6.48 (1H, m), 6.97 (1H, d, J=1.9 Hz), 7.02 (1H, t, J=8.7 Hz), 7.29-7.46 (6H, m), 7.52 (1H, dd, J=1.9, 12.8 Hz), 7.79 (1H, d, J=1.9 Hz), 8.48 (1H, d, J=1.9 Hz). LC-MS (ESI) m/z 445 [M+H]$^+$. Anal. Calcd for C$_{25}$H$_{21}$FN$_4$O$_3$: C, 67.56; H, 4.76; N, 12.61. Found: C, 67.31; H, 4.58; N, 12.52.

Reference Example 16

1-[2-Fluoro-4-(tetrahydro-2H-pyran-4-yl)phenyl]-5-methoxy-3-(1-phenyl-1H-pyrazol-5-yl)pyridazin-4(1H)-one

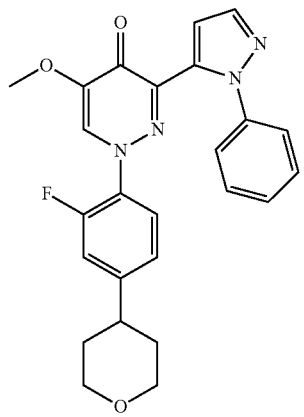 [SMILES: COc1cn(-c2ccc(C3CCOCC3)cc2F)nc(-c2ccnn2-c2ccccc2)c1=O]

A mixture of 1-[4-(3,6-dihydro-2H-pyran-4-yl)-2-fluorophenyl]-5-methoxy-3-(1-phenyl-1H-pyrazol-5-yl)pyridazin-4(1H)-one (300 mg, 0.675 mmol), 10% Pd—C (50% wet, 300 mg), THF (30 mL), and MeOH (30 mL) was hydrogenated for 2 hr at room temperature. The reaction mixture was filtered, and the filtrate was concentrated under reduced pressure. The residue was recrystallized from MeOH/H$_2$O to give the title compound (255 mg, 85% yield) as a white solid: mp 187-189° C.; $^1$H NMR (300 MHz, CDCl$_3$): δ ppm 1.57-1.83 (4H, m), 2.72-2.82 (1H, m), 3.45-3.58 (2H, m), 3.90 (3H, s), 4.09 (2H, td, J=3.0, 11.3 Hz), 6.35 (1H, t, J=8.3 Hz), 6.86 (1H, dd, J=1.5, 8.3 Hz), 7.03 (1H, dd, J=1.9, 12.8 Hz), 7.28 (1H, d, J=1.9 Hz), 7.35-7.46 (5H, m), 7.78 (1H, d, J=1.9 Hz), 7.79 (1H, d, J=2.6 Hz). LC-MS (ESI) m/z 447 [M+H]$^+$. Anal. Calcd for C$_{25}$H$_{23}$FN$_4$O$_3$: C, 67.25; H, 5.19; N, 12.55. Found: C, 67.13H, 5.13; N, 12.57.

Reference Example 17

1-[2-Fluoro-4-(3-fluoroazetidin-1-yl)phenyl]-5-methoxy-3-(1-phenyl-1H-pyrazol-5-yl)pyridazin-4(1H)-one

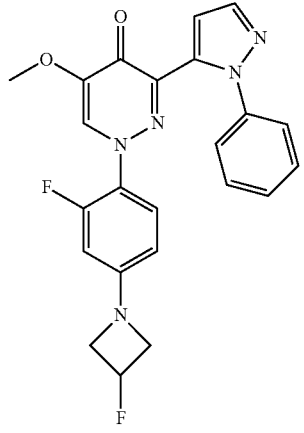 [SMILES: COc1cn(-c2ccc(N3CC(F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 3-fluoroazetidine hydrochloride (66.9 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 13 hr under N$_2$. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane to yield the title compound (88 mg, 40% yield) as a pale yellow solid: mp 162-163° C. $^1$H NMR (DMSO-d$_6$, 300 MHz): δ ppm 3.76 (3H, s), 3.86-4.04 (2H, m), 4.12-4.29 (2H, m), 5.36-5.64 (1H, m), 6.25 (1H, dd, J=8.5, 2.1 Hz), 6.48 (1H, dd, J=12.8, 2.3 Hz), 6.81-6.95 (2H, m), 7.25-7.48 (5H, m), 7.77 (1H, d, J=1.9 Hz), 8.36 (1H, d, J=1.9 Hz). Anal. Calcd for C$_{23}$H$_{19}$F$_2$N$_5$O$_2$: C, 63.44: H, 4.40: N, 16.08. Found: C, 63.62: H, 4.44: N, 15.92.

Reference Example 18

1-[4-(3,3-Difluoroazetidin-1-yl)-2-fluorophenyl]-5-methoxy-3-(1-phenyl-1H-pyrazol-5-yl)pyridazin-4(1H)-one

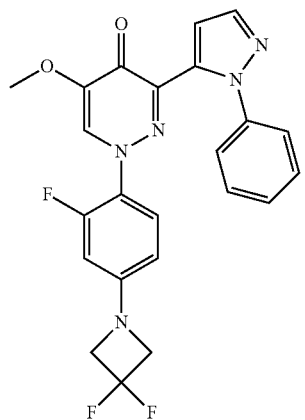 [SMILES: COc1cn(-c2ccc(N3CC(F)(F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 3,3-difluoroazetidine hydrochloride (77.7 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 16 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane to yield the title compound (123 mg, 54% yield) as a pale yellow solid: mp 204-206° C. $^1$H NMR (DMSO-d$_6$, 300 MHz): δ ppm 3.76 (3H, s), 4.35 (4H, t, J=12.4 Hz), 6.36 (1H, dd, J=8.9, 2.4 Hz), 6.61 (1H, dd, J=12.8, 2.3 Hz), 6.87-6.99 (2H, m), 7.25-7.49 (5H, m), 7.78 (1H, d, J=1.9 Hz), 8.38 (1H, d, J=1.5 Hz). Anal. Calcd for C$_{23}$H$_{18}$F$_3$N$_5$O$_2$: C, 60.93; H, 4.00; N, 15.45. Found: C, 61.00; H, 3.99; N, 15.50.

Reference Example 19

1-[4-(3,3-Difluoropyrrolidin-1-yl)-2-fluorophenyl]-5-methoxy-3-(1-phenyl-1H-pyrazol-5-yl)pyridazin-4(1H)-one

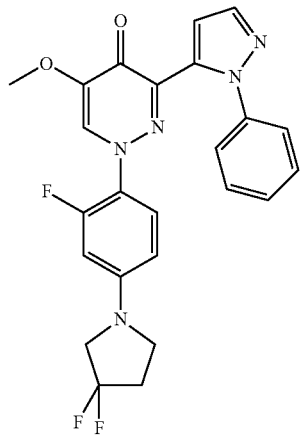 [SMILES: COc1cn(-c2ccc(N3CCC(F)(F)C3)cc2F)nc(-c2ccnn2-c2ccccc2)c1=O]

A suspension of 3-fluoro-4-[5-methoxy-4-oxo-3-(1-phenyl-1H-pyrazol-5-yl)pyridazin-1(4H)-yl]phenyl trifluoromethanesulfonate (204 mg, 0.4 mmol), 3,3-difluoropyrrolidine hydrochloride (71.8 mg, 0.5 mmol), Pd$_2$(dba)$_3$ (9.2 mg, 0.01 mmol), Xantphos (23.1 mg, 0.04 mmol), and NaO-t-Bu (96.1 mg, 1.0 mmol) in 1,4-dioxane (2 mL) was stirred for 3 hr at 90° C. under Ar atmosphere. The reaction mixture was poured into water and extracted with AcOEt. The extract was washed with brine, dried over MgSO$_4$, and concentrated under reduced pressure. The residue was subjected to basic silica gel column chromatography followed by purification by preparative HPLC. Recrystallization from MeOH/H$_2$O gave the title compound (21.0 mg, 11% yield) as a yellow solid: mp 195-197° C.; $^1$H NMR (300 MHz, CDCl$_3$): δ ppm 2.46-2.60 (2H, m), 3.52 (2H, t, J=7.2 Hz), 3.66 (2H, t, J=12.8 Hz), 3.89 (3H, s), 6.09 (1H, dd, J=2.6, 9.0 Hz), 6.23 (1H, dd, J=2.6, 13.9 Hz), 6.33 (1H, t, J=9.0 Hz), 7.25 (1H, d, J=1.9 Hz), 7.33-7.44 (5H, m), 7.71 (1H, d, J=2.3 Hz), 7.77 (1H, d, J=2.3 Hz). LC-MS (ESI) m/z 468 [M+H]$^+$. Anal. Calcd for C$_{24}$H$_{20}$F$_3$N$_5$O$_2$: C, 61.67; H, 4.31; N, 14.98. Found: C, 61.51; H, 4.38; N, 14.89.

Preparative HPLC was performed at the conditions described below.

Column: Waters SunFire Column C18 (30×50 mm S-5 μm)

Column temp: 25° C.

Mobile phase: (A) 0.1% TFA in distilled water, (B) 0.1% TFA in acetonitrile

Gradient: 0 min (A/B=60/40)→1 min (A/B=60/40)→4.75 min (A/B=0/100)→7.40 min (A/B=0/100)→7.41 min (A/B=60/40)→8.50 min (A/B=60/40)

Flow rate: 70 mL/min

Detector: UV 220 nm

Concentration: 50 mg/mL

Inject volume: 0.150 mL

Retention time: 2.44 min

Reference Example 20

1-[2-Fluoro-4-(3,3,4,4-tetrafluoropyrrolidin-1-yl)phenyl]-5-methoxy-3-(1-phenyl-1H-pyrazol-5-yl)pyridazin-4(1H)-one

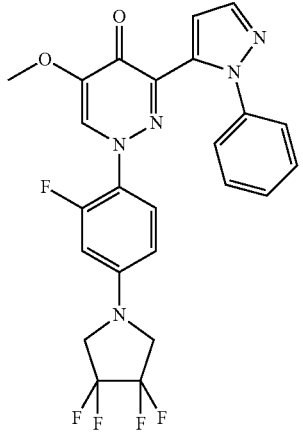 [SMILES: COc1cn(-c2ccc(N3CC(F)(F)C(F)(F)C3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (488 mg, 1.0 mmol), 3,3,4,4-tetrafluoropyrrolidine hydrochloride (215 mg, 1.2 mmol), Pd$_2$(dba)$_3$ (18.3 mg, 0.02 mmol), Xantphos (46.3 mg, 0.08 mmol), and NaO-t-Bu (250 mg, 2.6 mmol) in 1,4-dioxane (5 mL) was stirred for 6 hr at 90° C. under Ar atmosphere. The reaction mixture was poured into water and extracted with AcOEt. The extract was washed with brine, dried over MgSO$_4$, and concentrated under reduced pressure. The residue was subjected to basic silica gel column chromatography eluting with hexane/AcOEt (1/1-0/1) and crystallized from hexane/AcOEt to give the title compound (366 mg, 73% yield) as a white solid: mp 175-177° C.; $^1$H NMR (300 MHz, CDCl$_3$): δ ppm 3.75-3.89 (7H, m), 6.10 (1H, ddd, J=0.8, 2.6, 9.0 Hz), 6.26 (1H, dd, J=2.6, 13.6 Hz), 6.35 (1H, t, J=9.0 Hz), 7.27 (1H, d, J=1.9 Hz), 7.34-7.46 (5H, m), 7.71 (1H, d, J=2.6 Hz), 7.78 (1H, d, J=1.9 Hz). LC-MS (ESI) m/z 504 [M+H]$^+$. Anal. Calcd for C$_{24}$H$_{18}$F$_5$N$_5$O$_2$: C, 57.26; H, 3.60; N, 13.91. Found: C, 57.17; H, 3.61; N, 13.79.

Reference Example 21

1-[4-(3,3-Difluoropiperidin-1-yl)-2-fluorophenyl]-5-methoxy-3-(1-phenyl-1H-pyrazol-5-yl)pyridazin-4(1H)-one

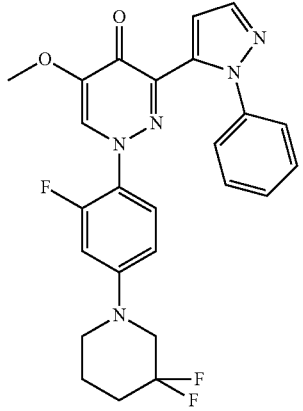 [SMILES: COc1cn(-c2ccc(N3CCCC(F)(F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 3,3-difluoropiperidine hydrochloride (94.6 mg, 0.6 mmol), Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 14 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane to yield the title compound (132 mg, 55% yield) as a yellow solid: mp 182-187° C. $^1$H NMR (DMSO-d$_6$, 300 MHz): δ ppm 1.68-1.81 (2H, m), 1.97-2.16 (2H, m), 3.34-3.43 (2H, m), 3.67 (2H, t, J=11.9 Hz), 3.76 (3H, s), 6.73-7.10 (4H, m), 7.24-7.50 (5H, m), 7.78 (1H, d, J=1.9 Hz), 8.39 (1H, d, J=1.9 Hz). Anal. Calcd for C$_{25}$H$_{22}$F$_3$N$_5$O$_2$: C, 62.36; H, 4.61; N, 14.55. Found: C, 62.60; H, 4.60; N, 14.31.

Reference Example 22

1-[4-(4,4-Difluoropiperidin-1-yl)-2-fluorophenyl]-5-methoxy-3-(1-phenyl-1H-pyrazol-5-yl)pyridazin-4(1H)-one

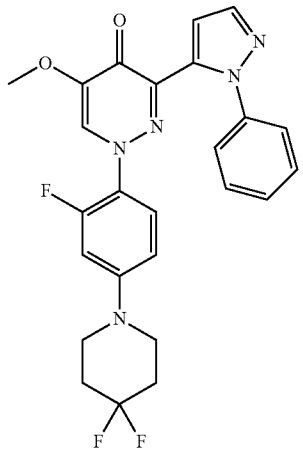 [SMILES: COc1cn(-c2ccc(N3CCC(F)(F)CC3)cc2F)nc(-c2ccnn2-c2ccccc2)c1=O]

A suspension of 3-fluoro-4-[5-methoxy-4-oxo-3-(1-phenyl-1H-pyrazol-5-yl)pyridazin-1(4H)-yl]phenyl trifluoromethanesulfonate (408 mg, 0.8 mmol), 4,4-difluoropiperidine hydrochloride (158 mg, 1.0 mmol), Pd$_2$(dba)$_3$ (36.6 mg, 0.04 mmol), Xantphos (92.6 mg, 0.16 mmol), and NaO-t-Bu (192 mg, 2.0 mmol) in 1,4-dioxane (4 mL) was stirred for 3 hr at 90° C. under Ar atmosphere. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/2-0/1) and crystallized from hexane/AcOEt to give the title compound (96.0 mg, 25% yield) as a yellow-green solid: mp 192-194° C.; $^1$H NMR (300 MHz, CDCl$_3$): δ ppm 2.01-2.14 (4H, m), 3.38-3.42 (4H, m), 3.89 (3H, s), 6.31 (1H, t, J=9.0 Hz), 6.47 (1H, dd, J=2.3, 9.0 Hz), 6.61 (1H, dd, J=2.6, 14.3 Hz), 7.25 (1H, d, J=1.9 Hz), 7.34-7.45 (5H, m), 7.73 (1H, d, J=2.3 Hz), 7.77 (1H, d, J=2.3 Hz). LC-MS (ESI) m/z 482 [M+H]$^+$. Anal. Calcd for C$_{25}$H$_{22}$F$_3$N$_5$O$_2$: C, 62.36; H, 4.61; N, 14.55. Found: C, 62.13; H, 4.62; N, 14.43.

Reference Example 23

1-[2-Fluoro-4-(2-oxo-1,3-oxazolidin-3-yl)phenyl]-5-methoxy-3-(1-phenyl-1H-pyrazol-5-yl)pyridazin-4(1H)-one

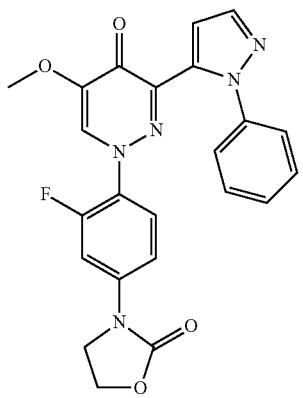 [SMILES: COc1cn(-c2ccc(N3CCOC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 2-oxazolidone (52.2 mg, 0.6 mmol), CuI (9.5 mg, 0.05 mmol), trans-1,2-diaminocyclohexane (0.012 mL, 0.1 mmol), and $K_3PO_4$ (212 mg, 1.0 mmol) in 1,4-dioxane (2 mL) was refluxed for 1.5 hr under Ar atmosphere. The reaction mixture was poured into water and extracted with AcOEt. The extract was washed with brine, dried over $MgSO_4$, and concentrated under reduced pressure. The residue was washed with AcOEt and recrystallized from MeOH/$H_2O$ to give the title compound (159 mg, 71% yield) as a pale yellow solid: mp 218-220° C.; $^1$H NMR (300 MHz, $CDCl_3$): δ ppm 3.90 (3H, s), 4.03-4.08 (2H, m), 4.51-4.56 (2H, m), 6.42 (1H, t, J=9.0 Hz), 7.01 (1H, ddd, J=1.1, 2.3, 9.0 Hz), 7.30 (1H, d, J=1.9 Hz), 7.35-7.45 (5H, m), 7.66 (1H, dd, J=2.3, 13.6 Hz), 7.78 (2H, d, J=1.9 Hz). LC-MS (ESI) m/z 448 [M+H]$^+$. Anal. Calcd for $C_{23}H_{18}FN_5O_4$: C, 61.74; H, 4.06; N, 15.65. Found: C, 61.48; H, 4.07; N, 15.54.

Reference Example 24

4-{3-Fluoro-4-[(5-methoxy-4-oxo-3-(1-phenyl-1H-pyrazol-5-yl)pyridazin-1(4H)-yl]phenyl}morpholin-3-one

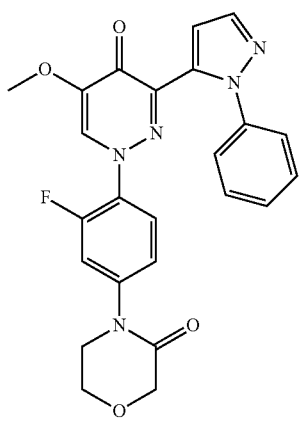 [SMILES: COc1cn(-c2ccc(N3CCOCC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 3-morpholinone (60.7 mg, 0.6 mmol), CuI (9.5 mg, 0.05 mmol), trans-1,2-diaminocyclohexane (0.012 mL, 0.1 mmol), and $K_3PO_4$ (212 mg, 1.0 mmol) in 1,4-dioxane (2 mL) was refluxed for 6 hr under Ar atmosphere. The reaction mixture was poured into water and extracted with AcOEt. The extract was washed with brine, dried over $MgSO_4$, and concentrated under reduced pressure. The residue was purified by basic silica gel column chromatography eluting with AcOEt and recrystallized from MeOH/$H_2O$ to give the title compound (136 mg, 59% yield) as a white solid: mp 193-195° C.; $^1$H NMR (300 MHz, $CDCl_3$): δ ppm 3.75-3.79 (2H, m), 3.90 (3H, s), 4.04-4.07 (2H, m), 4.35 (2H, s), 6.41 (1H, t, J=9.0 Hz), 7.00 (1H, ddd, J=1.1, 2.3, 9.0 Hz), 7.31 (1H, d, J=2.3 Hz), 7.33-7.46 (6H, m), 7.78-7.80 (2H, m). LC-MS (ESI) m/z 462 [M+H]$^+$. Anal. Calcd for $C_{24}H_{20}FN_5O_4$: C, 62.47; H, 4.37; N, 15.18. Found: C, 62.31; H, 4.33; N, 15.25.

Reference Example 25

1-[2-Fluoro-4-(1H-imidazol-1-yl)phenyl]-5-methoxy-3-(1-phenyl-1H-pyrazol-5-yl)pyridazin-4(1H)-one

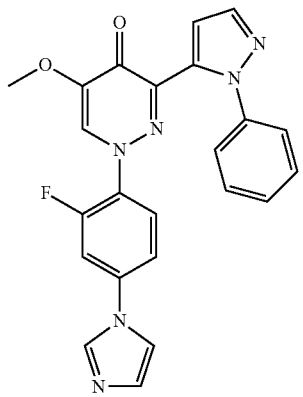 [SMILES: COc1cn(-c2ccc(-n3ccnc3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), imidazole (40.8 mg, 0.6 mmol), CuI (9.5 mg, 0.05 mmol), trans-1,2-diaminocyclohexane (0.012 mL, 0.1 mmol), and $Cs_2CO_3$ (326 mg, 1.0 mmol) in 1,4-dioxane (2 mL) was refluxed for 4 hr under Ar atmosphere. The reaction mixture was poured into water and extracted with AcOEt. The extract was washed with brine, dried over $MgSO_4$, and concentrated under reduced pressure. The residue was purified by basic silica gel column chromatography eluting with AcOEt/THF (1/0-0/1) and crystallized from MeOH to give the title compound (16.5 mg, 8% yield) as a white solid: mp 235-236° C. (dec); $^1$H NMR (300 MHz, $CDCl_3$): δ ppm 3.93 (3H, s), 6.49 (1H, t, J=8.7 Hz), 7.03 (1H, ddd, J=1.1, 2.3, 8.7 Hz), 7.22-7.27 (3H, m), 7.35 (1H, d, J=1.9 Hz), 7.38-7.49 (5H, m), 7.80 (1H, d, J=1.9 Hz), 7.82 (1H, d, J=2.6 Hz), 7.86 (1H, t, J=1.1 Hz). LC-MS (ESI) m/z 429 [M+H]$^+$. Anal. Calcd for $C_{23}H_{17}FN_6O_2$: C, 64.48; H, 4.00; N, 19.62. Found: C, 64.35; H, 3.90; N, 19.43.

Reference Example 26

1-[2-Fluoro-3-(1-methyl-1H-pyrazol-4-yl)phenyl]-5-methoxy-3-(1-phenyl-1H-pyrazol-5-yl)pyridazin-4(1H)-one

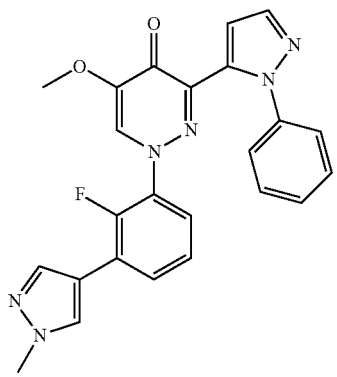 [SMILES: COc1cn(-c2cccc(-c3cnn(C)c3)c2F)nc(-c2ccnn2-c2ccccc2)c1=O]

A mixture of 3-acetyl-1-[2-fluoro-3-(1-methyl-1H-pyrazol-4-yl)phenyl]-5-methoxypyridazin-4(1H)-one (243 mg, 0.708 mmol) in N,N-dimethylformamide dimethyl acetal (2.4 mL) was heated to reflux for 2 hr. The mixture was concentrated under reduced pressure. To the residue were added AcOH (2.4 mL) and phenylhydrazine (0.139 mL, 1.42 mmol). The mixture was heated to reflux for 2 hr. The mixture was diluted with 1 M HCl aqueous solution, extracted with AcOEt, washed with saturated NaHCO$_3$ aqueous solution, dried over Na$_2$SO$_4$, filtered, concentrated under reduced pressure, purified by column chromatography on basic silica gel (hexane/AcOEt=20/80 to 0/100) and recrystallized with EtOH/AcOEt/hexane to yield the title compound (193 mg, 62% yield) as a pale yellow solid: mp 218-221° C. $^1$H NMR (DMSO-d$_6$, 300 MHz): δ ppm 3.78 (3H, s), 3.91 (3H, s), 6.97 (2H, d, J=1.9 Hz), 7.13-7.50 (6H, m), 7.72-7.84 (2H, m), 7.93 (1H, s), 8.18 (1H, d, J=2.3 Hz), 8.55 (1H, d, J=1.9 Hz).

Reference Example 27

1-[2-Fluoro-4-(1-methyl-1H-pyrazol-4-yl)phenyl]-5-methoxy-3-(1-phenyl-1H-pyrazol-5-yl)pyridazin-4(1H)-one

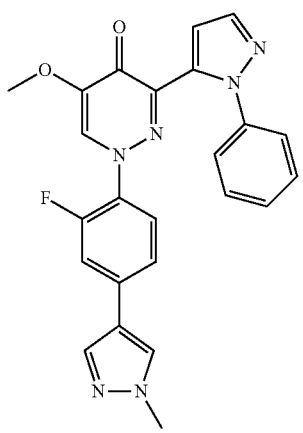 [SMILES: COc1cn(-c2ccc(-c3cnn(C)c3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (230 mg, 0.45 mmol), 1-methyl-1H-pyrazole-4-boronic acid pinacol ester (104 mg, 0.50 mmol), Pd(PPh$_3$)$_4$ (29 mg, 0.025 mmol), Na$_2$CO$_3$ (106 mg, 1.0 mmol), DME (4 mL), and H$_2$O (1 mL) was refluxed overnight under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with THF and recrystallized from MeOH/H$_2$O to give the title compound (162 mg, 81% yield) as a white solid: mp 195-197° C.; $^1$H NMR (300 MHz, CDCl$_3$): δ ppm 3.91 (3H, s), 3.96 (3H, s), 6.38 (1H, t, J=8.3 Hz), 7.06 (1H, ddd, J=0.8, 1.9, 8.3 Hz), 7.23 (1H, dd, J=1.9, 12.8 Hz), 7.30 (1H, d, J=1.9 Hz), 7.36-7.47 (5H, m), 7.64 (1H, s), 7.74 (1H, d, J=0.8 Hz), 7.79 (1H, d, J=1.9 Hz), 7.81 (1H, d, J=2.6 Hz). LC-MS (ESI) m/z 443 [M+H]% Anal. Calcd for C$_{24}$H$_{19}$FN$_6$O$_2$: C, 65.15; H, 4.33; N, 18.99. Found: C, 65.15; H, 4.30; N, 19.02.

Reference Example 28

1-[2-Fluoro-5-(1-methyl-1H-pyrazol-4-yl)phenyl]-5-methoxy-3-(1-phenyl-1H-pyrazol-5-yl)pyridazin-4(1H)-one

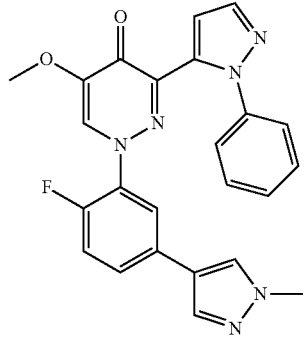

A mixture of 3-acetyl-1-[2-fluoro-5-(1-methyl-1H-pyrazol-4-yl)phenyl]-5-methoxypyridazin-4(1H)-one (200 mg, 0.585 mmol) in N,N-dimethylformamide dimethyl acetal (2.0 mL) was heated to reflux for 3 hr. The mixture was concentrated under reduced pressure. To the residue were added AcOH (2.0 mL) and phenylhydrazine (0.115 mL, 1.17 mmol). The mixture was heated to reflux for 3 hr. The mixture was diluted with 1 M HCl aqueous solution, extracted with AcOEt, washed with saturated NaHCO$_3$ aqueous solution, dried over Na$_2$SO$_4$, filtered, concentrated under reduced pressure, purified by column chromatography on basic silica gel (hexane/AcOEt=50/50 to 0/100) and by HPLC and recrystallized with EtOH/hexane to yield the title compound (118 mg, 46% yield) as a white solid: mp 93-102° C. $^1$H NMR (DMSO-d$_6$, 300 MHz): δ ppm 3.78 (3H, s), 3.89 (3H, s), 6.91 (1H, d, J=1.9 Hz), 7.20-7.52 (7H, m), 7.63-7.71 (1H, m), 7.78 (1H, d, J=1.9 Hz), 7.83 (1H, s), 8.10 (1H, s), 8.53 (1H, d, J=1.6 Hz). Anal. Calcd for C$_{24}$H$_{19}$FN$_6$O$_2$.1.3H$_2$O: C, 61.88; H, 4.67; N, 18.04. Found: C, 61.63; H, 4.64; N, 18.09.

Preparative HPLC was performed at the conditions described below.

Column: YMC CombiPrep Pro C18 RS (50×20 mmI.D. S-5 μm, 8 nm)

Column temp: 25° C.

Mobile phase: (A) 0.1% TFA in distilled water, (B) 0.1% TFA in acetonitrile

Gradient: 0 min (A/B=95/5)→1.00 min (A/B=95/5)→5.70 min (A/B=0/100)→7.30 min (A/B=0/100)→7.40 min (A/B=95/5)→8.00 min (A/B=95/5)

Flow rate: 20 mL/min

Detector: UV 220 nm

Concentration: 89 mg/mL

Inject volume: 100 μL

Reference Example 29

1-{4-[1-(Difluoromethyl)-1H-pyrazol-4-yl]-2-fluorophenyl}-5-methoxy-3-(1-phenyl-1H-pyrazol-5-yl)pyridazin-4(1H)-one

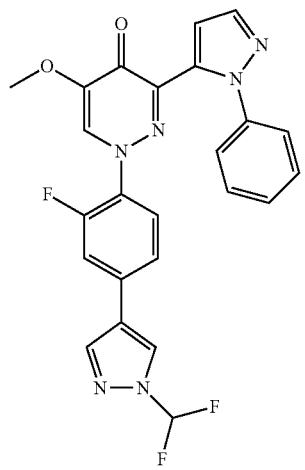 [SMILES: COc1cn(-c2ccc(-c3cnn(C(F)F)c3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (230 mg, 0.45 mmol), 1-(difluoromethyl)-1H-pyrazole-4-boronic acid pinacol ester (122 mg, 0.50 mmol), Pd(PPh$_3$)$_4$ (17 mg, 0.015 mmol), Na$_2$CO$_3$ (106 mg, 1.0 mmol), DME (4 mL), and H$_2$O (1 mL) was refluxed for 3 hr under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from MeOH/H$_2$O to give the title compound (183 mg, 85% yield) as a white solid: mp 185-187° C.; $^1$H NMR (300 MHz, CDCl$_3$): δ ppm 3.92 (3H, s), 6.41 (1H, t, J=8.3 Hz), 7.03-7.48 (10H, m), 7.79 (1H, d, J=1.9 Hz), 7.83 (1H, d, J=2.3 Hz), 7.91 (1H, d, J=0.8 Hz). LC-MS (ESI) m/z 479 [M+H]$^+$. Anal. Calcd for C$_{24}$H$_{17}$F$_3$N$_6$O$_2$: C, 60.25; H, 3.58; N, 17.57. Found: C, 60.19; H, 3.48; N, 17.52.

Reference Example 30

1-[2-Fluoro-4-(1,3-oxazol-2-yl)phenyl]-5-methoxy-3-(1-phenyl-1H-pyrazol-5-yl)pyridazin-4(1H)-one

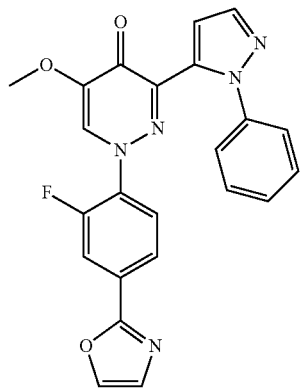 [SMILES: COc1cn(-c2ccc(-c3ncco3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 2-(tributylstannanyl)-1,3-oxazole (0.209 mL, 1.0 mmol) and Pd (PPh$_3$)$_4$ (57.8 mg, 0.05 mmol) in 1,4-dioxane (3 mL) was heated to reflux for 11 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100 and AcOEt/MeOH=100/0 to 70/30) and recrystallized with EtOH/hexane to yield the title compound (113 mg, 53% yield) as a yellow solid: mp 223-225° C. $^1$H NMR (DMSO-d$_6$, 300 MHz): δ ppm 3.79 (3H, s), 7.02 (1H, d, J=1.9 Hz), 7.16 (1H, t, J=8.3 Hz), 7.31-7.51 (6H, m), 7.77-7.83 (2H, m), 7.96 (1H, dd, J=11.5, 1.7 Hz), 8.34 (1H, s), 8.55 (1H, d, J=2.6 Hz). Anal. Calcd for C$_{23}$H$_{16}$FN$_5$O$_3$.0.1H$_2$O: C, 64.06; H, 3.79; N, 16.24. Found: C, 63.92; H, 3.67; N, 16.23.

Reference Example 31

1-(2-Fluoro-4-pyridin-2-ylphenyl)-5-methoxy-3-(1-phenyl-1H-pyrazol-5-yl)pyridazin-4(1H)-one

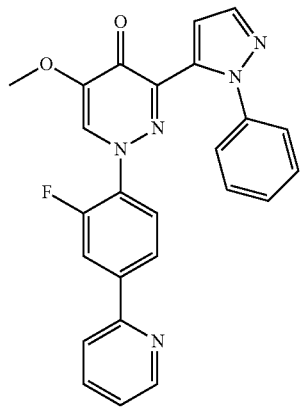 [SMILES: COc1cn(-c2ccc(-c3ccccn3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (200 mg, 0.392 mmol), (2-pyridine)cyclic-triolborate lithium salt (167 mg, 0.784 mmol), 2-(di-tert-butylphosphino)biphenyl (12.9 mg, 0.0431 mmol), CuI (14.9 mg, 0.0784 mmol) and Pd(OAc)$_2$ (4.4 mg, 0.0196 mmol) in DMF (1.2 mL) was heated to 80° C. for 13 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and on silica gel (hexane/AcOEt=50/50 to 0/100) and recrystallized with AcOEt/hexane to yield the title compound (68.9 mg, 40% yield) as a pale yellow solid: mp 206-208° C.; $^1$H NMR (DMSO-d$_6$, 300 MHz): δ ppm 3.80 (3H, s), 7.01 (1H, d, J=1.9 Hz), 7.11 (1H, t, J=8.3 Hz), 7.31-7.53 (6H, m), 7.80 (1H, d, J=1.9 Hz), 7.91-8.02 (2H, m), 8.08-8.20 (2H, m), 8.55 (1H, d, J=1.9 Hz), 8.72 (1H, d, J=4.5 Hz). Anal. Calcd for C$_{25}$H$_{18}$FN$_5$O$_2$: C, 68.33; H, 4.13; N, 15.94. Found: C, 68.15; H, 4.18; N, 15.83.

Reference Example 32

1-[4-(3,4-Difluoro-1H-pyrrol-1-yl)-2-fluorophenyl]-5-methoxy-3-(1-phenyl-1H-pyrazol-5-yl)pyridazin-4(1H)-one

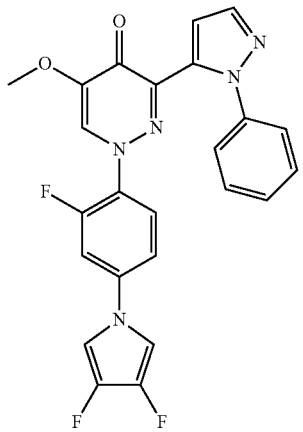 [SMILES: COc1cn(-c2ccc(-n3cc(F)c(F)c3)cc2F)nc(-c2ccnn2-c2ccccc2)c1=O]

KOtBu (236 mg, 2.1 mmol) was added portionwise at room temperature to a solution of 1-[2-fluoro-4-(3,3,4,4-tetrafluoropyrrolidin-1-yl)phenyl]-5-methoxy-3-(1-phenyl-1H-pyrazol-5-yl)pyridazin-4(1H)-one (352 mg, 0.7 mmol) in DMSO (3.5 mL). After stirring for 30 min, the reaction mixture was poured into water and extracted with AcOEt. The extract was washed with brine, dried over MgSO$_4$, and concentrated under reduced pressure. The residue was subjected to basic silica gel column chromatography eluting with hexane/AcOEt (1/1-0/1) followed by purification by preparative HPLC. Recrystallization from MeOH/H$_2$O afforded the title compound (105 mg, 32% yield) as a white solid: mp 212-214° C.; $^1$H NMR (300 MHz, CDCl$_3$): δ ppm 3.91 (3H, s), 6.42 (1H, t, J=9.0 Hz), 6.68-6.78 (2H, m), 6.87 (1H, ddd, J=1.1, 2.6, 9.0 Hz), 7.07 (1H, dd, J=2.6, 12.4 Hz), 7.33 (1H, d, J=2.3 Hz), 7.36-7.48 (5H, m), 7.78-7.79 (2H, m).

LC-MS (ESI) m/z 464 [M+H]$^+$. Anal. Calcd for C$_{24}$H$_{16}$F$_3$N$_5$O$_2$: C, 62.20; H, 3.48; N, 15.11. Found: C, 62.20; H, 3.51; N, 15.01.

Preparative HPLC was performed at the conditions described below.

Column: YMC CombiPrep ODS-A (20×50 mm S-5 μm)

Column temp: 25° C.

Mobile phase: (A) 0.1% TFA in distilled water, (B) 0.1% TFA in acetonitrile

Gradient: 0.00 min (A/B=60/40)→1.00 min (A/B=60/40)→4.75 min (A/B=0/100)→7.39 min (A/B=0/100)→7.40 min (A/B=100/0)→7.50 min (A/B=100/0)

Flow rate: 25 mL/min

Detector: UV 220 nm

Concentration: 33.3 mg/mL

Inject volume: 0.300 mL

Retention time: 2.35 min

Reference Example 33

1-[2-Fluoro-4-(1H-pyrazol-1-yl)phenyl]-5-methoxy-3-(1-phenyl-1H-pyrazol-5-yl)pyridazin-4(1H)-one

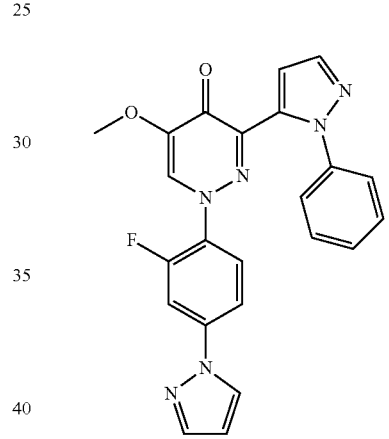

A suspension of 1-(2-fluoro-4-iodophenyl)-5-methoxy-3-(1-phenyl-1H-pyrazol-5-yl)pyridazin-4(1H)-one (4.88 g, 10 mmol), pyrazole (0.681 g, 10 mmol), Cu$_2$O (0.143 g, 1 mmol), salicylaldoxime (0.549 g, 4 mmol), and Cs$_2$CO$_3$ (6.52 g, 20 mmol) in CH$_3$CN (100 mL) was refluxed for 5 hr under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with hexane/THF (1/2) and recrystallized from EtOH/H$_2$O to give the title compound (1.90 g, 44% yield) as a pale yellow powder: mp 214-216° C.; $^1$H NMR (300 MHz, CDCl$_3$) δ ppm 3.92 (3H, s), 6.44 (1H, t, J=9.0 Hz), 6.53 (1H, dd, J=1.9, 2.3 Hz), 7.30 (1H, ddd, J=1.1, 2.3, 9.0 Hz), 7.34 (1H, d, J=1.9 Hz), 7.37-7.48 (5H, m), 7.61 (1H, dd, J=2.3, 12.4 Hz), 7.76 (1H, d, J=1.9 Hz), 7.79 (1H, d, J=1.9 Hz), 7.82 (1H, d, J=2.3 Hz), 7.92 (1H, d, J=2.3 Hz). LC-MS (ESI) m/z 429 [M+H]$^+$. Anal. Calcd for C$_{23}$H$_{17}$FN$_6$O$_2$: C, 64.48; H, 4.00; N, 19.62. Found: C, 64.41; H, 4.00; N, 19.54.

Reference Example 34

Ethyl 1-{3-fluoro-4-[5-methoxy-4-oxo-3-(1-phenyl-1H-pyrazol-5-yl)pyridazin-1(4H)-yl]phenyl}-5-hydroxy-1H-pyrazole-4-carboxylate

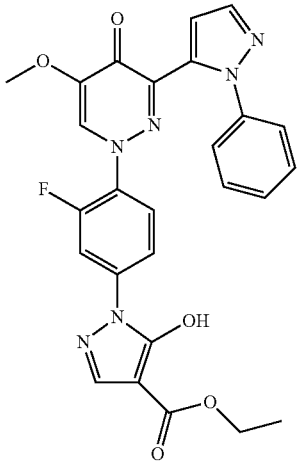 [SMILES: CCOC(=O)c1cnn(-c2ccc(-n3cc(OC)c(=O)c(-c4ccnn4-c4ccccc4)n3)c(F)c2)c1O]

A mixture of tert-butyl 1-{3-fluoro-4-[5-methoxy-4-oxo-3-(1-phenyl-1H-pyrazol-5-yl)pyridazin-1(4H)-yl]phenyl}hydrazinecarboxylate (2.02 g, 4.1 mmol), TFA (5 mL), and CH$_2$Cl$_2$ (10 mL) was stirred for 3 hr at room temperature. The reaction mixture was concentrated under reduced pressure.

A suspension of the residue, diethyl ethoxymethylenemalonate (0.829 mL, 4.1 mmol), and K$_2$CO$_3$ (1.70 g, 12.3 mmol) in EtOH (20 mL) was refluxed for 3 hr. After cooling to room temperature, the reaction mixture was poured into water and extracted with AcOEt. The extract was washed with brine, dried over MgSO$_4$, and concentrated under reduced pressure. The residue was washed with AcOEt and recrystallized from EtOH to give the title compound (1.43 g, 67% yield) as a pale orange solid: mp 188-193° C.; $^1$H NMR (300 MHz, CDCl$_3$): δ ppm 1.41 (3H, t, J=7.2 Hz), 3.92 (3H, s), 4.39 (2H, q, J=7.2 Hz), 6.45 (1H, t, J=9.0 Hz), 7.35 (1H, d, J=1.9 Hz), 7.37-7.48 (5H, m), 7.55 (1H, ddd, J=1.1, 2.3, 9.0 Hz), 7.77-7.82 (3H, m), 7.83 (1H, d, J=2.3 Hz). Anal. Calcd for C$_{26}$H$_{21}$FN$_6$O$_5$: C, 60.46; H, 4.10; N, 16.27. Found: C, 60.28; H, 4.17; N, 16.37.

Reference Example 35

1-[2-Fluoro-4-(5-hydroxy-1H-pyrazol-1-yl)phenyl]-5-methoxy-3-(1-phenyl-1H-pyrazol-5-yl)pyridazin-4(1H)-one

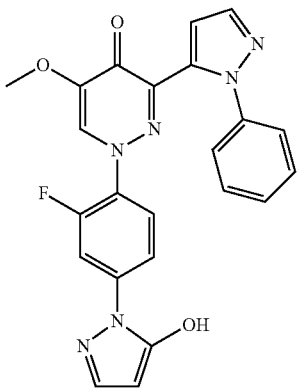 [SMILES: COc1cn(-c2ccc(-n3nccc3O)cc2F)nc(-c2ccnn2-c2ccccc2)c1=O]

A mixture of ethyl 1-{3-fluoro-4-[5-methoxy-4-oxo-3-(1-phenyl-1H-pyrazol-5-yl)pyridazin-1(4H)-yl]phenyl}-5-hydroxy-1H-pyrazole-4-carboxylate (1.41 g, 2.73 mmol), 4 M NaOH (40 mL), and EtOH (40 mL) was refluxed for 4 hr. After cooling to room temperature, conc. HCl (20 mL) was added slowly. The mixture was stirred for 30 min at room temperature and then refluxed for 1 hr. After cooling to room temperature, the reaction mixture was poured into water and extracted with AcOEt. The extract was washed with brine, dried over MgSO$_4$, and concentrated under reduced pressure. The residue was purified by silica gel column chromatography eluting with AcOEt/THF (2/1) and recrystallized from THF/MeOH to give the title compound (387 mg, 32% yield) as a pale yellow solid: mp 221-229° C.; $^1$H NMR (300 MHz, DMSO-d$_6$): δ ppm 3.78 (3H, s), 5.57 (1H, d, J=1.5 Hz), 6.99 (1H, d, J=1.9 Hz), 7.14 (1H, t, J=9.0 Hz), 7.31-7.51 (6H, m), 7.64-7.68 (1H, m), 7.79-7.84 (2H, m), 8.52 (1H, d, J=1.9 Hz), 12.17 (1H, brs). LC-MS (ESI) m/z 445 [M+H]$^+$.

Reference Example 36

1-{4-[5-(Difluoromethoxy)-1H-pyrazol-1-yl]-2-fluorophenyl}-5-methoxy-3-(1-phenyl-1H-pyrazol-5-yl)pyridazin-4(1H)-one

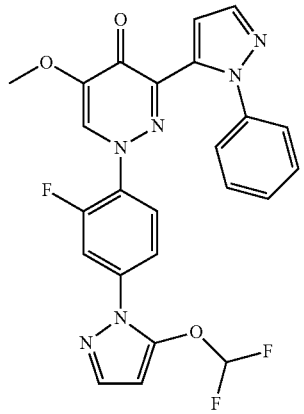 [SMILES: COc1cn(-c2ccc(-n3nccc3OC(F)F)cc2F)nc(-c2ccnn2-c2ccccc2)c1=O]

Reference Example 37

1-{4-[2-(Difluoromethyl)-5-oxo-2,5-dihydro-1H-pyrazol-1-yl]-2-fluorophenyl}-5-methoxy-3-(1-phenyl-1H-pyrazol-5-yl)pyridazin-4(1H)-one

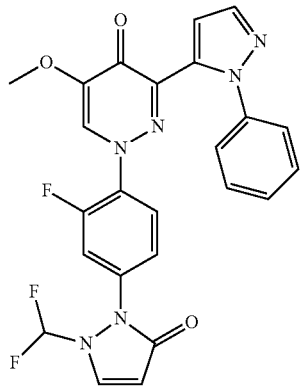 [SMILES: COc1cn(-c2ccc(-n3c(=O)ccn3C(F)F)cc2F)nc(-c2ccnn2-c2ccccc2)c1=O]

A mixture of 1-[2-fluoro-4-(5-hydroxy-1H-pyrazol-1-yl)phenyl]-5-methoxy-3-(1-phenyl-1H-pyrazol-5-yl)

pyridazin-4(1H)-one (373 mg, 0.84 mmol), CF$_2$ClCO$_2$Na (256 mg, 1.68 mmol), K$_2$CO$_3$ (232 mg, 1.68 mmol), DMF (2.5 mL), and H$_2$O (0.5 mL) was stirred for 2 hr at 100° C. The reaction mixture was poured into to water and extracted with AcOEt. The extract was washed with brine, dried over MgSO$_4$, and concentrated under reduced pressure. The residue was purified by basic silica gel column chromatography eluting with AcOEt and recrystallized from AcOEt to give 1-{4-[5-(difluoromethoxy)-1H-pyrazol-1-yl]-2-fluorophenyl}-5-methoxy-3-(1-phenyl-1H-pyrazol-5-yl)pyridazin-4(1H)-one (168 mg, 40% yield) as a pale yellow solid: mp 177-179° C.; $^1$H NMR (300 MHz, CDCl$_3$): δ ppm 3.92 (3H, s), 6.07-6.08 (1H, m), 6.45 (1H, t, J=9.0 Hz), 6.59 (1H, t, J=71.8 Hz), 7.34-7.47 (7H, m), 7.58 (1H, dd, J=2.3, 12.4 Hz), 7.61 (1H, d, J=1.9 Hz), 7.79 (1H, d, J=1.9 Hz), 7.83 (1H, d, J=2.3 Hz). LC-MS (ESI) m/z 495 [M+H]$^+$. Anal. Calcd for C$_{24}$H$_{17}$F$_3$N$_6$O$_3$: C, 58.30; H, 3.47; N, 17.00. Found: C, 58.17; H, 3.46; N, 16.91.

Further elution followed by recrystallization from MeOH/H$_2$O afforded 1-{4-[2-(difluoromethyl)-5-oxo-2,5-dihydro-1H-pyrazol-1-yl]-2-fluorophenyl}-5-methoxy-3-(1-phenyl-1H-pyrazol-5-yl)pyridazin-4(1H)-one (63.5 mg, 15% yield) as a white solid: mp 161-163° C.; $^1$H NMR (CDCl$_3$) δ 3.91 (3H, s), 5.99 (1H, d, J=4.1 Hz), 6.40 (1H, t, J=60.7 Hz), 6.47 (1H, t, J=8.7 Hz), 7.09 (1H, ddd, J=1.1, 2.3, 8.7 Hz), 7.32 (1H, d, J=1.9 Hz), 7.36-7.47 (6H, m), 7.79-7.81 (3H, m). LC-MS (ESI) m/z 495 [M+H]% Anal. Calcd for C$_{24}$H$_{17}$F$_3$N$_6$O$_3$.0.5H$_2$O: C, 57.26; H, 3.60; N, 16.69. Found: 57.38; H, 3.52; N, 16.78.

Reference Example 38

1-(2-Fluoro-5-iodophenyl)-5-methoxy-3-(1-phenyl-1H-pyrazol-5-yl)pyridazin-4(1H)-one

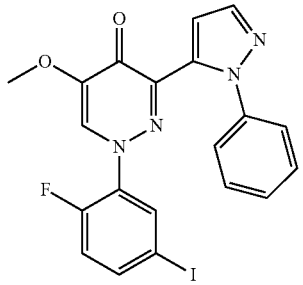 [SMILES: COc1cn(-c2cc(I)ccc2F)nc(-c2ccnn2-c2ccccc2)c1=O]

A mixture of 3-acetyl-1-(2-fluoro-5-iodophenyl)-5-methoxypyridazin-4(1H)-one (3.88 g, 10.0 mmol) in N,N-dimethylformamide dimethyl acetal (38.8 mL) was heated to reflux for 3 hr. The mixture was concentrated under reduced pressure. To the residue were added AcOH (38.8 mL) and phenylhydrazine (1.97 mL, 20.0 mmol). The mixture was heated to reflux for 5 hr. The mixture was concentrated under reduced pressure, diluted with 1 M HCl aqueous solution, extracted with AcOEt, washed with saturated NaHCO$_3$ aqueous solution, dried over Na$_2$SO$_4$, filtered, concentrated under reduced pressure, purified by column chromatography on basic silica gel (hexane/AcOEt=50/50 to 0/100) and triturated with AcOEt/hexane to yield the title compound (2.95 g, 60% yield) as a yellow solid: $^1$H NMR (DMSO-d$_6$, 300 MHz): δ ppm 3.77 (3H, s), 6.99 (1H, d, J=1.5 Hz), 7.23-7.50 (7H, m), 7.79 (1H, d, J=1.9 Hz), 7.84 (1H, ddd, J=8.7, 4.5, 2.3 Hz), 8.49 (1H, d, J=2.6 Hz).

Reference Example 39

3-[1-(2-Fluorophenyl)-1H-pyrazol-5-yl]-1-[2-fluoro-4-(1H-pyrazol-1-yl)phenyl]-5-methoxypyridazin-4(1H)-one

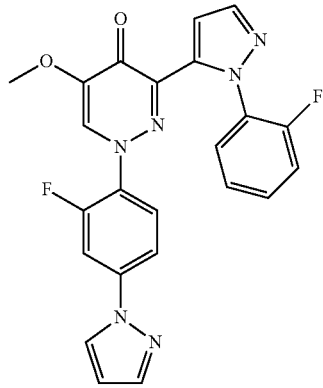 [SMILES: COc1cn(-c2ccc(-n3cccn3)cc2F)nc(-c2ccnn2-c2ccccc2F)c1=O]

A suspension of 3-acetyl-1-[2-fluoro-4-(1H-pyrazol-1-yl)phenyl]-5-methoxypyridazin-4(1H)-one (197 mg, 0.600 mmol) in N,N-dimethylformamide dimethyl acetal (2.0 mL) was stirred at 100° C. for 1 hr. The reaction mixture was concentrated under reduced pressure. To the residue were added AcOH (2.0 mL) and 2-fluorophenylhydrazine (151 mg, 1.20 mmol). The mixture was stirred at 100° C. for 1 hr. After solvent evaporated, the residue was diluted with saturated NaHCO$_3$ aqueous solution (25 mL) and extracted with AcOEt (25 mL×3). The combined organic phase was washed with brine (40 mL), dried with MgSO$_4$, and evaporated. The residue was crystallized from AcOEt to give a coarse solid, which was recrystallized from EtOH/hexane to give the title compound (125 mg, 47% yield) as a white solid: mp 202-206° C.; $^1$H NMR (300 MHz, DMSO-d$_6$): δ ppm 3.79 (3H, s), 6.64 (1H, d, J=1.9 Hz), 6.96 (1H, t, J=8.5 Hz), 7.23-7.33 (3H, m), 7.41-7.53 (2H, m), 7.71 (1H, d, J=9.1 Hz), 7.84 (2H, dd, J=4.0, 1.7 Hz), 7.94 (1H, dd, J=12.3, 2.5 Hz), 8.48 (1H, d, J=1.9 Hz), 8.65 (1H, d, J=2.6 Hz). LC-MS (ESI) m/z 447 [M+H]$^+$. Anal. Calcd for C$_{23}$H$_{16}$F$_2$N$_6$O$_2$.0.4H$_2$O: C, 60.90; H, 3.73; N, 18.53. Found: C, 60.68; H, 3.69; N, 18.39.

Reference Example 40

3-[1-(3-Chlorophenyl)-1H-pyrazol-5-yl]-1-[2-fluoro-4-(1H-pyrazol-1-yl)phenyl]-5-methoxypyridazin-4(1H)-one

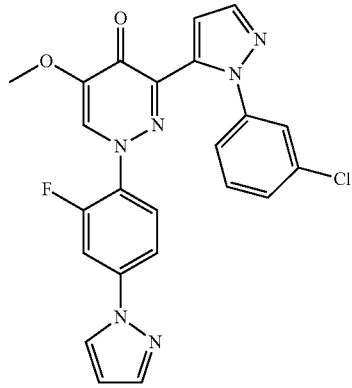 [SMILES: COc1cn(-c2ccc(-n3cccn3)cc2F)nc(-c2ccnn2-c2cccc(Cl)c2)c1=O]

A suspension of 3-acetyl-1-[2-fluoro-4-(1H-pyrazol-1-yl)phenyl]-5-methoxypyridazin-4(1H)-one (393 mg, 1.20 mmol) in N,N-dimethylformamide dimethyl acetal (4.0 mL) was stirred at 100° C. for 1 hr. The reaction mixture was concentrated under reduced pressure. To the residue were added AcOH (4 mL) and 3-chlorophenylhydrazine hydrochloride (429 mg, 2.40 mmol). The mixture was stirred at 100° C. for 1 hr. After solvent evaporated, the residue was diluted with saturated NaHCO$_3$ aqueous solution (25 mL) and extracted with AcOEt (25 mL×3). The combined organic phase was washed with brine (40 mL), dried with MgSO$_4$, and evaporated. The residue was crystallized from AcOEt to give a coarse solid, which was recrystallized from EtOH/hexane to give the title compound (242 mg, 44% yield) as an orange solid: mp 186-190° C.; $^1$H NMR (300 MHz, DMSO-d$_6$): δ ppm 3.80 (3H, s), 6.64 (1H, d, J=1.9 Hz), 7.05 (1H, d, J=1.9 Hz), 7.27-7.34 (1H, m), 7.44 (3H, dd, J=16.6, 10.2 Hz), 7.34-7.52 (1H, m), 7.84 (3H, dd, J=3.6, 1.7 Hz), 8.00 (1H, dd, J=12.3, 2.1 Hz), 8.56 (1H, d, J=1.9 Hz), 8.67 (1H, d, J=2.6 Hz): LC-MS (ESI) m/z 463 [M+H]$^+$. Anal. Calcd for C$_{23}$H$_{16}$ClFN$_6$O$_2$.0.03H$_2$O: C, 59.61; H, 3.49; N, 18.14. Found: C, 59.32; H, 3.50; N, 17.92.

Reference Example 41

1-[4-(3-tert-Butyl-2-oxoimidazolidin-1-yl)-2-fluorophenyl]-5-methoxy-3-(1-phenyl-1H-pyrazol-5-yl)pyridazin-4(1H)-one

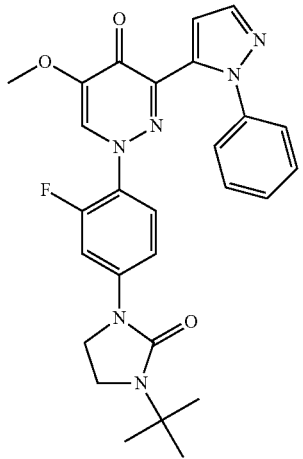 [SMILES: COc1cn(-c2ccc(N3CCN(C(C)(C)C)C3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (488 mg, 1.0 mmol), 1-tert-butylimidazolidin-2-one (171 mg, 1.2 mmol), CuI (19 mg, 0.1 mmol), trans-1,2-diaminocyclohexane (0.024 mL, 0.2 mmol), and K$_3$PO$_4$ (425 mg, 2.0 mmol) in toluene (5 mL) was stirred at 80° C. for 24 hr under N$_2$ atmosphere. After cooling to room temperature, the reaction mixture was purified by silica gel column chromatography eluting with hexane/AcOEt (1/1), AcOEt only and then AcOEt/MeOH (10/1) and recrystallized from AcOEt to give the title compound (198 mg, 39% yield) as a white solid: mp 238-239° C.; $^1$H NMR (300 MHz, DMSO-d$_6$): δ ppm 1.36 (9H, s), 3.29 (3H, s), 3.44-3.59 (2H, m), 3.64-3.76 (2H, m), 6.92-7.03 (2H, m), 7.23-7.51 (6H, m), 7.70 (1H, dd, J=14.1, 2.4 Hz), 7.78 (1H, d, J=1.9 Hz), 8.43 (1H, d, J=1.9 Hz). LC-MS (ESI) m/z 503 [M+H]$^+$. Anal. Calcd for C$_{27}$H$_{27}$FN$_6$O$_3$: C, 64.53; H, 5.42; N, 16.72. Found: C, 64.31; H, 5.38; N, 16.58.

Reference Example 42

1-[2-Fluoro-4-(2-oxoimidazolidin-1-yl)phenyl]-5-methoxy-3-(1-phenyl-1H-pyrazol-5-yl)pyridazin-4(1H)-one

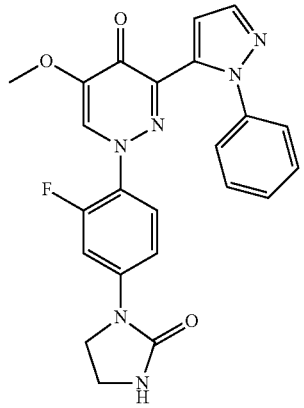 [SMILES: COc1cn(-c2ccc(N3CCNC3=O)cc2F)nc(-c2ccnn2-c2ccccc2)c1=O]

A mixture of 1-[4-(3-tert-butyl-2-oxoimidazolidin-1-yl)-2-fluorophenyl]-5-methoxy-3-(1-phenyl-1H-pyrazol-5-yl)pyridazin-4(1H)-one (503 mg, 1.0 mmol) in trifluoroacetic acid (3.0 mL) was stirred at 80° C. for 1 hr. After cooling to room temperature, the reaction mixture was evaporated. The residue was recrystallized from AcOEt/MeOH to give the title compound (334 mg, 75% yield) as a pale yellow solid: mp 259-260° C.; $^1$H NMR (300 MHz, DMSO-d$_6$): δ ppm 3.40-3.50 (2H, m), 3.77 (3H, s), 3.82-3.93 (2H, m), 6.95 (1H, d, J=2.3 Hz), 7.01 (1H, t, J=9.0 Hz), 7.23-7.49 (7H, m), 7.73 (1H, dd, J=14.1, 2.4 Hz), 7.78 (1H, d, J=1.9 Hz), 8.44 (1H, d, J=1.9 Hz). LC-MS (ESI) m/z 447 [M+H]$^+$. Anal. Calcd for C$_{23}$H$_{19}$FN$_6$O$_3$.0.75H$_2$O: C, 60.06; H, 4.49; N, 18.27. Found: C, 60.05; H, 4.26; N, 18.16.

Reference Example 43

1-{4-[3-(Difluoromethyl)-2-oxoimidazolidin-1-yl]-2-fluorophenyl}-5-methoxy-3-(1-phenyl-1H-pyrazol-5-yl)pyridazin-4(1H)-one

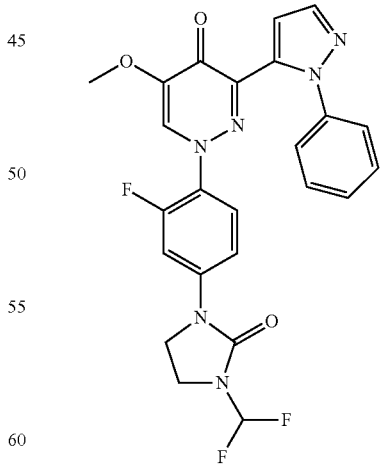

A mixture of 1-[2-fluoro-4-(2-oxoimidazolidin-1-yl)phenyl]-5-methoxy-3-(1-phenyl-1H-pyrazol-5-yl)pyridazin-4(1H)-one (100 mg, 0.22 mmol), sodium chlorodifluoroacetate (40 mg, 0.26 mmol), and 18-crown-6 (12 mg, 0.044 mmol) in acetonitrile (10 mL) was stirred at 90° C. for 20 hr.

After cooling to room temperature, to the reaction mixture was added silica gel. This mixture was evaporated, and purified by silica gel column chromatography eluting with AcOEt/MeOH (1/0 to 10/1) to give the title compound (2.5 mg, 2.3% yield) as a pale yellow powder: $^1$H NMR (300 MHz, DMSO-$d_6$): δ ppm 1.11-1.40 (4H, m), 3.61-3.86 (4H, m), 6.96 (1H, d, J=1.9 Hz), 7.01-7.15 (1H, m), 7.16-7.50 (6H, m), 7.71 (1H, dd, J=13.6, 2.3 Hz), 7.79 (1H, d, J=2.3 Hz), 8.47 (1H, d, J=1.9 Hz). LC-MS (ESI) m/z 497 [M+H]$^+$.

Reference Example 44

1-[3-(3,6-Dihydro-2H-pyran-4-yl)-2-fluorophenyl]-5-methoxy-3-(1-phenyl-1H-pyrazol-5-yl)pyridazin-4(1H)-one

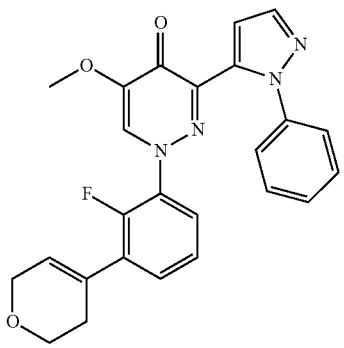 [SMILES: COc1cn(-c2cccc(C3=CCOCC3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (441 mg, 1.0 mmol), 4-(4,4,5,5-tetramethyl-1,3,2-dioxaborolan-2-yl)-3,6-dihydro-2H-pyran (231 mg, 1.1 mmol), Pd(PPh$_3$)$_4$ (57.8 mg, 0.05 mmol) and Na$_2$CO$_3$ (233 mg, 2.2 mmol) in DME (8.8 mL) and water (2.2 mL) was heated to reflux for 15 hr under N$_2$. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with EtOH/hexane to yield the title compound (380 mg, 85% yield) as a white solid: mp 138-141° C. $^1$H NMR (DMSO-$d_6$, 300 MHz): δ ppm 2.42 (2H, brs), 3.74-3.89 (5H, m), 4.21-4.29 (2H, m), 6.15 (1H, brs), 6.92-7.10 (2H, m), 7.17-7.59 (7H, m), 7.78 (1H, d, J=1.9 Hz), 8.52 (1H, s). Anal. Calcd for C$_{25}$H$_{21}$FN$_4$O$_3$: C, 67.56; H, 4.76; N, 12.61. Found: C, 67.42; H, 4.83; N, 12.44.

Reference Example 45

1-[2-Fluoro-3-(tetrahydro-2H-pyran-4-yl)phenyl]-5-methoxy-3-(1-phenyl-1H-pyrazol-5-yl)pyridazin-4(1H)-one

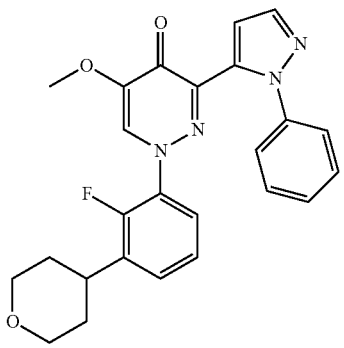 [SMILES: COc1cn(-c2cccc(C3CCOCC3)c2F)nc(-c2ccnn2-c2ccccc2)c1=O]

A mixture of 1-[3-(3,6-dihydro-2H-pyran-4-yl)-2-fluorophenyl]-5-methoxy-3-(1-phenyl-1H-pyrazol-5-yl)pyridazin-4(1H)-one (190 mg, 0.427 mmol) and Pd/C (10% Pd, 50% wet, 19 mg) in MeOH (10 mL) was stirred at room temperature for 16 hr under H$_2$. The mixture was filtered through a pad of Celite, concentrated under reduced pressure, purified by column chromatography on basic silica gel (hexane/AcOEt=50/50 to 0/100) and recrystallized with EtOH/hexane to yield the title compound (152 mg, 79% yield) as a pale yellow solid: $^1$H NMR (DMSO-$d_6$, 300 MHz): δ ppm 1.60-1.85 (4H, m), 3.39-3.56 (3H, m), 3.77 (3H, s), 3.91-4.04 (2H, m), 6.92-7.04 (2H, m), 7.21 (1H, t, J=8.1 Hz), 7.27-7.54 (6H, m), 7.78 (1H, d, J=1.9 Hz), 8.49 (1H, d, J=1.9 Hz).

Reference Example 46

1-(2-Fluoro-3-morpholin-4-ylphenyl)-5-methoxy-3-(1-phenyl-1H-pyrazol-5-yl)pyridazin-4(1H)-one

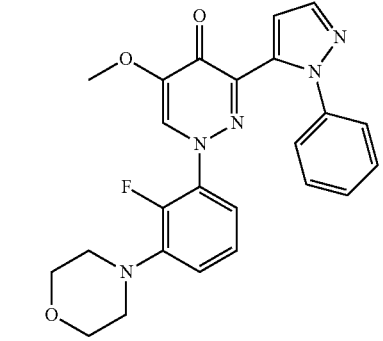 [SMILES: COc1cn(-c2cccc(N3CCOCC3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (221 mg, 0.5 mmol), morpholine (0.0525 mL, 0.6 mmol), NaO-t-Bu (67.3 mg, 0.7 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 18 hr under Ar. The mixture was diluted with NaHCO$_3$ aqueous solution, extracted with AcOEt, dried over Na$_2$SO$_4$, filtered, concentrated under reduced pressure, purified by column chromatography on basic silica gel (hexane/AcOEt=50/50 to 0/100) and recrystallized with AcOEt/hexane and EtOH/hexane to yield the title compound (139 mg, 59% yield) as a pale yellow solid: mp 187-189° C. $^1$H NMR (DMSO-$d_6$, 300 MHz): δ ppm 2.97-3.08 (4H, m), 3.70-3.80 (7H, m), 6.61-6.72 (1H, m), 6.96 (1H, d, J=1.5 Hz), 7.06-7.17 (2H, m), 7.26-7.47 (5H, m), 7.78 (1H, d, J=1.9 Hz), 8.50 (1H, d, J=1.9 Hz). Anal. Calcd for C$_{24}$H$_{22}$FN$_5$O$_3$: C, 64.42; H, 4.96; N, 15.65. Found: C, 64.47; H, 4.99; N, 15.55.

Reference Example 47

1-[3-(3,3-Difluoroazetidin-1-yl)-2-fluorophenyl]-5-methoxy-3-(1-phenyl-1H-pyrazol-5-yl)pyridazin-4(1H)-one

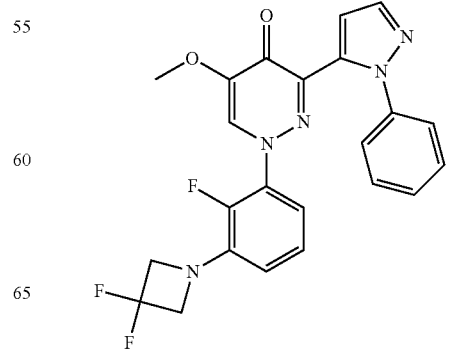

A mixture of 1-(3-bromo-2-fluorophenyl)-5-methoxy-3-(1-phenyl-1H-pyrazol-5-yl)pyridazin-4(1H)-one (177 mg, 0.4 mmol), 3,3-difluoroazetidine hydrochloride (62.2 mg, 0.48 mmol), NaO-t-Bu (99.9 mg, 1.04 mmol), Xantphos (99.9 mg, 0.173 mmol) and Pd$_2$(dba)$_3$ (39.7 mg, 0.043 mmol) in 1,4-dioxane (2 ml) was heated to 90° C. for 16 hr under N$_2$. The mixture was diluted with saturated NaHCO$_3$ aqueous solution, extracted with AcOEt, dried over Na$_2$SO$_4$, filtered, concentrated under reduced pressure and purified by column chromatography on basic silica gel (hexane/AcOEt=50/50 to 0/100) to yield the title compound (58.8 mg, 32% yield) as a pale yellow solid: $^1$H NMR (DMSO-d$_6$, 300 MHz): δ ppm 3.77 (3H, s), 4.42 (4H, t, J=12.6 Hz), 6.43-6.82 (1H, m), 6.90-7.49 (8H, m), 7.79 (1H, s), 8.39-8.60 (1H, m).

Reference Example 48

1-[3-(3,3-Difluoropyrrolidin-1-yl)-2-fluorophenyl]-5-methoxy-3-(1-phenyl-1H-pyrazol-5-yl)pyridazin-4(1H)-one

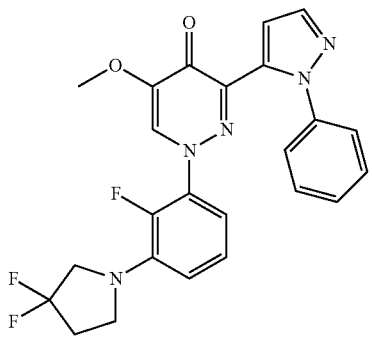 [SMILES: COc1cn(-c2cccc(N3CCC(F)(F)C3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (221 mg, 0.5 mmol), 3,3-difluoropyrrolidine hydrochloride (86.1 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 24 hr under N$_2$. The mixture was diluted with saturated NaHCO$_3$ aqueous solution, extracted with AcOEt, dried over Na$_2$SO$_4$, filtered, concentrated under reduced pressure and purified by column chromatography on basic silica gel (hexane/AcOEt=50/50 to 0/100) to yield the title compound (119 mg, 51% yield) as a pale yellow solid: $^1$H NMR (DMSO-d$_6$, 300 MHz): δ ppm 2.42-2.50 (2H, m), 3.56 (2H, t, J=7.4 Hz), 3.71-3.88 (5H, m), 6.43-6.54 (1H, m), 6.84-7.13 (3H, m), 7.27-7.49 (5H, m), 7.78 (1H, d, J=1.9 Hz), 8.47 (1H, d, J=2.3 Hz). Anal. Calcd for C$_{24}$H$_{20}$F$_3$N$_5$O$_2$.0.2H$_2$O: C, 61.20; H, 4.37; N, 14.87. Found: C, 61.36; H, 4.45; N, 14.56.

Reference Example 49

1-{2-Fluoro-3-[3-(trifluoromethyl)pyrrolidin-1-yl]phenyl}-5-methoxy-3-(1-phenyl-1H-pyrazol-5-yl)pyridazin-4(1H)-one

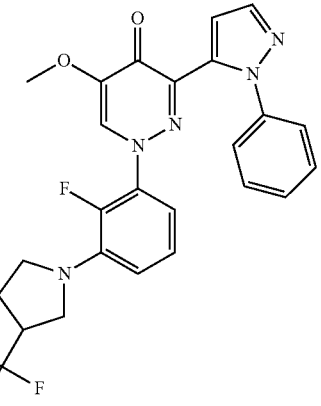

A mixture of 1-(3-bromo-2-fluorophenyl)-5-methoxy-3-(1-phenyl-1H-pyrazol-5-yl)pyridazin-4(1H)-one (300 mg, 0.68 mmol), 3-(trifluoromethyl)pyrrolidine hydrochloride (143 mg, 0.82 mmol), NaO-t-Bu (170 mg, 1.8 mmol), Xantphos (31 mg, 0.054 mmol) and Pd$_2$(dba)$_3$ (12 mg, 0.014 mmol) in 1,4-dioxane (4 mL) was heated at 90° C. for 14 hr under Ar. The mixture was extracted with AcOEt, dried over Na$_2$SO$_4$, filtered, concentrated under reduced pressure and purified by column chromatography on basic silica gel (hexane/AcOEt=10/90 to 0/100) to yield the title compound (131 mg, 39% yield) as a white amorphous solid: $^1$H NMR (300 MHz, CDCl$_3$): δ ppm 2.09-2.40 (2H, m), 3.05 (1H, s), 3.38-3.75 (4H, m), 3.83-3.99 (3H, m), 5.88-6.07 (1H, m), 6.65 (1H, td, J=8.3, 1.5 Hz), 6.80-6.95 (1H, m), 7.22 (1H, d, J=2.3 Hz), 7.30-7.49 (5H, m), 7.72 (1H, d, J=2.6 Hz), 7.74-7.80 (1H, m); MS Calcd.: 499; MS Found: 500 [M+H]$^+$.

Reference Example 50

1-{2-Fluoro-4-[3-(trifluoromethyl)pyrrolidin-1-yl]phenyl}-5-methoxy-3-(1-phenyl-1H-pyrazol-5-yl)pyridazin-4(1H)-one

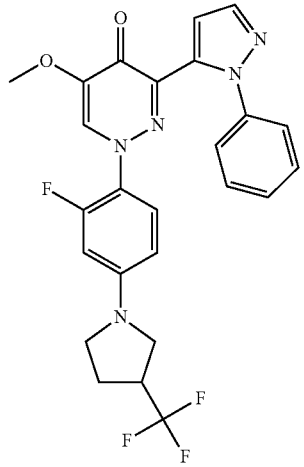 [SMILES: COc1cn(-c2ccc(N3CCC(C(F)(F)F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (300 mg, 0.61 mmol), 3-(trifluoromethyl)pyrrolidine hydrochloride (130 mg, 0.74 mmol), NaO-t-Bu (154 mg, 1.6 mmol), Xantphos (28 mg, 0.049 mmol) and $Pd_2(dba)_3$ (11 mg, 0.012 mmol) in 1,4-dioxane (4 mL) was heated to 90° C. for 12 hr under Ar. The mixture was extracted with AcOEt, dried over $Na_2SO_4$, filtered, concentrated under reduced pressure and purified by column chromatography on basic silica gel (hexane/AcOEt=10/90 to 0/100) to yield the title compound (138 mg, 45% yield) as a pale green solid: $^1$H NMR (300 MHz, $CDCl_3$): δ ppm 2.17-2.42 (2H, m), 3.01-3.21 (1H, m), 3.30-3.63 (4H, m), 3.89 (3H, s), 6.11 (1H, dd, J=8.9, 2.4 Hz), 6.20-6.37 (2H, m), 7.24 (1H, d, J=1.9 Hz), 7.33-7.47 (5H, m), 7.71 (1H, d, J=2.3 Hz), 7.77 (1H, d, J=1.9 Hz); MS Calcd.: 499; MS Found: 500 $[M+H]^+$.

Reference Example 51

1-[2-Fluoro-3-(3,3,4,4-tetrafluoropyrrolidin-1-yl)phenyl]-5-methoxy-3-(1-phenyl-1H-pyrazol-5-yl)pyridazin-4(1H)-one

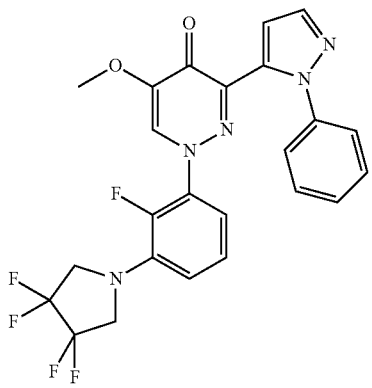 [SMILES: COc1cn(-c2cccc(N3CC(F)(F)C(F)(F)C3)c2F)nc(-c2ccnn2-c2ccccc2)c1=O]

A suspension of 1-(3-bromo-2-fluorophenyl)-5-methoxy-3-(1-phenyl-1H-pyrazol-5-yl)pyridazin-4(1H)-one (221 mg, 0.500 mmol), 3,3,4,4-tetrafluoropyrrolidine hydrochloride (108 mg, 0.600 mmol), sodium tert-butoxide (125 mg, 1.300 mmol), Xantphos (23 mg, 0.040 mmol), and tris(dibenzylideneacetone)dipalladium(0) (9 mg, 0.010 mmol) in 1,4-dioxane (2.5 mL) was stirred at 90° C. under Ar atmosphere. The reaction mixture was poured into 5% $NaHCO_3$ aqueous solution (20 mL) and extracted with AcOEt (20 mL×3). The combined organic phase was washed with brine (40 mL), dried with $MgSO_4$, and evaporated. The residue was purified by silica gel column chromatography (AcOEt/hexane=60%-100%) to give the title compound (95.4 mg, 38% yield) as an amorphous solid: $^1$H NMR (300 MHz, $CDCl_3$): δ ppm 3.84-3.96 (7H, m), 6.11 (1H, t, J=7.5 Hz), 6.60 (1H, td, J=8.3, 1.5 Hz), 6.90-6.98 (1H, m), 7.25 (1H, d, J=1.9 Hz), 7.33-7.41 (5H, m), 7.70 (1H, d, J=2.6 Hz), 7.78 (1H, d, J=1.9 Hz). LC-MS (ESI) m/z 504 $[M+H]^+$.

Reference Example 52

1-(2-Fluoro-3-pyridin-3-ylphenyl)-5-methoxy-3-(1-phenyl-1H-pyrazol-5-yl)pyridazin-4(1H)-one

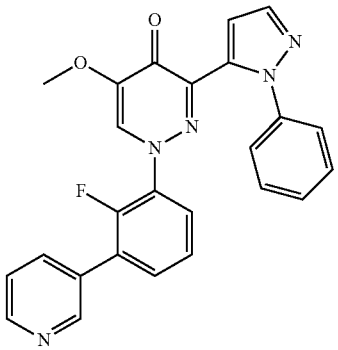 [SMILES: COc1cn(-c2cccc(-c3cccnc3)c2F)nc(-c2ccnn2-c2ccccc2)c1=O]

A solution of 1-(3-bromo-2-fluorophenyl)-5-methoxy-3-(1-phenyl-1H-pyrazol-5-yl)pyridazin-4(1H)-one (177 mg, 0.400 mmol), 3-pyridineboronic acid (54.1 mg, 0.440 mmol), tetrakis(triphenylphosphine)palladium(0) (23 mg, 0.020 mmol) and $Na_2CO_3$ (93 mg, 0.88 mmol) in DME (3.6 mL) and water (0.9 mL) was stirred at 85° C. for 5 hr under Ar atmosphere. The mixture was poured into 5% $NaHCO_3$ aqueous solution (20 mL) and extracted with AcOEt (20 mL×3). The combined organic phase was washed with brine (30 mL), dried with $MgSO_4$, and evaporated. The residue was purified by basic silica gel column chromatography (MeOH/AcOEt=0%-10%) and crystallized from AcOEt to give the title compound (84.8 mg, 48% yield) as a colorless solid: mp 147-153° C.; $^1$H NMR (300 MHz, DMSO-$d_6$): δ ppm 3.78 (3H, s), 7.01 (1H, d, J=1.9 Hz), 7.04-7.17 (1H, m), 7.28-7.51 (6H, m), 7.56 (1H, dd, J=7.7, 5.1 Hz), 7.63-7.75 (1H, m), 7.79 (1H, d, J=1.9 Hz), 8.03 (1H, dd, J=7.9, 1.9 Hz), 8.58-8.68 (2H, m), 8.81 (1H, s). LC-MS (ESI) m/z 440 $[M+H]^+$. Anal. Calcd for $C_{25}H_{18}FN_5O_2$: C, 68.33; H, 4.13; N, 15.94. Found: C, 68.04; H, 4.03; N, 15.80.

Reference Example 53

1-[2-fluoro-4-(3-methyl-2-oxoimidazolidin-1-yl)phenyl]-5-methoxy-3-(1-phenyl-1H-pyrazol-5-yl)pyridazin-4(1H)-one

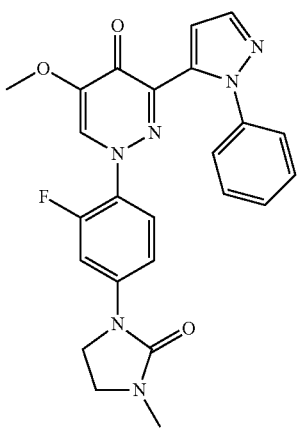 [SMILES: COc1cn(-c2ccc(N3CCN(C)C3=O)cc2F)nc(-c2ccnn2-c2ccccc2)c1=O]

A mixture of 1-[2-fluoro-4-(2-oxoimidazolidin-1-yl)phenyl]-5-methoxy-3-(1-phenyl-1H-pyrazol-5-yl)pyridazin-4(1H)-one (40 mg, 0.09 mmol), iodomethane (0.02 mL, 0.36 mmol), and sodium hydride (60% in oil) (7.0 mg, 0.18 mmol) in DMF (4.0 mL) was stirred at 0° C. for 2 hr. The reaction mixture was quenched with H₂O, and extracted with AcOEt. The organic layer was dried over MgSO₄, and concentrated under reduced pressure. The residue was recrystallized from $^i$Pr₂O/AcOEt to give the title compound (24 mg, 59% yield) as a white solid: mp 208-209° C.; ¹H NMR (300 MHz, DMSO-d₆): δ ppm 2.79 (3H, s), 3.42-3.58 (2H, m), 3.77 (3H, s), 3.78-3.86 (2H, m), 6.95 (1H, d, J=1.9 Hz), 7.01 (1H, t, J=9.0 Hz), 7.22-7.51 (6H, m), 7.73 (1H, dd, J=14.1, 2.4 Hz), 7.78 (1H, d, J=1.9 Hz), 8.44 (1H, d, J=1.9 Hz). LC-MS (ESI) m/z 461 [M+H]⁺. Anal. Calcd for C₂₄H₂₁FN₆O₃·0.75H₂O: C, 60.06; H, 4.49; N, 18.27. Found: C, 60.05; H, 4.26; N, 18.16.

Reference Example 54

1-[4-(2,5-Dihydro-1H-pyrrol-1-yl)-2-fluorophenyl]-5-methoxy-3-(1-phenyl-1H-pyrazol-5-yl)pyridazin-4(1H)-one

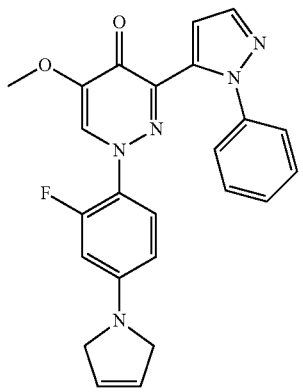 [SMILES: COc1cn(-c2ccc(N3CC=CC3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 3-pyrroline (0.046 mL, 0.6 mmol), Pd₂(dba)₃ (18.3 mg, 0.02 mmol), Xantphos (46.3 mg, 0.08 mmol), and NaO-t-Bu (67.3 mg, 0.7 mmol) in 1,4-dioxane (2.5 mL) was stirred for 2 hr at 90° C. under Ar atmosphere. The reaction mixture was poured into water and extracted with AcOEt. The extract was washed with brine, dried over MgSO₄, and concentrated under reduced pressure. The residue was purified by basic silica gel column chromatography eluting with hexane/THF (1/2) and recrystallized from MeOH/H₂O to give the title compound (109 mg, 51% yield) as a yellow solid: mp 204-207° C.; ¹H NMR (300 MHz, CDCl₃): δ ppm 3.89 (3H, s), 4.09 (4H, s), 5.97 (2H, t, J=4.1 Hz), 6.07 (1H, dd, J=2.6, 9.0 Hz), 6.19 (1H, dd, J=2.6, 14.3 Hz), 6.32 (1H, t, J=9.0 Hz), 7.24 (1H, d, J=1.9 Hz), 7.33-7.45 (5H, m), 7.72 (1H, d, J=2.3 Hz), 7.77 (1H, d, J=1.9 Hz). LC-MS (ESI) m/z 430 [M+H]⁺. Anal. Calcd for C₂₄H₂₀FN₅O₂: C, 67.12; H, 4.69; N, 16.31. Found: C, 67.03; H, 4.76; N, 16.16.

Reference Example 55

1-[4-(4-Chloro-1H-pyrazol-1-yl)-2-fluorophenyl]-5-methoxy-3-(1-phenyl-1H-pyrazol-5-yl)pyridazin-4(1H)-one

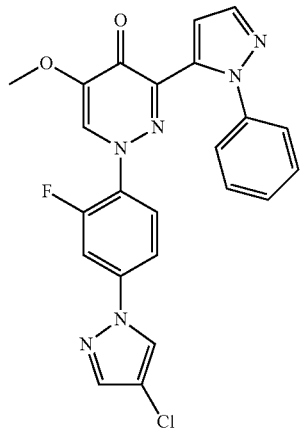 [SMILES: COc1cn(-c2ccc(-n3cc(Cl)cn3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (488 mg, 1.0 mmol), 4-chloro-1H-pyrazole (103 mg, 1.0 mmol), Cu₂O (14.3 mg, 0.1 mmol), salicylaldoxime (54.9 mg, 0.4 mmol), and Cs₂CO₃ (652 mg, 2.0 mmol) in CH₃CN (10 mL) was refluxed overnight under Ar atmosphere. After cooling to room temperature, the reaction mixture was poured into water and extracted with AcOEt. The extract was washed with brine, dried over MgSO₄, and concentrated under reduced pressure. The residue was subjected to basic silica gel column chromatography eluting with AcOEt followed by purification by preparative HPLC. Recrystallization from MeOH/H₂O gave the title compound (68.1 mg, 15% yield) as a pale yellow powder: mp 190-192° C.; ¹H NMR (300 MHz, CDCl₃): δ ppm 3.92 (3H, s), 6.43 (1H, t, J=9.0 Hz), 7.23 (1H, ddd, J=1.1, 2.3, 9.0 Hz), 7.35 (1H, d, J=1.9 Hz), 7.36-7.48 (5H, m), 7.57 (1H, dd, J=2.6, 12.4 Hz), 7.68 (1H, s), 7.79 (1H, d, J=1.9 Hz), 7.82 (1H, d, J=2.3 Hz), 7.92 (1H, d, J=0.8 Hz). LC-MS (ESI) m/z 463 [M+H]⁺. Anal. Calcd for C₂₃H₁₆ClFN₆O₂: C, 59.68; H, 3.48; N, 18.16. Found: C, 59.81; H, 3.50; N, 18.14.

Preparative HPLC was performed at the conditions described below.

Column: CHIRALPAK AS CC001 (50 mm ID×500 mL)

Column temp: 30° C.

Mobile phase: MeOH

Flow rate: 60 mL/min

Detector: UV 220 nm

Concentration: 111 mg/mL

Inject volume: 1 mL

Retention time: 18.8 min

Reference Example 56

1-[5-(3,3-Difluoroazetidin-1-yl)-2-fluorophenyl]-5-methoxy-3-(1-phenyl-1H-pyrazol-5-yl)pyridazin-4(1H)-one

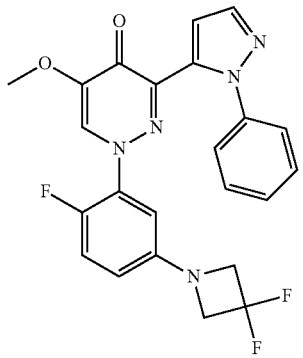 [SMILES: COc1cn(-c2cc(N3CC(F)(F)C3)ccc2F)nc(-c2ccnn2-c2ccccc2)c1=O]

A mixture of 1-(2-fluoro-5-iodophenyl)-5-methoxy-3-(1-phenyl-1H-pyrazol-5-yl)pyridazin-4(1H)-one (244 mg, 0.5 mmol), 3,3-difluoroazetidine hydrochloride (77.7 mg, 0.6 mmol), NaO-t-Bu (125 mg, 1.3 mmol), Xantphos (46.3 mg, 0.08 mmol) and $Pd_2(dba)_3$ (18.3 mg, 0.02 mmol) in 1,4-dioxane (2.5 mL) was heated to 90° C. for 13 hr under Ar. The mixture was diluted with saturated $NaHCO_3$ aqueous solution, extracted with AcOEt, dried over $Na_2SO_4$, filtered, concentrated under reduced pressure, purified by column chromatography on basic silica gel (hexane/AcOEt=50/50 to 0/100) and recrystallized with EtOH/hexane to yield the title compound (92 mg, 41% yield) as a white solid: $^1$H NMR (DMSO-$d_6$, 300 MHz): δ ppm 3.77 (3H, s), 4.25 (4H, t, J=12.2 Hz), 6.48 (1H, dd, J=6.4, 3.0 Hz), 6.63-6.72 (1H, m), 6.90 (1H, d, J=1.5 Hz), 7.25-7.48 (6H, m), 7.79 (1H, d, J=1.9 Hz), 8.45 (1H, d, J=1.9 Hz). Anal. Calcd for $C_{23}H_{18}F_3N_5O_2$: C, 60.93; H, 4.00; N, 15.45. Found: C, 60.97; H, 3.94; N, 15.47.

Reference Example 57

1-[2-Fluoro-5-(1H-pyrazol-1-yl)phenyl]-5-methoxy-3-(1-phenyl-1H-pyrazol-5-yl)pyridazin-4(1H)-one

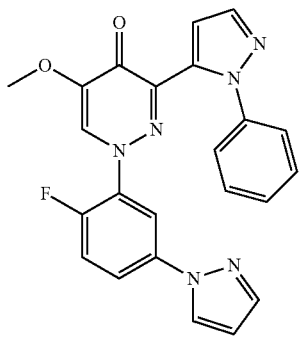 [SMILES: COc1cn(-c2cc(-n3cccn3)ccc2F)nc(-c2ccnn2-c2ccccc2)c1=O]

A mixture of 1-(2-fluoro-5-iodophenyl)-5-methoxy-3-(1-phenyl-1H-pyrazol-5-yl)pyridazin-4(1H)-one (244 mg, 0.5 mmol), pyrazole (34.0 mg, 0.5 mmol), 2-hydroxybenzaldehyde oxime (27.4 mg, 0.2 mmol), $Cu_2O$ (7.2 mg, 0.05 mmol) and $Cs_2CO_3$ (326 mg, 1.0 mmol) in acetonitrile (1 mL) was heated to reflux for 14 hr under Ar. The mixture was diluted with saturated $NaHCO_3$ aqueous solution, extracted with AcOEt, dried over $Na_2SO_4$, filtered, concentrated under reduced pressure, purified by column chromatography on basic silica gel (hexane/AcOEt=50/50 to 0/100) and on silica gel (hexane/AcOEt=50/50 to 0/100) and recrystallized with AcOEt/hexane to yield the title compound (8.3 mg, 4% yield) as a white solid: mp 186-187° C. $^1$H NMR (DMSO-$d_6$, 300 MHz): δ ppm 3.78 (3H, s), 6.59-6.66 (1H, m), 6.95 (1H, d, J=1.9 Hz), 7.17-7.27 (1H, m), 7.30-7.42 (4H, m), 7.56-7.67 (1H, m), 7.76-7.90 (3H, m), 7.93-8.02 (1H, m), 8.47 (1H, d, J=2.6 Hz), 8.59 (1H, d, J=1.9 Hz). Anal. Calcd for $C_{23}H_{17}FN_6O_2$: C, 64.48; H, 4.00; N, 19.62. Found: C, 64.21; H, 4.08; N, 19.42.

Reference Example 58

1-[2-Fluoro-4-(4-hydroxy-4-methylpiperidin-1-yl)phenyl]-5-methoxy-3-(1-phenyl-1H-pyrazol-5-yl)pyridazin-4(1H)-one

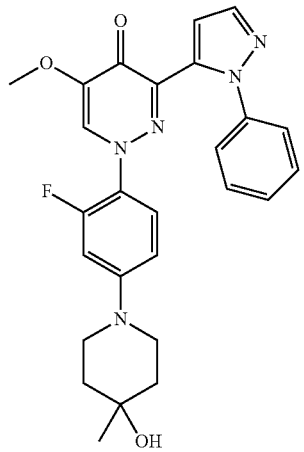 [SMILES: COc1cn(-c2ccc(N3CCC(C)(O)CC3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.500 mmol), 4-methylpiperidin-4-ol hydrochloride (91 mg, 0.60 mmol), sodium tert-butoxide (187 mg, 1.95 mmol), Xantphos (23 mg, 0.040 mmol), and tris(dibenzylideneacetone)dipalladium(0) (9 mg, 0.010 mmol) in 1,4-dioxane (2.5 mL) was stirred at 90° C. under Ar atmosphere. The reaction mixture was poured into 5% $NaHCO_3$ aqueous solution (20 mL) and extracted with AcOEt (20 mL×3). The combined organic phase was washed with brine (40 mL), dried with $MgSO_4$, and evaporated. The residue was purified by basic silica gel column chromatography (MeOH/AcOEt=0%-20%). The residue was recrystallized from AcOEt/hexane to give the title compound (76.2 mg, 32% yield) as a pale yellow solid: $^1$H NMR (300 MHz, DMSO-$d_6$): δ ppm 1.14 (3H, s), 1.39-1.60 (4H, m), 3.20 (2H, ddd, J=13.2, 8.7, 5.3 Hz), 3.40-3.52 (2H, m), 3.76 (3H, s), 4.36 (1H, s), 6.70 (1H, dd, J=9.0, 2.6 Hz), 6.91 (2H, d, J=1.9 Hz), 6.79-6.94 (1H, m), 7.29 (1H, s), 7.32 (1H, d, J=1.9 Hz), 7.35-7.47 (3H, m), 7.77 (1H, d, J=1.9 Hz), 8.37 (1H, d, J=1.9 Hz). LC-MS (ESI) m/z 476 [M+H]$^+$. Anal. Calcd for $C_{26}H_{26}FN_5O_3$: C, 65.67; H, 5.51; N, 14.73. Found: C, 65.53; H, 5.50; N, 14.66.

Reference Example 59

1-(4-Bromo-2,5-difluorophenyl)-5-methoxy-3-(1-phenyl-1H-pyrazol-5-yl)pyridazin-4(1H)-one

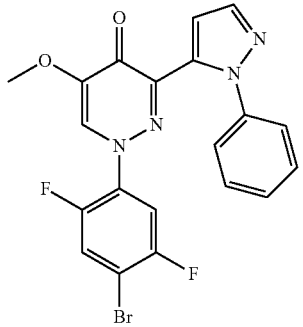 [SMILES: COc1cn(-c2cc(F)c(Br)cc2F)nc(-c2ccnn2-c2ccccc2)c1=O]

A mixture of 3-acetyl-1-(4-bromo-2,5-difluorophenyl)-5-methoxypyridazin-4(1H)-one (3.57 g, 10 mmol) and N,N-dimethylformamide dimethyl acetal (16 mL) was stirred at 100° C. for 5 hr. After cooling to room temperature, the reaction mixture was concentrated under reduced pressure. The residue was dissolved in AcOH (20 mL) and added phenylhydrazine (2.0 mL, 20 mmol). This mixture was stirred at 130° C. for 3 hr. After cooling to room temperature, the reaction mixture was concentrated under reduced pressure. The residue was purified by silica gel column chromatography eluting with hexane/AcOEt (1/0 to 0/1) and recrystallized from $^i$Pr$_2$O/AcOEt to give the title compound (1.05 g, 23% yield) as a pale yellow solid: mp 211-213° C.; $^1$H NMR (300 MHz, DMSO-d$_6$): δ ppm 3.77 (3H, s), 7.02 (1H, d, J=1.9 Hz), 7.09 (1H, dd, J=8.9, 6.6 Hz), 7.22-7.62 (5H, m), 7.80 (1H, d, J=1.9 Hz), 8.07 (1H, dd, J=10.2, 6.0 Hz), 8.49 (1H, d, J=2.3 Hz). LC-MS (ESI) m/z 460 [M+H]$^+$. Anal. Calcd for $C_{20}H_{13}BrF_2N_4O_2$: C, 52.31; H, 2.85; N, 12.20. Found: C, 52.51; H, 2.95; N, 12.20.

Reference Example 60

1-[4-(5,5-Dimethyl-2-oxo-1,3-oxazolidin-3-yl)-2-fluorophenyl]-5-methoxy-3-(1-phenyl-1H-pyrazol-5-yl)pyridazin-4(1H)-one

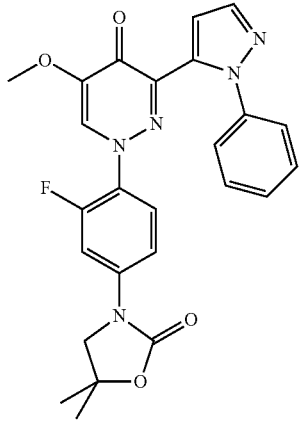 [SMILES: COc1cn(-c2ccc(N3CC(C)(C)OC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.500 mmol), 5,5-dimethyl-1,3-oxazolidin-2-one (69.1 mg, 0.600 mmol), trans-1,2-diaminocyclohexane (0.012 mL, 0.100 mmol), CuI (9.5 mg, 0.050 mmol), and K$_3$PO$_4$ (212 mg, 1.00 mmol) in 1,4-dioxane (2.0 mL) was stirred at 110° C. under Ar atmosphere. The reaction mixture was poured into 5% NaHCO$_3$ aqueous solution (20 mL) and extracted with AcOEt (20 mL×3). The combined organic phase was washed with brine (40 mL), dried with MgSO$_4$, and evaporated. The residue was purified by basic silica gel column chromatography (MeOH/AcOEt=0%-10%) to give the title compound (157.4 mg, 66% yield): $^1$H NMR (300 MHz, DMSO-d$_6$): δ ppm 1.49 (6H, s), 3.78 (3H, s), 3.89 (2H, s), 6.97 (1H, d, J=1.9 Hz), 7.05 (1H, t, J=9.0 Hz), 7.31 (1H, d, J=8.7 Hz), 7.31 (1H, t, J=1.7 Hz), 7.33 (1H, s), 7.37-7.48 (3H, m), 7.68 (1H, dd, J=13.4, 2.5 Hz), 7.79 (1H, d, J=1.9 Hz), 8.46 (1H, d, J=2.3 Hz). LC-MS (ESI) m/z 476 [M+H]$^+$. Anal. Calcd for $C_{25}H_{22}FN_5O_4$: C, 63.15; H, 4.66; N, 14.73. Found: C, 63.09; H, 4.70; N, 14.85.

Reference Example 61

5-Methoxy-1-[2-methoxy-4-(1H-pyrazol-1-yl)phenyl]-3-(1-phenyl-1H-pyrazol-5-yl)pyridazin-4(1H)-one

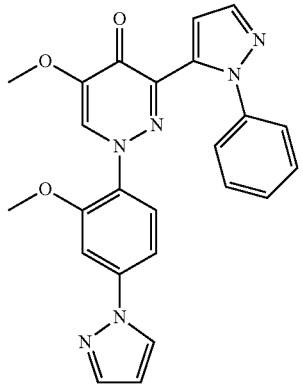 [SMILES: COc1cc(-n2cccn2)ccc1-n1cc(OC)c(=O)c(-c2ccnn2-c2ccccc2)n1]

A mixture of 3-acetyl-5-methoxy-1-[2-methoxy-4-(1H-pyrazol-1-yl)phenyl]pyridazin-4(1H)-one (1.50 g, 4.41 mmol), N,N-dimethylformamide dimethyl acetal (15 mL), and MeOH (15 mL) was refluxed for 3 hr. After cooling to room temperature, the reaction mixture was concentrated under reduced pressure.

A solution of the residue and phenylhydrazine (0.868 mL, 8.82 mmol) in AcOH (15 mL) was refluxed for 2 hr. After cooling to room temperature, the reaction mixture was poured into 1 M HCl aqueous solution and extracted with AcOEt. The extract was washed with 1 M NaOH aqueous solution and brine, dried over MgSO$_4$, and concentrated under reduced pressure. The residue was purified by basic silica gel column chromatography eluting with AcOEt and crystallized from hexane/AcOEt to give the title compound (0.921 g, 47% yield) as an off-white solid: mp 133-135° C.; $^1$H NMR (300 MHz, CDCl$_3$): δ ppm 3.90 (3H, s), 3.93 (3H, s), 6.39 (1H, d, J=8.7 Hz), 6.52 (1H, dd, J=1.9, 2.6 Hz), 6.99 (1H, dd, J=2.3, 8.7 Hz), 7.26 (1H, d, J=1.9 Hz), 7.36-7.46 (5H, m), 7.49 (1H, d, J=2.3 Hz), 7.75 (1H, d, J=1.9 Hz), 7.77 (1H, d, J=1.9 Hz), 7.86 (1H, s), 7.94 (1H, d, J=2.6 Hz). LC-MS (ESI) m/z 441 [M+H]$^+$. Anal. Calcd for $C_{24}H_{20}N_6O_3$: C, 65.45; H, 4.58; N, 19.08. Found: C, 65.37; H, 4.65; N, 18.88.

Reference Example 62

1-(2,3-Difluoro-4-morpholin-4-ylphenyl)-5-methoxy-3-(1-phenyl-1H-pyrazol-5-yl)pyridazin-4(1H)-one

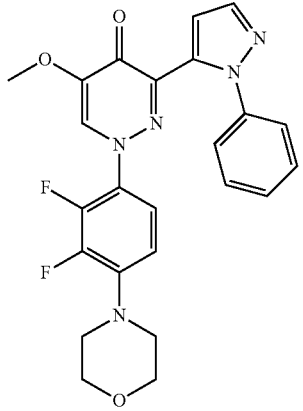 [SMILES: COc1cn(-c2ccc(N3CCOCC3)c(F)c2F)nc(-c2ccnn2-c2ccccc2)c1=O]

A mixture of 3-acetyl-1-(2,3-difluoro-4-morpholin-4-yl-phenyl)-5-methoxypyridazin-4(1H)-one (200 mg, 0.55 mmol) and N,N-dimethylformamide dimethyl acetal (2.0 mL) was stirred at 120° C. for 2.5 hr. After cooling to room temperature, the reaction mixture was concentrated under reduced pressure. The residue was dissolved in AcOH (2.0 mL) and phenylhydrazine (0.11 mL, 1.1 mmol) was added. This mixture was stirred at room temperature for 1 hr, and then the reaction mixture was concentrated under reduced pressure. The residue was purified by silica gel column chromatography eluting with AcOEt/MeOH (1/0 to 10/1) and recrystallized from $^i$Pr$_2$O/AcOEt to give the title compound (141 mg, 55% yield) as a yellow solid: mp 182-183° C.; $^1$H NMR (300 MHz, DMSO-d$_6$): δ ppm 2.98-3.22 (4H, m), 3.62-3.87 (7H, m), 6.78-6.92 (2H, m), 6.95 (1H, d, J=1.9 Hz), 7.21-7.54 (5H, m), 7.78 (1H, d, J=1.9 Hz), 8.48 (1H, d, J=1.9 Hz). LC-MS (ESI) m/z 466 [M+H]$^+$. Anal. Calcd for C$_{24}$H$_{21}$F$_2$N$_5$O$_3$: C, 61.93; H, 4.55; N, 15.05. Found: C, 61.90; H, 4.58; N, 14.87.

Reference Example 63

1-(2,5-Difluoro-4-morpholin-4-ylphenyl)-5-methoxy-3-(1-phenyl-1H-pyrazol-5-yl)pyridazin-4(1H)-one

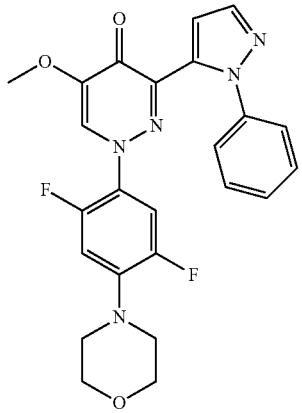 [SMILES: COc1cn(-c2cc(F)c(N3CCOCC3)cc2F)nc(-c2ccnn2-c2ccccc2)c1=O]

A mixture of 3-acetyl-1-(2,5-difluoro-4-morpholin-4-yl-phenyl)-5-methoxypyridazin-4(1H)-one (340 mg, 0.93 mmol) and N,N-dimethylformamide dimethyl acetal (3.4 mL) was stirred at 120° C. for 2.5 hr. After cooling to room temperature, the reaction mixture was concentrated under reduced pressure. The residue was dissolved in AcOH (3.4 mL) and phenylhydrazine (0.18 mL, 1.9 mmol) was added. This mixture was stirred at room temperature for 1 hr. The reaction mixture was diluted with AcOEt, and washed with saturated NaHCO$_3$ aqueous solution and brine. The organic layer was dried over MgSO$_4$, and concentrated under reduced pressure. The residue was recrystallized from AcOEt/MeOH to give the title compound (156 mg, 36% yield) as a pale orange solid: mp 211-212° C.; $^1$H NMR (300 MHz, DMSO-d$_6$): δ ppm 2.99-3.15 (4H, m), 3.60-3.88 (7H, m), 6.85 (1H, dd, J=12.8, 7.2 Hz), 6.99 (1H, d, J=2.3 Hz), 7.09 (1H, dd, J=12.8, 7.6 Hz), 7.24-7.50 (5H, m), 7.79 (1H, d, J=1.9 Hz), 8.43 (1H, d, J=2.3 Hz). LC-MS (ESI) m/z 466 [M+H]$^+$. Anal. Calcd for C$_{24}$H$_{21}$F$_2$N$_5$O$_3$.0.5H$_2$O: C, 60.75; H, 4.67; N, 14.76. Found: C, 60.98; H, 4.71; N, 14.63.

Reference Example 64

1-(1-benzyl-1,2,3,6-tetrahydropyridin-4-yl)-5-methoxy-3-(1-phenyl-1H-pyrazol-5-yl)pyridazin-4(1H)-one A) 1-benzyl-4-[4-oxo-3-(1-phenyl-1H-pyrazol-5-yl)pyridazin-1(4H)-yl]pyridinium bromide 5-Methoxy-3-(1-phenyl-1H-pyrazol-5-yl)-1-pyridin-4-ylpyridazin-4(1H)-one (0.49 g) and benzyl bromide (0.25 mL) were dissolved in acetonitrile (30 mL), and the mixture was heated under reflux overnight. The solvent was removed under reduced pressure, and the obtained crystals were washed with ethyl acetate to give the title compound (0.73 g).

$^1$H NMR (300 MHz, DMSO-d$_6$) δ 3.90 (3H, s), 5.76 (2H, s), 7.26 (1H, d, J=1.9 Hz), 7.37-7.52 (10H, m), 7.79 (2H, d, J=7.4 Hz), 7.86 (1H, d, J=1.9 Hz), 8.72 (1H, s), 9.15 (2H, d, J=7.4 Hz).

B) 1-(1-benzyl-1,2,3,6-tetrahydropyridin-4-yl)-5-methoxy-3-(1-phenyl-1H-pyrazol-5-yl)pyridazin-4(1H)-one To the solution of 1-benzyl-4-[4-oxo-3-(1-phenyl-1H-pyrazol-5-yl)pyridazin-1(4H)-yl]pyridinium bromide (0.73 g) in methanol (30 mL) was added sodium borohydride (0.21 g) at 0° C., and the mixture was stirred at room temperature overnight. Water was added to the reaction mixture, and the mixture was extracted with ethyl acetate. The extract was washed with brine, dried over anhydrous magnesium sulfate, and concentrated under reduced pressure. The obtained crystals were washed with ethyl acetate and recrystallized from ethyl acetate to give the title compound (0.15 g).

MS (ESI+), found: 440.2

Reference Example 65

5-methoxy-3-(1-phenyl-1H-pyrazol-5-yl)-1-(1-prop-2-en-1-yl-1,2,3,6-tetrahydropyridin-4-yl)pyridazin-4(1H)-one By a method similar to Reference Example 64, the title compound was obtained.

MS (ESI+), found: 390.2

Reference Example 66

5-methoxy-3-(1-phenyl-1H-pyrazol-5-yl)-1-piperidin-4-ylpyridazin-4(1H)-one

To a solution of 1-(1-benzyl-1,2,3,6-tetrahydropyridin-4-yl)-5-methoxy-3-(1-phenyl-1H-pyrazol-5-yl)pyridazin-4(1H)-one (1.3 g) in methanol (25 mL) was added palladium hydroxide on carbon (10% wet, 0.40 g). The reaction mixture was stirred under hydrogen atmosphere at 50° C. for 4 hr. The reaction mixture was filtered through celite pad, and the filtrate was concentrated under reduced pressure. The residue was purified by silica gel column chromatography (NH, ethyl acetate/methanol), and crystallized from 2-propanol/heptane to give the title compound (0.41 g).

MS (ESI+), found: 352.1

Reference Example 67

1-[1-(4-fluorophenyl)piperidin-4-yl]-5-methoxy-3-(1-phenyl-1H-pyrazol-5-yl)pyridazin-4(1H)-one A suspension of 5-methoxy-3-(1-phenyl-1H-pyrazol-5-yl)-1-piperidin-4-ylpyridazin-4(1H)-one (150 mg), 1-bromo-4-fluorobenzene (0.094 mL), tris(dibenzylideneacetone)dipalladium (0) (20 mg), dicyclohexyl[2',4',6'-tris(1-methylethyl)biphenyl-2-yl]phosphane (21 mg) and sodium tert-butoxide (61 mg) in toluene (8 mL) was stirred under argon atmosphere at 120° C. for 8 hr. The reaction mixture was poured into water, and the mixture was extracted with ethyl acetate. The extract was washed with brine, dried over anhydrous magnesium sulfate, and concentrated under reduced pressure. The residue was purified by silica gel column chromatography (ethyl acetate/hexane) and recrystallized from ethyl acetate/hexane to give the title compound (12 mg).

MS (ESI+), found: 446.2

Reference Example 68

2-{4-[(5-methoxy-4-oxo-3-(1-phenyl-1H-pyrazol-5-yl)pyridazin-1(4H)-yl]piperidin-1-yl}benzonitrile By a method similar to Reference Example 67, the title is compound was obtained.

MS (ESI+), found: 453.2

Reference Example 69

5-methoxy-3-(1-phenyl-1H-pyrazol-5-yl)-1-(1,2,3,6-tetrahydropyridin-4-yl)pyridazin-4(1H)-one A suspension of 5-methoxy-3-(1-phenyl-1H-pyrazol-5-yl)-1-(1-prop-2-en-1-yl-1,2,3,6-tetrahydropyridin-4-yl)pyridazin-4(1H)-one (1.5 g), tetrakis(triphenylphosphine)palladium (0) (500 mg) and 1,3-dimethylbarbituric acid (1.8 g) in toluene (30 mL) was heated under reflux for 8 hr. under nitrogen atmosphere. The reaction mixture was concentrated under reduced pressure. The residue was purified by silica gel column chromatography (NH, methanol/ethyl acetate) and recrystallized from acetonitrile to give the title compound (0.28 g).

MS (ESI+), found: 350.2

Reference Example 70

1-[1-(2,3-difluorophenyl)piperidin-4-yl]-5-methoxy-3-(1-phenyl-1H-pyrazol-5-yl)pyridazin-4(1H)-one By a method similar to Reference Example 67, the title compound was obtained.

MS (ESI+), found: 464.2

Reference Example 71

5-methoxy-3-(1-phenyl-1H-pyrazol-5-yl)-1-[1-(1,3-thiazol-2-yl)piperidin-4-yl]pyridazin-4(1H)-one By a method similar to Reference Example 67, the title compound was obtained.

MS (ESI+), found: 435.1

Reference Example 72

1-[1-(3-chloropyridin-2-yl)piperidin-4-yl]-5-methoxy-3-(1-phenyl-1H-pyrazol-5-yl)pyridazin-4(1H)-one By a method similar to Reference Example 67, the title compound was obtained.

MS (ESI+), found: 463.1

Reference Example 73

2-{4-[5-methoxy-4-oxo-3-(1-phenyl-1H-pyrazol-5-yl)pyridazin-1(4H)-yl]piperidin-1-yl}pyridine-3-carbonitrile By a method similar to Reference Example 67, the title compound was obtained.

MS (ESI+), found: 454.1

Reference Example 74

1-(3'-chloro-3,6-dihydro-2H-1,2'-bipyridin-4-yl)-5-methoxy-3-(1-phenyl-1H-pyrazol-5-yl)pyridazin-4(1H)-one By a method similar to Reference Example 67, the title compound was obtained.

MS (ESI+), found: 461.0.

The structural formulas of the compounds obtained in Reference Examples 64-74 are shown in the following Tables 1-1 to 1-3

TABLE 1-1

| Ref. Ex. No. | IUPAC name | Structural Formula | MS |
|---|---|---|---|
| 64 | 1-(1-benzyl-1,2,3,6-tetrahydropyridin-4-yl)-5-methoxy-3-(1-phenyl-1H-pyrazol-5-yl)pyridazin-4(1H)-one | | 440.2 |
| 65 | 5-methoxy-3-(1-phenyl-1H-pyrazol-5-yl)-1-(1-prop-2-en-1-yl-1,2,3,6-tetrahydropyridin-4-yl)pyridazin-4(1H)-one | | 390.2 |
| 66 | 5-methoxy-3-(1-phenyl-1H-pyrazol-5-yl)-1-piperidin-4-ylpyridazin-4(1H)-one | | 352.1 |
| 67 | 1-[1-(4-fluorophenyl)piperidin-4-yl]-5-methoxy-3-(1-phenyl-1H-pyrazol-5-yl)pyridazin-4(1H)-one | | 446.2 |

TABLE 1-1-continued

| Ref. Ex. No. | IUPAC name | Structural Formula | MS |
|---|---|---|---|
| 68 | 2-{4-[5-methoxy-4-oxo-3-(1-phenyl-1H-pyrazol-5-yl)pyridazin-1(4H)-yl]piperidin-1-yl}benzonitrile | | 453.2 |

TABLE 1-2

| Ref. Ex. No. | IUPAC name | Structural Formula | MS |
|---|---|---|---|
| 69 | 5-methoxy-3-(1-phenyl-1H-pyrazol-5-yl)-1-(1,2,3,6-tetrahydropyridin-4-yl)pyridazin-4(1H)-one | | 350.2 |
| 70 | 1-[1-(2,3-difluorophenyl)piperidin-4-yl]-5-methoxy-3-(1-phenyl-1H-pyrazol-5-yl)pyridazin-4(1H)-one | | 464.2 |

TABLE 1-2-continued

| Ref. Ex. No. | IUPAC name | Structural Formula | MS |
|---|---|---|---|
| 71 | 5-methoxy-3-(1-phenyl-1H-pyrazol-5-yl)-1-[1-(1,3-thiazol-2-yl)piperidin-4-yl]pyridazin-4(1H)-one | | 435.1 |
| 72 | 1-[1-(3-chloropyridin-2-yl)piperidin-4-yl]-5-methoxy-3-(1-phenyl-1H-pyrazol-5-yl)pyridazin-4(1H)-one | | 463.1 |
| 73 | 2-{4-[5-methoxy-4-oxo-3-(1-phenyl-1H-pyrazol-5-yl)pyridazin-1(4H)-yl]piperidin-1-yl}pyridine-3-carbonitrile | | 454.1 |

TABLE 1-3

| Ref. Ex. No. | IUPAC name | Structural Formula | MS |
|---|---|---|---|
| 74 | 1-(3'-chloro-3,6-dihydro-2H-1,2'-bipyridin-4-yl)-5-methoxy-3-(1-phenyl-1H-pyrazol-5-yl)pyridazin-4(1H)-one | | 461 |

Reference Example 75 and Reference Example 76

1-[2-fluoro-4-(1H-pyrazol-1-yl)phenyl]-5-methoxy-3-(3-methyl-1-phenyl-1H-pyrazol-5-yl)pyridazin-4(1H)-one Reference Example 75

5-methoxy-1-[2-methoxy-4-(1H-pyrazol-1-yl)phenyl]-3-(3-methyl-1-phenyl-1H-pyrazol-5-yl)pyridazin-4(1H)-one Reference Example 76

A mixture of 3-acetyl-1-[2-fluoro-4-(1H-pyrazol-1-yl)phenyl]-5-methoxypyridazin-4(1H)-one (300 mg), N,N-dimethylacetamide dimethyl acetal (3 mL) and acetonitrile (3 mL) was stirred at 80° C. for 12 hr and the solvent was evaporated under reduced pressure. The residue was dissolved in acetic acid (5 mL), and phenylhydrazine (98.8 mg) was added at room temperature. The reaction mixture was stirred at 80° C. for 3 hr, and the solvent was evaporated under reduced pressure. The residue was treated with water and extracted with ethyl acetate. The extract was dried over anhydrous magnesium sulfate and concentrated under reduced pressure. The residue was purified by silica gel column chromatography (ethyl acetate/methanol) to give 1-[2-fluoro-4-(1H-pyrazol-1-yl)phenyl]-5-methoxy-3-(3-methyl-1-phenyl-1H-pyrazol-5-yl)pyridazin-4(1H)-one (69 mg) and a mixture containing 5-methoxy-1-[2-methoxy-4-(1H-pyrazol-1-yl)phenyl]-3-(3-methyl-1-phenyl-1H-pyrazol-5-yl)pyridazin-4(1H)-one. The obtained mixture was purified by preparative HPLC to give 5-methoxy-1-[2-methoxy-4-(1H-pyrazol-1-yl)phenyl]-3-(3-methyl-1-phenyl-1H-pyrazol-5-yl)pyridazin-4(1H)-one (28 mg).

1-[2-fluoro-4-(1H-pyrazol-1-yl)phenyl]-5-methoxy-3-(3-methyl-1-phenyl-1H-pyrazol-5-yl)pyridazin-4(1H)-one $^1$H NMR (300 MHz, DMSO-$d_6$) δ 2.29 (3H, s), 3.78 (3H, s), 6.59-6.66 (1H, m), 6.79 (1H, s), 7.08-7.21 (1H, m), 7.25-7.49 (5H, m), 7.74 (1H, d, J=8.7 Hz), 7.83 (1H, d, J=1.5 Hz), 7.91-8.04 (1H, m), 8.52 (1H, d, J=1.9 Hz), 8.66 (1H, d, J=2.7 Hz)

5-methoxy-1-[2-methoxy-4-(1H-pyrazol-1-yl)phenyl]-3-(3-methyl-1-phenyl-1H-pyrazol-5-yl)pyridazin-4(1H)-one $^1$H NMR (300 MHz, DMSO-d$_6$) δ 2.29 (3H, s), 3.76 (3H, s), 3.91 (3H, s), 6.60 (1H, s), 6.75 (1H, s), 6.93 (1H, d, J=8.7 Hz), 7.20-7.49 (6H, m), 7.64 (1H, d, J=1.9 Hz), 7.80 (1H, s), 8.38 (1H, s), 8.66 (1H, d, J=2.7 Hz).

Reference Example 77

3-[1-(3-chloro-2-fluorophenyl)-1H-pyrazol-5-yl]-1-[2-fluoro-4-(1H-pyrazol-1-yl)phenyl]-5-methoxy-pyridazin-4(1H)-one A) 3-[3-(dimethylamino)prop-2-enoyl]-1-[2-fluoro-4-(1H-pyrazol-1-yl)phenyl]-5-methoxypyridazin-4(1H)-one A mixture of 3-acetyl-1-[2-fluoro-4-(1H-pyrazol-1-yl)phenyl]-5-methoxypyridazin-4(1H)-one (600 mg), N,N-dimethylformamide dimethyl acetal (3 mL) and acetonitrile (3 mL) was stirred at 80° C. for 12 hr, cooled to room temperature and further stirred for 12 hr. The precipitate was collected by filtration, and washed with diisopropyl ether to give the title compound (600 mg).

$^1$H NMR (300 MHz, DMSO-d$_6$) δ 2.82 (3H, s), 3.09 (3H, s), 3.79 (3H, s), 5.25 (1H, brs), 6.64 (1H, dd, J=2.5, 1.8 Hz), 7.51 (1H, brs), 7.79-7.95 (3H, m), 7.99-8.10 (1H, m), 8.50 (1H, d, J=1.8 Hz), 8.68 (1H, d, J=2.5 Hz).

B) 3-[1-(3-chloro-2-fluorophenyl)-1H-pyrazol-5-yl]-1-[2-fluoro-4-(1H-pyrazol-1-yl)phenyl]-5-methoxy-pyridazin-4(1H)-one To a solution of 3-[3-(dimethylamino)prop-2-enoyl]-1-[2-fluoro-4-(1H-pyrazol-1-yl)phenyl]-5-methoxypyridazin-4(1H)-one (200 mg) in trifluoroacetic acid/ethanol (5/95, 8 mL) was added (3-chloro-2-fluorophenyl)hydrazine hydrochloride (98.8 mg) under ice-cooling. The reaction mixture was stirred at room temperature for 3 hr, water was added, and the mixture was extracted with ethyl acetate. The extract was dried over anhydrous magnesium sulfate and the solvent was evaporated under reduced pressure. The residue was purified by silica gel column chromatography (ethyl acetate/methanol) to give the title compound (97 mg).

$^1$H NMR (300 MHz, DMSO-d$_6$) δ 3.80 (3H, s), 6.57-6.71 (1H, m), 7.12-7.22 (1H, m), 7.23-7.32 (1H, m), 7.38-7.49 (2H, m), 7.55-7.69 (1H, m), 7.72-7.81 (1H, m), 7.81-8.01 (3H, m), 8.50 (1H, d, J=1.9 Hz), 8.67 (1H, d, J=2.6 Hz).

Reference Example 78

3-[1-(5-chloro-2-fluorophenyl)-1H-pyrazol-5-yl]-1-[2-fluoro-4-(1H-pyrazol-1-yl)phenyl]-5-methoxy-pyridazin-4(1H)-one To a solution of 3-[3-(dimethylamino)prop-2-enoyl]-1-[2-fluoro-4-(1H-pyrazol-1-yl)phenyl]-5-methoxypyridazin-4(1H)-one (200 mg) in trifluoroacetic acid/ethanol (5/95, 8 mL) was added (5-chloro-2-fluorophenyl)hydrazine hydrochloride (88.8 mg) under ice-cooling. The reaction mixture was stirred at room temperature for 3 hr, treated with water, and extracted with ethyl acetate. The extract was dried over anhydrous magnesium sulfate and concentrated under reduced pressure. The residue was purified by silica gel column chromatography (ethyl acetate/methanol) to give the title compound (98 mg).

$^1$H NMR (300 MHz, DMSO-d$_6$) δ 3.80 (3H, s), 6.52-6.71 (1H, m), 7.10-7.26 (1H, m), 7.27-7.41 (2H, m), 7.45-7.54 (1H, m), 7.60-7.68 (1H, m), 7.74-7.81 (1H, m), 7.82-7.90 (2H, m), 7.92-8.00 (1H, m), 8.51 (1H, d, J=1.9 Hz), 8.67 (1H, d, J=2.6 Hz).

Reference Example 79

1-[2-fluoro-4-(1H-pyrazol-1-yl)phenyl]-5-methoxy-3-{1-[3-(trifluoromethyl)phenyl]-1H-pyrazol-5-yl}pyridazin-4(1H)-one To a solution of 3-[3-(dimethylamino)prop-2-enoyl]-1-[2-fluoro-4-(1H-pyrazol-1-yl)phenyl]-5-methoxypyridazin-4(1H)-one (200 mg) in trifluoroacetic acid/ethanol (5/95, 8 mL) was added [3-(trifluoromethyl)phenyl]hydrazine (96.5 mg) under ice-cooling. The reaction mixture was stirred at room temperature for 3 hr, treated with water, and extracted with ethyl acetate. The extract was dried over anhydrous magnesium sulfate and concentrated under reduced pressure. The residue was purified by silica gel column chromatography (ethyl acetate/methanol) to give the title compound (185 mg).

$^1$H NMR (300 MHz, DMSO-d$_6$) δ 3.79 (3H, s), 6.63 (1H, s), 7.11 (1H, s), 7.30-7.44 (1H, m), 7.56-7.82 (5H, m), 7.80-7.92 (2H, m), 7.93-8.04 (1H, m), 8.56 (1H, s), 8.66 (1H, d, J=2.3 Hz).

Reference Example 80

1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one A) [3-(trifluoromethoxy)phenyl]hydrazine hydrochloride 3-(Trifluoromethoxy)aniline (3.68 mL) was dissolved in 6 M hydrochloric acid (71 mL), and an aqueous solution (4.7 mL) of sodium nitrite (2.08 g) was added dropwise at −5° C. over 20 min. To the mixture was added a solution of Tin (II) chloride (1.954 mL) in 6 M hydrochloric acid (25 mL) at −5° C. The mixture was stirred at −5° C. for 2 hr, and the precipitated solid was collected by filtration, washed with 0.1 M hydrochloric acid and dried under reduced pressure to give the title compound (2.72 g).

$^1$H NMR (300 MHz, CDCl$_3$) δ 6.81-7.03 (3H, m), 7.41 (1H, t, J=8.3 Hz), 8.64 (1H, brs), 10.35 (2H, brs).

B) 1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one To a suspension of 3-[3-(dimethylamino)prop-2-enoyl]-5-methoxy-1-[2-fluoro-4-(1H-pyrazol-1-yl)phenyl]pyridazin-4(1H)-one (200 mg) in ethanol (2.0 mL) was added dropwise a solution of [3-(trifluoromethoxy)phenyl]hydrazine hydrochloride (139 mg) and trifluoroacetic acid (0.2 mL) in ethanol (2.0 mL), and the mixture was stirred at room temperature for 24 hr. To the reaction mixture was added a solution of [3-(trifluoromethoxy)phenyl]hydrazine hydrochloride (16.7 mg) in ethanol (0.3 mL) and the mixture was stirred at room temperature for 24 hr. The precipitate was collected by filtration and the mother liquor was concentrated. The precipitate from mother liquor was collected by filtration. The precipitates were combined and recrystallized from acetone-water to give the title compound (96.1 mg).

$^1$H NMR (300 MHz, CDCl$_3$) δ 3.79 (3H, s), 6.64 (1H, d, J=2.6 Hz), 7.03 (1H, d, J=1.9 Hz), 7.27-7.49 (4H, m), 7.57 (1H, t, J=8.1 Hz), 7.74-7.88 (3H, m), 7.99 (1H, dd, J=12.1, 2.3 Hz), 8.57 (1H, d, J=1.9 Hz), 8.66 (1H, d, J=2.6 Hz). mp 148-150° C.

Anal. Calcd for C$_{24}$H$_{16}$F$_4$N$_6$O$_3$.0.5H$_2$O: C, 55.28; H, 3.29; N, 16.11. Found: C, 55.25; H, 3.07; N, 16.05.

Reference Example 81

5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one A) 3-[3-(dimethylamino)prop-2-enoyl]-5-methoxy-1-[2-methoxy-4-(1H-pyrazol-1-yl)phenyl]pyridazin-4(1H)-one A mixture of 3-acetyl-5-methoxy-1-[2-methoxy-4-(1H-pyrazol-1-yl)phenyl]pyridazin-4(1H)-one (264 mg), N,N-dimethylformamide dimethyl acetal (1.5 mL) and acetonitrile (1.5 mL) was heated under reflux for 3 hr. The reaction mixture was concentrated under reduced pressure, and the residue was crystallized from ethanol to give the title compound (274 mg).

$^1$H NMR (300 MHz, CDCl$_3$) δ 2.90 (3H, s), 3.12 (3H, s), 3.89 (3H, s), 3.97 (3H, s), 5.89 (1H, brs), 6.52 (1H, dd, J=2.6, 1.9 Hz), 7.26 (1H, dd, J=8.3, 2.3 Hz), 7.59 (1H, d, J=1.9 Hz), 7.63 (1H, d, J=8.7 Hz), 7.76 (1H, d, J=1.9 Hz), 7.79 (1H, brs), 7.82 (1H, s), 7.98 (1H, d, J=2.3 Hz).

B) 5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one To a suspension of 3-[3-(dimethylamino)prop-2-enoyl]-5-methoxy-1-[2-methoxy-4-(1H-pyrazol-1-yl)phenyl]pyridazin-4(1H)-one (136 mg) in ethanol (1.5 mL) was added dropwise a solution of 3-(trifluoromethyl)phenylhydrazine (0.049 mL) and trifluoroacetic acid (0.15 mL) in ethanol (1.5 mL), and the mixture was stirred at room temperature for 3 hr. The reaction mixture was concentrated under reduced pressure, and the residue was purified by silica gel column chromatography (NH, ethyl acetate) and recrystallized from ethanol/water to give the title compound (123 mg).

mp 215-217° C.

$^1$H NMR (300 MHz, CDCl$_3$) δ 3.89 (3H, s), 3.93 (3H, s), 6.53 (1H, dd, J=2.6, 1.9 Hz), 6.62 (1H, d, J=8.7 Hz), 7.03 (1H, dd, J=8.7, 2.3 Hz), 7.30 (1H, d, J=1.9 Hz), 7.48-7.53 (2H, m), 7.57-7.62 (2H, m), 7.67-7.68 (1H, m), 7.76 (1H, d, J=1.5 Hz), 7.80 (1H, d, J=1.9 Hz), 7.82 (1H, s), 7.93 (1H, d, J=2.3 Hz).

Anal. Calcd for C$_{25}$H$_{19}$F$_3$N$_6$O$_3$: C, 59.06; H, 3.77; N, 16.53. Found: C, 58.97; H, 3.85; N, 16.40.

Reference Example 82

3-[1-(3-chlorophenyl)-1H-pyrazol-5-yl]-5-methoxy-1-[2-methoxy-4-(1H-pyrazol-1-yl)phenyl]pyridazin-4(1H)-one To a suspension of 3-[3-(dimethylamino)prop-2-enoyl]-5-methoxy-1-[2-methoxy-4-(1H-pyrazol-1-yl)phenyl]pyridazin-4(1H)-one (136 mg) in ethanol (1.5 mL) was added dropwise a solution of 3-chlorophenylhydrazine hydrochloride (67.7 mg) and trifluoroacetic acid (0.15 mL) in ethanol (1.5 mL), and the mixture was stirred at room temperature for 5 hr. The reaction mixture was concentrated under reduced pressure, and the residue was purified by silica gel column chromatography (NH, ethyl acetate) and crystallized from ethyl acetate. Recrystallization from ethanol/water gave the title compound (68.0 mg).

mp 167-168° C.

$^1$H NMR (300 MHz, CDCl$_3$) δ 3.90 (3H, s), 3.95 (3H, s), 6.53 (1H, dd, J=2.6, 1.9 Hz), 6.68 (1H, d, J=8.7 Hz), 7.08 (1H, dd, J=8.7, 2.3 Hz), 7.27-7.36 (4H, m), 7.44-7.45 (1H, m), 7.53 (1H, d, J=2.3 Hz), 7.76 (1H, d, J=1.9 Hz), 7.77 (1H, d, J=1.9 Hz), 7.84 (1H, s), 7.96 (1H, d, J=2.6 Hz).

Anal. Calcd for C$_{24}$H$_{19}$ClN$_6$O$_3$: C, 60.70; H, 4.03; N, 17.70. Found: C, 60.73; H, 4.08; N, 17.58.

Reference Example 83

1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one A) 4-bromo-2-(tert-butoxy)-1-nitrobenzene To a solution of 4-bromo-2-fluoro-1-nitrobenzene (25.2 g) in tetrahydrofuran (250 mL) was added potassium tert-butoxide (25.3 g) at 0° C., and the mixture was stirred at 0° C. for 30 min. The reaction mixture was poured into water, and the mixture was extracted with ethyl acetate. The extract was washed with water and brine, dried over anhydrous magnesium sulfate, and concentrated under reduced pressure. The residue was purified by silica gel column chromatography (hexane/ethyl acetate) to give the title compound (28.6 g).

$^1$H NMR (300 MHz, CDCl$_3$) δ 1.44 (9H, s), 7.26 (1H, dd, J=8.7, 2.3 Hz), 7.38 (1H, d, J=2.3 Hz), 7.62 (1H, d, J=8.7 Hz).

B) 1-(3-tert-butoxy-4-nitrophenyl)-3,4-difluoro-1H-pyrrole

A suspension of 4-bromo-2-(tert-butoxy)-1-nitrobenzene (13.7 g), 3,3,4,4-tetrafluoropyrrolidine hydrochloride (9.87 g), Pd$_2$(dba)$_3$ (0.916 g), Xantphos (2.31 g) and sodium tert-butoxide (19.2 g) in 1,4-dioxane (150 mL) was stirred under an argon atmosphere at 90° C. for 4 hr. The reaction mixture was poured into water, and the mixture was extracted with ethyl acetate. The extract was washed with brine, dried over anhydrous magnesium sulfate, and concentrated under reduced pressure. The residue was purified by silica gel column chromatography (NH, hexane/ethyl acetate) and recrystallized from hexane/ethyl acetate to give the title compound (8.35 g).

$^1$H NMR (300 MHZ, CDCl$_3$) δ 1.47 (9H, s), 6.72-6.82 (2H, m), 7.00 (1H, dd, J=8.7, 2.6 Hz), 7.04 (1H, d, J=2.6 Hz), 7.88 (1H, d, J=8.7 Hz).

C) 5-(3,4-difluoro-1H-pyrrol-1-yl)-2-nitrophenol

A mixture of 1-(3-tert-butoxy-4-nitrophenyl)-3,4-difluoro-1H-pyrrole (8.30 g), trifluoroacetic acid (30 mL) and tetrahydrofuran (60 mL) was heated under reflux for 3 hr. The reaction mixture was concentrated under reduced pressure, and the residue was washed with hexane/ethyl acetate (10/1) to give the title compound (6.43 g).

¹H NMR (300 MHz, CDCl₃) δ 6.80-6.91 (3H, m), 6.98 (1H, d, J=2.6 Hz), 8.18 (1H, d, J=9.4 Hz), 10.85 (1H, s).

D) 1-[3-(benzyloxy)-4-nitrophenyl]-3,4-difluoro-1H-pyrrole

A suspension of 5-(3,4-difluoro-1H-pyrrol-1-yl)-2-nitrophenol (6.39 g), benzyl bromide (3.48 mL) and potassium carbonate (5.51 g) in N,N-dimethylformamide (60 mL) was stirred at room temperature overnight. The reaction mixture was poured into water, and the mixture was extracted with ethyl acetate. The extract was washed with water and brine, dried over anhydrous magnesium sulfate, and concentrated under reduced pressure. The residue was recrystallized from hexane/ethyl acetate to give the title compound (8.57 g).

¹H NMR (300 MHz, CDCl₃) δ 5.30 (2H, s), 6.67-6.77 (2H, m), 6.88-6.92 (2H, m), 7.33-7.51 (5H, m), 8.02 (1H, d, J=8.3 Hz).

E) 2-(benzyloxy)-4-(3,4-difluoro-1H-pyrrol-1-yl) aniline

To a mixture of zinc (33.7 g), tetrahydrofuran (40 mL) and acetic acid (80 mL) was added dropwise a mixture of 1-[3-(benzyloxy)-4-nitrophenyl]-3,4-difluoro-1H-pyrrole (8.52 g), tetrahydrofuran (80 mL) and acetic acid (40 mL) at 0° C. The mixture was stirred at 0° C. for 15 min, and filtered. The filtrate was concentrated under reduced pressure. The residue was purified by silica gel column chromatography (NH, hexane/ethyl acetate) and recrystallized from hexane/ethyl acetate to give the title compound (7.53 g).

¹H NMR (300 MHz, CDCl₃) δ 3.86 (2H, s), 5.10 (2H, s), 6.50-6.60 (2H, m), 6.69-6.76 (3H, m), 7.33-7.46 (5H, m).

F) methyl 2-{[2-(benzyloxy)-4-(3,4-difluoro-1H-pyrrol-1-yl)phenyl]hydrazono}-4-methoxy-3-oxobutanoate To a mixture of 2-(benzyloxy)-4-(3,4-difluoro-1H-pyrrol-1-yl)aniline (7.51 g) and 6M hydrochloric acid (50 mL) was added dropwise a solution of sodium nitrite (3.45 g) in water (10 mL) at 0° C. and the mixture was stirred for 15 min. The reaction mixture was added to a suspension of methyl 4-methoxyacetoacetate (3.24 mL) and sodium acetate (24.6 g) in methanol (50 mL) at 0° C. The reaction mixture was stirred for 15 min, poured into water, and the mixture was extracted with ethyl acetate. The extract was washed with saturated aqueous sodium hydrogen carbonate solution and brine, dried over anhydrous magnesium sulfate, and concentrated under reduced pressure. The residue was washed with hexane/ethyl acetate, and recrystallized from hexane/tetrahydrofuran to give the title compound (4.87 g).

¹H NMR (300 MHz, CDCl₃) δ 3.51 (3H, s), 3.90 (3H, s), 4.68 (2H, s), 5.27 (2H, s), 6.59-6.69 (2H, m), 6.87 (1H, d, J=2.3 Hz), 6.94 (1H, dd, J=8.7, 2.3 Hz), 7.34-7.52 (5H, m), 7.61 (1H, d, J=8.7 Hz), 13.27 (1H, s).

G) methyl 1-[2-(benzyloxy)-4-(3,4-difluoro-1H-pyrrol-1-yl)phenyl]-5-methoxy-4-oxo-1,4-dihydropyridazine-3-carboxylate A mixture of methyl 2-{[2-(benzyloxy)-4-(3,4-difluoro-1H-pyrrol-1-yl)phenyl]hydrazono}-4-methoxy-3-oxobutanoate (4.85 g) and N,N-dimethylformamide dimethyl acetal (100 mL) was heated under reflux for 3 hr. After cooling to room temperature, the precipitate was collected by filtration and recrystallized from methanol to give the title compound (4.57 g).

¹H NMR (300 MHz, CDCl₃) δ 3.64 (3H, s), 3.97 (3H, s), 5.17 (2H, s), 6.69-6.79 (2H, m), 6.99-7.03 (2H, m), 7.32-7.43 (5H, m), 7.59-7.62 (1H, m), 7.80 (1H, s).

H) 1-[2-(benzyloxy)-4-(3,4-difluoro-1H-pyrrol-1-yl) phenyl]-5-methoxy-4-oxo-1,4-dihydropyridazine-3-carboxylic acid A mixture of methyl 1-[2-(benzyloxy)-4-(3,4-difluoro-1H-pyrrol-1-yl)phenyl]-5-methoxy-4-oxo-1,4-dihydropyridazine-3-carboxylate (4.54 g), 1M aqueous sodium hydroxide solution (15 mL), tetrahydrofuran (30 mL) and methanol (30 mL) was stirred at room temperature for 30 min. The reaction mixture was neutralized with 1M hydrochloric acid, and the precipitate was collected by filtration and washed with water to give the title compound (0.5 tetrahydrofuran solvate, 4.70 g).

¹H NMR (300 MHz, DMSO-d₆) δ3.78 (3H, s), 5.32 (2H, s), 7.31-7.45 (6H, m), 7.59 (1H, d, J=2.3 Hz), 7.69-7.71 (3H, m), 8.89 (1H, s), 15.18 (1H, brs).

I) 1-[2-(benzyloxy)-4-(3,4-difluoro-1H-pyrrol-1-yl) phenyl]-N,5-dimethoxy-N-methyl-4-oxo-1,4-dihydropyridazine-3-carboxamide A suspension of 1-[2-(benzyloxy)-4-(3,4-difluoro-1H-pyrrol-1-yl)phenyl]-5-methoxy-4-oxo-1,4-dihydropyridazine-3-carboxylic acid (0.5 tetrahydrofuran solvate, 4.67 g), N,O-dimethylhydroxylamine hydrochloride (1.11 g), WSC (2.19 g), HOBt (1.54 g) and triethylamine (1.59 mL) in N,N-dimethylformamide (75 mL) was stirred at room temperature for 6 hr. The reaction mixture was poured into water, and the mixture was extracted with ethyl acetate. The extract was washed with water and brine, dried over anhydrous magnesium sulfate, and concentrated under reduced pressure. The residue was purified by silica gel column chromatography (NH, tetrahydrofuran) and recrystallized from hexane/tetrahydrofuran to give the title compound (4.51 g).

¹H NMR (300 MHz, CDCl₃) δ 3.38 (3H, s), 3.62 (3H, s), 3.67 (3H, s), 5.17 (2H, s), 6.69-6.79 (2H, m), 6.97-7.01 (2H, m), 7.32-7.44 (5H, m), 7.59-7.64 (1H, m), 7.86 (1H, s).

J) 3-acetyl-1-[2-(benzyloxy)-4-(3,4-difluoro-1H-pyrrol-1-yl)phenyl]-5-methoxypyridazin-4(1H)-one To a solution of 1-[2-(benzyloxy)-4-(3,4-difluoro-1H-pyrrol-1-yl)phenyl]-N,5-dimethoxy-N-methyl-4-oxo-1,4-dihydropyridazine-3-carboxamide (4.47 g) in tetrahydrofuran (270 mL) was added dropwise a 1M solution of methylmagnesium bromide in tetrahydrofuran (27 mL) at −78° C. and the mixture was stirred for 15 min. To the reaction mixture was added 1M hydrochloric acid, and the mixture was extracted with ethyl acetate. The extract was washed with water and brine, dried over anhydrous magnesium sulfate, and concentrated under reduced pressure. The residue was washed with tetrahydrofuran, and recrystallized from methanol to give the title compound (3.75 g).

¹H NMR (300 MHz, CDCl₃) δ 2.68 (3H, s), 3.63 (3H, s), 5.18 (2H, s), 6.71-6.81 (2H, m), 7.00-7.04 (2H, m), 7.32-7.44 (5H, m), 7.59-7.62 (1H, m), 7.80 (1H, s).

K) 1-[2-(benzyloxy)-4-(3,4-difluoro-1H-pyrrol-1-yl)phenyl]-3-[3-(dimethylamino)prop-2-enoyl]-5-methoxypyridazin-4(1H)-one A mixture of 3-acetyl-1-[2-(benzyloxy)-4-(3,4-difluoro-1H-pyrrol-1-yl)phenyl]-5-methoxypyridazin-4(1H)-one (3.70 g), N,N-dimethylformamide dimethyl acetal (40 mL) and acetonitrile (40 mL) was heated under reflux for 6 hr. The reaction mixture was concentrated under reduced pressure, and the residue was crystallized from ethanol to give the title compound (3.85 g).

$^1$H NMR (300 MHz, DMSO-d$_6$) δ 2.78 (3H, brs), 3.05 (3H, brs), 3.65 (3H, s), 5.26 (1H, brs), 5.31 (2H, s), 7.30-7.47 (6H, m), 7.54 (1H, d, J=2.3 Hz), 7.61 (1H, d, J=8.7 Hz), 7.66 (2H, d, J=1.5 Hz), 8.40 (1H, s).

L) 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one A solution of 1-[2-(benzyloxy)-4-(3,4-difluoro-1H-pyrrol-1-yl)phenyl]-3-[3-(dimethylamino)prop-2-enoyl]-5-methoxypyridazin-4(1H)-one (3.80 g) and phenylhydrazine (1.48 mL) in acetic acid (30 mL) was heated under reflux for 2 hr. The reaction mixture was concentrated under reduced pressure, and the residue was purified by silica gel column chromatography (NH, ethyl acetate) and crystallized from hexane/ethyl acetate. Recrystallization from dimethyl sulfoxide/ethanol gave the title compound (3.29 g).

mp 221-223° C.

$^1$H NMR (300 MHz, CDCl$_3$) δ 3.57 (3H, s), 5.10 (2H, s), 6.31 (1H, d, J=8.7 Hz), 6.65-6.75 (3H, m), 6.92 (1H, d, J=2.3 Hz), 7.27-7.46 (11H, m), 7.78 (1H, d, J=2.3 Hz), 7.88 (1H, s).

Anal. Calcd for C$_{31}$H$_{23}$F$_2$N$_5$O$_3$: C, 67.51; H, 4.20; N, 12.70. Found: C, 67.48; H, 4.27; N, 12.62.

Reference Example 84

1-[4-(3,4-difluoro-1H-pyrrol-1-yl)-2-methoxyphenyl]-5-methoxy-3-(1-phenyl-1H-pyrazol-5-yl)pyridazin-4(1H)-one

A) 1-[4-(3,4-difluoro-1H-pyrrol-1-yl)-2-hydroxyphenyl]-5-methoxy-3-(1-phenyl-1H-pyrazol-5-yl)pyridazin-4(1H)-one Under a hydrogen atmosphere, a mixture of 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one (3.20 g) and 10% Pd—C (3.20 g) in AcOH (100 mL) was stirred at room temperature for 3 hr, and then filtered. The filtrate was concentrated under reduced pressure and the residue was purified by supercritical fluid chromatography (column: CHIRALPAK ADH, 20 mmID×250 mL, manufactured by DAICEL CHEMICAL INDUSTRIES, LTD., mobile phase: CO$_2$/2-propanol/acetonitrile-=700/150/150(v/v/v)). Crystallization from acetone gave the title compound (1.24 g).

$^1$H NMR (300 MHz, DMSO-d$_6$) δ 3.75 (3H, s), 6.80 (1H, d, J=8.7 Hz), 6.90-6.99 (2H, m), 7.02 (1H, d, J=2.3 Hz), 7.29-7.49 (7H, m), 7.78 (1H, d, J=1.9 Hz), 8.35 (1H, s), 10.90 (1H, brs).

B) 1-[4-(3,4-difluoro-1H-pyrrol-1-yl)-2-methoxyphenyl]-5-methoxy-3-(1-phenyl-1H-pyrazol-5-yl)pyridazin-4(1H)-one A suspension of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (231 mg), iodomethane (0.0375 mL) and potassium carbonate (138 mg) in N,N-dimethylformamide (2.5 mL) was stirred at room temperature overnight. The reaction mixture was poured into water, and extracted with ethyl acetate. The extract was washed with brine, dried over anhydrous magnesium sulfate, and concentrated under reduced pressure. The residue was purified by silica gel column chromatography (NH, tetrahydrofuran) and recrystallized from methanol/water to give the title compound (232 mg).

mp 206-207° C.

$^1$H NMR (300 MHz, CDCl$_3$) δ 3.89 (6H, s), 6.36 (1H, d, J=8.7 Hz), 6.65-6.77 (3H, m), 6.81 (1H, d, J=2.3 Hz), 7.25 (1H, d, J=1.9 Hz), 7.35-7.46 (5H, m), 7.77 (1H, d, J=1.9 Hz), 7.81 (1H, s).

Anal. Calcd for C$_{25}$H$_{19}$F$_2$N$_5$O$_3$: C, 63.15; H, 4.03; N, 14.73. Found: C, 62.96; H, 3.98; N, 14.66.

Reference Example 85

1-[2-(difluoromethoxy)-4-(3,4-difluoro-1H-pyrrol-1-yl)phenyl]-5-methoxy-3-(1-phenyl-1H-pyrazol-5-yl)pyridazin-4(1H)-one A mixture of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (231 mg), sodium chlorodifluoroacetate (152 mg), potassium carbonate (104 mg), N,N-dimethylformamide (2.5 mL) and water (0.5 mL) was stirred at reflux overnight. The reaction mixture was poured into water, and extracted with ethyl acetate. The extract was washed with saturated brine, dried over anhydrous magnesium sulfate, and concentrated under reduced pressure. The residue was purified by silica gel column chromatography (NH, ethyl acetate) and crystallized from hexane/ethyl acetate to give the title compound (193 mg).

mp 168-170° C.

$^1$H NMR (300 MHz, CDCl$_3$) δ 3.89 (3H, s), 6.41 (1H, t, J=72.0 Hz), 6.56 (1H, d, J=8.7 Hz), 6.69-6.79 (2H, m), 6.99 (1H, dd, J=8.7, 2.6 Hz), 7.12 (1H, d, J=2.6 Hz), 7.25 (1H, d, J=1.9 Hz), 7.34-7.46 (5H, m), 7.74 (1H, s), 7.78 (1H, d, J=1.9 Hz).

Anal. Calcd for C$_{25}$H$_{17}$F$_4$N$_5$O$_3$: C, 58.71; H, 3.35; N, 13.69. Found: C, 58.68; H, 3.41; N, 13.55.

Reference Example 86

1-[4-(3,4-difluoro-1H-pyrrol-1-yl)-2-(2,2,2-trifluoroethoxy)phenyl]-5-methoxy-3-(1-phenyl-1H-pyrazol-5-yl)pyridazin-4(1H)-one A suspension of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (138 mg), 2,2,2-trifluoroethyl trifluoromethanesulfonate (104 mg) and potassium carbonate (82 mg) in N,N-dimethylformamide (1.5 mL) was stirred at room temperature for 30 min. The reaction mixture was poured into water, and extracted with ethyl acetate. The extract was washed with brine, dried over anhydrous magnesium sulfate, and concentrated under reduced pressure. The residue was purified by silica gel column chromatography (NH, tetrahydrofuran) and crystallized from methanol to give the title compound (131 mg).

mp 220-222° C.

$^1$H NMR (300 MHz, CDCl$_3$) δ 3.86 (3H, s), 4.41 (2H, q, J=7.9 Hz), 6.37-6.41 (1H, m), 6.67-6.80 (4H, m), 7.28 (1H, d, J=1.9 Hz), 7.35-7.47 (5H, m), 7.78 (1H, d, J=1.9 Hz), 7.83 (1H, s).

Anal. Calcd for $C_{26}H_{18}F_5N_5O_3$: C, 57.46; H, 3.34; N, 12.89. Found: C, 57.38; H, 3.38; N, 12.83.

Reference Example 87

5-methoxy-1-[2-methoxy-4-(3,3,4,4-tetrafluoropyrrolidin-1-yl)phenyl]-3-(1-phenyl-1H-pyrazol-5-yl)pyridazin-4(1H)-one A) 3-acetyl-1-(4-iodo-2-methoxyphenyl)-5-methoxypyridazin-4(1H)-one To a solution of 1-(4-iodo-2-methoxyphenyl)-N,5-dimethoxy-N-methyl-4-oxo-1,4-dihydropyridazine-3-carboxamide (8.90 g) in tetrahydrofuran (150 mL) was added dropwise 1M methylmagnesium bromide tetrahydrofuran solution (30 mL) at −78° C., and the mixture was stirred for 20 min. To the reaction mixture was added 1M hydrochloric acid, and the mixture was extracted with ethyl acetate. The extract was washed with water and saturated brine, dried over anhydrous magnesium sulfate, and concentrated under reduced pressure. The residue was washed with ethyl acetate, and recrystallized from methanol/water to give the title compound (5.12 g).
$^1$H NMR (300 MHz, CDCl$_3$) δ 2.66 (3H, s), 3.87 (3H, s), 3.90 (3H, s), 7.21 (1H, d, J=8.3 Hz), 7.40 (1H, d, J=1.9 Hz), 7.47 (1H, dd, J=8.3, 1.9 Hz), 7.71 (1H, s).

B) 1-(4-iodo-2-methoxyphenyl)-5-methoxy-3-(1-phenyl-1H-pyrazol-5-yl)pyridazin-4(1H)-one A mixture of 3-acetyl-1-(4-iodo-2-methoxyphenyl)-5-methoxypyridazin-4(1H)-one (2.00 g), N,N-dimethylformamide dimethyl acetal (10 mL) and acetonitrile (10 mL) was heated under reflux for 8 hr. After cooling to room temperature, the reaction mixture was concentrated under reduced pressure.
To a solution of the obtained residue in ethanol (20 mL) was added dropwise a solution of phenylhydrazine (0.541 mL) and trifluoroacetic acid (0.743 mL) in ethanol (5 mL) at 0° C., and the mixture was stirred at room temperature for 3 hr. The reaction mixture was concentrated under reduced pressure, and the residue was purified by silica gel column chromatography (ethyl acetate) and recrystallized from ethanol/water to give the title compound (1.36 g).
$^1$H NMR (300 MHz, CDCl$_3$) δ 3.84 (3H, s), 3.88 (3H, s), 5.98 (1H, d, J=8.3 Hz), 7.13 (1H, dd, J=8.3, 1.9 Hz), 7.25-7.28 (2H, m), 7.34-7.45 (5H, m), 7.77 (1H, d, J=1.9 Hz), 7.79 (1H, s).

C) 5-methoxy-1-[2-methoxy-4-(3,3,4,4-tetrafluoropyrrolidin-1-yl)phenyl]-3-(1-phenyl-1H-pyrazol-5-yl)pyridazin-4(1H)-one A suspension of 1-(4-iodo-2-methoxyphenyl)-5-methoxy-3-(1-phenyl-1H-pyrazol-5-yl)pyridazin-4(1H)-one (186 mg), 3,3,4,4-tetrafluoropyrrolidine hydrochloride (80.0 mg), Pd$_2$(dba)$_3$ (6.8 mg), Xantphos (17.4 mg) and sodium tert-butoxide (93.0 mg) in 1,4-dioxane (2 mL) was stirred under an argon atmosphere at 90° C. for 30 min. The reaction mixture was poured into water, and the mixture was extracted with ethyl acetate. The extract was washed with brine, dried over anhydrous magnesium sulfate, and concentrated under reduced pressure. The residue was purified by silica gel column chromatography (NH, ethyl acetate) and purified by preparative HPLC (L-Column 2 ODS, mobile phase: water/acetonitrile (5% ammonium acetate-containing system)). The obtained fraction was concentrated under reduced pressure, and to the residue was added saturated aqueous sodium hydrogen carbonate solution, and the mixture was extracted with ethyl acetate. The extract was washed with brine, dried over anhydrous magnesium sulfate, and concentrated under reduced pressure. The residue was crystallized from methanol/water to give the title compound (41.1 mg).
mp 209-213° C.
$^1$H NMR (300 MHz, CDCl$_3$) δ 3.76-3.93 (10H, m), 5.91 (1H, dd, J=8.7, 2.6 Hz), 6.00 (1H, d, J=2.6 Hz), 6.31 (1H, d, J=8.7 Hz), 7.19 (1H, d, J=1.9 Hz), 7.31-7.45 (5H, m), 7.73 (1H, s) 7.76 (1H, d, J=1.9 Hz).
Anal. Calcd for $C_{25}H_{21}F_4N_5O_3$: C, 58.25; H, 4.11; N, 13.59. Found: C, 58.24; H, 4.10; N, 13.62.

Reference Example 88

5-methoxy-3-(1-phenyl-1H-pyrazol-5-yl)-1-(1,3-thiazol-2-yl)pyridazin-4(1H)-one

A) 1-benzyl-3-chloro-5-methoxypyridazin-4(1H)-one

To a solution of 3-chloro-5-methoxypyridazin-4-ol (10.0 g) in DMF (300 mL) were added NaH (55 wt %, 3.26 g) and n-Bu$_4$NI (4.60 g) at 0° C. The mixture was stirred for 10 min at 0° C., and then BnBr (12.3 g) was added at 0° C. The reaction mixture was stirred for 20 hr at room temperature, treated with water and extracted with CH$_2$Cl$_2$. The combined organic layers were washed with water and brine, dried over anhydrous sodium sulfate, filtered and concentrated under reduced pressure. The residue was purified by recrystallization from ethyl acetate/hexane to give the title compound (19.8 g) as a white solid.
$^1$H NMR (400 MHz, CDCl$_3$) δ 3.82 (3H, s), 5.31 (2H, s), 7.34-7.42 (5H, m), 7.89 (1H, s).

B) 1-benzyl-5-methoxy-3-(1-phenyl-1H-pyrazol-5-yl)pyridazin-4(1H)-one

A mixture of 1-benzyl-3-chloro-5-methoxypyridazin-4(1H)-one (13.6 g), 1-phenyl-5-(4,4,5,5-tetramethyl-1,3,2-dioxaborolan-2-yl)-1H-pyrazole (22.0 g), potassium carbonate (51.0 g) and PdCl$_2${Pt—Bu$_2$(Ph-p-NMe$_2$)}$_2$ (1.92 g) in toluene (330 ml) and water (33.0 ml) was stirred at reflux for 24 hr under nitrogen atmosphere. The reaction mixture was diluted with water and saturated sodium hydrogen carbonate aqueous solution, extracted with ethyl acetate, dried over anhydrous sodium sulfate, filtered and concentrated under reduced pressure. The residue was purified by recrystallization from ethyl acetate/hexane to give the title compound (15.1 g) as a pale yellow solid.
$^1$H NMR (400 MHz, DMSO-d$_6$) δ 3.81 (3H, s), 5.10 (2H, s), 6.95 (1H, d, J=1.6 Hz), 7.05-7.07 (2H, m), 7.24-7.38 (8H, m), 7.74 (1H, d, J=1.6 Hz), 8.33 (1H, s).

C) 5-methoxy-3-(1-phenyl-1H-pyrazol-5-yl)pyridazin-4-ol

A mixture of 1-benzyl-5-methoxy-3-(1-phenyl-1H-pyrazol-5-yl)pyridazin-4(1H)-one (15.0 g) and Pd(OH)$_2$/C (50% wet, 5.88 g) in THF (500 mL) and methanol (300 ml) was stirred at room temperature for 2 days under a hydrogen atmosphere. After filtration, the filtrate was concentrated under reduced pressure. The residue solid was suspended in ethanol/hexane and collected by filtration to give the title compound (9.10 g) as a brown solid.

MS (ESI+): [M+H]+269.2.

$^1$H NMR (400 MHz, DMSO-d$_6$) δ 3.74 (3H, s), 6.79 (1H, d, J=1.6 Hz), 7.27-7.40 (5H, m), 7.76 (1H, d, J=2.0 Hz), 8.15 (1H, s), 13.4 (1H, brs).

D) 5-methoxy-3-(1-phenyl-1H-pyrazol-5-yl)-1-(1,3-thiazol-2-yl)pyridazin-4(1H)-one A mixture of 5-methoxy-3-(1-phenyl-1H-pyrazol-5-yl)pyridazin-4-ol (70 mg), 2-chloro-1,3-thiazole (62 mg) and cesium carbonate (255 mg) in DMF (2 mL) was stirred at 100° C. for 12 h, treated with water and extracted with ethyl acetate. The organic layer was dried over anhydrous magnesium sulfate and concentrated under reduced pressure. The residue was purified by silica gel chromatography (ethyl acetate/methanol) to give the title compound (44 mg).

MS (API+): [M+H]$^+$352.3

Reference Example 89

1-(1-benzyl-1H-pyrazol-4-yl)-5-methoxy-3-(1-phenyl-1H-pyrazol-5-yl)pyridazin-4(1H)-one A) 1-methoxy-3-(1-phenyl-1H-pyrazol-5-yl)propan-2-ol To a solution of 1-phenylpyrazole (15 g) in THF (450 mL) was added 1.6M n-butyllithium in hexane (100 mL) at −78° C., and the mixture was stirred at −78° C. for 1 hr. To the reaction mixture was added 2-(methoxymethyl)oxirane (27.8 mL) at −78° C., and the mixture was warmed to room temperature and stirred for 1 hr. To the reaction mixture was added 1N hydrochloric acid and the mixture was extracted with ethyl acetate. The extract was concentrated under reduced pressure and the residue was purified by silica gel column chromatography (ethyl acetate/hexane) to give the title compound (12.2 g).

$^1$H NMR (300 MHz, CDCl$_3$) δ 2.33 (1H, d, J=4.1 Hz), 2.88 (2H, dd, J=6.6, 3.2 Hz), 3.19-3.28 (1H, m), 3.33 (3H, s), 3.34-3.40 (1H, m), 3.94-4.06 (1H, m, J=10.0, 6.8, 3.4, 3.4 Hz), 6.30-6.38 (1H, m), 7.34-7.53 (5H, m), 7.63 (1H, s).

B) 1-methoxy-3-(1-phenyl-1H-pyrazol-5-yl)propan-2-one

To a solution of DMSO (14.2 mL) in THF (100 mL) was added dropwise trifluoroacetic acid anhydride (12.6 g) at −42° C. over 15 min, and the mixture was stirred at −42° C. for 15 min. To the reaction mixture was added dropwise a solution of 1-methoxy-3-(1-phenyl-1H-pyrazol-5-yl)propan-2-ol (9.3 g) in THF (66 mL) at −42° C. over 1 hr, and the mixture was stirred at 0° C. for 15 min. To the reaction mixture was added dropwise triethylamine (22.3 mL) at 0° C. over 15 min and the mixture was stirred at 0° C. for 1 hr. To the reaction mixture was added 10% aqueous sodium carbonate solution and the mixture was extracted with ethyl acetate. The extract was concentrated under reduced pressure and the residue was purified by silica gel column chromatography (ethyl acetate/hexane) to give the title compound (4.11 g).

$^1$H NMR (300 MHz, CDCl$_3$) δ 3.33 (3H, s), 3.88 (2H, s), 3.95 (2H, s), 6.34 (1H, d, J=1.9 Hz), 7.35-7.52 (5H, m), 7.66 (1H, d, J=1.9 Hz).

C) 1-(1-benzyl-1H-pyrazol-4-yl)-5-methoxy-3-(1-phenyl-1H-pyrazol-5-yl)pyridazin-4(1H)-one To a mixture of 1-benzyl-1H-pyrazole-4-amine (75 mg) and 6M hydrochloric acid (1 mL) was added dropwise a solution of sodium nitrite (24 mg) in water (0.5 mL) at 0° C., and the mixture was stirred for 30 min. The obtained aqueous solution was added to a suspension of 1-methoxy-3-(1-phenyl-1H-pyrazol-5-yl)propan-2-one (100 mg) and sodium acetate (354 mg) in methanol (2 mL) at 0° C. The reaction mixture was stirred for 3 hr, poured into water, and extracted with ethyl acetate. The extract was dried over anhydrous magnesium sulfate, and concentrated under reduced pressure. The obtained residue was dissolved in acetonitrile (2 mL), and N,N-dimethylformamide dimethyl acetal (0.3 mL) was added. The reaction mixture was stirred at 80° C. for 12 hr, treated with water, and extracted with ethyl acetate. The extract was dried over anhydrous magnesium sulfate, and concentrated under reduced pressure. The residue was purified by silica gel column chromatography (ethyl acetate/methanol) to give the title compound (11 mg).

MS (API+): [M+H]$^+$425.3

Reference Example 90

5-methoxy-3-(1-phenyl-1H-pyrazol-5-yl)-1-[6-(3,3,4,4-tetrafluoropyrrolidin-1-yl)pyridin-3-yl]pyridazin-4(1H)-one A) 5-nitro-2-(3,3,4,4-tetrafluoropyrrolidin-1-yl)pyridine A mixture of cesium carbonate (100 g), tetrafluoropyrrolidine hydrochloride (10 g) and 2-chloro-5-nitropyridine (20 g) in DMF (200 mL) was stirred at room temperature for 90 hr, treated with water and extracted with ethyl acetate. The extract was dried over anhydrous magnesium sulfate, and concentrated under reduced pressure. The residue was purified by silica gel column chromatography (ethyl acetate/hexane) to give the title compound as yellow crystals.

MS (ESI+): [M+H]$^+$266.1

B) 6-(3,3,4,4-tetrafluoropyrrolidin-1-yl)pyridine-3-amine

Under a hydrogen atmosphere, a mixture of 5-nitro-2-(3,3,4,4-tetrafluoropyrrolidin-1-yl)pyridine (2.17 g) and 10% palladium on carbon (533 mg) in methanol (100 mL) was stirred at room temperature for 4 hr, and then filtered. The filtrate was concentrated under reduced pressure to give the title compound (1.88 g).

MS (API+): [M+H]$^+$236.2

C) 5-methoxy-3-(1-phenyl-1H-pyrazol-5-yl)-1-[6-(3,3,4,4-tetrafluoropyrrolidin-1-yl)pyridin-3-yl]pyridazin-4(1H)-one By a method similar to Reference Example 90, step C, the title compound was obtained.

MS (API+): [M+H]$^+$487.1

Reference Example 91

5-methoxy-3-(1-phenyl-1H-pyrazol-5-yl)-1-[1-(2,2,2-trifluoroethyl)-1H-pyrazol-4-yl]pyridazin-4(1H)-one

A) 1-(2,2,2-trifluoroethyl)-1H-pyrazole-4-amine

To a suspension of 4-nitro-1H-pyrazole (500 mg) and potassium carbonate (1.22 g) in DMF (5 mL) was added dropwise 2,2,2-trifluoroethyl trifluoromethanesulfonate (1.54 g). The reaction mixture was stirred at room temperature for 4 hr, treated with water, and extracted with ethyl acetate. The extract was dried over anhydrous magnesium sulfate, and concentrated under reduced pressure. A mixture of the residue obtained above and 10% palladium on carbon (1 g) in methanol (30 mL) was stirred under a hydrogen atmosphere at room temperature for 12 hr, filtered, and concentrated under reduced pressure. The residue was purified by preparative HPLC to give the title compound (490 mg).

$^1$H NMR (300 MHz, DMSO-$d_6$) δ 3.97 (2H, brs), 4.88 (2H, q, J=9.1 Hz), 7.04 (1H, s), 7.10 (1H, s).

B) 5-methoxy-3-(1-phenyl-1H-pyrazol-5-yl)-1-[1-(2,2,2-trifluoroethyl)-1H-pyrazol-4-yl]pyridazin-4(1H)-one By a method similar to Reference Example 89, step C, the title compound was obtained.

MS (API+): [M+H]$^+$417.4

Reference Example 92

1-[1-(cyclopropylmethyl)-1H-pyrazol-4-yl]-5-methoxy-3-(1-phenyl-1H-pyrazol-5-yl)pyridazin-4(1H)-one

A) 1-(cyclopropylmethyl)-1H-pyrazol-4-amine

By a method similar to Reference Example 91, step A, the title compound was obtained.

$^1$H NMR (300 MHz, DMSO-$d_6$) δ 0.24-0.33 (2H, m), 0.42-0.54 (2H, m), 1.02-1.20 (1H, m), 3.70-3.88 (4H, m), 6.87 (1H, s), 7.06 (1H, s).

B) 1-[1-(cyclopropylmethyl)-1H-pyrazol-4-yl]-5-methoxy-3-(1-phenyl-1H-pyrazol-5-yl)pyridazin-4(1H)-one By a method similar to Reference Example 89, step C, the title compound was obtained.

MS (API+): [M+H]$^+$389.2

Reference Example 93

1-[1-(dicyclopropylmethyl)-1H-pyrazol-4-yl]-5-methoxy-3-(1-phenyl-1H-pyrazol-5-yl)pyridazin-4(1H)-one

A) 1-(dicyclopropylmethyl)-1H-pyrazol-4-amine

To a solution of 4-nitro-1H-pyrazole (500 mg), dicyclopropylmethanol (0.92 g) and triphenylphosphine (2.3 g) in THF (10 mL) was added a solution of diisopropyl azodicarboxylate in toluene (1.9 M, 4.6 mL) at room temperature. The reaction mixture was stirred at room temperature for 2 hr, treated with water, and extracted with ethyl acetate. The extract was dried over anhydrous magnesium sulfate, and concentrated under reduced pressure. A suspension of the obtained residue and 10% palladium on carbon (1 g) in methanol (30 mL) was stirred under a hydrogen atmosphere at room temperature for 12 hr, filtered, and concentrated under reduced pressure. The residue was purified by preparative HPLC to give the title compound (140 mg).

$^1$H NMR (300 MHz, DMSO-$d_6$) δ 0.11-0.24 (2H, m), 0.26-0.42 (4H, m), 0.47-0.63 (2H, m), 1.19-1.37 (2H, m), 2.80 (1H, t, J=8.7 Hz), 3.73 (2H, s), 6.87 (1H, s), 7.08 (1H, s).

B) 1-[1-(dicyclopropylmethyl)-1H-pyrazol-4-yl]-5-methoxy-3-(1-phenyl-1H-pyrazol-5-yl)pyridazin-4(1H)-one By a method similar to Reference Example 89, step C, the title compound was obtained.

MS (API+): [M+H]$^+$429.1

Reference Example 94

5-methoxy-1-[1-(1-phenylethyl)-1H-pyrazol-4-yl]-3-(1-phenyl-1H-pyrazol-5-yl)pyridazin-4(1H)-one

A) 1-(1-phenylethyl)-1H-pyrazol-4-amine

By a method similar to Reference Example 91, step A, the title compound was obtained.

B) 5-methoxy-1-[1-(1-phenylethyl)-1H-pyrazol-4-yl]-3-(1-phenyl-1H-pyrazol-5-yl)pyridazin-4(1H)-one By a method similar to Reference Example 89, step C, the title compound was obtained.

MS (API+): [M+H]$^+$439.4

Reference Example 95

5-methoxy-1-[1-(1-methylethyl)-1H-pyrazol-4-yl]-3-(1-phenyl-1H-pyrazol-5-yl)pyridazin-4(1H)-one

A) 1-(1-methylethyl)-1H-pyrazol-4-amine

By a method similar to Reference Example 91, step A, the title compound was obtained.

B) 5-methoxy-1-[1-(1-methylethyl)-1H-pyrazol-4-yl]-3-(1-phenyl-1H-pyrazol-5-yl)pyridazin-4(1H)-one By a method similar to Reference Example 89, step C, the title compound was obtained.

MS (API+): [M+H]$^+$377.0

Reference Example 96

1-[1-(1-cyclopropylethyl)-1H-pyrazol-4-yl]-5-methoxy-3-(1-phenyl-1H-pyrazol-5-yl)pyridazin-4(1H)-one A) 1-(1-cyclopropylethyl)-1H-pyrazol-4-amine By a method similar to Reference Example 93, step A, the title compound was obtained.
$^1$H NMR (300 MHz, DMSO-d$_6$) δ 0.39-0.50 (2H, m), 0.52-0.63 (1H, m), 0.65-0.76 (1H, m), 1.24-1.37 (1H, m), 1.60 (3H, d, J=6.8 Hz), 3.56-3.70 (1H, m), 3.97 (2H, brs), 7.08 (1H, s), 7.28 (1H, s).

B) 1-[1-(1-cyclopropylethyl)-1H-pyrazol-4-yl]-5-methoxy-3-(1-phenyl-1H-pyrazol-5-yl)pyridazin-4(1H)-one By a method similar to Reference Example 89, step C, the title compound was obtained.
MS (API+): [M+H]$^+$403.1

Reference Example 97

5-methoxy-1-[1-(2-methylpropyl)-1H-pyrazol-4-yl]-3-(1-phenyl-1H-pyrazol-5-yl)pyridazin-4(1H)-one A) 1-(2-methylpropyl)-1H-pyrazol-4-amine By a method similar to Reference Example 91, step A, the title compound was obtained.
MS (API+): [M+H]$^+$140.3

C) 5-methoxy-1-[1-(2-methylpropyl)-1H-pyrazol-4-yl]-3-(1-phenyl-1H-pyrazol-5-yl)pyridazin-4(1H)-one By a method similar to Reference Example 89, steps A, B and C, the title compound was obtained.
MS (API+): [M+H]$^+$391.1

Reference Example 98

1-[1-(cyclobutylmethyl)-1H-pyrazol-4-yl]-5-methoxy-3-(1-phenyl-1H-pyrazol-5-yl)pyridazin-4(1H)-one By a method similar to Reference Example 97, steps A to C, the title compound (196 mg) was obtained.
MS (API+): [M+H]$^+$403.1

Reference Example 99

1-[1-(1-cyclopropylethyl)-1H-pyrazol-4-yl]-5-methoxy-3-(1-phenyl-1H-pyrazol-5-yl)pyridazin-4(1H)-one (Retention Time Shorter)

A racemate (140 mg) of 1-[1-(1-cyclopropylethyl)-1H-pyrazol-4-yl]-5-methoxy-3-(1-phenyl-1H-pyrazol-5-yl)pyridazin-4(1H)-one was separated by HPLC (column: CHIRALCEL OJ (MC001), 50 mmID×500 mL, manufactured by DAICEL CHEMICAL INDUSTRIES, LTD., mobile phase: hexane/ethanol=1/9) to give the title compound (63 mg) having a shorter retention time.
MS (API+): [M+H]$^+$403.1

Reference Example 100

1-[1-(1-cyclopropylethyl)-1H-pyrazol-4-yl]-5-methoxy-3-(1-phenyl-1H-pyrazol-5-yl)pyridazin-4(1H)-one (Retention Time Longer)

A racemate (140 mg) of 1-[1-(1-cyclopropylethyl)-1H-pyrazol-4-yl]-5-methoxy-3-(1-phenyl-1H-pyrazol-5-yl)pyridazin-4(1H)-one was separated by HPLC (column: CHIRALCEL OJ (MC001), 50 mmID×500 mL, manufactured by DAICEL CHEMICAL INDUSTRIES, LTD., mobile phase: hexane/ethanol=1/9) to give the title compound (63 mg) having a longer retention time.
MS (API+): [M+H]$^+$403.1

Reference Example 101

1-[1-(cyclopropylmethyl)-1H-pyrazol-4-yl]-5-methoxy-3-(3-methyl-1-phenyl-1H-pyrazol-5-yl)pyridazin-4(1H)-one A) 1-methoxy-3-(3-methyl-1-phenyl-1H-pyrazol-5-yl)propan-2-one By a method similar to Reference Example 89, steps A and B, the title compound was obtained.
MS (API+), found: 247.4

B) 1-[1-(cyclopropylmethyl)-1H-pyrazol-4-yl]-5-methoxy-3-(3-methyl-1-phenyl-1H-pyrazol-5-yl)pyridazin-4(1H)-one By a method similar to Reference Example 92, the title compound was obtained.
MS (API+), found: 403.4

Reference Example 102

5-methoxy-1-{1-[(1-methylcyclopropyl)methyl]-1H-pyrazol-4-yl}-3-(1-phenyl-1H-pyrazol-5-yl)pyridazin-4(1H)-one By a method similar to Reference Example 92, the title compound was obtained.
MS (API+), found: 403.1

Reference Example 103

5-methoxy-1-[1-(2,2,3,3,3-pentafluoropropyl)-1H-pyrazol-4-yl]-3-(1-phenyl-1H-pyrazol-5-yl)pyridazin-4(1H)-one By a method similar to Reference Example 92, the title compound was obtained.
MS (API+), found: 467.3

The structural formulas of the compounds obtained in Reference Examples 75-103 are shown in the following Tables 2-1 to 2-6.

TABLE 2-1

| Ref. Ex. No. | IUPAC name | Structural Formula | MS |
|---|---|---|---|
| 75 | 1-[2-fluoro-4-(1H-pyrazol-1-yl)phenyl]-5-methoxy-3-(3-methyl-1-phenyl-1H-pyrazol-5-yl)pyridazin-4(1H)-one | | 443.3 |
| 76 | 5-methoxy-1-[2-methoxy-4-(1H-pyrazol-1-yl)phenyl]-3-(3-methyl-1-phenyl-1H-pyrazol-5-yl)pyridazin-4(1H)-one | | 455.3 |
| 77 | 3-[1-(3-chloro-2-fluorophenyl)-1H-pyrazol-5-yl]-1-[2-fluoro-4-(1H-pyrazol-1-yl)phenyl]-5-methoxypyridazin-4(1H)-one | | 481.3 |

TABLE 2-1-continued

| Ref. Ex. No. | IUPAC name | Structural Formula | MS |
|---|---|---|---|
| 78 | 3-[1-(5-chloro-2-fluorophenyl)-1H-pyrazol-5-yl]-1-[2-fluoro-4-(1H-pyrazol-1-yl)phenyl]-5-methoxypyridazin-4(1H)-one | | 481.3 |
| 79 | 1-[2-fluoro-4-(1H-pyrazol-1-yl)phenyl]-5-methoxy-3-{1-[3-(trifluoromethyl)phenyl]-1H-pyrazol-5-yl}pyridazin-4(1H)-one | | 497.2 |

TABLE 2-2

| Ref. Ex. No. | IUPAC name | Structural Formula | MS |
|---|---|---|---|
| 80 | 1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one | | |

$^1$H NMR (300 MHz, CDCl$_3$) δ 3.79 (3H, s), 6.64 (1H, d, J = 2.6 Hz), 7.03 (1H, d, J = 1.9 Hz), 7.27-7.49 (4H, m), 7.57 (1H, t, J = 8.1 Hz), 7.74-7.88 (3H, m), 7.99 (1H, dd, J = 12.1, 2.3 Hz), 8.57 (1H, d, J = 1.9 Hz), 8.66 (1H, d, J = 2.6 Hz).

TABLE 2-2-continued

| Ref. Ex. No. | IUPAC name | Structural Formula | MS |
|---|---|---|---|
| 81 | 5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one | | 509.5 |
| 82 | 3-[1-(3-chlorophenyl)-1H-pyrazol-5-yl]-5-methoxy-1-[2-methoxy-4-(1H-pyrazol-1-yl)phenyl]pyridazin-4(1H)-one | | 475.5 |
| 83 | 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one | | 552.6 |

TABLE 2-3

| Ref. Ex. No. | IUPAC name | Structural Formula | MS |
|---|---|---|---|
| 84 | 1-[4-(3,4-difluoro-1H-pyrrol-1-yl)-2-methoxyphenyl]-5-methoxy-3-(1-phenyl-1H-pyrazol-5-yl)pyridazin-4(1H)-one | | 476.4 |
| 85 | 1-[2-(difluoromethoxy)-4-(3,4-difluoro-1H-pyrrol-1-yl)phenyl]-5-methoxy-3-(1-phenyl-1H-pyrazol-5-yl)pyridazin-4(1H)-one | | 512.5 |
| 86 | 1-[4-(3,4-difluoro-1H-pyrrol-1-yl)-2-(2,2,2-trifluoroethoxy)phenyl]-5-methoxy-3-(1-phenyl-1H-pyrazol-5-yl)pyridazin-4(1H)-one | | 544.5 |

TABLE 2-3-continued

| Ref. Ex. No. | IUPAC name | Structural Formula | MS |
|---|---|---|---|
| 87 | 5-methoxy-1-[2-methoxy-4-(3,3,4,4-tetrafluoropyrrolidin-1-yl)phenyl]-3-(1-phenyl-1H-pyrazol-5-yl)pyridazin-4(1H)-one | | 516.5 |
| 88 | 5-methoxy-3-(1-phenyl-1H-pyrazol-5-yl)-1-(1,3-thiazol-2-yl)pyridazin-4(1H)-one | | 352.3 |
| 89 | 1-(1-benzyl-1H-pyrazol-4-yl)-5-methoxy-3-(1-phenyl-1H-pyrazol-5-yl)pyridazin-4(1H)-one | | 425.3 |

TABLE 2-4

| Ref. Ex. No. | IUPAC name | Structural Formula | MS |
|---|---|---|---|
| 90 | 5-methoxy-3-(1-phenyl-1H-pyrazol-5-yl)-1-[6-(3,3,4,4-tetrafluoropyrrolidin-1-yl)pyridin-3-yl]pyridazin-4(1H)-one | | 487.1 |
| 91 | 5-methoxy-3-(1-phenyl-1H-pyrazol-5-yl)-1-[1-(2,2,2-trifluoroethyl)-1H-pyrazol-4-yl]pyridazin-4(1H)-one | | 417.4 |
| 92 | 1-[1-(cyclopropylmethyl)-1H-pyrazol-4-yl]-5-methoxy-3-(1-phenyl-1H-pyrazol-5-yl)pyridazin-4(1H)-one | | 389.2 |

TABLE 2-4-continued

| Ref. Ex. No. | IUPAC name | Structural Formula | MS |
|---|---|---|---|
| 93 | 1-[1-(dicyclopropylmethyl)-1H-pyrazol-4-yl]-5-methoxy-3-(1-phenyl-1H-pyrazol-5-yl)pyridazin-4(1H)-one | | 429.1 |
| 94 | 5-methoxy-1-[1-(1-phenylethyl)-1H-pyrazol-4-yl]-3-(1-phenyl-1H-pyrazol-5-yl)pyridazin-4(1H)-one | | 439.4 |
| 95 | 5-methoxy-1-[1-(1-methylethyl)-1H-pyrazol-4-yl]-3-(1-phenyl-1H-pyrazol-5-yl)pyridazin-4(1H)-one | | 377.0 |

TABLE 2-5

| Ref. Ex. No. | IUPAC name | Structural Formula | MS |
|---|---|---|---|
| 96 | 1-[1-(1-cyclopropylethyl)-1H-pyrazol-4-yl]-5-methoxy-3-(1-phenyl-1H-pyrazol-5-yl)pyridazin-4(1H)-one | | 403.1 |
| 97 | 5-methoxy-1-[1-(2-methylpropyl)-1H-pyrazol-4-yl]3-(1-phenyl-1H-pyrazol-5-yl)pyridazin-4(1H)-one | | 391.1 |
| 98 | 1-[1-(cyclobutylmethyl)-1H-pyrazol-4-yl]-5-methoxy-3-(1-phenyl-1H-pyrazol-5-yl)pyridazin-4(1H)-one | | 403.1 |
| 99 | 1-[1-(1-cyclopropylethyl)-1H-pyrazol-4-yl]-5-methoxy-3-(1-phenyl-1H-pyrazol-5-yl)pyridazin-4(1H)-one | | 403.1 |

TABLE 2-5-continued

| Ref. Ex. No. | IUPAC name | Structural Formula | MS |
|---|---|---|---|
| 100 | 1-[1-(1-cyclopropylethyl)-1H-pyrazol-4-yl]-5-methoxy-3-(1-phenyl-1H-pyrazol-5-yl)pyridazin-4(1H)-one | | 403.1 |
| 101 | 1-[1-(cyclopropylmethyl)-1H-pyrazol-4-yl]-5-methoxy-3-(3-methyl-1-phenyl-1H-pyrazol-5-yl)pyridazin-4(1H)-one | | 403.4 |

TABLE 2-6

| Ref. Ex. No. | IUPAC name | Structural Formula | MS |
|---|---|---|---|
| 102 | 5-methoxy-1-{1-[(1-methylcyclopropyl)methyl]-1H-pyrazol-4-yl}-3-(1-phenyl-1H-pyrazol-5-yl)pyridazin-4(1H)-one | | 403.1 |

TABLE 2-6-continued

| Ref. Ex. No. | IUPAC name | Structural Formula | MS |
|---|---|---|---|
| 103 | 5-methoxy-1-[1-(2,2,3,3,3-pentafluoropropyl)-1H-pyrazol-4-yl]-3-(1-phenyl-1H-pyrazol-5-yl)pyridazin-4(1H)-one | | 467.3 |

Reference Examples 104-121

In the same manner as in Reference Examples 75-103, the compounds of Reference Examples 104-121 were obtained. The structural formulas of the compounds are shown in the following Tables 3-1 to 3-4.

TABLE 3-1

| Ref. Ex. No. | IUPAC name | Structural Formula | MS |
|---|---|---|---|
| 104 | 1-[2-(difluoromethoxy)-4-(3,3,4,4-tetrafluoropyrrolidin-1-yl)phenyl]-5-methoxy-3-(1-phenyl-1H-pyrazol-5-yl)pyridazin-4(1H)-one | | 552.2 |
| 105 | 1-[2-fluoro-4-(5-methoxy-1H-pyrazol-1-yl)phenyl]-5-methoxy-3-(1-phenyl-1H-pyrazol-5-yl)pyridazin-4(1H)-one | | 459.2 |

TABLE 3-1-continued

| Ref. Ex. No. | IUPAC name | Structural Formula | MS |
|---|---|---|---|
| 106 | 1-{4-[5-(cyclopropylmethoxy)-1H-pyrazol-1-yl]-2-fluorophenyl}-5-methoxy-3-(1-phenyl-1H-pyrazol-5-yl)pyridazin-4(1H)-one | | 499.3 |
| 107 | 1-{2-fluoro-4-[5-(2,2,2-trifluoroethoxy)-1H-pyrazol-1-yl]phenyl}-5-methoxy-3-(1-phenyl-1H-pyrazol-5-yl)pyridazin-4(1H)-one | | 527.3 |

TABLE 3-1-continued

| Ref. Ex. No. | IUPAC name | Structural Formula | MS |
|---|---|---|---|
|  | 1-[4-(3,3-difluoropiperidin-1-yl)-2-fluorophenyl]-5-methoxy-3-(1-phenyl-1H-pyrazol-5-yl)pyridazin-4(1H)-one |  | 482.2 |

TABLE 3-2

| Ref. Ex. No. | IUPAC name | Structural Formula | MS |
|---|---|---|---|
| 109 | 3-[1-(3-chlorophenyl)-1H-pyrazol-5-yl]-1-(2-fluoro-4-iodophenyl)-5-methoxypyridazin-4(1H)-one |  | 523.1 |
| 110 | 1-(2-fluoro-4-iodophenyl)-3-[1-(2-fluorophenyl)-1H-pyrazol-5-yl]-5-methoxypyridazin-4(1H)-one |  | 506.9 |

TABLE 3-2-continued

| Ref. Ex. No. | IUPAC name | Structural Formula | MS |
|---|---|---|---|
| 111 | 1-[2-(difluoromethoxy)-4-iodophenyl]-5-methoxy-3-(1-phenyl-1H-pyrazol-5-yl)pyridazin-4(1H)-one | | 537.2 |
| 112 | 1-[2-(difluoromethoxy)-4-(1H-pyrazol-1-yl)phenyl]-5-methoxy-3-(1-phenyl-1H-pyrazol-5-yl)pyridazin-4(1H)-one | | 477.3 |
| 113 | 5-methoxy-3-(1-phenyl-1H-pyrazol-5-yl)-1-[4-(1H-pyrazol-1-yl)-2-(2,2,2-trifluoroethoxy)phenyl]pyridazin-4(1H)-one | | 509.3 |
| 114 | 1-[2-(2,2-difluoroethoxy)-4-(1H-pyrazol-1-yl)phenyl]-5-methoxy-3-(1-phenyl-1H-pyrazol-5-yl)pyridazin-4(1H)-one | | 491.3 |

TABLE 3-3

| Ref. Ex. No. | IUPAC name | Structural Formula | MS |
|---|---|---|---|
| 115 | 1-(4-iodo-phenyl)-5-methoxy-3-(1-phenyl-1H-pyrazol-5-yl)pyridazin-4(1H)-one | | 471.2 |
| 116 | 1-{4-[(2R,6S)-2,6-dimethyl-morpholin-4-yl]-2-fluorophenyl}-5-methoxy-3-(1-phenyl-1H-pyrazol-5-yl)pyridazin-4(1H)-one | | 476.3 |
| 117 | 1-(4-iodo-2-methoxyphenyl)-5-methoxy-3-(1-phenyl-1H-pyrazol-5-yl)pyridazin-4(1H)-one | | 501.1 |
| 118 | 1-[2-fluoro-4-(1H-pyrazol-1-yl)phenyl]-5-methoxy-3-(1H-pyrazol-5-yl)pyridazin-4(1H)-one | | 353.3 |

TABLE 3-3-continued

| Ref. Ex. No. | IUPAC name | Structural Formula | MS |
|---|---|---|---|
| 119 | 1-[2-fluoro-4-(8-oxa-3-azabicyclo[3.2.1]oct-3-yl)phenyl]-5-methoxy-3-(1-phenyl-1H-pyrazol-5-yl)pyridazin-4(1H)-one | | 474.5 |
| 120 | 1-[2-fluoro-4-(1,4-oxazepan-4-yl)phenyl]-5-methoxy-3-(1-phenyl-1H-pyrazol-5-yl)pyridazin-4(1H)-one | | 462.4 |

TABLE 3-4

| Ref. Ex. No. | IUPAC name | Structural Formula | MS |
|---|---|---|---|
| 121 | 5-methoxy-3-(1-phenyl-1H-pyrazol-5-yl)-1-[4-(1H-pyrazol-1-yl)phenyl]pyridazin-4(1H)-one | | 411.4 |

Reference Example 122

5-(Fluoromethoxy-d$_2$)-1-{2-fluoro-4-(tetrahydro-2H-pyran-4-yl)phenyl}-3-(1-phenyl-1H-pyrazol-5-yl)pyridazin-4(1H)-one

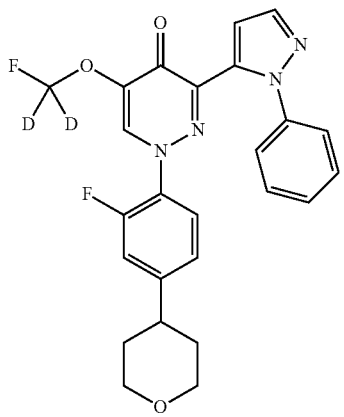 [SMILES: [2H]C([2H])(F)Oc1cn(-c2ccc(C3CCOCC3)cc2F)nc(-c2ccnn2-c2ccccc2)c1=O]

1) Fluoroiodomethane-d$_2$

Diiodomethane-d$_2$ (10 g) was charged under argon flow into the oven dried two neck round bottomed flask equipped with solid addition system and water-cooled condenser before the receiver flask. Ampoules were rinsed with Et$_2$O (2 ml) to complete the transfer. HgF (6.8 g) was charged into the solid addition system and the system was evacuated to residual pressure 75 Torr while slow flow of argon was maintained through the system. Flask containing diiodomethane-d$_2$ was heated to 40° C. Receiver flask was placed then into dry ice alcohol bath and temperature in the reaction flask was raised to 65° C. HgF was added portionwise over 105 min to the stirred mixture at 65-75° C. maintaining the pressure in the system at 75 Torr. Heating was then continued for 2 hr raising the temperature gradually from 75° C. to 100° C. System was filled with argon and the content in the receiver flask was distilled at ambient pressure to give the title compound (0.101 g) as colorless liquid.

2) 5-(Fluoromethoxy-d$_2$)-1-{2-fluoro-4-(tetrahydro-2H-pyran-4-yl)phenyl}-3-(1-phenyl-1H-pyrazol-5-yl)pyridazin-4(1H)-one 1-{2-Fluoro-4-(tetrahydro-2H-pyran-4-yl)phenyl}-5-hydroxy-3-(1-phenyl-1H=pyrazol-5-yl)pyridazin-4(1H)-one (51 mg) was weighed into 10 ml oven dried round bottomed flask. The flask was purged with argon. DMF (0.7 ml) was added and the resulting suspension was stirred briefly at 0° C. A suspension of 60% NaH (9 mg) in DMF was added to the mixture in one portion under flow of argon. The mixture was stirred at 0° C. for 5 min, and then a solution of fluoroiodomethane-d$_2$ (20 mg) in DMF (0.2 ml) was added dropwise. The syringe and reagent vial were rinsed with DMF (0.5 ml) to complete the addition. The mixture was stirred at 0° C. for 10 min and then at room temperature for 2.5 hr. The ice cooled light yellow solution was quenched with water (1 ml), stirred for 5 min and partitioned then between water (35 ml) and EtOAc (20 ml). Organic layer was separated and the water layer was extracted with EtOAc (2×10 ml). Combined organic layers were washed with mixture of brine (10 ml) and water (20 ml), then with mixture of brine (10 ml), water (10 ml) and 5% Na$_2$S$_2$O$_3$ solution and finally with brine (15 ml), dried over MgSO$_4$, and filtered through cotton, and the filtrate was concentrated in vacuo. The residue was purified by silica gel column chromatography eluting with EtOAc/1% Et$_3$N to give the title compound (53 mg) as white powder.

$^1$H-NMR (200 MHz, CDCl$_3$) δ 1.66-1.82 (4H, m), 2.77 (1H, m), 3.40-3.61 (2H, m), 4.02-4.15 (2H, m), 6.37 (1H, t, J=8.2 Hz), 6.87 (1H, d, J=8.4 Hz), 7.03 (1H, m), 7.26-7.51 (6H, m), 7.79 (1H, d, J=1.8 Hz), 8.13 (1H, d, J=1.8 Hz).

Reference Example 123

5-(2-Fluoroethoxy-d$_4$)-1-{2-fluoro-4-(tetrahydro-2H-pyran-4-yl)phenyl}-3-(1-phenyl-1H-pyrazol-5-yl)pyridazin-4(1H)-one

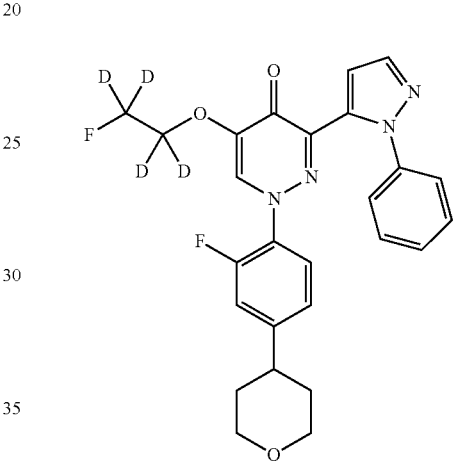

1) 2-Fluoroethyl-d$_4$-tosylate

To the stirred solution of ethylene-d$_4$ glycol (1.1 g) in CH$_2$Cl$_2$ (20 ml) was added under flow of argon over 3 min a solution of p-toluenesulfonyl chloride (7.3 g) and pyridine (8 g) in CH$_2$Cl$_2$ (20 ml). The mixture was stirred at room temperature for 18 hr. To the mixture was added CH$_2$Cl$_2$ (20 ml) and the mixture was stirred at room temperature for 48 hr. The reaction mixture was poured into water (40 ml) and extracted with CH$_2$Cl$_2$ (10+5 ml). Combined organic layers were washed with 1 M HCl (40 ml), water (20 ml) and brine (40 ml), dried over Na$_2$SO$_4$, and filtered through cotton, and the filtrate was concentrated in vacuo. Crystalline solid was removed from the flask walls, crushed and dried further in vacuo. To the resulting fine crystalline solid was added hot EtOAc (40 ml) and the mixture was heated until all the material dissolved. Hot hexane (10 ml) was added to the solution, and the mixture was gently shaken and left to crystallize at room temperature for 2.5 days. The mixture was cooled at 4° C. for 2 hr and filtered. Crystals were washed with hexane (2×15 ml), with mixture of EtOAc/hexane (1/1, 15 ml) and again with hexane (2×15 ml) to give white crystal of ethylene-d$_4$ ditosylate (4.9 g).

To the stirred solution of ethylene-d$_4$ ditosylate (0.52 g) in CH$_3$CN (16 ml) was added with syringe 1 M tetrabutylammonium fluoride solution in THF (1.8 ml) under argon atmosphere. The syringe was rinsed with CH$_3$CN (0.5 ml). The mixture was refluxed for 70 min and concentrated in vacuo. The residue was dissolved in EtOAc (30 ml) and washed with water (30 ml). Water layer was extracted with EtOAc (10 ml). Combined organic layers were washed with brine (2×15 ml), dried over Na$_2$SO$_4$, and filtered through cotton, and the filtrate was concentrated in vacuo. The residue was purified by silica gel column chromatography eluting with EtOAc/hexane to give the title compound (0.12 g) as colorless oil.

2) 5-(2-Fluoroethoxy-d$_4$)-1-{2-fluoro-4-(tetrahydro-2H-pyran-4-yl)phenyl}-3-(1-phenyl-1H-pyrazol-5-yl)pyridazin-4(1H)-one 1-{2-Fluoro-4-(tetrahydro-2H-pyran-4-yl)phenyl}-5-hydroxy-3-(1-phenyl-1H-pyrazol-5-yl)pyridazin-4(1H)-one (50 mg) was weighed into 4 ml glass vial and K$_2$CO$_3$ (35 mg) was added. Vial was flushed with argon and DMF (0.6 ml) was added. To the stirred yellowish suspension was added a solution of 2-fluoroethyl-d$_4$-tosylate (51 mg) in DMF (0.2 ml). The transfer pipette and the reagent vial were rinsed additionally with DMF (0.1 ml). The mixture was stirred at room temperature for 20 hr, at 75° C. for 3 hr and at room temperature for 43 hr. The mixture was treated with water and EtOAc was added. Organic layer was separated and water layer was extracted with EtOAc. Combined organic layers were washed with a mixture of sat. NaHCO$_3$ (15 ml) and water (5 ml) then with brine (20 ml), dried over MgSO$_4$ and concentrated in vacuo. The residue was purified by silica gel column chromatography eluting with EtOAc/ 1% Et$_3$N to give a turbid solid. The turbid solid was dissolved in hot toluene (2 ml) and the obtained solution was concentrated in vacuo to give a solid foam. The solid was triturated with Et$_2$O and hexane, and the liquid was removed with pipette. The residue was washed with hexane and then dried in vacuo to give the title compound (51 mg) as an off-white fine powder.

$^1$H-NMR (400 MHz, CDCl$_3$) δ 1.70-1.82 (4H, m), 2.77 (1H, m), 3.48-3.54 (2H, m), 4.07-4.11 (2H, m), 6.38 (1H, t, J=8.4 Hz), 6.86 (1H, d, J=8.4 Hz), 7.02 (1H, m), 7.26 (1H, m), 7.36-7.48 (5H, m), 7.77 (1H, d, J=2.0 Hz), 8.00 (1H, d, J=2.0 Hz).

Reference Example 124

5-(Fluoromethoxy)-1-{2-fluoro-4-(tetrahydro-2H-pyran-4-yl)phenyl}-3-(1-phenyl-1H-pyrazol-5-yl)pyridazin-4(1H)-one

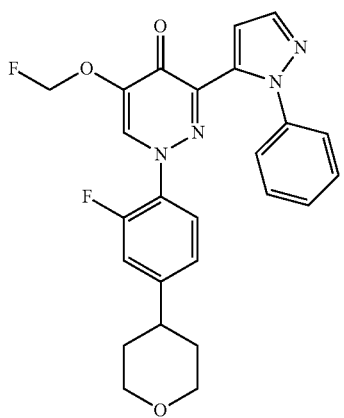 [SMILES: O=c1c(OCF)cn(-c2ccc(C3CCOCC3)cc2F)nc1-c1ccnn1-c1ccccc1]

To a stirred mixture of 1-{2-fluoro-4-(tetrahydro-2H-pyran-4-yl)phenyl}-5-hydroxy-3-(1-phenyl-1H-pyrazol-5-yl)pyridazin-4(1H)-one (70 mg) in DMF (2 mL) was added 60% sodium hydride (7.12 mg) at room temperature. The mixture was stirred at room temperature for 30 min, and bromofluoromethane (27.4 mg) was added. The mixture was stirred at room temperature for 12 hr, treated with water and extracted with EtOAc. The organic layer was dried over MgSO$_4$ and concentrated in vacuo. The residue was purified by silica gel column chromatography eluting with EtOAc/ MeOH and crystallized from EtOAc/Hexane to give the title compound (40 mg) as white crystal.

$^1$H-NMR (300 MHz, DMSO-d$_6$) δ 1.56-1.78 (4H, m), 2.78-2.94 (1H, m), 3.36-3.51 (2H, m), 3.87-4.01 (2H, m), 5.74 (1H, s), 5.92 (1H, s), 6.94 (1H, t, J=8.3 Hz), 7.05 (1H, d, J=1.5 Hz), 7.09-7.19 (1H, m), 7.29-7.49 (6H, m), 7.81 (1H, d, J=1.9 Hz), 8.75 (1H, d, J=1.9 Hz).

MS (API+): [M+H]+465.2

Reference Example 125

5-(2-Fluoroethoxy)-1-{2-fluoro-4-(tetrahydro-2H-pyran-4-yl)phenyl}-3-(1-phenyl-1H-pyrazol-5-yl)pyridazin-4(1H)-one

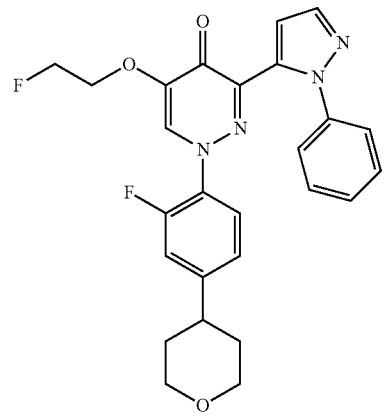 [SMILES: O=c1c(OCCF)cn(-c2ccc(C3CCOCC3)cc2F)nc1-c1ccnn1-c1ccccc1]

To a stirred mixture of 1-{2-fluoro-4-(tetrahydro-2H-pyran-4-yl)phenyl}-5-hydroxy-3-(1-phenyl-1H-pyrazol-5-yl)pyridazin-4(1H)-one (85 mg), 2-fluoroethanol (25.2 mg) and triphenylphosphine (103 mg) in THF (3 mL) was added 1.9 M diisopropyl azodicaroxylate in toluene (0.21 mL) at room temperature. The mixture was stirred at room temperature for 1 hr, treated with water and extracted with EtOAc. The organic layer was dried over MgSO$_4$ and concentrated in vacuo. The residue was purified by silica gel column chromatography eluting with EtOAc/Hexane and crystallized from EtOAc/IPE to give the title compound (40 mg) as white crystal.

$^1$H-NMR (300 MHz, DMSO-d$_6$) δ 1.61-1.76 (4H, m), 2.80-2.95 (1H, m), 3.36-3.50 (2H, m), 3.88-4.01 (2H, m), 4.15-4.36 (2H, m), 4.59-4.84 (2H, m), 6.89-7.06 (2H, m), 7.14 (1H, dd, J=8.3, 1.9 Hz), 7.28-7.48 (6H, m), 7.79 (1H, d, J=1.9 Hz), 8.55 (1H, d, J=2.3 Hz).

MS (API+): [M+H]+479.2

Examples

Example 1

Production of [$^{11}$C]CH$_3$OTf from [$^{11}$C]CH$_4$

[$^{11}$C]CH$_4$ was obtained via the $^{14}$N(p,α)$^{11}$C reaction on nitrogen with 10% hydrogen, with 16.4 MeV protons. Typically, the target gas was irradiated for 10-20 minutes with a beam intensity of 35 μA. The recirculation system was flushed with helium for 10-20 minutes before radioactivity release. [$^{11}$C]CH$_3$I was produced according to previously published methods (Applied Radiation and Isotopes, 1997. 48(2): 153-157; Applied Radiation and Isotopes, 2009. 67(1): 106-110.). In short, [$^{11}$C]CH$_4$ was released and passed through a phosphorous pentoxide trap (to remove trace amounts of ammonia and water produced in the target) and collected in a HayeSep D trap cooled with liquid nitrogen. The nitrogen and hydrogen were flushed to waste using helium. Following collection the [$^{11}$C]CH$_4$ was released from the trap by heating, into a recirculation system consisting of a micro diaphragm gas pump (NMP830 KVDC, KNF Neuberger, Freiburg, Germany), three ovens, a HayeSep D trap and a Quartz tube containing iodine and ascarite. First the [$^{11}$C]CH$_4$ was pumped to the quartz tube where it was mixed with vapours from iodine crystals at 60° C. and then reaction occurred at 720° C. After the reaction the iodine and HI were trapped in ascarite while the [$^{11}$C]CH$_3$I was collected in the HayeSep D trap at room temperature and the unreacted [$^{11}$C]CH$_4$ was recirculated for five minutes. [$^{11}$C]CH$_3$I was released from the HayeSep D trap by heating the trap to 200° C. [$^{11}$C]CH$_3$OTf was prepared by sweeping [$^{11}$C]CH$_3$I vapour through a soda-glass column (i.d 3.7 mm; length 150 mm; oven temp. 165° C.) containing silver-triflate-impregnated graphitized carbon, as previously described (Nucl Med Biol, 1995. 22(2): 235-239). The [$^{11}$C]CH$_3$OTf was trapped at room temperature in a vessel containing the precursor where labeling occurred.

Example 2

1-[4-(3,3-Difluoroazetidin-1-yl)-2-fluorophenyl]-5-[$^{11}$C]methoxy)-3-(1-phenyl-1H-pyrazol-5-yl)pyridazin-4(1H)-one

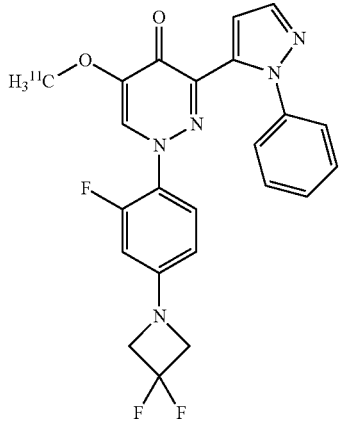 [SMILES: [11CH3]Oc1cn(-c2ccc(N3CC(F)(F)C3)cc2F)nc(-c2ccnn2-c2ccccc2)c1=O]

(1) Methyl 2-(benzyloxy)acetate

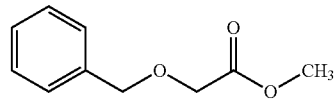

A mixture of 2-(benzyloxy)acetic acid (20 g) and H$_2$SO$_4$ (10 μL) in MeOH (200 mL) was stirred at 70° C. for 2 hr and evaporated. The residue was treated with saturated NaHCO$_3$ solution, and extracted with AcOEt. The organic layer was dried over MgSO$_4$, passed through silica gel pad and concentrated under reduced pressure to give the title compound (18.1 g).

$^1$H-NMR (300 MHz, DMSO-d$_6$) δ 3.67 (3H, s), 4.17 (2H, s), 4.54 (2H, s), 7.16-7.54 (5H, m).

(2) 1-(Benzyloxy)pentane-2,4-dione

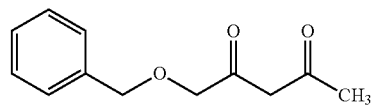

To a stirred mixture of methyl 2-(benzyloxy)acetate (17.6 g) and acetone (7.17 mL) in THF (20 mL) was added dropwise a suspension of sodium tert-butoxide (9.39 g) in THF (20 mL) at 0° C. The mixture was stirred at 0° C. for 30 min, and evaporated. The residue was treated with 1N HCl, and extracted with AcOEt. The organic layer was dried over MgSO$_4$ and concentrated under reduced pressure. The residue was purified by column chromatography on silica gel eluting with AcOEt/hexane=1/10 to give the title compound (11.3 g) as colorless oil.

$^1$H-NMR (300 MHz, CDCl$_3$) δ 2.03-2.32 (3H, s), 4.09 (2H, s), 4.57 (2H, s), 5.86 (1H, s), 7.30-7.50 (5H, m).

(3) 1-(Benzyloxy)-3-[(2-fluoro-4-iodophenyl)hydrazono]pentane-2,4-dione

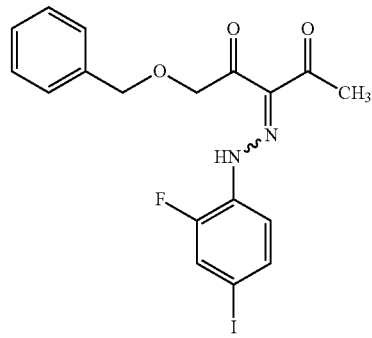 [SMILES: CC(=O)C(=NNc1ccc(I)cc1F)C(=O)COCc1ccccc1]

To a stirred mixture of 2-fluoro-4-iodoaniline (5.75 g) and 6 N HCl aq (24.3 mL) was added dropwise a solution of sodium nitrite (2.0 g) in water (6.1 mL) at 0° C., and the mixture was stirred at 0° C. for 20 min. The mixture was poured into a stirred suspension of 1-(benzyloxy)pentane-2,4-dione (5 g) and sodium acetate (11.9 g) in MeOH (48 mL). The mixture was stirred at 0° C. for 20 min. To the mixture was added water (76 mL) and the precipitate was collected by filtration to give the title compound (10.7 g) as a yellow powder.

$^1$H-NMR (300 MHz, DMSO-$d_6$) δ 2.39-2.53 (3H, m), 4.58 (2H, d, J=6.4 Hz), 4.67 (1H, s), 4.80 (1H, s), 7.13-7.47 (5H, m), 7.47-7.78 (2H, m), 7.78-8.00 (1H, m), 14.31 (1H, d, J=5.3 Hz).

(4) 5-(Benzyloxy)-1-(2-fluoro-4-iodophenyl)-3-(1-phenyl-1H-pyrazol-5-yl)pyridazin-4(1H)-one

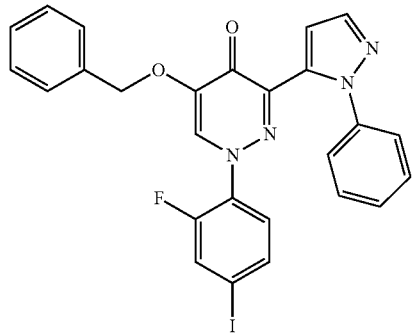 [SMILES: O=c1c(OCc2ccccc2)cn(-c2ccc(I)cc2F)nc1-c1ccnn1-c1ccccc1]

To a solution of 1-(benzyloxy)-3-[(2-fluoro-4-iodophenyl)hydrazono]pentane-2,4-dione (10.7 g) in DMA (30 mL) was added N,N-dimethylformamide dimethyl acetal (9.38 mL). The mixture was stirred at 80° C. for 2 hr and then evaporated. To the residue was added EtOH (200 mL). To the stirred mixture was added a solution of phenylhydrazine (2.46 mL) and TFA (20 mL) in EtOH (180 mL) at 0° C. The mixture was stirred at room temperature for 16 hr. The precipitate was collected by filtration and washed with EtOH to give the title compound (8.95 g).

MS (API+): [M+H]+565.3

$^1$H-NMR (300 MHz, DMSO-$d_6$) δ 5.08 (2H, s), 6.76 (1H, t, J=8.3 Hz), 7.00 (1H, d, J=1.9 Hz), 7.30-7.34 (2H, m), 7.35-7.43 (8H, m), 7.61 (1H, d, J=8.3 Hz), 7.79 (1H, d, J=1.9 Hz), 7.92 (1H, dd, J=10.2, 1.5 Hz), 8.60 (1H, d, J=1.9 Hz).

(5) 5-(Benzyloxy)-1-[4-(3,3-difluoroazetidin-1-yl)-2-fluorophenyl]-3-(1-phenyl-1H-pyrazol-5-yl)pyridazin-4(1H)-one

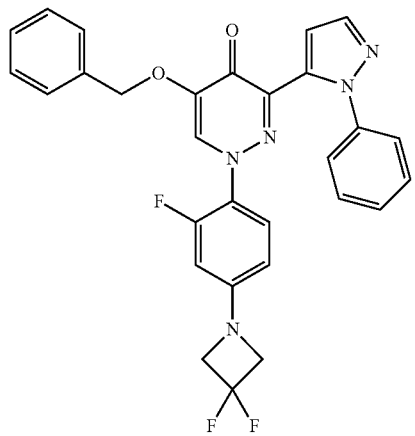 [SMILES: O=c1c(OCc2ccccc2)cn(-c2ccc(N3CC(F)(F)C3)cc2F)nc1-c1ccnn1-c1ccccc1]

Under argon atmosphere, a suspension of 5-(benzyloxy)-1-(2-fluoro-4-iodophenyl)-3-(1-phenyl-1H-pyrazol-5-yl)pyridazin-4(1H)-one (564 mg), 3,3-difluoroazetidine hydrochloride (155 mg), Pd$_2$(dba)$_3$ (220 mg), Xantphos (278 mg), and sodium tert-butoxide (250 mg) in 1,4-dioxane (5 mL) was stirred at room temperature for 48 hr. The reaction mixture was poured into water and extracted with AcOEt. The organic layer was washed with brine, dried over MgSO$_4$, and concentrated under reduced pressure. The residue was purified by silica gel column chromatography eluting with hexane/AcOEt and crystallized from hexane/AcOEt to give the title compound (145 mg) as an off-white powder.

MS (API+): [M+H]+530.1

$^1$H-NMR (300 MHz, DMSO-$d_6$) δ 4.35 (4H, t, J=12.5 Hz), 5.09 (2H, s), 6.35 (1H, dd, J=8.5, 2.1 Hz), 6.60 (1H, dd, J=12.8, 2.3 Hz), 6.79-6.99 (2H, m), 7.24-7.52 (10H, m), 7.78 (1H, d, J=1.9 Hz), 8.49 (1H, d, J=1.9 Hz).

(6) 1-[4-(3,3-Difluoroazetidin-1-yl)-2-fluorophenyl]-5-hydroxy-3-(1-phenyl-1H-pyrazol-5-yl)pyridazin-4(1H)-one

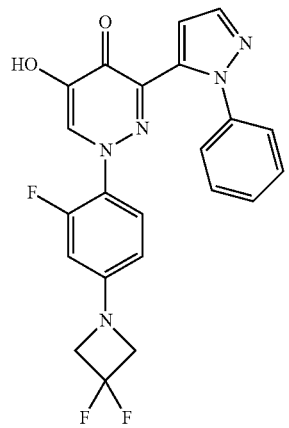 [SMILES: O=c1c(O)cn(-c2ccc(N3CC(F)(F)C3)cc2F)nc1-c1ccnn1-c1ccccc1]

Under H$_2$ atmosphere, a mixture of 5-(benzyloxy)-1-[4-(3,3-difluoroazetidin-1-yl)-2-fluorophenyl]-3-(1-phenyl-1H-pyrazol-5-yl)pyridazin-4(1H)-one (135 mg) and 10% Pd—C (50 mg) in AcOEt (5 mL) and MeOH (5 mL) was stirred at room temperature for 2 hr, and filtered. The filtrate was concentrated under reduced pressure and the residue was crystallized from CH$_3$CN/H$_2$O. The crystals obtained were recrystallized from CH$_3$CN to give the title compound (70 mg) as a white powder.

MS (API+): [M+H]+440.1

$^1$H-NMR (300 MHz, DMSO-$d_6$) δ 4.35 (4H, t, J=12.3 Hz), 6.35 (1H, dd, J=8.7, 1.9 Hz), 6.60 (1H, dd, J=13.0, 2.5 Hz), 6.86-7.00 (2H, m), 7.24-7.47 (5H, m), 7.79 (1H, d, J=1.9 Hz), 8.32 (1H, d, J=2.3 Hz).

(7) 1-[4-(3,3-Difluoroazetidin-1-yl)-2-fluorophenyl]-5-[$^{11}$C]methoxy)-3-(1-phenyl-1H-pyrazol-5-yl)pyridazin-4(1H)-one

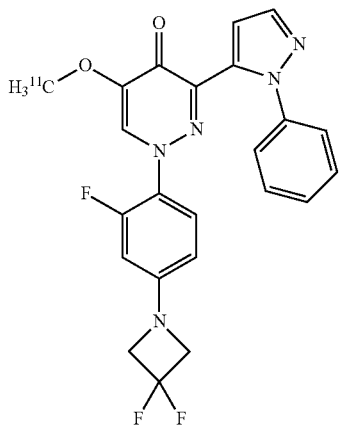 [SMILES: [11CH3]Oc1cn(-c2ccc(N3CC(F)(F)C3)cc2F)nc(-c2ccnn2-c2ccccc2)c1=O]

Sodium hydroxide (0.5 M, 3-4 μL) was added to 1-[4-(3,3-difluoroazetidin-1-yl)-2-fluorophenyl]-5-hydroxy-3-(1-phenyl-1H-pyrazol-5-yl)pyridazin-4(1H)-one (0.2-0.5 mg) in a glass vial, and then acetone (500 μL) was added to the same vial and the mixture was thoroughly mixed. The [$^{11}$C]CH$_3$OTf (10-25 GBq), prepared in Example 1, was trapped into the vial at room temperature and incubated for 40 to 60 seconds. Then the reaction mixture was diluted with mobile phase used for HPLC purification. The diluted mixture was transferred to the Ascentis RP-Amide reverse-phase HPLC column and eluted with acetonitrile (MeCN)/0.1% aqueous triethylamine mixture as mobile phase. The fraction containing $^{11}$C-labelled compound was collected in a vial containing sterile water (50 ml) and sodium ascorbate (300 mg) and then pushed trough Waters Oasis HLB cartridge to adsorb labelled compound. The cartridge was then washed with distilled water (8 ml) and $^{11}$C-labelled ligand was eluted with 99.6% ethanol (1.0 ml) into a vial containing sterile PBS (10 ml). The solution was then filtered though sterile 0.22 μm particle filter to obtain sterile injectable formulation. Sample for radiochemical purity/pyrogen determination was taken from the final composition.

Example 3

1-[2-Fluoro-4-(tetrahydro-2H-pyran-4-yl)phenyl]-5-[$^{11}$C]methoxy-3-(1-phenyl-1H-pyrazol-5-yl)pyridazin-4(1H)-one

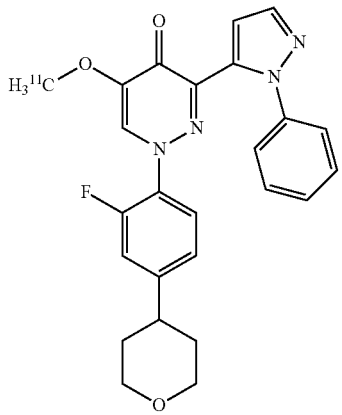 [SMILES: [11CH3]Oc1cn(-c2ccc(C3CCOCC3)cc2F)nc(-c2ccnn2-c2ccccc2)c1=O]

(1) 4-(3,6-Dihydro-2H-pyran-4-yl)-2-fluoroaniline

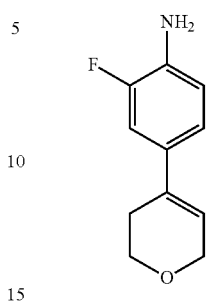

To a mixture of 2-fluoro-4-iodoaniline (5.37 g), 2-(3,6-dihydro-2H-pyran-4-yl)-4,4,5,5-tetramethyl-1,3,2-dioxaborolane (5 g), palladium acetate (0.25 g) and X-phos (1.08 g) in DME (84 mL) was added a solution of cesium carbonate (18.5 g) in water (28 mL). Under argon atmosphere, the mixture was stirred at 90° C. for 12 hr, diluted with water and extracted with AcOEt. The organic layer was dried over MgSO$_4$ and concentrated under reduced pressure. The residue was purified by column chromatography on silica gel eluting with hexane/AcOEt=10/1 to 5/1 to give the title compound (3.2 g).

$^1$H-NMR (300 MHz, DMSO-d$_6$) δ 2.29-2.40 (2H, m), 3.77 (2H, d, J=11.0 Hz), 4.17 (2H, q, J=2.9 Hz), 5.15 (2H, s), 6.05 (1H, dt, J=3.0, 1.5 Hz), 6.72 (1H, dd, J=9.5, 8.3 Hz), 6.99 (1H, dd, J=8.3, 2.3 Hz), 7.08 (1H, dd, J=13.4, 2.1 Hz).

(2) 2-Fluoro-4-(tetrahydro-2H-pyran-4-yl)aniline

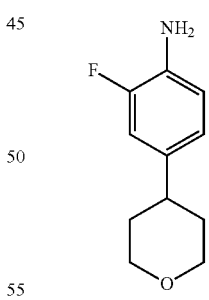

Under H$_2$ atmosphere, a mixture of 4-(3,6-dihydro-2H-pyran-4-yl)-2-fluoroaniline (3.62 g) and 10% Pd—C (0.36 g) in EtOH (75 mL) was stirred at room temperature for 5 hr, and then filtered. The filtrate was concentrated under reduced pressure to give the title compound (3.53 g) as white solid.

$^1$H-NMR (300 MHz, DMSO-d$_6$) δ 1.46-1.70 (4H, m), 2.55-2.69 (1H, m), 3.33-3.47 (2H, m), 3.84-3.99 (2H, m), 4.88 (2H, brs), 6.61-6.80 (2H, m), 6.86 (1H, d, J=12.8 Hz).

(3) 1-(Benzyloxy)-3-{[2-fluoro-4-(tetrahydro-2H-pyran-4-yl)phenyl]hydrazono}pentane-2,4-dione

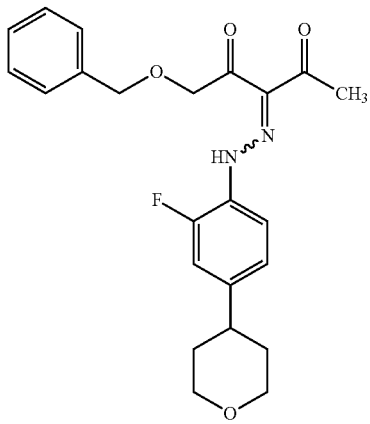 [SMILES: CC(=O)C(=NNc1ccc(C2CCOCC2)cc1F)C(=O)COCc1ccccc1]

To a stirred suspension of 2-fluoro-4-(tetrahydro-2H-pyran-4-yl)aniline (4 g) in 6N HCl (20 ml) was added a solution of sodium nitrite (2.1 g) in water (10 mL) with ice-cooling. The mixture was stirred at 0° C. for 2 hr and then poured into a stirred mixture of 1-(benzyloxy)pentane-2,4-dione (4.23 g) and sodium acetate trihydrate (16.7 g) in MeOH (40 mL). The mixture was stirred at 0° C. for 1 hr and at room temperature for 2 hr. The precipitate was collected by filtration, and washed with water and IPE to give the title compound (6.8 g).

MS (API+): [M+H]+440.1

$^1$H NMR (300 MHz, DMSO-d$_6$) δ 1.53-1.79 (4H, m), 2.31-2.42 (3H, m), 2.72-2.93 (1H, m), 3.37-3.57 (2H, m), 3.89-3.99 (2H, m), 4.58 (2H, s), 4.71 (2H, brs), 7.02-7.47 (7H, m), 7.72 (1H, brs), 14.44 (1H, brs).

(4) 5-(Benzyloxy)-1-[2-fluoro-4-(tetrahydro-2H-pyran-4-yl)phenyl]-3-(1-phenyl-1H-pyrazol-5-yl)pyridazin-4(1H)-one

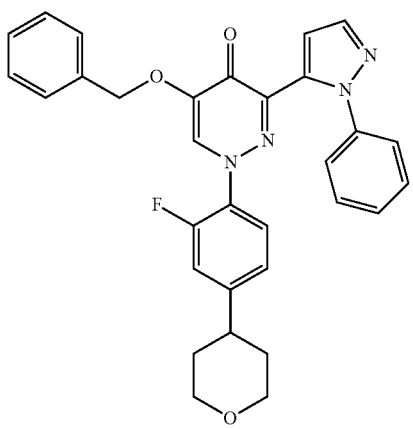 [SMILES: O=c1c(OCc2ccccc2)cn(-c2ccc(C3CCOCC3)cc2F)nc1-c1ccnn1-c1ccccc1]

A mixture of 1-(benzyloxy)-3-{[2-fluoro-4-(tetrahydro-2H-pyran-4-yl)phenyl]hydrazono}pentane-2,4-dione (1.2 g) and N,N-dimethylformamide dimethyl acetal (1.2 mL) in DMF (15 mL) was stirred at 80° C. for 5 hr and concentrated under reduced pressure. The residue was dissolved in EtOH (15 mL), and then TFA (1.5 mL) was added. To the stirred suspension was added phenylhydrazine (0.33 g) at 0° C. The mixture was stirred at room temperature for 72 h, treated with saturated NaHCO$_3$ solution, and extracted with AcOEt. The organic layer was dried over MgSO$_4$ and concentrated under reduced pressure. The residue was purified by column chromatography on silica gel eluting with AcOEt/Hexane=1/1 to 3/1 to give the title compound (0.8 g).

MS (API+): [M+H]+523.1

$^1$H-NMR (300 MHz, DMSO-d$_6$) δ 1.59-1.76 (4H, m), 2.77-2.94 (1H, m), 3.36-3.51 (2H, m), 3.89-4.00 (2H, m), 5.09 (2H, s), 6.88-7.00 (2H, m), 7.14 (1H, d, J=8.3 Hz), 7.29-7.51 (11H, m), 7.79 (1H, d, J=1.9 Hz), 8.60 (1H, d, J=2.3 Hz).

(5) 1-[2-Fluoro-4-(tetrahydro-2H-pyran-4-yl)phenyl]-5-hydroxy-3-(1-phenyl-1H-pyrazol-5-yl)pyridazin-4(1H)-one

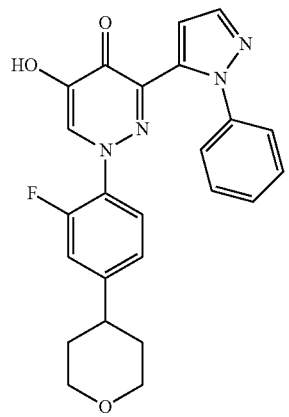 [SMILES: O=c1c(O)cn(-c2ccc(C3CCOCC3)cc2F)nc1-c1ccnn1-c1ccccc1]

A mixture of 5-(benzyloxy)-1-[2-fluoro-4-(tetrahydro-2H-pyran-4-yl)phenyl]-3-(1-phenyl-1H-pyrazol-5-yl)pyridazin-4(1H)-one (5.7 g) and 25% HBr in AcOH (40 mL) was stirred at 50° C. for 12 hr. After cooling to room temperature, the mixture was diluted with water and extracted with AcOEt. The organic layer was washed with saturated NaHCO$_3$ solution and an aqueous solution of Na$_2$S$_2$O$_3$ (11.4 g), dried over MgSO$_4$ and concentrated under reduced pressure. The residue was suspended in AcOEt (25 ml) and then IPE (25 mL) was added. The mixture was stirred at room temperature for 30 min. The precipitate was collected by filtration, and recrystallized from DMSO/EtOH to give the title compound (1.8 g).

MS (API+): [M+H]+433.2

$^1$H-NMR (300 MHz, DMSO-d$_6$) δ 1.56-1.80 (4H, m), 2.76-2.94 (1H, m), 3.35-3.51 (3H, m), 3.88-4.02 (2H, m), 6.87-7.07 (2H, m), 7.11-7.15 (1H, m), 7.28-7.49 (6H, m), 7.79 (1H, d, J=1.9 Hz), 8.41 (1H, d, J=2.3 Hz).

(6) 1-[2-Fluoro-4-(tetrahydro-2H-pyran-4-yl)phenyl]-5-[$^{11}$C]methoxy-3-(1-phenyl-1H-pyrazol-5-yl)pyridazin-4(1H)-one

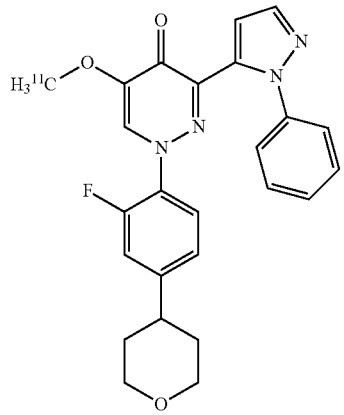

Sodium hydroxide (0.5 M, 3-4 μL) was added to 1-[2-fluoro-4-(tetrahydro-2H-pyran-4-yl)phenyl]-5-hydroxy-3-(1-phenyl-1H-pyrazol-5-yl)pyridazin-4(1H)-one (0.2-0.5 mg) in a glass vial, and then acetone (500 μL) was added to the same vial and the mixture was thoroughly mixed. The [$^{11}$C]CH$_3$OTf (10-25 GBq), prepared in Example 1, was trapped into the vial at room temperature and incubated for 40 to 60 seconds. Then the reaction mixture was diluted with mobile phase used for HPLC purification. The diluted mixture was transferred to the Ascentis RP-Amide reverse-phase HPLC column and eluted with acetonitrile (MeCN)/0.1% aqueous triethylamine mixture as mobile phase. The fraction containing $^{11}$C-labelled compound was collected in a vial containing sterile water (50 ml) and sodium ascorbate (300 mg) and then pushed trough Waters Oasis HLB cartridge to adsorb labelled compound. The cartridge was then washed with distilled water (8 ml) and $^{11}$C-labelled ligand was eluted with 99.6% ethanol (1.0 ml) into a vial containing sterile PBS (10 ml). The solution was then filtered though sterile 0.22 μm particle filter to obtain sterile injectable formulation. Sample for radiochemical purity/pyrogen determination was taken from the final composition.

Examples 4-118

In the same manner as in Examples 2-3, the compounds of Reference Examples 1-4 and 11-121 are radiolabeled with $^{11}$C.

Example 119

Synthesis of 5-([$^{18}$F]fluoro-methyloxy-d$_2$)-1-(2-fluoro-4-(tetrahydro-2H-pyran-4-yl)phenyl)-3-(1-phenyl-1H-pyrazol-5-yl)pyridazin-4(1H)-one (1) Production of bromo[$^{18}$F]fluoromethane from [$^{18}$F]fluoride Aqueous [$^{18}$F]fluoride was produced via the $^{18}$O(p,n)$^{18}$F nuclear reaction, transferred from the cyclotron target by means of helium flow (in a 1.5 mL bolus of [$^{18}$O]H$_2$O) and trapped on an ion-exchange resin cartridge to remove [$^{18}$O] H$_2$O. [$^{18}$F]fluoride was then eluted into the reaction vessel using 2 mL of acetonitrile/water (96/4 v/v) containing 9.8 mg of Kryptofix 2.2.2 and 1.8 mg of potassium carbonate. The solvents were evaporated by heating at 140° C. under a stream of nitrogen. To the dried [$^{18}$F]fluoride/Kryptofix complex 10-25 μl of deuterated dibromomethane dissolved in 1.0 ml of acetonitrile (MeCN) was added. The reaction mixture was heated for 5 min at 100° C. in the sealed 10 ml conical reaction vial without stirring. Following the reaction bromo[$^{18}$F]fluoromethane-d$_2$ was distilled, under nitrogen flow, from the reaction mixture into a vial containing 250-350 μL of dimethylformamide (DMF), with receiving vial cooled to −15° C.

(2) 5-([$^{18}$F]fluoro-methyloxy-d$_2$)-1-(2-fluoro-4-(tetrahydro-2H-pyran-4-yl)phenyl)-3-(1-phenyl-1H-pyrazol-5-yl)pyridazin-4(1H)-one

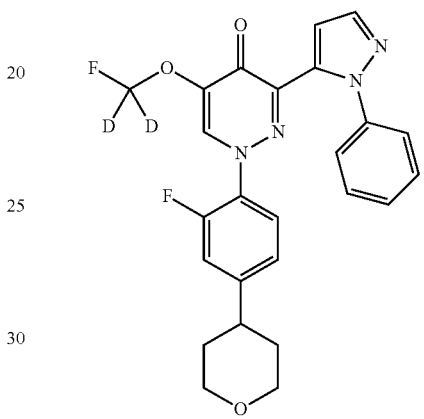

5-10 μL of aqueous 0.5 M NaOH was added to 0.75-1.50 mg of compound obtained in Example 3 (5), the mixture was then dissolved in approximately 300 μL of DMF and the solution was added to the DMF solution of bromo[$^{18}$F] fluoromethane-d$_2$. The resulting reaction mixture was heated to 130° C. for 10-15 minutes, cooled to room temperature and diluted with the mobile phase used for HPLC purification. The diluted mixture was transferred to the Ascentis RP-Amide reverse-phase HPLC column and eluted with acetonitrile (MeCN)/0.1% aqueous triethylamine mixture as mobile phase. The fraction containing $^{18}$F-labelled compound was collected in a vial containing 50 ml of sterile water and 300 mg of sodium ascorbate and then pushed trough Waters Oasis HLB cartridge to concentrate labelled compound. The cartridge was then washed with 10 ml of distilled water and $^{18}$F-labelled ligand was eluted with 1.0 ml of 99.6% ethanol into a vial containing 10 ml of sterile PBS. The solution was then filtered though sterile 0.22 μm particle filter to obtain sterile injectable formulation. Sample for radiochemical purity/pyrogen determination is taken from the final formulation.

Example 120

Synthesis of 5-(2-[$^{18}$F]fluoro-ethyloxy-d$_4$)-1-(2-fluoro-4-(tetrahydro-2H-pyran-4-yl)phenyl)-3-(1-phenyl-1H-pyrazol-5-yl)pyridazin-4(1H)-one (1) Production of 1-bromo-2-[$^{18}$F]fluoroethane-d$_4$ from [$^{18}$F]fluoride Aqueous [$^{18}$F]fluoride was produced via the $^{18}$O(p,n)$^{18}$F nuclear reaction, transferred from the cyclotron target by means of helium flow (in a 1.5 mL bolus of [$^{18}$O]H$_2$O) and trapped on an ion-exchange resin cartridge to remove [$^{18}$O]H$_2$O. [$^{18}$F]fluoride was then eluted into the reaction vessel using 2 mL of acetonitrile/water (96/4 v/v) containing 9.8 mg of Kryptofix 2.2.2 and 1.8 mg of potassium carbonate. The solvents were evaporated by heating at 140° C. under a stream of nitrogen. To the dried [$^{18}$F]fluoride/Kryptofix complex 10-25 μL of deuterated 1-tosyl-2-bromoethane dissolved in 0.7 ml of o-dichlorobenzene (o-DCB) was added. The reaction mixture was heated for 5 min at 135° C. (o-DCB) in the sealed 10 ml conical reaction vial without stirring. Following the reaction 1-bromo-2-[$^{18}$F]fluoroethane-d$_4$ was distilled, under nitrogen flow, from the reaction mixture into a vial containing 250-350 μL of dimethylformamide (DMF), with receiving vial cooled to −15° C.

(2) 5-(2-[$^{18}$F]fluoro-ethyloxy-d$_4$)-1-(2-fluoro-4-(tetrahydro-2H-pyran-4-yl)phenyl)-3-(1-phenyl-1H-pyrazol-5-yl)pyridazin-4(1H)-one

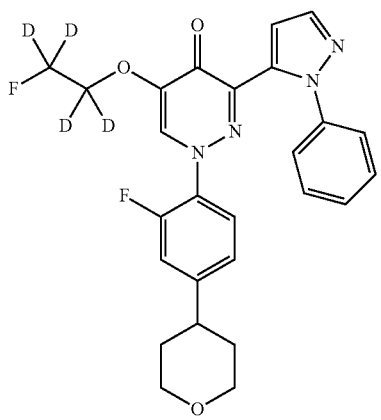 [SMILES: [2H]C([2H])(F)C([2H])([2H])Oc1cn(-c2ccc(C3CCOCC3)cc2F)nc(-c2ccnn2-c2ccccc2)c1=O]

5-10 μL of aqueous 0.5 M NaOH was added to 0.75-1.50 mg of compound obtained in Example 3 (5), the mixture was then dissolved in approximately 300 μL of DMF and the solution was added to the DMF solution of 1-bromo-2-[$^{18}$F]fluoroethane-d$_4$. The resulting reaction mixture was heated to 130° C. for 10-15 minutes, cooled to room temperature and diluted with the mobile phase used for HPLC purification. The diluted mixture was transferred to the Ascentis RP-Amide reverse-phase HPLC column and eluted with acetonitrile (MeCN)/0.1% aqueous triethylamine mixture as mobile phase. The fraction containing $^{18}$F-labelled compound was collected in a vial containing 50 ml of sterile water and 300 mg of sodium-ascorbate and then pushed trough Waters Oasis HLB cartridge to concentrate labelled compound. The cartridge was then washed with 10 ml of distilled water and $^{18}$F-labelled ligand was eluted with 1.0 ml of 99.6% ethanol into a vial containing 10 ml of sterile PBS. The solution was then filtered though sterile 0.22 μm particle filter to obtain sterile injectable formulation. Sample for radiochemical purity/pyrogen determination is taken from the final formulation.

Experimental Examples

Experimental Example 1

PET Measurements ([$^{11}$C]Compound)

PET measurements were performed with the High Resolution Research Tomograph system (HRRT) (Siemens Molecular Imaging) using two rhesus monkeys with body weight of 4450 g and 5000 g. The monkeys were maintained under gas anesthesia of sevoflurane, oxygen, and medical air during PET measurements. 123-min dynamic brain PET data were acquired in List mode after 150 and 162 MBq of [$^{11}$C] compound of Example 2 and 159 and 162 MBq of [$^{11}$C] compound of Example 3 were injected intravenously. List-mode data were reconstructed using the ordinary Poisson-3D-ordered subset expectation maximization (OP-3D-OSEM) algorithm, with 10 iterations and 16 subsets including modelling of the point spread function (PSF). During PET acquisition, venous blood sampling was performed for the metabolite analysis. The results are shown in FIGS. 1 and 2.

The fraction of parent compound of Example 2 was 70-76% at 30 min and 52-58% at 90 min.

The fraction of parent compound of Example 3 was 56-57% at 30 min and 45-53% at 90 min.

PET Measurements ([$^{18}$F]Compound)

PET measurements were performed with the High Resolution Research Tomograph system (HRRT) (Siemens Molecular Imaging) using three cynomolgus monkeys with body weight of 3730 g to 4845 g. The monkeys were maintained under gas anesthesia of sevoflurane, oxygen, and medical air during PET measurements.

180-min dynamic brain PET data were acquired in List mode after 148 and 157 MBq of [$^{18}$F]compound of Example 119 and 159 and 163 MBq of [$^{18}$F]compound of Example 120 were injected intravenously. List-mode data were reconstructed using the ordinary Poisson-3D-ordered subset expectation maximization (OP-3D-OSEM) algorithm, with 10 iterations and 16 subsets including modelling of the point spread function (PSF). During PET acquisition, venous blood sampling was performed for the metabolite analysis. The results are shown in FIGS. 11 and 12.

Figure 11:
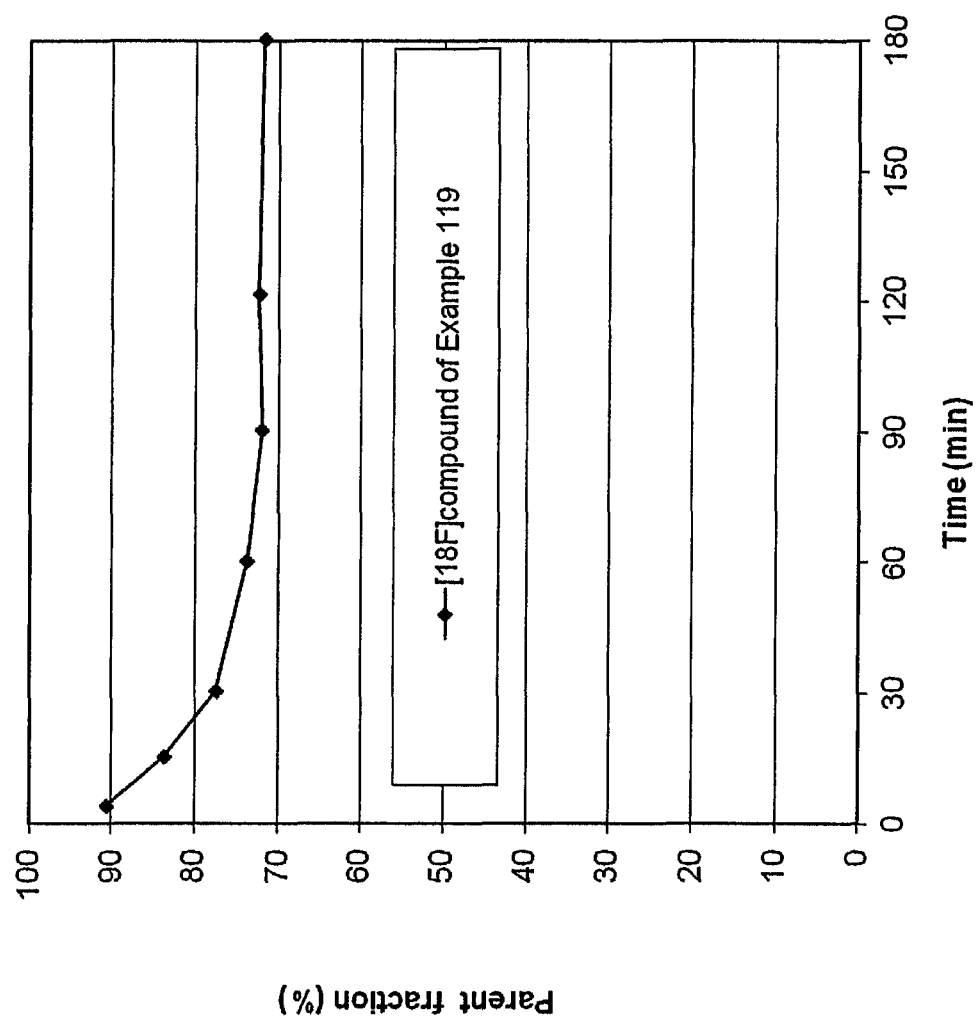

FIG. 11 shows parent fraction of the radioligands of Example 119.

Figure 12:
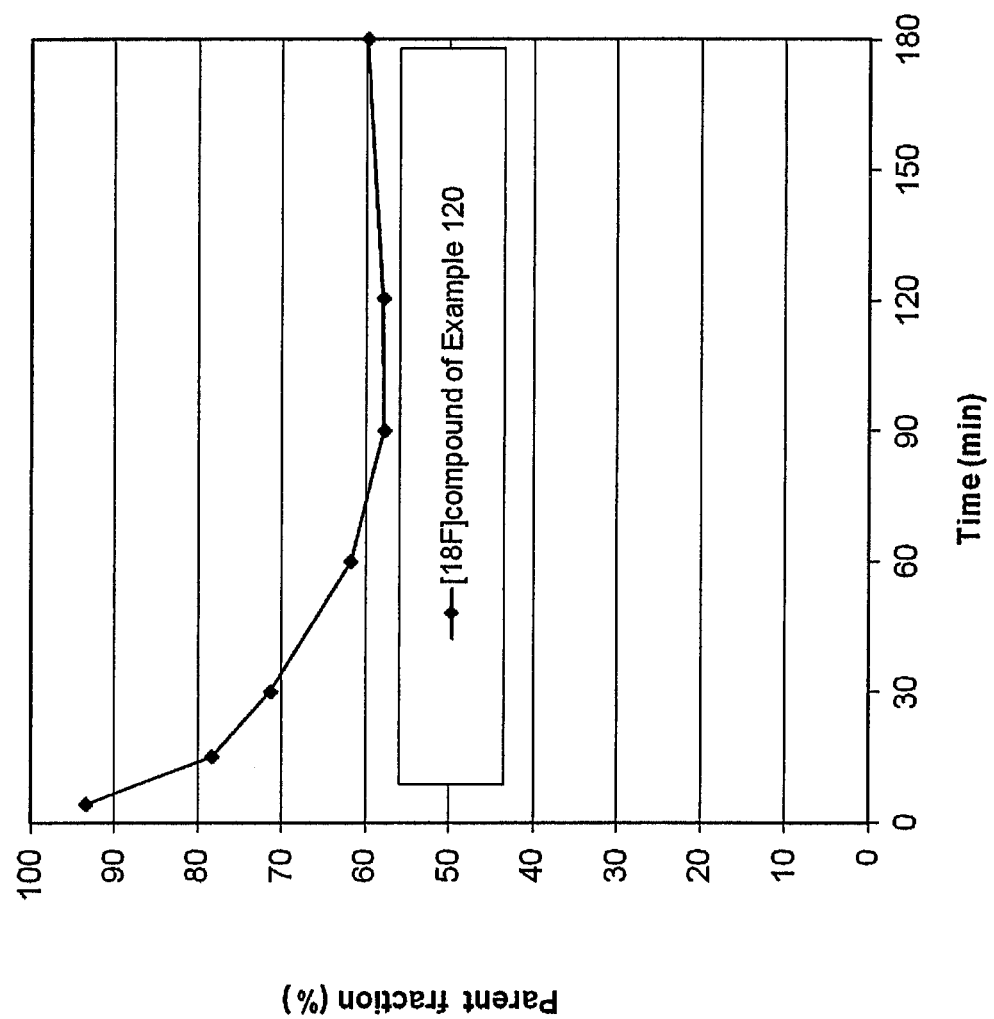

FIG. 12 shows parent fraction of the radioligands of Example 120.

The fraction of parent compound of Example 119 was 62-71% at 60 min and 60-63% at 180 min.

The fraction of parent compound of Example 120 was 64-74% at 60 min and 51-72% at 180 min.

Experimental Example 2

MRI Measurements

T1-weighted MR images were acquired with an MRI system GE 1.5 T Signa unit (Milwaukee, Wis., USA). The T1 sequence was a 3-D SPGR protocol with the following settings: repetition time (TR) 21 ms, flip angle 35°, FOV 12.8, matrix 256×256×128, 128×1.0 mm slices.

Experimental Example 3

Data Analysis ([$^{11}$C]Compound)

Regions of interest (ROIs) for Caudate, Putamen, Nucleus Accumbens, Thalamus, Cerebellum, Frontal cortex, Temporal cortex, and whole brain were delineated on MRI/PET coregistered images using PMOD software (v3.1 PMOD Technologies Ltd. Zurich, Switzerland). Time activity curves were generated for these regions. The uptake was expressed as % ID (=total radioactivity in the brain (MBq) *100/injected radioactivity (MBq)) or % SUV (=radioactivity in the region (MBq/cc)*100/(injected radioactivity (MBq)/Body weight (g))). Metabolite fraction in the plasma was measured by a radio LC analysis. The results are shown in FIGS. 3, 4, 5, 6, 7, 8, 9 and 10.

Figure 1:
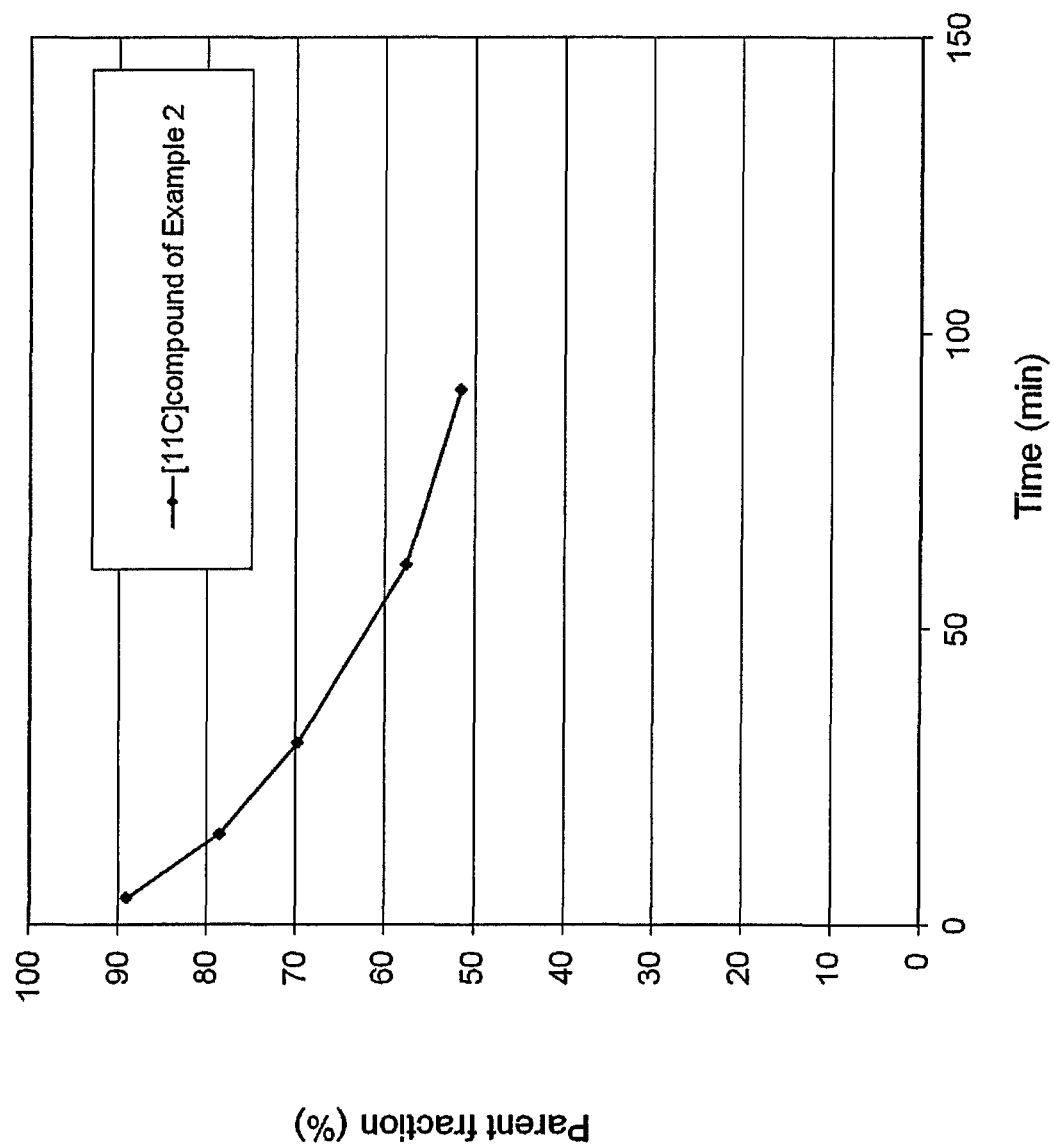
FIG. 1 shows parent fraction of the radioligands of Example 2.
Figure 2:
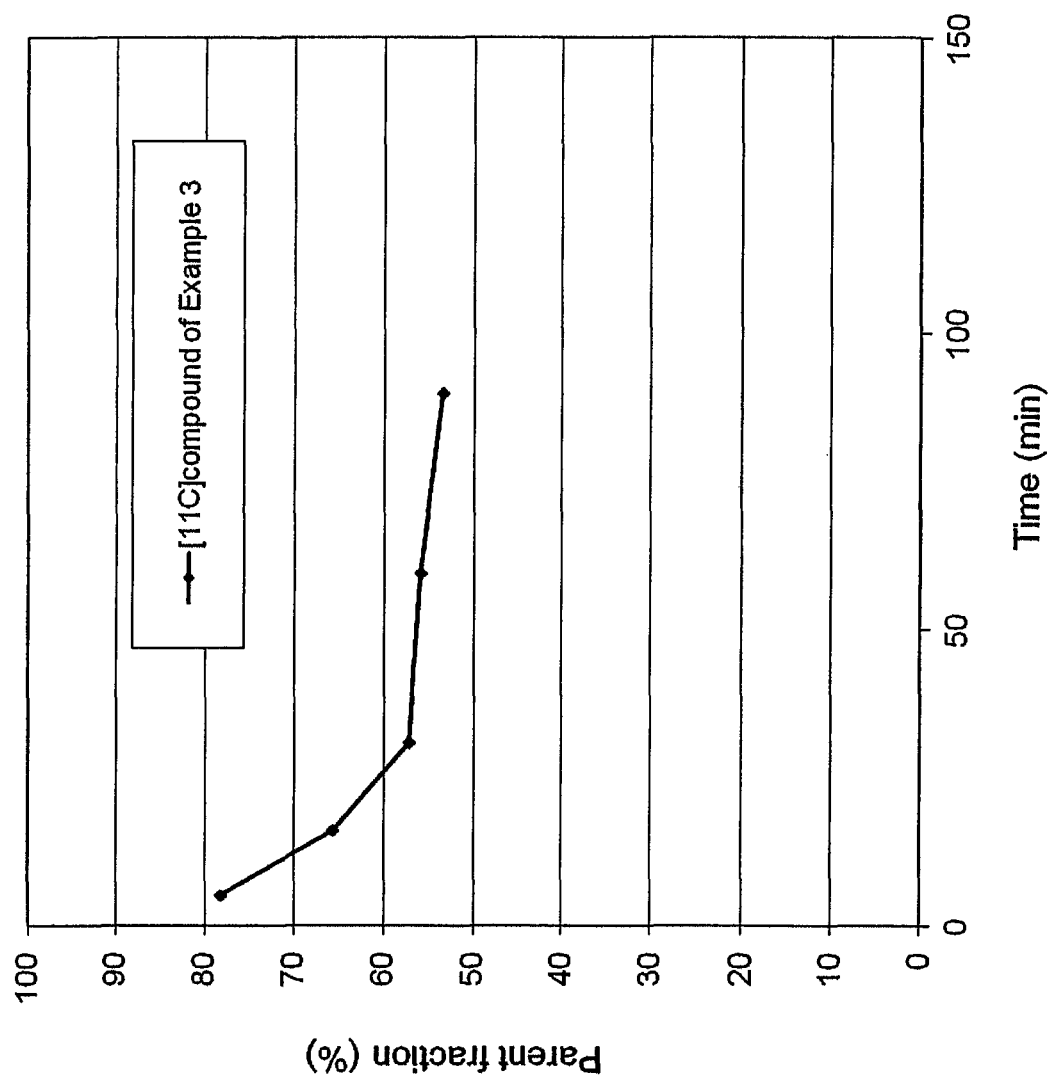
FIG. 2 shows parent fraction of the radioligands of Example 3.
Figure 3:
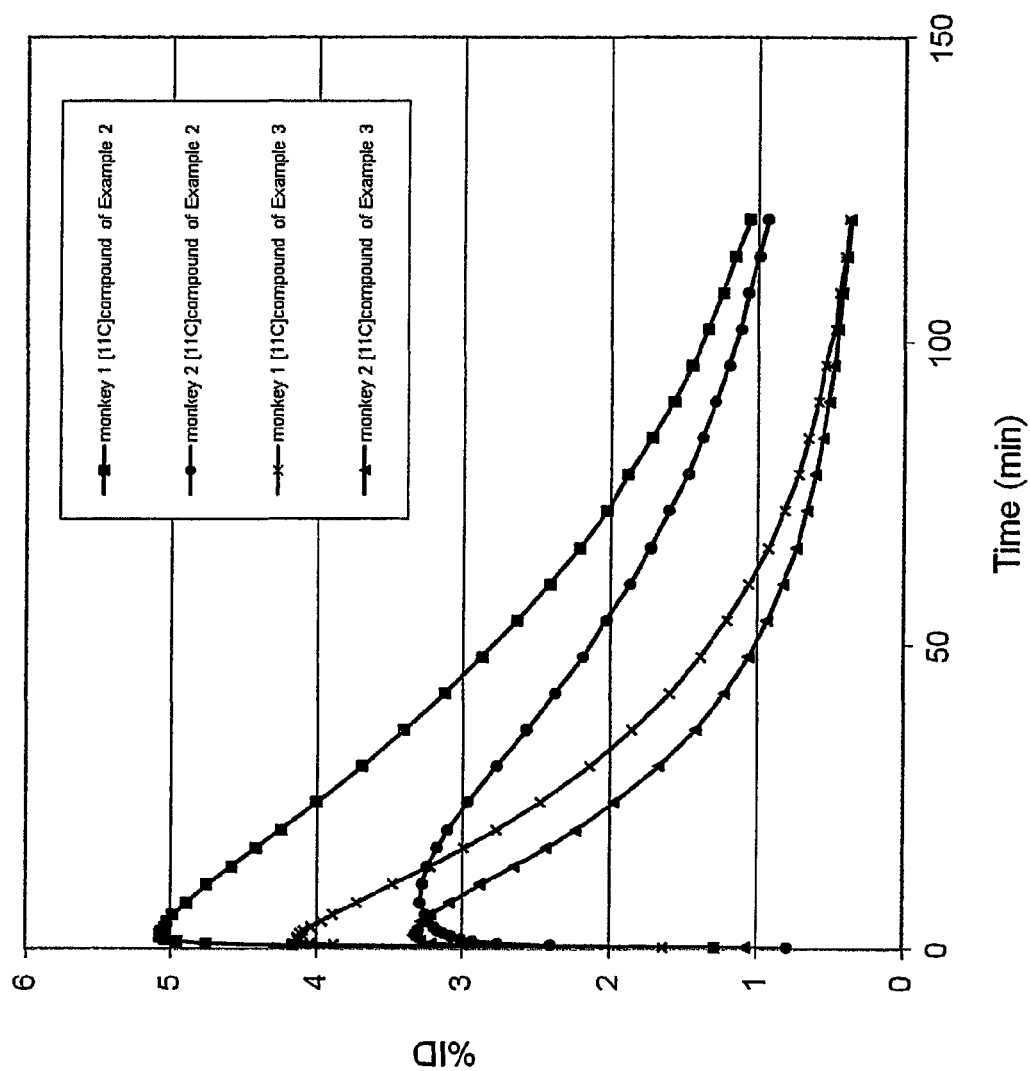

FIG. 3 shows whole brain uptake of Examples 2 and 3 (% ID, two rhesus monkeys).

Figure 4:
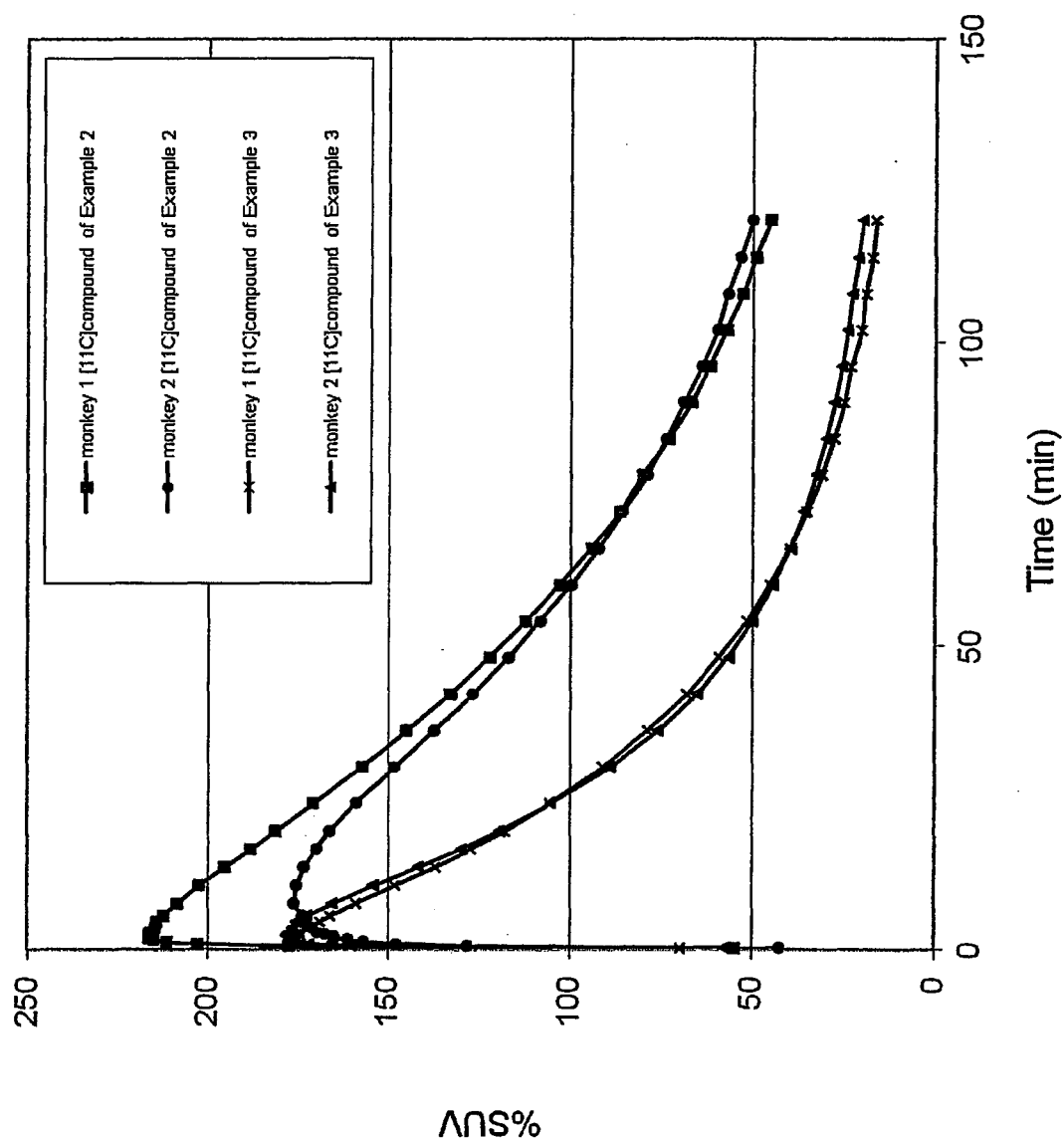

FIG. 4 shows whole brain uptake of Examples 2 and 3 (% SUV, two rhesus monkeys).

Figure 5:
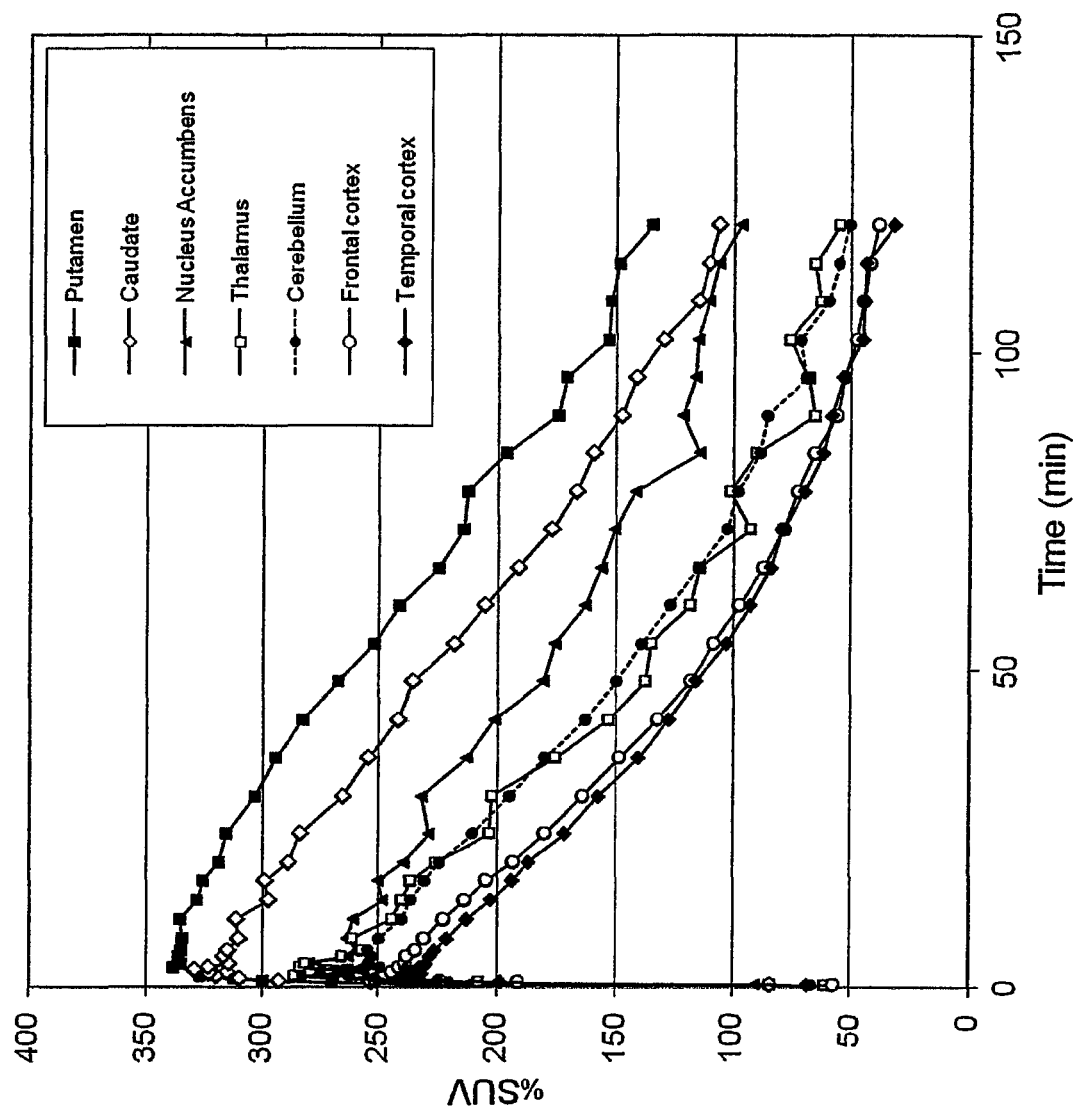

FIG. 5 shows regional brain uptake of Example 2 (% SUV).

Figure 6:
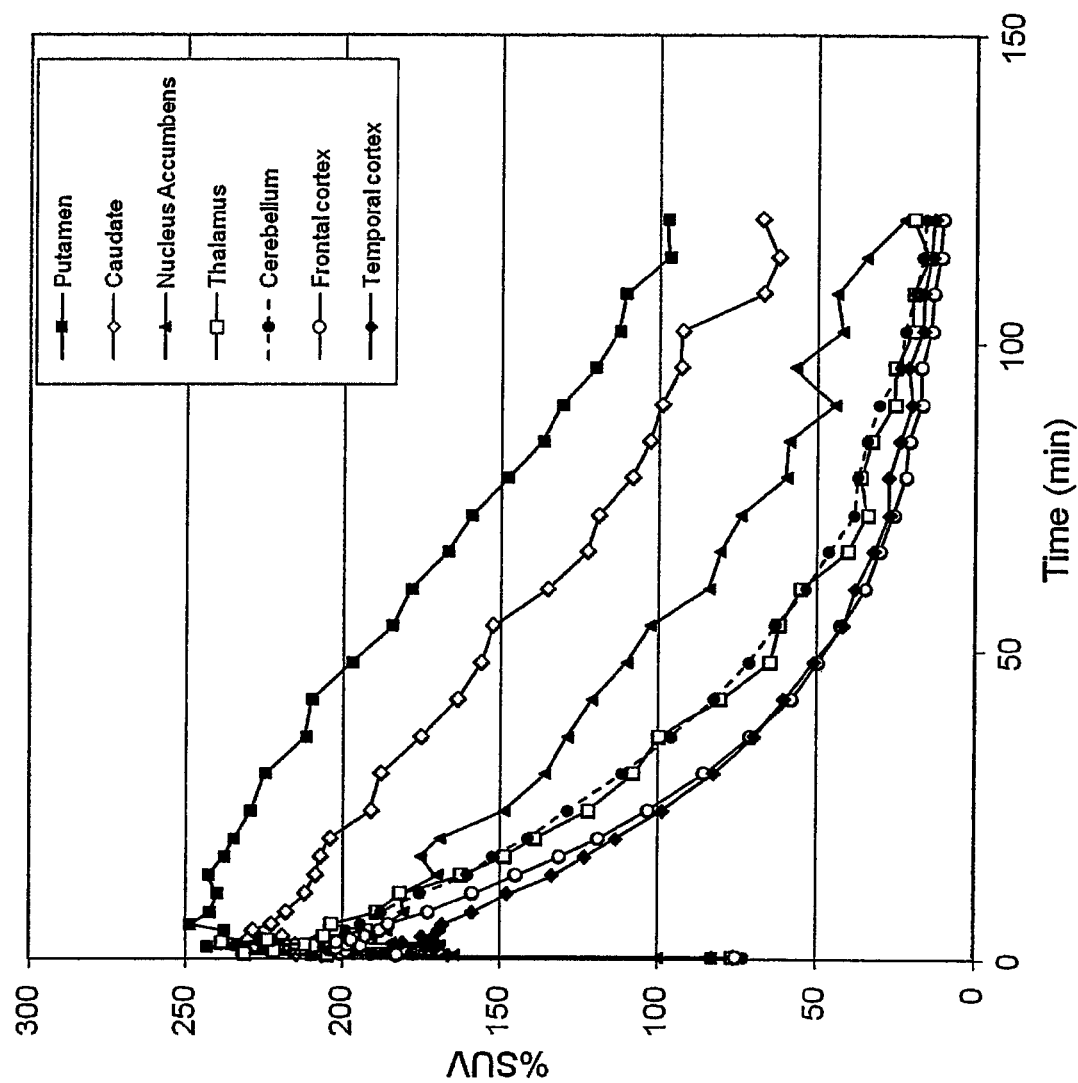

FIG. 6 shows regional brain uptake of Example 3 (% SUV).

Figure 7:
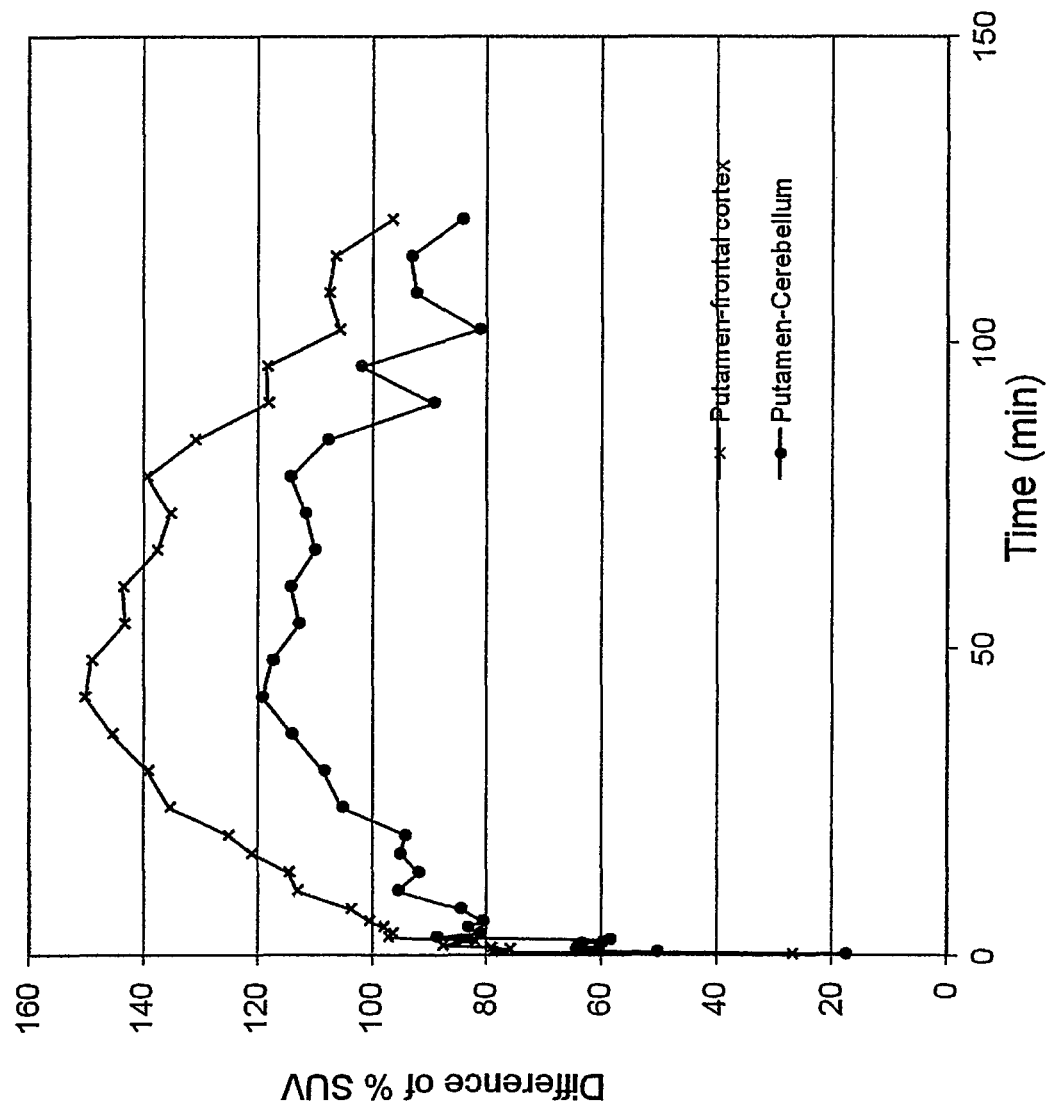

FIG. 7 shows time course of specific radioligand binding of Example 2.

Figure 8:
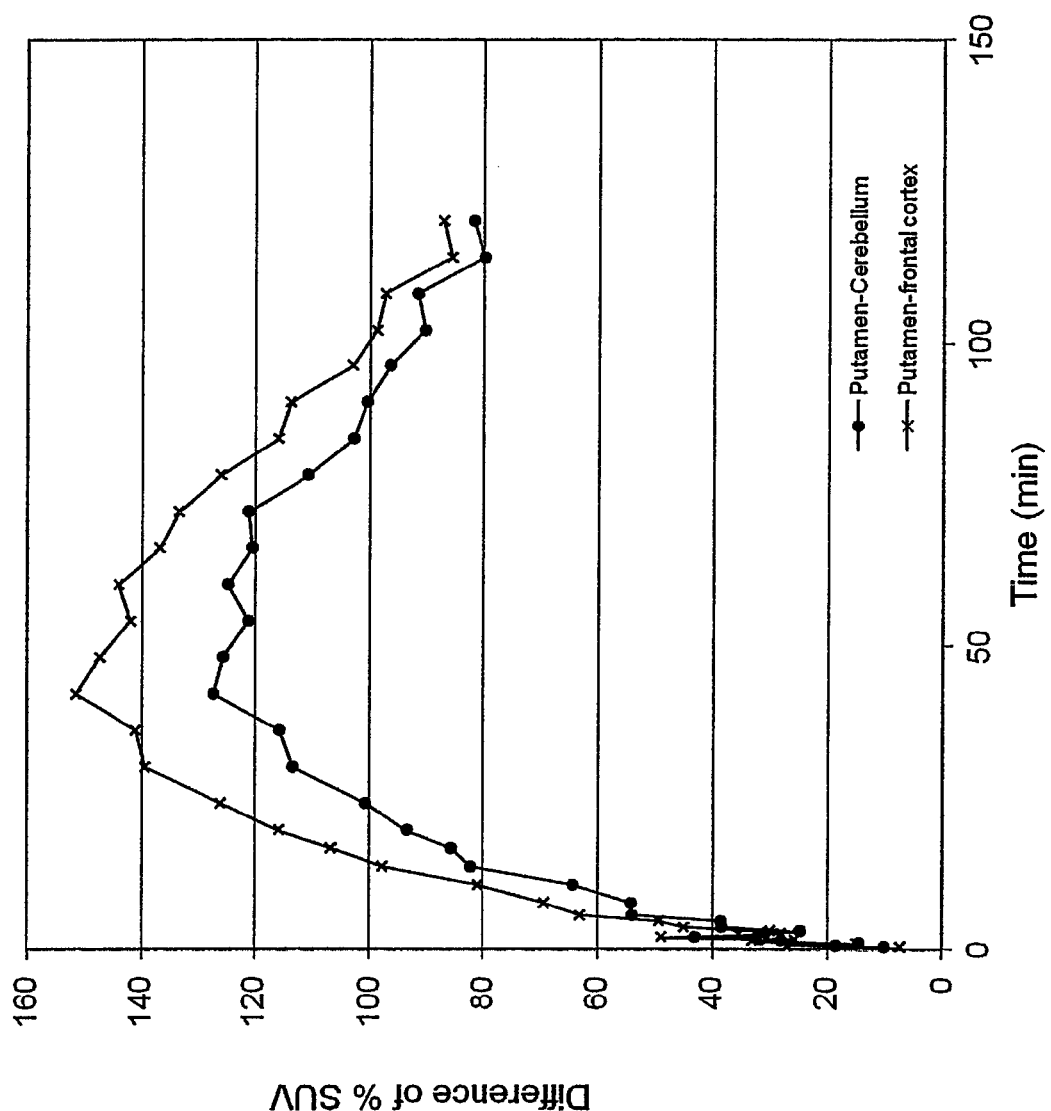

FIG. 8 shows time course of specific radioligand binding of Example 3.

Figure 9:
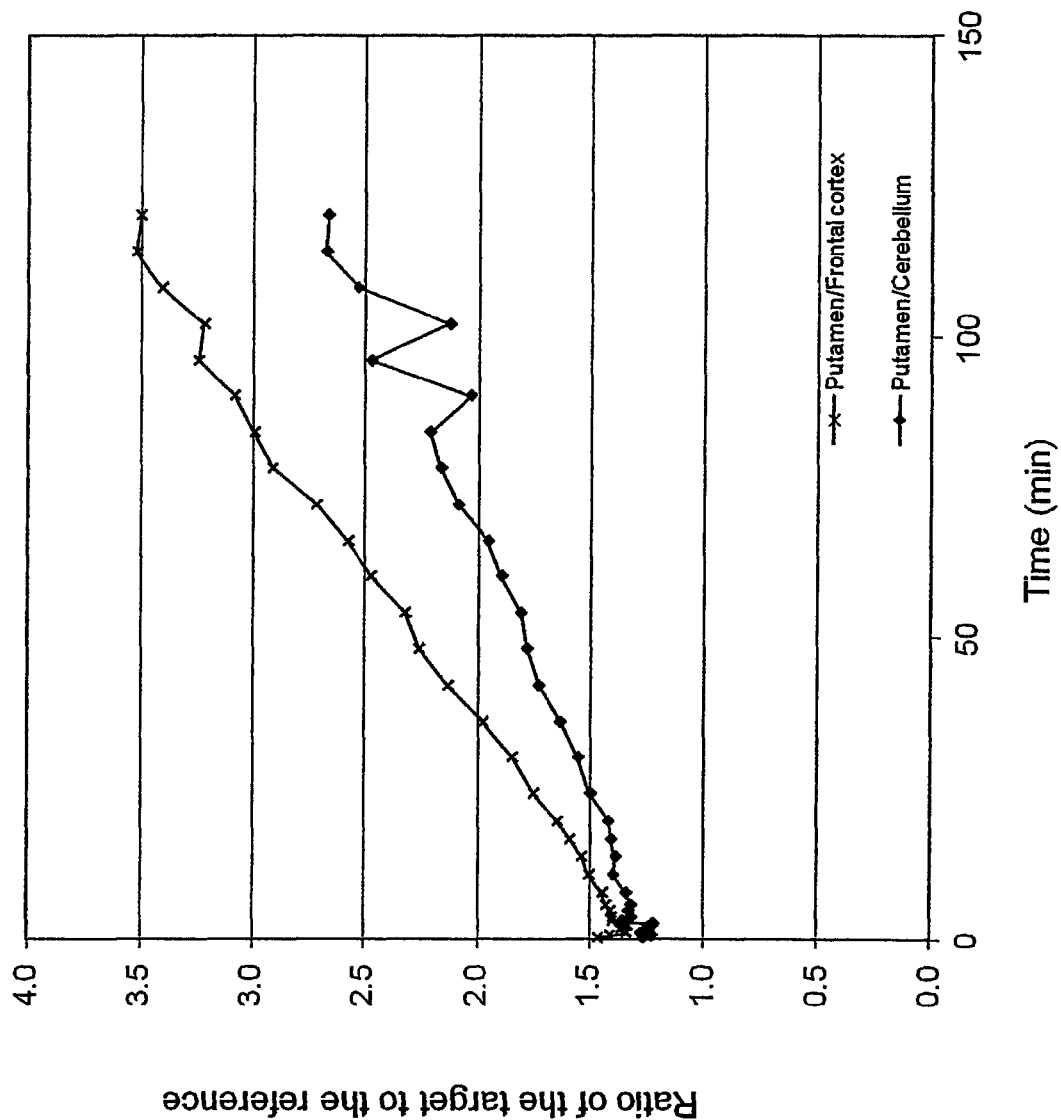

FIG. 9 shows time course of ratio between the target region to the reference region (Example 2).

Figure 10:
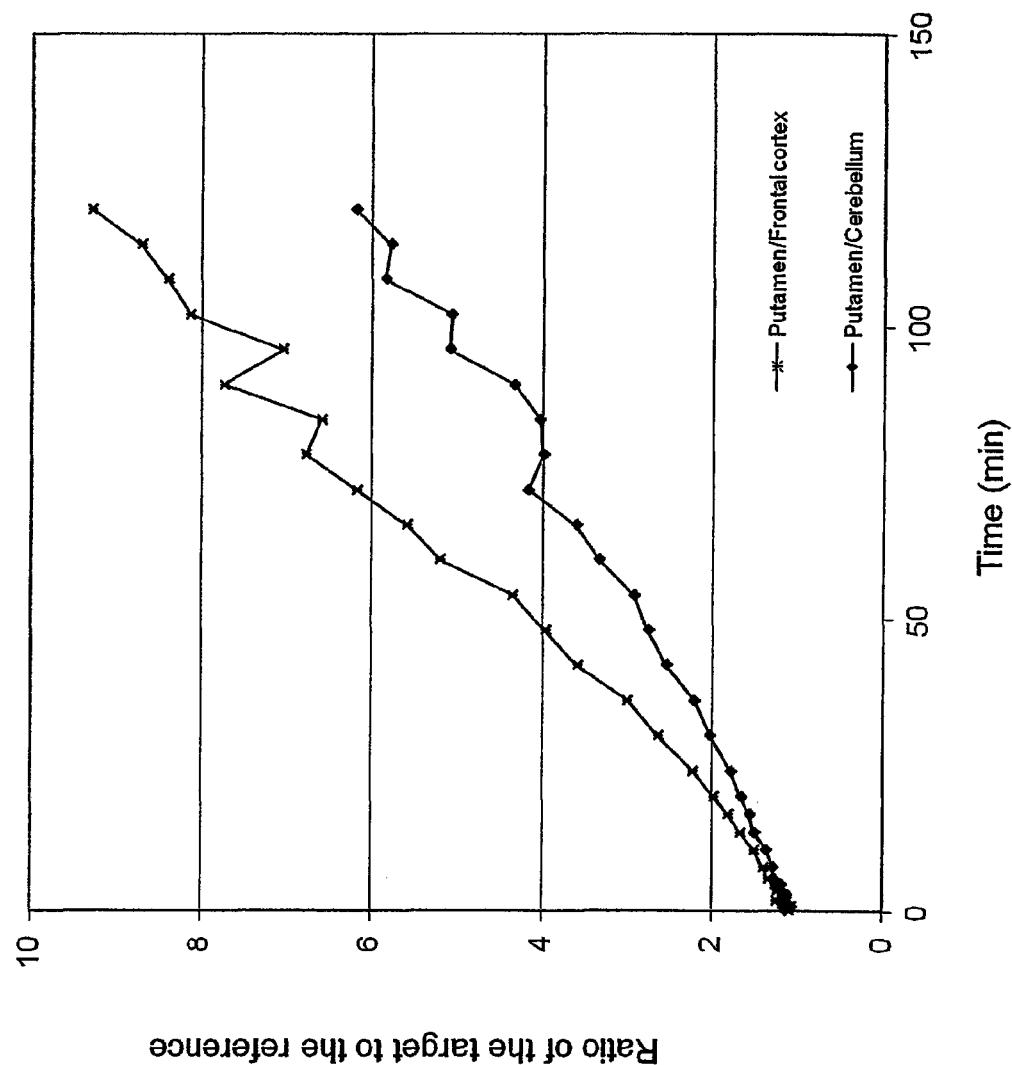

FIG. 10 shows time course of ratio between the target region to the reference region (Example 3).

The uptake of Example 2 of whole brain reached at peak at 2.5-7.5 min. The uptake at the peak was 3.3-5.1% ID. Then the uptake decreased to half at 60-66 min. For regional brain uptake of Example 2, all the regions reached the peak during PET measurements. Putamen showed highest uptake, followed by Caudate, Nuclear Accumbens and Thalamus. The lowest uptake was Cerebellum, Frontal cortex and Temporal cortex. The specific binding of Example 2 in Putamen, which was the uptake of the putamen minus the cerebellum, had a peak at 48 min. The ratio of the specific binding between the uptake of Example 2 in the target region and the uptake in the cerebellum increased up to approximately 2.5-2.7 during 123 min PET measurements.

The uptake of Example 3 of whole brain reached at peak at 2 min. The uptake at the peak was 3.3-4.1% ID. Then the washout of the uptake was rapid, and the uptake decreased to half at 30 min. For regional brain uptake of Example 3, all the regions reached the peak during PET measurements. Putamen showed highest uptake, followed by Caudate, Nuclear Accumbens and Thalamus. The lowest uptake was Cerebellum, Frontal cortex and Temporal cortex. The specific binding of Example 3 in Putamen, which was the uptake of the putamen minus the cerebellum, had a peak at 42 min. The ratio of the specific binding between the uptake of Example 3 in the target region and the uptake in the cerebellum increased up to approximately six during 123 min PET measurements.

Data Analysis ([$^{18}$F]Compound)

Regions of interest (ROIs) for Caudate, Putamen, Nucleus Accumbens, Thalamus, Cerebellum, Frontal cortex, Temporal cortex, and whole brain were delineated on MRI/PET coregistered images using PMOD software (v3.2PMOD Technologies Ltd. Zurich, Switzerland). Time activity curves were generated for these regions. The uptake was expressed as % ID (=total radioactivity in the brain (MBq) *100/injected radioactivity (MBq)) or % SUV (=radioactivity in the region (MBq/cc)*100/(injected radioactivity (MBq)/Body weight (g))). Metabolite fraction in the plasma was measured by a radio LC analysis. The results are shown in FIGS. 13, 14, 15, 16, 17, 18, 19 and 20.

Figure 13:
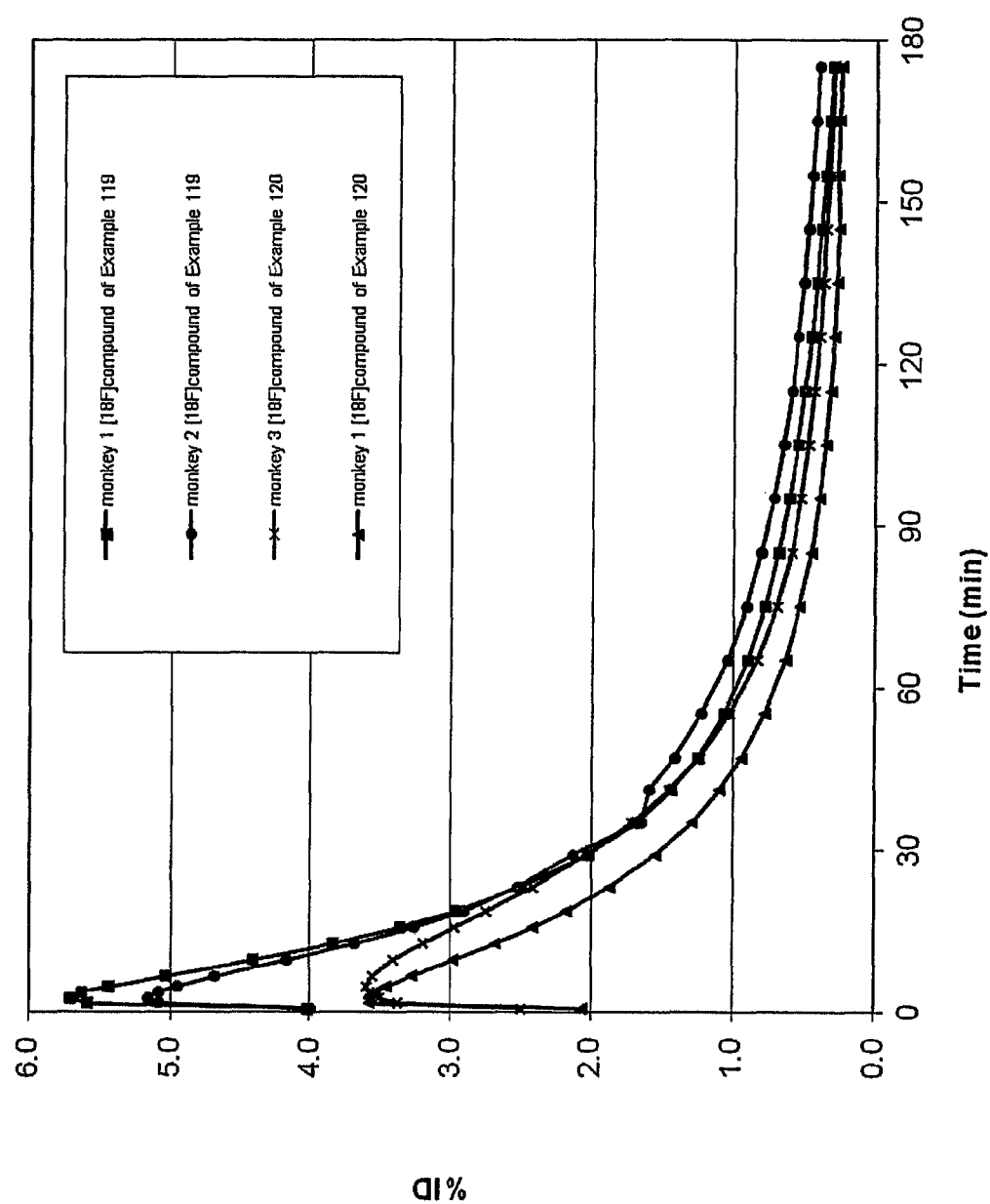

FIG. 13 shows whole brain uptake of Examples 119 and 120 (% ID, three cynomolgus monkeys).

Figure 14:
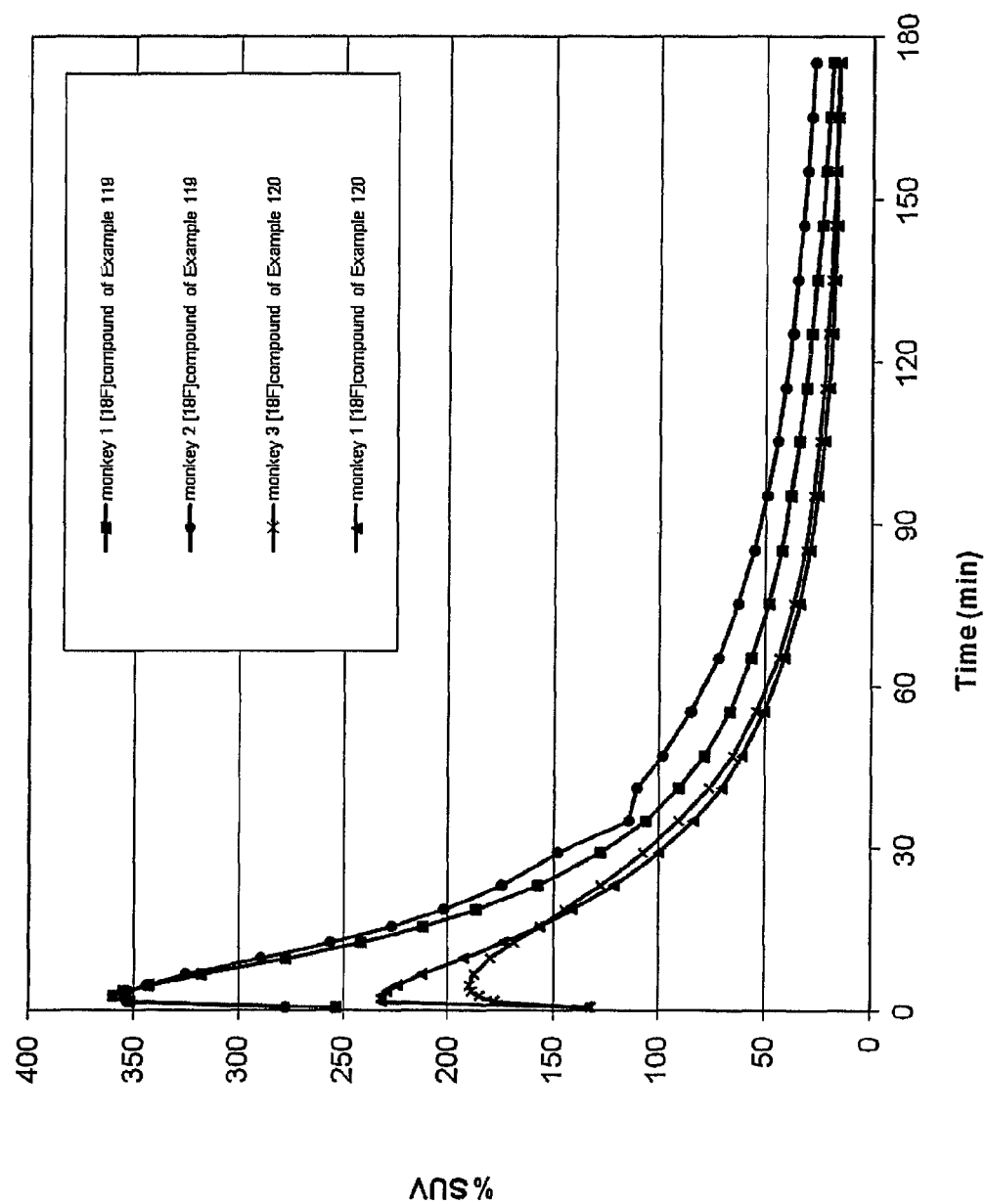

FIG. 14 shows whole brain uptake Examples 119 and 120 (% SUV, three cynomolgus monkeys).

Figure 15:
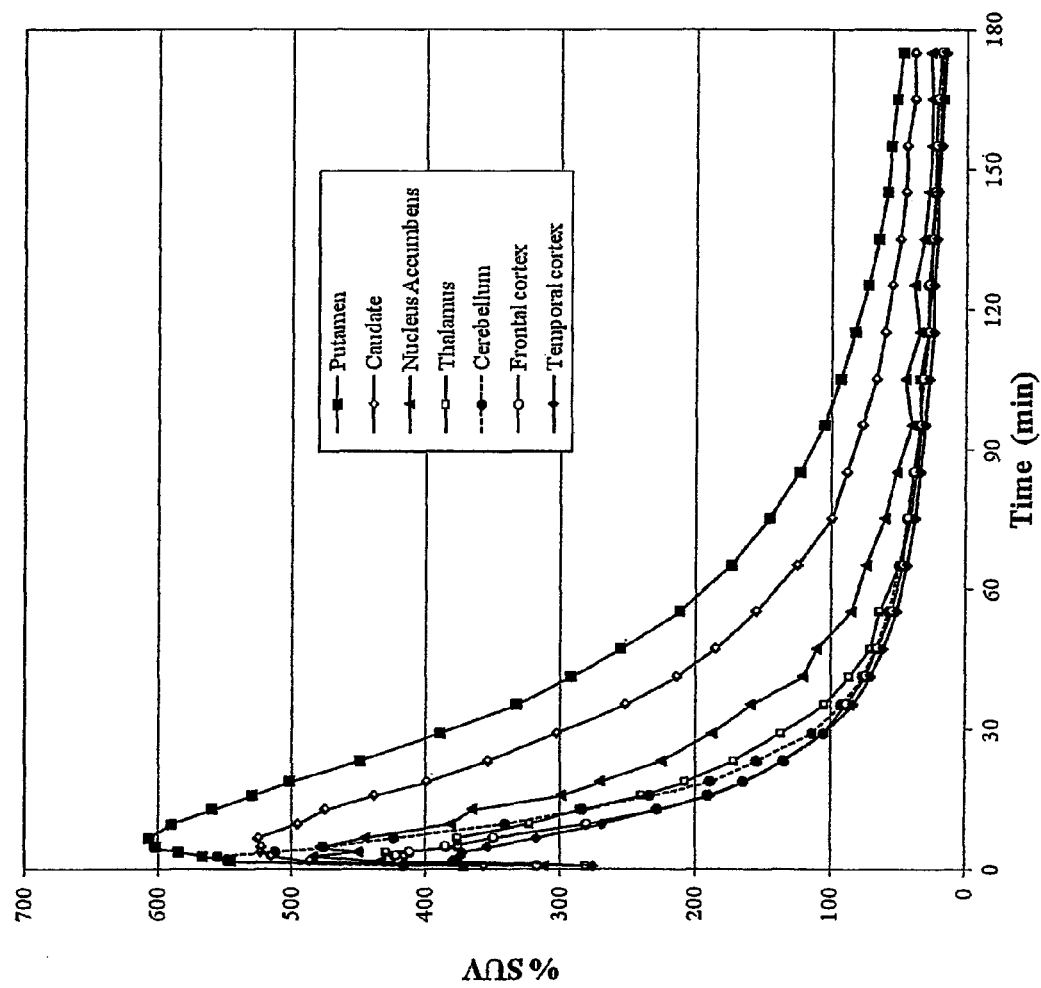

FIG. 15 shows regional brain uptake of Example 119 (% SUV).

Figure 16:
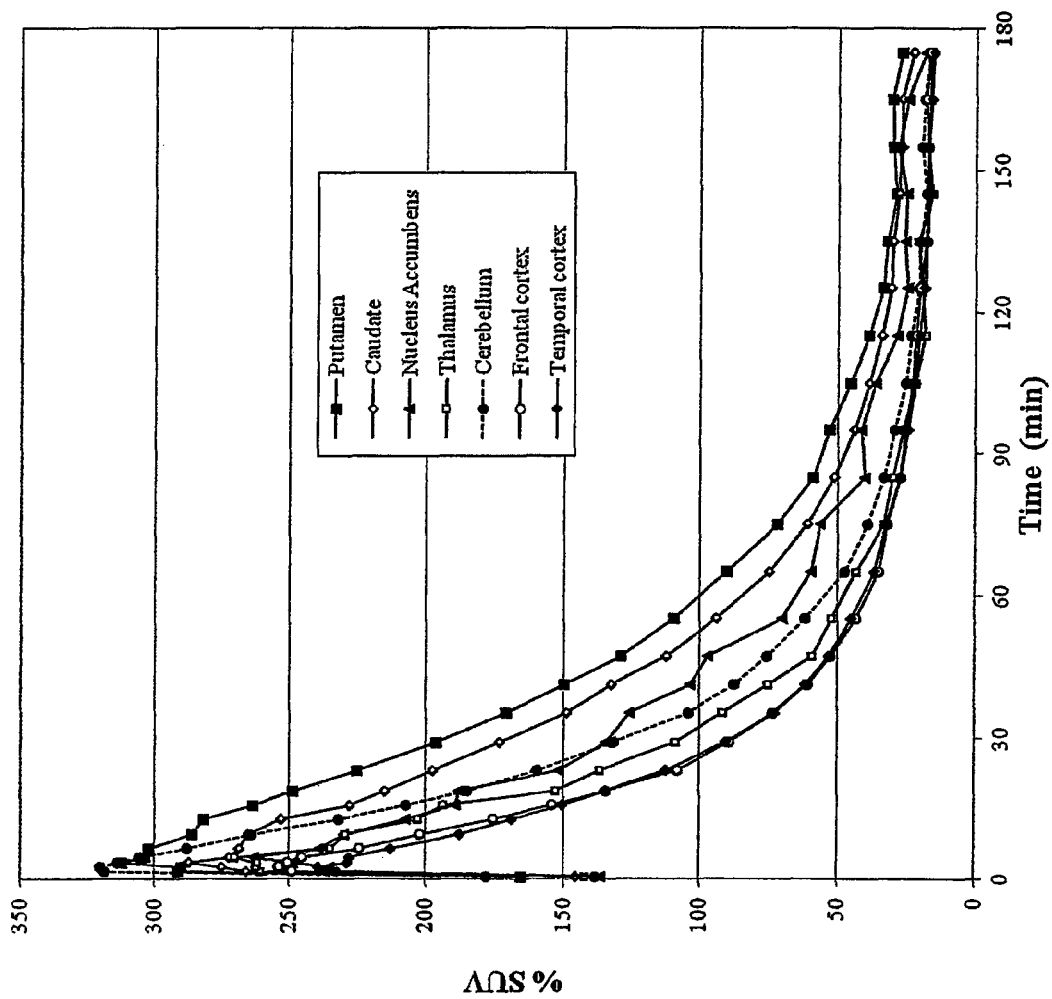

FIG. 16 shows regional brain uptake of Example 120 (% SUV).

Figure 17:
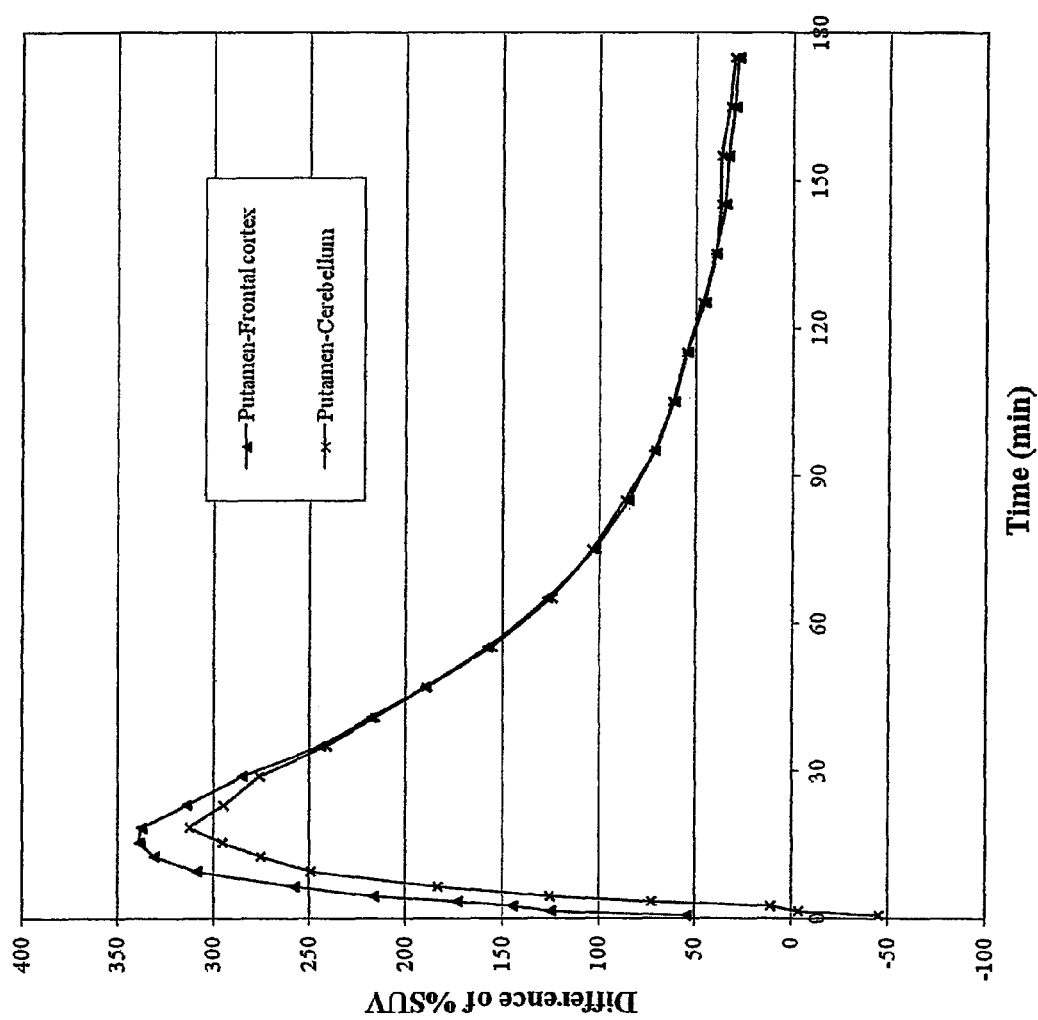

FIG. 17 shows time course of specific radioligand binding of Example 119.

Figure 18:
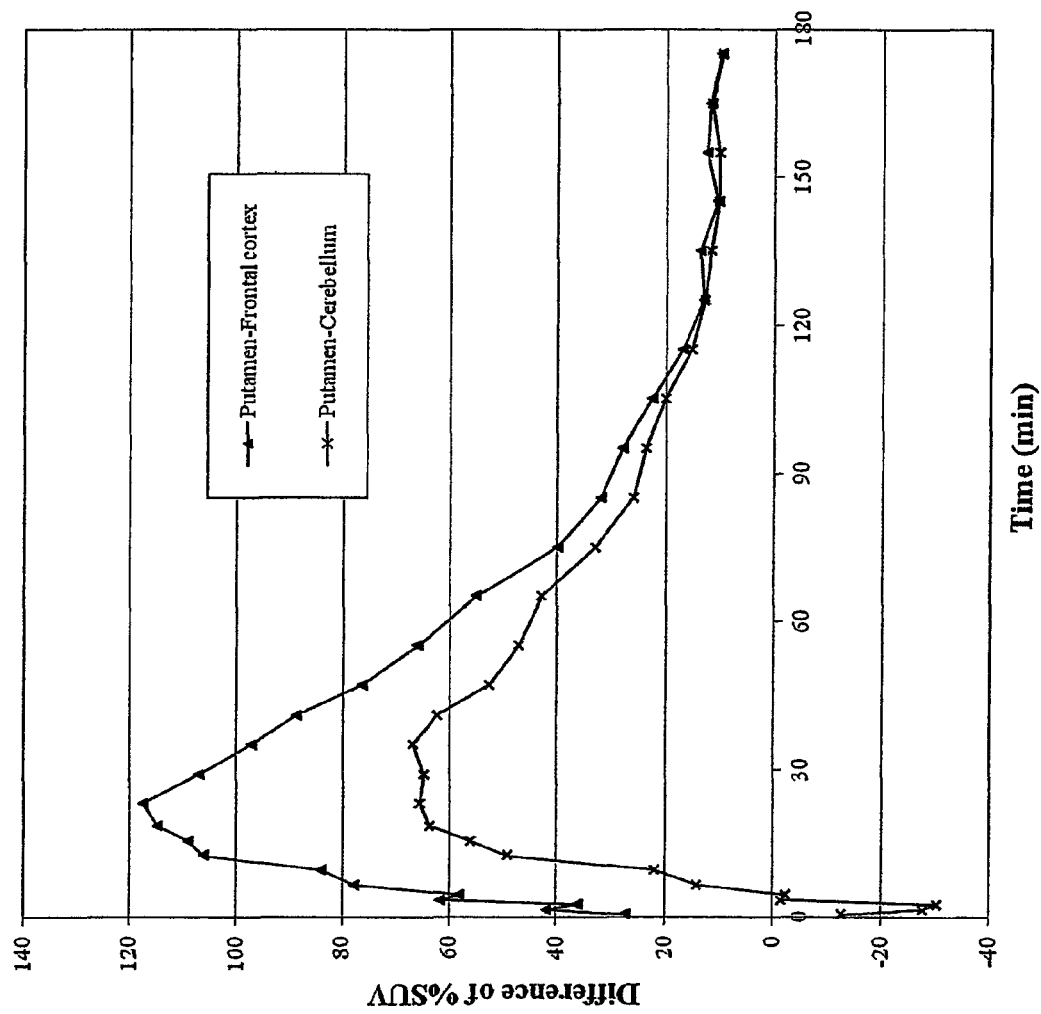

FIG. 18 shows time course of specific radioligand binding of Example 120.

Figure 19:
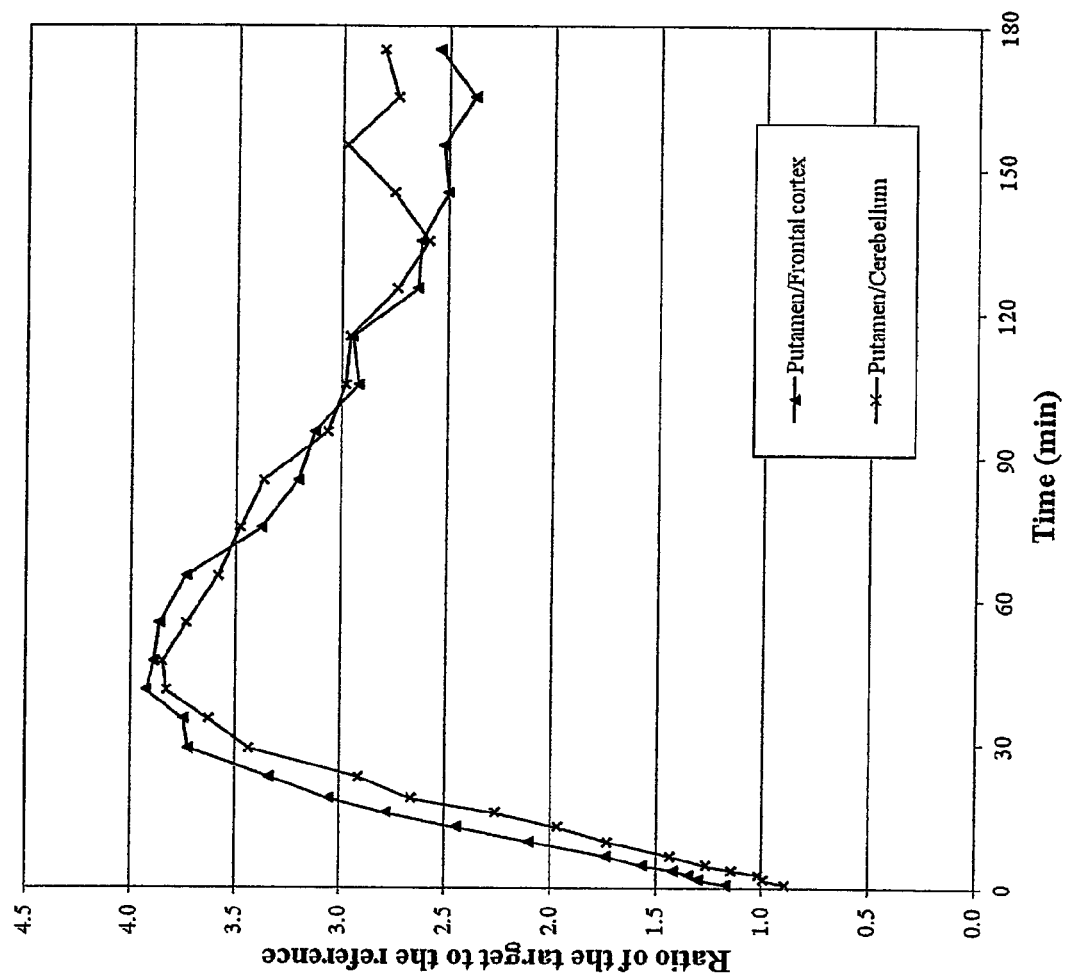

FIG. 19 shows time course of ratio between the target region to the reference region (Example 119).

Figure 20:
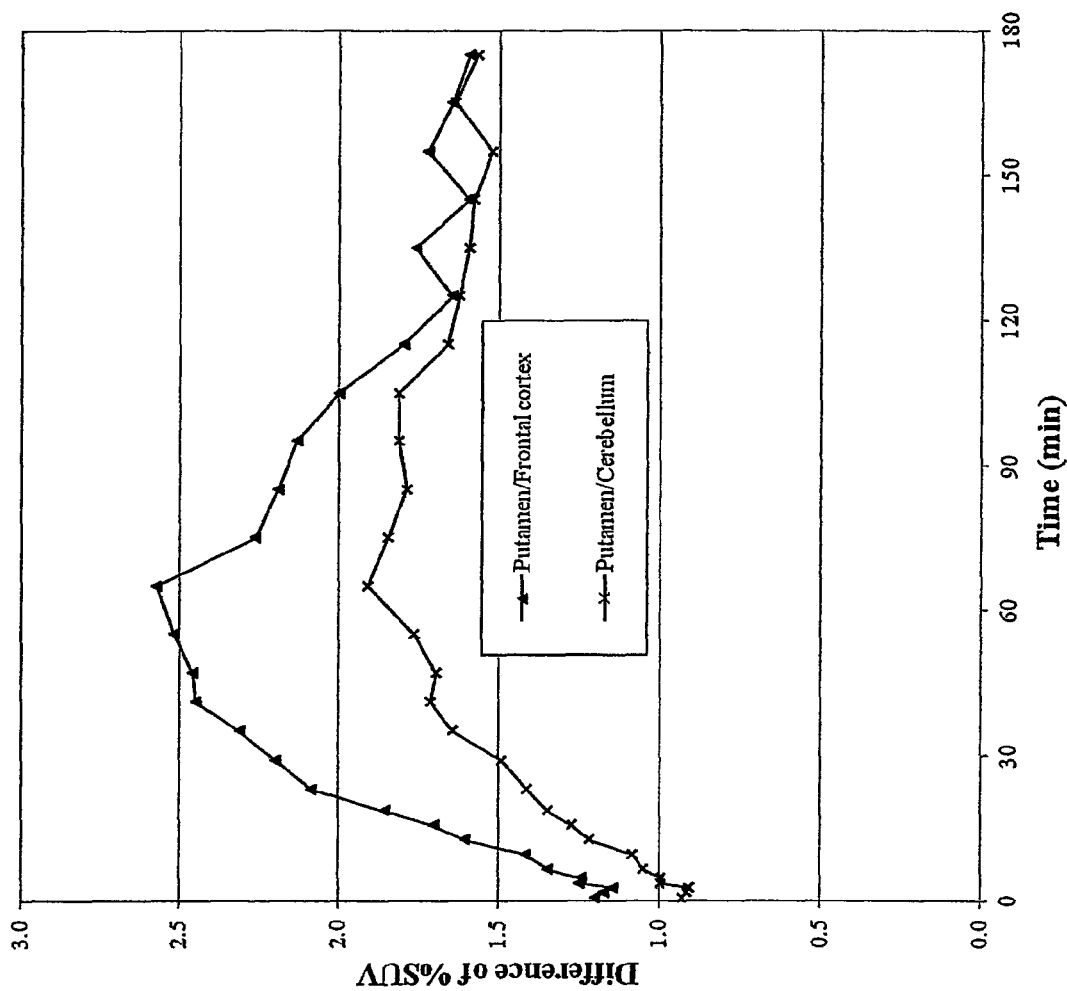

FIG. 20 shows time course of ratio between the target region to the reference region (Example 120).

The uptake of Example 119 of whole brain reached at peak at 2.5 min. The uptake at the peak was 5.2-5.7% ID. Then the uptake decreased to half at 23 min. For regional brain uptake of Example 119, all the regions reached the peak during PET measurements. Putamen showed highest uptake, followed by Caudate, Nuclear Accumbens and Thalamus. The lowest uptake was Cerebellum, Frontal cortex and Temporal cortex. The specific binding of Example 119 in Putamen, which was the uptake of the putamen minus the cerebellum, had a peak at 18.5-29 min. The ratio of the specific binding between the uptake of Example 119 in the target region and the uptake in the cerebellum increased up to approximately 3.0-3.9 during 47-65 min PET measurements.

The uptake of Example 120 of whole brain reached at peak at 2.5-4.5 min. The uptake at the peak was 3.6% ID. Then the uptake decreased to half at 23-35 min. For regional brain uptake of Example 120, all the regions reached the peak during PET measurements. Putamen showed highest uptake, followed by Caudate, Nuclear Accumbens and Thalamus. The lowest uptake was Cerebellum, Frontal cortex and Temporal cortex. The specific binding of Example 120 in Putamen, which was the uptake of the putamen minus the cerebellum, had a peak at 35-41 min. The ratio of the specific binding between the uptake of Example 120 in the target region and the uptake in the cerebellum increased up to approximately 1.5-1.9 during 65-75 min PET measurements.

Experimental Example 4

PDE10A Enzyme Inhibition

Human PDE10A enzyme was generated from Sf9 or COS-7 cells transfected with the full-length gene. Cloned enzyme was extracted from homogenized cell pellets. The extracted enzyme from sf9 cells was partially purified using His-tag affinity column. The enzyme was stored at −70° C. until use. PDE activity was measured using a SPA (Scintillation Proximity Assay) (GE Healthcare). To evaluate the inhibitory activity, 10 µL of serial diluted compounds were incubated with 20 µL of PDE enzyme in assay buffer (50 mM HEPES-NaOH, 8.3 mM $MgCl_2$, 1.7 mM EGTA, 0.1% BSA (pH 7.4)) for 30 min. at room temperature. Final concentration of DMSO in the assay was 1% as compounds were tested in duplicate in 96-well half-area plates (Corning). To start the reaction, 10 µL of substrate [$^3$H] cGMP (25 or 50 nM; enclosed in SPA kits from GE Healthcare or purchased from PerkinElmer, respectively) was added for a final assay volume of 40 µL. After 60 min incubation at room temperature, yttrium SPA beads containing zinc sulphate were added (20 µL at 6 mg/mL) to terminate the PDE reaction. After being settled for 60 min., assay plates were counted in a scintillation counter (PerkinElmer) to allow calculation of inhibition rate. $IC_{50}$ values were calculated on the basis of 0% control wells with DMSO and 100% control wells without enzyme. The results are shown in Table 4.

Experimental Example 5

PDE Family Enzyme Inhibition

Selectivity Assay

Human PDE1A, 3A, 4D2, 5A1, 7B, 8A1, 9A2, and 11A4 enzymes were purchased from BPS Bioscience. Human PDE6AB enzyme was purchased from Scottish Biomedical. Human PDE2A3 was generated from Sf9 transfected with the full-length gene in house. PDE activities were measured using a SPA (Scintillation Proximity Assay) (PerkinElmer). To evaluate the inhibitory activity, 10 μL of serial diluted compounds were incubated with 20 μL of PDE enzyme in assay buffer (50 mM HEPES-NaOH, 8.3 mM $MgCl_2$, 1.7 mM EGTA, 0.1% BSA (pH 7.4)) for 30 min. at room temperature. Final concentration of DMSO in the assay was 1% as compounds were tested in duplicate in 96-well half-area plates (Corning). To start the reaction, 10 μL of substrate [$^3$H] cGMP (PerkinElmer) for PDE1A, 2A3, 5A1, 6AB, 9A2, and 11A4 or [$^3$H] cAMP (PerkinElmer) for PDE3A, 4D2, 7B, and 8A1 was added for a final assay volume of 40 μL. After 60 min incubation at room temperature, yttrium SPA beads containing zinc sulphate were added (20 μL at 6 mg/mL) to terminate the PDE reaction. After being settled for 60 min., assay plates were counted in a scintillation counter (PerkinElmer) to allow calculation of inhibition rate. $IC_{50}$ values were calculated on the basis of 0% control wells with DMSO and 100% control wells without enzyme. Selectivity was defined as the ratio of $IC_{50}$ for each PDE other than PDE10A to $IC_{50}$ for PDE10A. The results are shown in Table 4.

TABLE 4

| Structure | name | PDE10A enzyme $IC_{50}$ (nM) | Selectivity over other PDEs |
|---|---|---|---|
| Ref. Ex. 18 | 1-[4-(3,3-difluoroazetidin-1-yl)-2-fluorophenyl]-5-methoxy-3-(1-phenyl-1H-pyrazol-5-yl)pyridazin-4(1H)-one | <1 | >1000-fold |
| Ref. Ex. 16 | 1-[2-fluoro-4-(tetrahydro-2H-pyran-4-yl)phenyl]-5-methoxy-3-(1-phenyl-1H-pyrazol-5-yl)pyridazin-4(1H)-one | <1 | >1000-fold |

TABLE 4-continued

| Structure | name | PDE10A enzyme IC$_{50}$ (nM) | Selectivity over other PDEs |
|---|---|---|---|
| Ref. Ex. 122 | 5-(fluoro-methyloxy-d$_2$)-1-(2-fluoro-4-(tetrahydro-2H-pyran-4-yl)phenyl)-3-(1-phenyl-1H-pyrazol-5-yl)pyridazin-4(1H)-one | <10 | >1000-fold |
| Ref. Ex. 123 | 5-(2-fluoro-ethyloxy-d$_4$)-1-(2-fluoro-4-(tetrahydro-2H-pyran-4-yl)phenyl)3-(1-phenyl-1H-pyrazol-5-yl)pyridazin-4(1H)one | <10 | >100-fold |

INDUSTRIAL APPLICABILITY

The radiolabeled compounds of the present invention are useful as radiotracers for quantitative imaging of PDE10A in mammals.

This application is based on patent application Nos. 1150757-1 and 1250925-3 filed in Sweden, the contents of which are incorporated in full herein.

The invention claimed is:

1. 1-[2-Fluoro-4-(tetrahydro-2H-pyran-4-yl)phenyl]-5-$^{11}$C-methoxy-3-(1-phenyl-1H-pyrazol-5-yl)pyridazin-4(1H)-one or a salt thereof.

2. 1-[4-(3,3-Difluoroazetidin-1-yl)-2-fluorophenyl]-5-$^{11}$C-methoxy-3-(1-phenyl-1H-pyrazol-5-yl)pyridazin-4(1H)-one or a salt thereof.

3. 5-([$^{18}$F]Fluoro-methyloxy-d$_2$)-1-(2-fluoro-4-(tetrahydro-2H-pyran-4-yl)phenyl)-3-(1-phenyl-1H-pyrazol-5-yl)pyridazin-4(1H)-one or a salt thereof.

4. 5-(2-[$^{18}$F]Fluoro-ethyloxy-d$_4$)-1-(2-fluoro-4-(tetrahydro-2H-pyran-4-yl)phenyl)-3-(1-phenyl-1H-pyrazol-5-yl)pyridazin-4(1H)-one or a salt thereof.

5. A method for quantitative imaging of PDE10A in a mammal, which comprises administering to the mammal in need of such imaging an effective amount of the compound of any one of claims 1-4, or a salt thereof, and obtaining an image useful for quantifying PDE10A in the mammal using positron emission tomography.

6. A method for quantitative imaging of PDE10A in the brain in a mammal, which comprises administering to the mammal in need of such imaging an effective amount of the compound of any one of claims 1-4, or a salt thereof, and obtaining an image useful for quantifying PDE10A in the brain in the mammal using positron emission tomography.

7. A method for diagnostic imaging of a neurological or psychiatric disorder associated with PDE10A dysfunction in a mammal, which comprises administering to the mammal in need of such diagnostic imaging an effective amount of the compound of any one of claims 1-4, or a salt thereof, and obtaining an image useful for quantifying PDE10A in the brain in the mammal using positron emission tomography.

8. A method for diagnostic imaging of a neurological or psychiatric disorder associated with striatal hypofunction or basal ganglia dysfunction in a mammal, which comprises administering to the mammal in need of such diagnostic imaging an effective amount of the compound of any one of claims 1-4, or a salt thereof, and obtaining an image useful for quantifying PDE10A in the brain in the mammal using positron emission tomography.

9. A method for the quantification of PDE10A in mammalian tissue, which comprises contacting such mammalian tissue in which quantification is desired with an effective amount of the compound of any one of claims 1-4, or a salt thereof, and detecting or quantifying the PDE10A using positron emission tomography.

10. A sterile composition which comprises a compound of any one of claims 1-4, or a salt thereof, dissolved in saline.

11. A method of imaging a tissue, cells or a host, which comprises contacting a compound of any one of claims 1-4, or a salt thereof, with or administering a compound of any one of claims 1-4, or a salt thereof to a tissue, cells or a host, and imaging the tissue, cells or host with a PET imaging system.

12. A compound of any one of claims 1-4, or a salt thereof, which is for use of quantitative imaging of PDE10A.

* * * * *